(12) United States Patent
Wang et al.

(10) Patent No.: US 12,344,611 B2
(45) Date of Patent: Jul. 1, 2025

(54) BRIDGED CYCLOFORMYLPYRIDINE DERIVATIVES AND USES THEREOF

(71) Applicant: BroadenBio Co., Ltd., Beijing (CN)

(72) Inventors: Qi Wang, Beijing (CN); Gongping Duan, Beijing (CN); Wei Hua, Beijing (CN); Xingmin Zhang, Beijing (CN)

(73) Assignee: BroadenBio Co., Ltd., Beijing (CN)

( * ) Notice: Subject to any disclaimer, the term of this patent is extended or adjusted under 35 U.S.C. 154(b) by 723 days.

(21) Appl. No.: 17/755,337

(22) PCT Filed: Oct. 21, 2020

(86) PCT No.: PCT/CN2020/122569
§ 371 (c)(1),
(2) Date: Apr. 27, 2022

(87) PCT Pub. No.: WO2021/083011
PCT Pub. Date: May 6, 2021

(65) Prior Publication Data
US 2023/0012600 A1    Jan. 19, 2023

(30) Foreign Application Priority Data

Nov. 1, 2019   (CN) .................. 201911061801.8

(51) Int. Cl.
*C07D 471/18*     (2006.01)
*A61P 35/00*      (2006.01)

(52) U.S. Cl.
CPC ............ *C07D 471/18* (2013.01); *A61P 35/00* (2018.01)

(58) Field of Classification Search
None
See application file for complete search history.

(56) References Cited

U.S. PATENT DOCUMENTS

2018/0044338 A1    2/2018  Blum et al.

FOREIGN PATENT DOCUMENTS

| CN | 105392788 A   | 3/2016  |
|----|---------------|---------|
| CN | 107207496 A   | 9/2017  |
| CN | 107304210 A   | 10/2017 |
| CN | 109745321 A   | 5/2019  |
| CN | 109922804 A   | 6/2019  |
| WO | 2018083603 A1 | 5/2018  |

OTHER PUBLICATIONS

Chinese Office Action issued in 202080075456.8 dated Sep. 29, 2023.
Singaporean Office Action issued in 11202204587W dated Aug. 28, 2023.

*Primary Examiner* — Kortney L. Klinkel
*Assistant Examiner* — Donna M Nestor
(74) *Attorney, Agent, or Firm* — Fox Rothschild LLP

(57) ABSTRACT

Provided are a compound of formula (I), or a pharmaceutically acceptable salt, solvate, active metabolite, polymorph, isotopic label, isomer or prodrug thereof, and a use thereof. The above-mentioned compound has a very strong inhibitory effect on the FGFR4 kinase activity and the proliferative activity of Hep 3B cells with high FGFR4 expression.

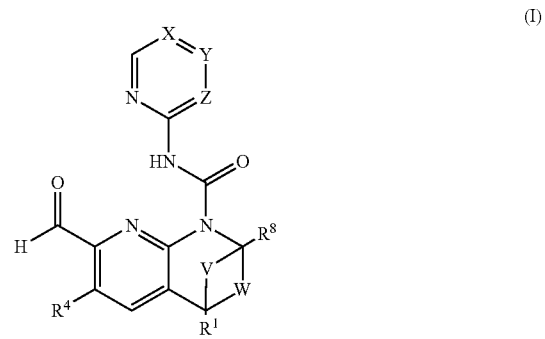

13 Claims, 1 Drawing Sheet

BRIDGED CYCLOFORMYLPYRIDINE DERIVATIVES AND USES THEREOF

CROSS-REFERENCE TO RELATED APPLICATIONS

This application is the U.S. National Phase of International Patent Application No. PCT/CN2020/122569, filed on Oct. 21, 2020, which claims priority to Chinese Patent Application No. 201911061801.8, filed on Nov. 1, 2019. The contents of the applications are incorporated herein by reference in their entirety.

TECHNICAL FIELD

This disclosure relates to formylpyridine derivatives, in particular to a bridged cycloformylpyridine derivative with FGFR4 inhibitory activity.

BACKGROUND OF ART

Fibroblast growth factor (FGF) is a family consisting of more than twenty kinds of polypeptides with similar structures while different biological activities, and plays an important role in stimulating cell proliferation, migration and differentiation as well as bone and limb development, tissue repair, angiogenesis and tumorigenesis.

Fibroblast growth factor receptor (FGFR) belongs to the receptor tyrosine kinase family, including FGFR1, FGFR2, FGFR3 and FGFR4 (Turner, N., Grose, R., Nat. Rev. Cancer, 2010, 10: 116-129). FGFR4 consists of a ligand-binding extracellular domain, a transmembrane domain, and a receptor phosphorylated intracellular domain. When the ligand specifically binds to the receptor, it induces FGFR4 autophosphorylation and then dimerization, so that its domain changes from an inactive state to an active state. Activated FGFR4 in turn phosphorylates with intracellular kinases, thereby activating a series of downstream related signaling pathways, such as mitogen-activated protein kinase (MAPK), phosphatidylinositol-3 kinase/protein kinase B (PI3K/Akt) etc., ultimately stimulate cell proliferation, differentiation, inhibit cell apoptosis, regulate cell proliferation, differentiation and metastasis (Haugsten, E. M. et al., Mol. Cancer Res., 2010, 8: 1439-1452; Carter, E. P. et al., Trends Cell Biol., 2015, 25: 221-233).

Abnormal signal transduction such as overexpression or mutation of FGFR4 gene or overexpression of its ligand FGF19 plays an important role in the occurrence and development of certain tumors. FGF19 can bind to FGFR4 with high specificity and activate FGFR4 (Harmer, N. J. et al., Biochemistry, 2004, 43: 629-640.), and this signaling pathway has a very important role in liver cancer. About 50% of patients with hepatocellular carcinoma has abnormally high expression of FGFR4 gene and has a poor prognosis (French, D. M. et al., PLoS One, 2012, 7: e36713). In addition, FGFR4/FGF19 overexpression has also been reported to be related with the metastasis and invasiveness of other cancers such as breast cancer (Jaakko, S. et al, Int. J. Cancer, 1993, 54: 378-382), glioblastoma (Masica, D. L. et al., Cancer Res., 2011, 71: 4550-4561), prostate cancer (Wang, J. et al., Clin. Cancer Res., 2004, 10: 6169-6178), rhabdomyosarcoma (Crose, L. E. S. et al., Clin. Cancer Res., 2012, 18: 3780-3790), gastric cancer (Ye, Y. et al., Ann. Surg. Oncol., 2010, 17: 3354-3361), ovarian cancer (Zaid, T. M. et al., Clin. Cancer Res., 2013, 19: 809-820), lung cancer (Fawdara, S. et al., PNAS, 2013, 110: 12426-12431), colorectal cancer (Desnoyers, L. R. et al., Oncogene, 2008, 27: 85-97), and skin cancer.

In addition, mutations in the FGFR4 kinase region have been found in rhabdomyosarcoma, non-small cell lung cancer, malignant glioma and other tumors. Mutations that persistently activate FGFR4 kinase activity are found in 7% to 8% of patients with rhabdomyosarcoma, which mainly occur at K535 and E550, increase FGFR4 kinase activity, and are associated with metastases in advanced tumors (Taylor VI, J. G. et al., J. Clin. Invest., 2009, 119: 3395-3407). The $FGFR4^{Y367C}$ mutation in breast cancer cell MDA-MB453 causes FGFR4 to spontaneously form a dimer, which leads to constitutive activation of ERK, enhancement of MAPK signaling pathway, promotion of cell proliferation, and induction of tumor formation (Roidl, A. et al., Oncogene, 2010, 29: 1543-1552).

Although a series of patent applications for FGFR4 inhibitors have been published, including WO2014011900, WO2015061572, WO2016064960, WO2016134294, WO2016134314, etc., the FGFR4 inhibitory activity of the existing compounds is not good enough, so new compounds with better activities and efficacy need to be developed.

SUMMARY

A primary object of the present disclosure is to provide a compound of formula (I) or a pharmaceutically acceptable salt, solvate, active metabolite, polymorph, isotopic label, isomer or prodrug thereof,

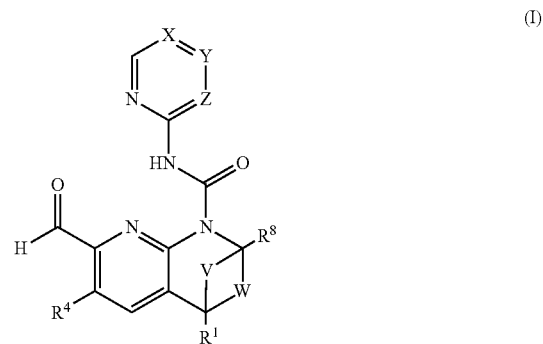

(I)

wherein, V and W are independently selected from $C_1$~$C_4$ alkylene or cyclopropylene, and V, W and the carbon atom connecting $R^8$ and the carbon atom connecting $R^1$ together form a 4-6 membered carbocyclic group;

X is selected from $C(R^X)$ or N; Y is selected from $C(R^Y)$ or N; Z is selected from CH or N; and at most one of X, Y, Z is N;

$R^X$ is selected from:
1) hydrogen, halogen, cyano, $C_3$~$C_6$ cycloalkyl, ethynyl; or
2) $C_1$~$C_6$ alkyl, which is unsubstituted or substituted by one or more groups selected from halogen and hydroxyl;

$R^Y$ is selected from:
1) hydrogen, halogen, cyano, $C_1$~$C_3$ alkylthio;
2) $C_1$~$C_6$ alkyl, which is unsubstituted or substituted by one or more hydroxyl groups;
3) $C_3$~$C_6$ cycloalkyl, which is unsubstituted or substituted by one or more hydroxyl groups;

4) $C_3\sim C_6$ cycloalkoxy, which is unsubstituted or substituted by one or more groups selected from the group consisting of hydroxyl, $C_1\sim C_3$ alkoxy and $CH_3OCH_2$—;

5) $C_1\sim C_6$ alkoxy, which is unsubstituted or substituted by one or more groups selected from the group consisting of hydroxyl, halogen, $C_1\sim C_3$ alkoxy, $C_1\sim C_3$ alkoxy substituted by one or more $C_1\sim C_3\sim C_3\sim C_6$ cycloalkoxy, —$NR^{Y1}R^{Y2}$; or 6) —$NR^{Y1}R^{Y3}$, —O—$(CH_2)_{0-1}$—$R^{Y7}$ or —$CHR^{Y8}R^{Y9}$;

$R^{Y1}$ is selected from hydrogen or $C_1\sim C_6$ alkyl;

$R^{Y2}$ is selected from hydrogen, unsubstituted or hydroxy-substituted $C_1\sim C_3$ alkyl;

$R^{Y3}$ is selected from:

1) $C_1\sim C_6$ alkyl, which is unsubstituted or substituted by one or more selected from the group consisting of hydroxyl, halogen, $C_1\sim C_3$ alkoxy, $C_1\sim C_3$ alkoxy optionally substituted by one or more $C_1\sim C_3$ alkoxy, $C_1\sim C_3$ haloalkoxy, —$S(=O)_2R^{Y5}$, cyclopropyl optionally substituted by one or more $C_1\sim C_3$ alkoxy, —$NR^{Y1}R^{Y2}$;

2) $C_3\sim C_6$ cycloalkyl, which is unsubstituted or substituted by one or more selected from the group consisting of hydroxyl, halogen, $C_1\sim C_3$ alkoxy, $C_1\sim C_3$ haloalkoxy, —$NHS(=O)_2CH_3$, —$NR^{Y1}R^{Y2}$;

3) $C_5\sim C_8$ bicycloalkyl, which is unsubstituted or substituted with one or more groups selected from the group consisting of hydroxy, hydroxymethyl, $C_1\sim C_3$ alkyl; or 4) —$(CH_2)_{0-1}$—$R^{Y4}$, —$C(=O)R^{Y5}$, —$S(=O)_2R^{Y5}$; or $R^{Y1}$, $R^{Y3}$ and the N atom to which they are attached together form a 4-6 membered aliphatic heterocyclyl that is unsubstituted or optionally substituted by one or more $R^{Y6}$; $R^{Y4}$ is selected from:

1) 4-6 membered saturated heterocyclyl which is unsubstituted or substituted by one or more groups selected from the group consisting of $C_1\sim C_3$ alkyl, —$S(=O)_2R^{Y5}$ and oxo;

2) phenyl, which is unsubstituted or substituted by one or more —$S(=O)_2R^{Y5}$;

$R^{Y5}$ is selected from $C_1\sim C_3$ alkyl; $R^{Y6}$ is selected from:

1) hydroxyl, $C_1\sim C_3$ alkoxy;

2) $C_1\sim C_3$ alkyl which is unsubstituted or substituted by one or more —$NR^{Y1}R^{Y2}$; or 3) Two $R^{Y6}$ connected to the same carbon atom together with the carbon atom to which they are connected form an 5-membered saturated heterocyclyl which is unsubstituted or substituted with one or more $C_1\sim C_3$ alkyl;

$R^{Y7}$ is selected from:

1) quinuclidinyl; or 2) 4-6 membered saturated heterocyclyl, which is unsubstituted or optionally substituted by one or more groups selected from the group consisting of $C_1\sim C_3$ alkyl and oxo;

$R^{Y8}$, $R^{Y9}$ and the carbon atoms to which they are attached together form a 6-membered saturated aliphatic heterocyclyl;

or $R^X$, $R^Y$ and the carbon atoms to which they are attached together form a fused heterocyclyl that is unsubstituted or optionally substituted by one or more $C_1\sim C_3$ alkyl, and the fused heterocyclyl includes two fused cyclic groups, and the number of ring atoms of the fused heterocyclyl is 9-10;

$R_1$ is selected from:

1) hydrogen, halogen, cyano, —$N_3$, carboxyl, ethynyl; or

2) $C_1\sim C_3$ alkyl, which is unsubstituted or substituted by one or more groups selected from the group consisting of hydroxyl and halogen;

3) —$OR^2$, —$(CH_2)_{0-1}NR^2R^3$ or —$C(=O)$—$NR^2R^3$;

$R^2$ is selected from:

1) hydrogen; or

2) $C_3\sim C_6$ cycloalkyl, which is unsubstituted or substituted by one or more groups selected from the group consisting of hydroxyl, halogen, $C_1\sim C_3$ alkoxy, and —$NR^{Y1}R^{Y2}$;

3) $C_1\sim C_3$ alkyl, which is unsubstituted or substituted by one or more groups selected from the group consisting of hydroxyl, halogen, $C_1\sim C_3$ alkoxy, $C_1\sim C_3$ alkoxy optionally substituted by one or more $C_1\sim C_3$ alkoxy, $C_1\sim C_3$ haloalkoxy, —$NR^{Y1}R^{Y3}$ and —$C(=O)$—$NR^{Y1}R^{Y3}$; or

4) —$(CH_2)_{0-1}$—$R^{Y4}$;

$R^3$ is selected from:

1) hydrogen, $C_1\sim C_3$ alkyl; or

2) $C_1\sim C_4$ acyl, which is unsubstituted or substituted by one or more groups selected from the group consisting of hydroxyl, $C_3\sim C_6$ cycloalkyl, $C_1\sim C_3$ alkoxy, —$NR^{Y1}R^{Y3}$, and $R^{Y4}$;

3) —$C(=O)$—$R^9$, —$S(=O)_2R^{Y5}$;

or $R^2$, $R^3$ and the N atom to which they are attached together form a 4-6 membered saturated heterocyclyl which is unsubstituted or substituted with one or more $R^7$;

$R^4$ is selected from:

1) hydrogen, halogen, —$CH_2CO_2H$, —$C(=O)H$;

2) $C_1\sim C_3$ alkyl, which is unsubstituted or substituted by one or more groups selected from the group consisting of hydroxyl, halogen, $C_1\sim C_3$ alkoxy, $C_1\sim C_3$ haloalkoxy;

3) $C_3\sim C_6$ cycloalkyl, which is unsubstituted or substituted by one or more groups selected from the group consisting of hydroxyl, halogen, $C_1\sim C_3$ alkoxy, $C_1\sim C_3$ haloalkoxy;

4) 5-membered or 6-membered heterocyclyl, which is unsubstituted or substituted by one or more groups selected from the group consisting of $C_1\sim C_3$ alkyl, $C_1\sim C_3$ haloalkyl, oxetanyl or oxo; or

5) —$CH_2NR^5R^6$, —$CH(CH_3)NR^5R^6$, —$C(CH_3)_2NR^5R^6$;

$R^5$ is selected from $C_3\sim C_6$ cycloalkyl, $C_1\sim C_3$ alkyl which is unsubstituted or substituted by one or more —$NR^{Y1}R^{Y2}$;

$R^6$ is selected from:

1) $C_1\sim C_3$ alkyl, $C_4\sim C_7$ cycloalkylformyl, —$S(=O)_2R^{Y5}$; or

2) $C_1\sim C_4$ acyl, which is unsubstituted or substituted by one or more groups selected from the group consisting of hydroxyl, $C_1\sim C_3$ alkoxy, —$NR^{Y1}R^{Y2}$;

or $R^5$, $R^6$ and the N atom to which they are attached together form a 4-7 membered saturated heterocyclyl which is unsubstituted or substituted with one or more $R^7$;

$R^7$ is selected from:

1) $C_1\sim C_4$ acyl, hydroxyl, oxo, —$NR^{Y1}R^{Y2}$; or

2) $C_1\sim C_3$ alkyl, which is unsubstituted or substituted by one or more hydroxyl groups;

or

Two $R^7$ connected to the same carbon atom and the carbon atom connected to them together form a 4-6 membered saturated heterocyclyl;

$R^8$ is selected from hydrogen or $C_1\sim C_3$ alkyl;

R⁹ is 4-6 membered saturated heterocyclic or aromatic heterocyclyl, which is unsubstituted or substituted by one or more groups selected from the group consisting of $C_1$~$C_3$ alkyl and oxo.

One embodiment of the present disclosure provides a pharmaceutical composition, containing the above-mentioned compound of formula (I) or a pharmaceutically acceptable salt, solvate, active metabolite, polymorph, isotopic label, isomer or pro-drug thereof, and a pharmaceutically acceptable carrier.

One embodiment of the present disclosure provides use of the above-mentioned compound of formula (I) or a pharmaceutically acceptable salt, solvate, active metabolite, polymorph, isotopic label, isomer or prodrug thereof, or the above-mentioned pharmaceutical composition in the prevention or treatment of a disease mediated by FGFR4, FGF19 or KLB (β-Klotho).

One embodiment of the present disclosure provides use of the above-mentioned compound of formula (I) or a pharmaceutically acceptable salt, solvate, active metabolite, polymorph, isotopic label, isomer or prodrug thereof, or the above-mentioned pharmaceutical composition in the manufacture of a medicament for preventing or treating a disease mediated by FGFR4, FGF19 or KLB (β-Klotho).

One embodiment of the present disclosure provides use of the above-mentioned compound of formula (I) or a pharmaceutically acceptable salt, solvate, active metabolite, polymorph, isotopic label, isomer or prodrug thereof, or the above-mentioned pharmaceutical composition in the treatment of benign or malignant tumors or obesity.

One embodiment of the present disclosure provides use of the above-mentioned compound of formula (I) or a pharmaceutically acceptable salt, solvate, active metabolite, polymorph, isotopic label, isomer or prodrug thereof, or the above-mentioned pharmaceutical composition in the preparation of a medicament for the treatment of benign or malignant tumors or obesity.

According to One embodiment of the present disclosure, the malignant tumor includes one or more of hepatocellular carcinoma, cholangiocarcinoma, breast cancer, glioblastoma, prostate cancer, rhabdomyosarcoma, esophageal squamous cell carcinoma, malignant peripheral nerve sheath tumor, gastric cancer, ovary cancer, lung cancer, colorectal cancer, and skin cancer.

One embodiment of the present disclosure provides a method of preventing or treating a disease mediated by FGFR4, FGF19, or KLB (β-Klotho), including administering to a patient suffering from a disease mediated by FGFR4, FGF19, or KLB (β-Klotho) a therapeutically effective amount of a compound of formula (I).

The compound of one embodiment of the present disclosure has a strong inhibitory effect on the activity of FGFR4 kinase and the proliferation of Hep 3B cells and HuU-7 cells with high FGFR4 expression.

DETAILED DESCRIPTION

Figure 1:
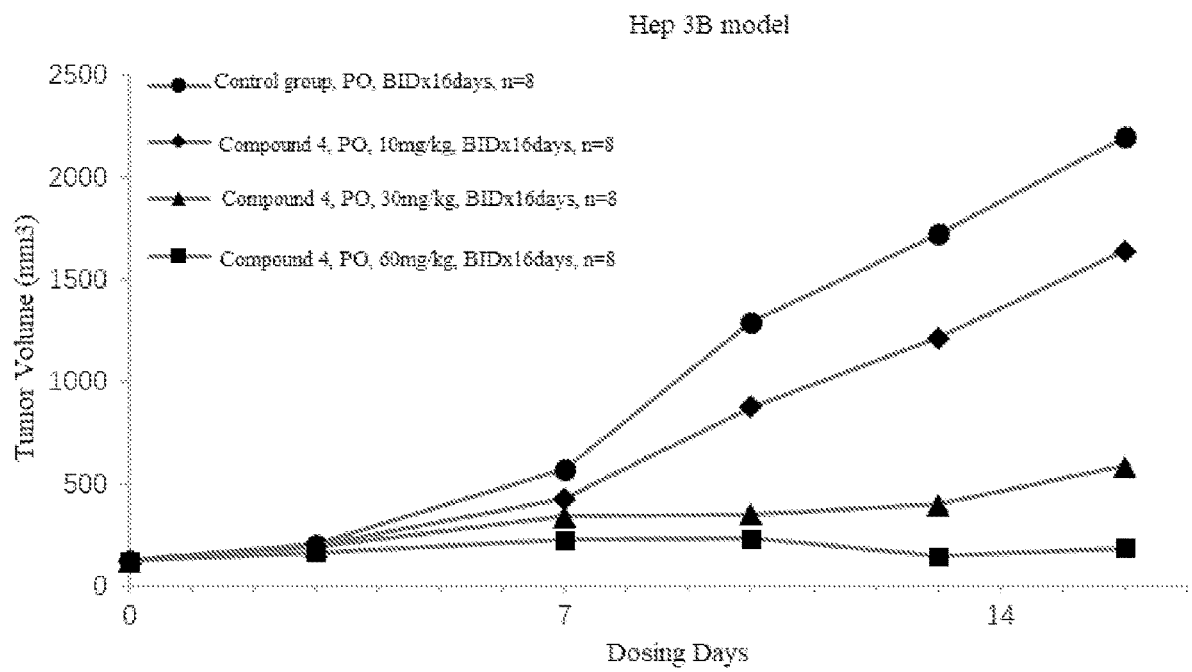
FIGS. 1 and 2 show the in vivo pharmacodynamic data of compound 4 of the present disclosure.

Exemplary embodiments embodying the features and advantages of the present disclosure will be described in detail in the following description, and it is to be understood that the present disclosure is capable of varying in various embodiments without departing from the scope of the present disclosure, and that the description is intended to be illustrative in nature and not to limit the present disclosure.

One embodiment of the disclosure provides a bridged cycloformylpyridine derivative shown in formula (I), which has FGFR4 inhibitory activity and can be used as an FGFR4 inhibitor.

(I)

[Chemical structure]

wherein V, W, X, Y, Z, $R_1$, $R_4$, and $R_8$ are defined as above.

In one embodiment, V, W together with the carbon atom to which the $R^8$ is attached and the carbon atom to which the $R^1$ is attached together form a 4-membered, a 5-membered or a 6-membered carbocyclic group.

In one embodiment, V and W may independently be a linear or branched alkylene or a cycloalkylene containing 1 to 4 carbon atoms, for example, the number of carbon atoms in V, W may be 2 or 3.

In one embodiment, V and W may independently be linear alkylene —$(CH_2)_n$—, and n may be 1~2.

In one embodiment, V and W may independently be a branched alkylene, for example, —HC(CH₃)—,

—C(CH₃)₂, (CH₃)₂, —CH₂(CH₃)CH—, or —CH₂(CH₃)₂C—.

In one embodiment, V and W may independently be a cycloalkylene (C(CH₂)₂).

In one embodiment, only one of X, Y and Z is N; for example, X is N, Y is C($R^Y$), and Z is CH; X is C($R^X$), Y is N, and Z is CH; X is C($R^X$), Y is C($R^Y$), and Z is N.

In one embodiment, X is C($R^X$), Y is C($R^Y$), and Z is CH.

In one embodiment, the number of carbon atoms contained in $R^X$ may be 1-6, for example, 2, 3, 4, and 5.

In one embodiment, $C_1$~$C_6$ alkyl as a substituent of $R^X$ may be a $C_1$~$C_3$ or a $C_1$-$C_6$ alkyl substituted with hydroxy.

In one embodiment, the number of substituents of $R^X$ may be 1, 2, 3, 4, 5 or 6.

In one embodiment, the number of carbon atoms contained in $R^Y$ may be 1-20, such as 2, 3, 4, 5, 6, 7, 8, 9, 10, 12, 14, 15, 16, and 18.

In one embodiment, the number of substituents of $R^Y$ may be 1, 2, 3, 4, 5 or 6.

In one embodiment, $R^Y$ may be $C_1$~$C_3$ alkyl, $C_1$~$C_3$ alkoxy substituted with hydroxyl, $C_1$~$C_3$ alkoxy substituted with $C_1$~$C_3$ alkoxy, $C_1$~$C_3$ alkoxy substituted with $C_3$~$C_6$ cycloalkoxy, $C_3$~$C_6$ cycloalkoxy substituted with $C_1$~$C_3$ alkoxy, $C_1$~$C_3$ alkoxy substituted with both $C_1$~$C_3$ alkoxy and halogen, $C_1$~$C_6$ alkoxy substituted with both hydroxyl and halogen.

In one embodiment, $R^{Y3}$ may contain 1~20, for example, 2, 3, 4, 5, 6, 7, 8, 9, 10, 12, 14, 15, 16, 18 carbon atoms.

In one embodiment, $R^{Y3}$, $R^{Y4}$ or $R^{Y6}$ may have 1, 2, 3, 4, 5 or 6 substituents.

In one embodiment, $R^{Y3}$ may be $C_1$~$C_6$ haloalkyl substituted with hydroxyl, $C_5$~$C_8$ bicycloalkyl substituted with hydroxymethyl.

In one embodiment, $R^{Y1}$ and $R^{Y3}$ together with the N atom to which they are attached form an 5- or 6-membered aliphatic heterocyclyl, unsubstituted or substituted with one or two $R^{Y6}$;

In one embodiment, each $R^{Y6}$ may be the same or different.

In one embodiment, the unsubstituted or substituted 5- or 6-membered aliphatic heterocyclyl formed by $R^{Y1}$, $R^{Y3}$ and N atoms may contain one oxygen atom.

In one embodiment, 5- or 6-membered aliphatic heterocyclyl formed by $R^{Y1}$, $R^{Y3}$ and N atoms may be saturated or unsaturated 5- or 6-membered aliphatic heterocyclyl.

In one embodiment, the unsaturated 5- or 6-membered aliphatic heterocyclyl formed by $R^{Y1}$, $R^{Y3}$ and N atoms may be tetrahydropyridyl, dihydropyranyl, dihydrothiopyranyl.

In one embodiment, two $R^{Y6}$ attached to the same carbon atom together with the carbon atoms to which they are attached form a 5-membered saturated heterocyclyl which is unsubstituted or substituted with one or two $C_1$~$C_3$ alkyl.

In one embodiment, $R^X$, $R^Y$ and the carbon atoms to which they are attached together form an unsubstituted or substituted fused heterocyclyl comprising two fused cyclic groups, may be two heterocyclyls or one is a carbocyclic group and the other is a heterocyclyl; a heterocyclyl may be an aromatic heterocyclyl.

In one embodiment, the fused heterocyclyl formed by $R^X$, $R^Y$ and the carbon atoms to which they are attached may be imidazopyridine, isothiazolopyridine.

In one embodiment, the fused heterocyclyl formed by $R^X$, $R^Y$ contains one or two heteroatoms selected from the group consisting of N, O and S.

In one embodiment, the unsubstituted or substituted 5- or 6-membered saturated heterocyclyl formed by $R^2$, $R^3$ and the N atom to which they are attached may contain one or two heteroatoms. The two heteroatoms include a first heteroatom and a second heteroatom, wherein the first heteroatom is the N atom connected to $R^2$, $R^3$, and the second heteroatom is selected from N, O or S.

In one embodiment, the unsubstituted or substituted 5- or 6-membered saturated heterocyclyl formed by $R^2$, $R^3$ and together with the N atom to which they are attached may be pyrrolidinyl, oxazolidinyl, piperazinyl, morpholinyl or thiomorpholinyl.

In one embodiment, the number of substituent $R^7$ in the substituted 5- or 6-membered saturated heterocyclyl formed by $R^2$, $R^3$ together with the N atom to which they are attached may be 1, 2, 3, or 4.

In one embodiment, $R^2$ is selected from:
1) hydrogen; or
2) $C_3$~$C_6$ cycloalkyl, which is unsubstituted or substituted with one or more groups selected from the group consisting of hydroxyl, halogen, $C_1$~$C_3$ alkoxy, and —$NR^{Y1}R^{Y2}$;
3) $C_1$~$C_3$ alkyl, which is unsubstituted or substituted with one or more groups selected from the group consisting of hydroxyl, halogen, $C_1$~$C_3$ alkoxy, $C_1$~$C_3$ alkoxy optionally substituted with one or more $C_1$~$C_3$ alkoxy, $C_1$~$C_3$ haloalkoxy, —$NR^{Y1}R^{Y2}$, or —C(=O)—$NR^{Y1}R^{Y2}$; or
4) —$(CH_2)_{0-1}$—$R^{Y4}$.

$R^3$ is selected from:
1) hydrogen, $C_1$~$C_3$ alkyl; or
2) $C_1$~$C_4$ acyl, which is unsubstituted or substituted with one or more groups selected from the group consisting of hydroxyl, $C_3$~$C_6$ cycloalkyl, $C_1$~$C_3$ alkoxy, and —$NR^{Y1}R^{Y2}$, $R^{Y4}$;
3) —C(=O)—$R^9$, —S(=O)$_2R^{Y5}$;
or $R^2$, $R^3$ and the N atom to which they are attached together form a 4-6 membered saturated heterocyclyl unsubstituted or optionally substituted with one or more $R^7$.

In one embodiment, each $R^7$ may be the same or different.

In one embodiment, $R^7$ may be attached to a carbon atom on the ring, and may also be attached to a heteroatom on the ring.

In one embodiment, $R_4$ may be an unsubstituted or substituted 5- or 6-membered heterocyclyl, which may be a saturated heterocyclyl, and may also be an aromatic heterocyclyl, wherein heteroatoms include one or more of N, O or S. For example, $R^4$ may be pyrrolidinyl, oxazolidinyl, piperazinyl, morpholinyl or thiomorpholinyl.

In one embodiment, the unsubstituted or substituted 5- or 6-membered saturated heterocyclyl formed by $R^5$, $R^6$ and the N atom to which they are attached contain two heteroatoms, a first heteroatom and a second heteroatom. The first heteroatom is the N atom connected to $R^5$, $R^6$, and the second heteroatom is selected from N, O or S.

In one embodiment, the unsubstituted or substituted 4-, 5-, 6- or 7-membered saturated heterocyclyl formed by $R^5$, $R^6$ and together with the N atom to which they are attached may be azetidinyl, pyrrolidinyl, oxazolidinyl, piperazinyl, morpholinyl or thiomorpholinyl.

In one embodiment, the number of substituent $R^7$ in the substituted 4- to 7-membered saturated heterocyclyl formed by $R^5$, $R^6$ together with the N atom to which they are attached may be 1, 2, 3, or 4.

In one embodiment, in the substituted $C_1$~$C_6$ alkyl, the number of substituents may be one or more, for example, 2, 3, etc.

In one embodiment, the substituted $C_1$~$C_6$ alkyl may be $C_1$~$C_6$ haloalkyl, hydroxyl substituted $C_1$~$C_6$ alkyl, hydroxyl substituted $C_1$~$C_6$ haloalkyl, $C_1$~$C_3$ alkoxy substituted $C_1$~$C_6$ alkyl, $C_1$~$C_3$ haloalkoxy substituted $C_1$~$C_6$ alkyl.

In one embodiment, $C_1$~$C_3$ haloalkyl, $C_1$~$C_6$ haloalkyl may be, for example, trifluoromethyl, difluoromethyl, fluoromethyl, trichloromethyl, 2,2,2-trifluoroethyl, 1-fluoromethyl-2-fluoroethyl, 3-bromo-2-fluoropropyl (—$CH_2$—CHF—$CH_2$Br) and 1-bromomethyl-2-bromoethyl.

In one embodiment, hydroxyl substituted $C_1$~$C_6$ alkyl may be, for example, hydroxymethyl (—$CH_2$OH), 2-hydroxyl ethyl(—$CH_2CH_2$OH), 2-hydroxyl propyl (—$CH_2$(OH)$CHCH_3$), 3-hydroxyl propyl (—$CH_2CH_2CH_2$OH) and 5-hydroxyl amyl (—$CH_2CH_2CH_2CH_2CH_2$OH).

In one embodiment, hydroxyl substituted $C_1$~$C_6$ haloalkyl may be for example, —$CHClCH_2$OH, —$CH_2$(OH)$CH_2CH_2$Cl.

In one embodiment, $C_1$~$C_6$ alkyl substituted with hydroxyl substituted —$NR^{Y1}R^{Y2}$ may be —$OCH_3$N$(CH_2$OH$)_2$, —$OCH_3$N$(CH_3)(CH_2$OH).

In one embodiment, $C_1$~$C_3$ alkoxy substituted $C_1$~$C_6$ alkyl may be methoxymethyl, methoxyethyl, ethoxyethyl, 1-methoxypropyl, 2-methoxypropyl.

In one embodiment, $C_1$~$C_3$ haloalkoxy substituted $C_1$~$C_6$ alkyl may be —$CH_2OCF_3$, —$CH_2OCHF_2$, —$CH_2CH_2OCF_3$.

In one embodiment, substituted $C_1$~$C_6$ alkoxy may be hydroxyl substituted $C_1$~$C_3$ alkoxy, for example, hydroxyl methoxy(—$OCH_2OH$), hydroxyl ethoxy(—$OCH_2CH_2OH$); may be $C_1$~$C_3$ alkoxy substituted $C_1$~$C_3$ alkoxy, for example, —$OCH_2OCH_3$, —$OCH_2CH_2OCH_3$; may be $C_6$ cycloalkoxy substituted $C_1$~$C_3$ alkoxy, for example, cyclopropoxymethoxy (—$OCH_2OC_3H_5$); may be $C_1$~$C_3$ alkoxy substituted with both $C_1$~$C_3$ alkoxy and halogen, for example, methoxytrifluoropropoxy; may be —$NR^{Y1}R^{Y2}$ substituted $C_1$~$C_6$ alkoxy, for example, —$OCH_2N(CH_3)_2$, —$OCH_2CH_2N(CH_3)_2$, —$OCH_2N(CH_2CH_3)_2$, etc.; and may be $C_1$~$C_6$ alkoxy substituted with both hydroxyl and halogen, for example, —$OCH_2CHClCH_2OH$.

In one embodiment, hydroxyl substituted $C_3$~$C_6$ cycloalkyl may be 3-hydroxyl cyclobutyl, 3-hydroxyl cyclopentyl, 4-hydroxyl cyclohexyl.

In one embodiment, halogen-substituted $C_3$~$C_6$ cycloalkyl may be chlorocyclopropyl (—$C_3H_4$~$C_1$), fluorocyclobutyl (—$C_4H_6$—F).

In one embodiment, the substituent of $C_3$~$C_6$ cycloalkyl substituted by $C_1$~$C_3$ alkoxy may be methoxy, ethoxy, n-propoxy, isopropoxy, for example, $C_3$~$C_6$ cycloalkyl substituted by $C_1$~$C_3$ alkoxy may be methoxycyclopropyl (—$C_3H_4$—$OCH_3$), methoxycyclobutyl (—$C_4H_6$—$OCH_3$), methoxycyclopentyl (—$C_5H_8$—$OCH_3$), methoxycyclohexyl (—$C_6H_{10}$—$OCH_3$), ethoxycyclohexyl (—$C_6H_{10}$—$OC_2H_5$).

In one embodiment, the substituent of $C_3$~$C_6$ cycloalkoxy substituted by $C_1$~$C_3$ alkoxy may be methoxy, ethoxy, n-propoxy, isopropoxy, for example, $C_3$~$C_6$ cycloalkoxy substituted by $C_1$~$C_3$ alkoxy may be methoxycyclopropoxy (—$OC_3H_4$—$OCH_3$), methoxycyclobutoxy (—$OC_4H_6$—$OCH_3$), methoxycyclopentyloxy (—$OC_5H_8$—$OCH_3$), methoxycyclohexyloxy (—$OC_6H_{10}$—$OCH_3$), ethoxycyclohexyloxy (—$OC_6H_{10}$—$OC_2H_5$).

In one embodiment, the heteroatoms in a saturated heterocyclyl may be selected from one or more of N, O or S, for example, 2, 3, 4, 5, 6, etc.

In one embodiment, a 4-6 membered saturated heterocyclyl refers to a saturated heterocyclyl containing 4-6 atoms in the ring. A 4-6-membered saturated heterocyclyl may be a 4-membered saturated heterocyclyl, a 5-membered saturated heterocyclyl, or a 6-membered saturated heterocyclyl.

In one embodiment, a 4-6 membered saturated heterocyclyl may be azetidinyl, oxetanyl, pyrrolidinyl, tetrahydrofuranyl, tetrahydrothienyl, piperidinyl, piperazinyl, tetrahydropyranyl, morpholinyl.

In one embodiment, a 5- or 6-membered saturated heterocyclyl may be pyrrolidinyl, oxazolidinyl, piperazinyl, morpholinyl, thiomorpholinyl.

In one embodiment, the 6-membered unsaturated aliphatic heterocyclyl may be tetrahydropyridyl, dihydropyranyl, dihydrothiopyranyl.

In one embodiment, the substituent of a substituted 4-6 membered saturated heterocyclyl may be $C_1$~$C_3$ alkyl, for example, methyl, ethyl, n-propyl, isopropyl, or may be oxo (═O). In one embodiment, the fused heterocyclyl may be a bicyclic group, for example, a benzene ring fused to a heterocyclic ring, or two heterocyclic rings fused.

In one embodiment, the number of carbon atoms contained in the $C_1$~$C_4$ acyl is 1 to 4, and the $C_1$~$C_4$ acyl may be a $C_2$~$C_3$ acyl or $C_2$~$C_4$ acyl, for example, $C_1$~$C_4$ acyl may be acetyl (—$C(═O)CH_3$), propionyl (—$C(═O)CH_2CH_3$), butyryl (—$C(═O)CH_2CH_2CH_3$), 2-methylpropionyl (—$C(═O)CH(CH_3)_2$) etc.

In one embodiment, $C_4$~$C_7$ cycloalkyl formyl contains 4 to 7 carbon atoms, wherein the cycloalkyl is $C_3$~$C_6$ cycloalkyl, for example, $C_4$~$C_7$ cycloalkyl formyl group may be cyclopropylformyl, cyclobutylformyl, cyclopentylformyl, cyclohexylformyl.

In one embodiment, $R^X$ is selected from halogen, cyano (—CN), ethynyl CH) or $C_1$~$C_3$ haloalkyl, for example, —CN, —$CF_3$ and the like.

In one embodiment, $R^Y$ may be cyclopropoxy (—$OC_3H_5$), isopropylthio (—$SCH(CH_3)_2$).

In one embodiment, $R^Y$ may be $C_1$~$C_3$ alkoxy substituted $C_1$~$C_3$ alkyl, for example, —$CH_2CH_2OCH_3$, —$CH(CH_3)CH_2OCH_3$.

In one embodiment, $R^Y$ may be $C_1$~$C_3$ alkoxy, for example, methoxy ($CH_3O$—), ethoxy ($CH_3CH_2O$—), isopropoxy (($CH_3$)$_2$CHO—).

In one embodiment, $R^Y$ may be $C_1$~$C_3$ alkoxy substituted $C_1$~$C_3$ alkoxy, for example, —$OCH_2CH_2OCH_3$, —$OCH(CH_3)CH_2OCH_3$.

In one embodiment, $R^Y$ may be substituted $C_1$~$C_6$ alkoxy, and the substituent may be $C_1$~$C_3$ alkoxy substituted $C_1$~$C_3$ alkoxy, for example, $R^Y$ may be —$OCH_2CH_2OCH_2CH_2OCH_3$. In one embodiment, $R^Y$ may be —O—$(CH_2)_{0-1}$—$R^{Y7}$, $R^{Y7}$ is an unsubstituted 4-, 5-, or 6-membered saturated heterocyclyl with O as the heteroatom in the ring.

In one embodiment, $R^{Y7}$ may be a substituted or unsubstituted 4-, 5-, or 6-membered saturated heterocyclyl, which may contain a heteroatom, for example, an oxygen atom or a nitrogen atom as the heteroatom.

In one embodiment, $R^{Y1}$ may be hydrogen or $C_1$~$C_3$ alkyl.

In one embodiment, $R^{Y3}$ may be $C_1$~$C_3$ alkyl, for example, —$CH(CH_3)_2$.

In one embodiment, $R^{Y3}$ may be halogen substituted $C_1$~$C_3$ alkyl, for example, —$CH_2CH_2F$. In one embodiment, $R^{Y3}$ may be $C_1$~$C_3$ substituted $C_1$~$C_3$ alkyl, for example, —$CH_2CH_2OCF_3$.

In one embodiment, $R^{Y3}$ may be —$S(═O)_2R^{Y5}$ substituted $C_1$~$C_3$ alkyl, for example, —$CH_2CH_2S(═O)_2CH_3$.

In one embodiment, $R^{Y3}$ may be —$NR^{Y1}R^{Y2}$ substituted $C_1$~$C_3$ alkyl; $R^{Y1}$ may selected from hydrogen, $C_1$~$C_3$ alkyl; $R^{Y2}$ may be $C_1$~$C_3$ alkyl; $R^{Y3}$ may be, for example, —$CH_2CH_2N(CH_3)_2$, —$CH_2CH_2NHCH_3$.

In one embodiment, $R^{Y3}$ may be substituted $C_1$~$C_3$ alkyl, and the substituent may be cyclopropyl substituted with methoxy, for example, $R^{Y3}$ may be —$CH_2C_3H_4OCH_3$.

In one embodiment, $R^{Y3}$ may be substituted $C_1$~$C_6$ alkyl, and the substituent may be $C_3$ alkoxy substituted $C_1$~$C_3$ alkoxy, for example, $R^{Y3}$ may be —$CH_2CH_2OCH_2CH_2OCH_3$.

In one embodiment, $R^{Y3}$ may be substituted or un substituted $C_3$~$C_6$ cycloalkyl, for example, cyclopropyl, cyclobutyl, cyclopentyl, cyclohexyl; and the substituent may be $C_1$~$C_3$ alkoxy (for example, methoxy), hydroxyl, —$NHS(═O)_2CH_3$, —$NR^{Y1}R^{Y2}$.

In one embodiment, —$NR^{Y1}R^{Y2}$ may be —$N(CH_3)_2$.

In one embodiment, $R^{Y3}$ may be —$NHS(═O)_2CH_3$ substituted cyclobutyl, hydroxyl substituted cyclobutyl, —$N(CH_3)_2$ substituted cyclobutyl, methoxy substituted cyclobutyl, methoxy substituted cyclopentyl, hydroxyl substituted cyclopentyl.

In one embodiment, $R^Y$ is —$NR^{Y1}R^{Y3}$, $R^{Y1}$ is hydrogen, $R^{Y3}$ is a substituted cyclopentyl, the ring carbon atom (chiral carbon atom) connected to N on the cyclopentyl group and the ring carbon atom connected to the substituent on the cyclopentyl group (chiral carbon atom) may be independently R— or S—, wherein the substituent on the cyclopentyl group may be one group, for example, a methoxy group or a hydroxyl, and the ring carbon atom attached to the substituent may be located ortho to the ring carbon atom to which N is attached.

In one embodiment, $R^{Y3}$ may be substituted or unsubstituted $C_5$~$C_8$ bicycloalkyl substituent may be hydroxyl substituted $C_1$~$C_3$ alkyl, for example, —$CH_2OH$.

In one embodiment, $R^{Y3}$ may be —$(CH_2)_{0-1}$—$R^{Y4}$.

In one embodiment, $R^{Y4}$ may be a substituted or unsubstituted 4-, 5- or 6-membered saturated heterocyclyl, which may contain a heteroatom, for example, an oxygen atom or a nitrogen atom.

In one embodiment, the substituent on the saturated heterocyclyl of $R^{Y4}$ may be oxo, methyl, —$S(=O)_2R^{Y5}$ (for example, —$S(=O)_2CH_3$), and the substituent may be located on the carbon adjacent to the ring heteroatom, and may also be attached to the ring heteroatom.

In one embodiment, $R^{Y4}$ may be a substituted or unsubstituted 4-membered, 5-membered or 6-membered saturated heterocyclyl that may contain a ring heteroatom, for example, N, O or S. The saturated heterocyclyl may be substituted by $C_1$~$C_3$ alkyl (for example, methyl), oxo. The substituent may be connected to a carbon atom on the ring, or connected to a heteroatom on the ring; wherein, when the heteroatom is S, it may be substituted by two oxo groups to form sulfuryl-$S(=O)_2$— on the ring.

In one embodiment, $R^{Y4}$ may be substituted phenyl, and the substituent may be —$S(=O)_2R^{Y5}$, for example, —$S(=O)_2CH_3$, —$S(=O)_2CH(CH_3)_2$.

In one embodiment, $R^{Y1}$, $R^{Y3}$ and the N atom to which they are attached together form a 4-, 5- or 6-membered saturated aliphatic heterocyclyl unsubstituted or substituted with one or two $R^{Y6}$, which may contain a heteroatom (N).

In one embodiment, the substituent $R^{Y6}$ on the aliphatic heterocyclyl formed by $R^{Y1}$, $R^{Y3}$ and the N atom to which they are attached may be one or both of methyl, hydroxyl, and methoxy.

In one embodiment, two $R^{Y6}$ connected to the same carbon atom together with the carbon atom to which they are connected form a 5-membered saturated heterocyclyl substituted by a $C_1$-$C_3$ alkyl (for example, methyl). The 5-membered saturated heterocyclyl may contain one heteroatom, for example, N, and the substituent $C_1$~$C_3$ alkyl may be attached to N.

In one embodiment, $R^1$ may be hydrogen, fluorine, hydroxyl, —$N_3$, ethynyl, cyano, amino.

In one embodiment, $R^1$ may be —$OR^2$, wherein $R^2$ may be $C_1$~$C_3$ alkyl, $C_1$~$C_3$ alkoxy, —$NR^{Y1}R^{Y2}$ substituted $C_1$~$C_3$ alkyl, and $R^{Y1}$, $R^{Y2}$ may independently be $C_1$~$C_3$ alkyl, for example, —$OCH_3$, —$OCH_2CH_2OCH_3$, —$OCH_2CH_2N(CH_3)_2$.

In one embodiment, $R^1$ may be hydroxyl substituted $C_1$~$C_3$ alkyl, for example, —$CH_2OH$.

In one embodiment, $R^1$ may be —$(CH_2)_{0-1}NR^2R^3$ or —$C(=O)$—$NR^2R^3$.

In one embodiment, $R^2$ may be hydrogen, $C_1$~$C_3$ alkyl (for example, methyl), $C_3$~$C_6$ cycloalkyl (for example, cyclopropyl, cyclobutyl, cyclopentyl, cyclohexyl), $C_1$~$C_3$ alkoxy substituted $C_1$~$C_3$ alkyl (for example, —$CH_2CH_2OCH_3$), —$NR^{Y1}R^{Y2}$ substituted $C_1$~$C_3$ alkyl (for example, —$CH_2CH_2N(CH_3)_2$).

In one embodiment, $R^2$ may be substituted $C_1$~$C_3$ alkyl, and the substituent may be $C_1$-$C_3$ alkoxy substituted $C_1$~$C_3$ alkoxy, for example, $R^2$ may be —$CH_2CH_2OCH_2CH_2OCH_3$.

In one embodiment, $R^2$ may be —$NR^{Y1}R^{Y2}$ substituted $C_3$~$C_6$ cycloalkyl (for example, cyclobutyl, cyclopentyl) —$NR^{Y1}R^{Y2}$ may be —$N(CH_3)_2$.

In one embodiment, $R^2$ may be —$(CH_2)_{0-1}$—$R^{Y4}$.

In one embodiment, $R^2$ may be —$C(=O)NR^{Y1}R^{Y2}$ substituted $C_1$~$C_3$ alkyl, —$NR^{Y1}R^{Y2}$ may be —$N(CH_3)_2$, for example, $R^2$ may be —$CH_2C(=O)N(CH_3)_2$.

In one embodiment, $R^3$ may be hydrogen.

In one embodiment, $R^3$ may be substituted or unsubstituted $C_1$~$C_4$ acyl, for example, may be substituted or unsubstituted $C_2$~$C_4$ acyl, and the substituent may be —$NR^{Y1}R^{Y2}$, for example, $R^3$ may be —$C(=O)CH_2N(CH_3)_2$.

In one embodiment, $R^2$, $R^3$ and the N atom to which they are attached together form a 4-, 5- or 6-membered saturated heterocyclyl that is unsubstituted or substituted by one or more $R^7$, and the saturated heterocyclyl may contain one or two ring heteroatoms, for example, two nitrogen atoms, one nitrogen atom and one oxygen atom.

In one embodiment, $R^7$ may be hydroxyl, methyl, ethyl, oxo, —$N(CH_3)_2$, —$C(=O)CH_2OH$, $C_4$ acyl (for example, —$C(=O)CH_3$).

In one embodiment, $R^7$ may be attached to the carbon atom ortho to the ring heteroatom.

In one embodiment, $R^9$ may be an unsubstituted or substituted 4-, 5 or 6-membered saturated heterocyclyl or aromatic heterocyclyl, and the number of heteroatoms on the ring may be one or two, for example, a nitrogen atom or two nitrogen atoms, and the substituents may be $C_1$~$C_3$ alkyl, for example, methyl.

In one embodiment, $R^4$ may be an unsubstituted or substituted 5- or 6-membered heterocyclyl whose ring heteroatoms may include one or two, for example, two nitrogen atoms, one nitrogen atom and one oxygen atom, or one nitrogen atom and one sulfur atom.

In one embodiment, in $R^4$, the substituent of the 5- or 6-membered heterocyclyl may be oxo.

In one embodiment, $R^4$ may be hydrogen or —$CH_2NR^5R^6$.

In one embodiment, $R^6$ may be $C_2$~$C_4$ acyl, for example, —$C(=O)CH_3$.

In one embodiment, $R^6$ may be —$NR^{Y1}R^{Y2}$ substituted $C_2$~$C_4$ acyl, $R^{Y1}$, $R^{Y2}$ may independently be $C_1$~$C_3$ alkyl, for example, $R^6$ may be —$C(=O)CH_2N(CH_3)_2$.

In one embodiment, $R^6$ may be hydroxyl substituted $C_2$~$C_4$ acyl, for example, —$C(=O)CH_2OH$.

In one embodiment, $R^6$ may be $C_1$~$C_3$ alkoxy substituted $C_2$~$C_4$ acyl, for example, —$C(=O)CH_2OCH_3$.

In one embodiment, $R^5$ may be $C_1$~$C_3$ alkyl, for example, methyl, ethyl.

In one embodiment, $R^5$, $R^6$ and the N atom to which they are attached together form a 4-, 5-, 6- or 7-membered saturated heterocyclyl that is unsubstituted or substituted with one or more $R^7$.

In one embodiment, the ring heteroatoms of the heterocyclyl formed by $R^5$, $R^6$ and the N atom to which they are attached may include one or two, for example, two nitrogen atoms, one nitrogen atom and one oxygen atom, or one nitrogen atom and one sulfur atom.

In one embodiment, the substituent $R^7$ on the saturated heterocyclyl formed by $R^5$, $R^6$ may be oxo (=O), and the oxo group may be connected with a carbon atom to form a carbonyl group, and the carbonyl group may be located in the ortho position of the ring heteroatom; the oxo group may also be attached to a ring heteroatom, for example, two oxo groups attached to the same sulfur atom to form a sulfuryl group.

In one embodiment, the substituent $R^7$ on the saturated heterocyclyl formed by $R^5$, $R^6$ may be $C_1$~$C_3$ alkyl (for example, methyl, ethyl), $C_2$~$C_4$ acyl (for example, acetyl $CH_3(C=O)$—), hydroxyl, and the substituent can be located in the ortho position to the ring heteroatom, or directly attached to the ring heteroatom.

In one embodiment, the compound of formula (I) may have the following structure:

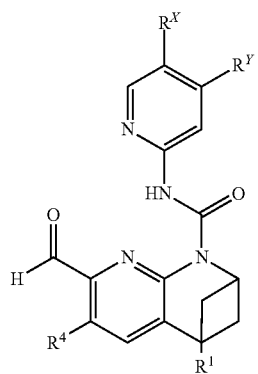

(Ia)

wherein, $R^X$ is selected from the group consisting of halogen, cyano (—CN), $C_1$~$C_3$ haloalkyl; and $R^1$, $R^4$, $R^Y$ are defined as above.

In one embodiment, the compound of formula (I) may have the following structure:

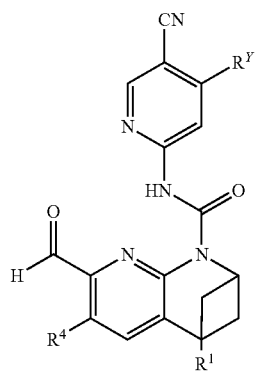

(Ia-1)

Wherein, $R^1$, $R^4$, $R^Y$ are defined as above.

In one embodiment, the compound of formula (I) may have the following structure:

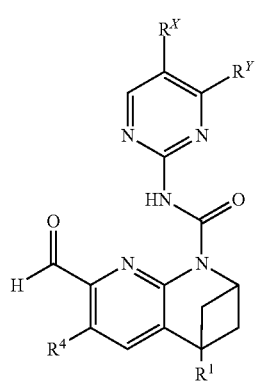

(Ib)

$R^X$ is selected from hydrogen, halogen, cyano or $C_1$~$C_3$ haloalkyl;

$R^Y$ is selected from hydrogen, halogen, cyano, $C_1$~$C_3$ alkyl, $C_3$~$C_6$ cycloalkyl, $C_1$~$C_6$ alkoxy, $C_1$~$C_6$ alkyl hydroxyl, $C_1$~$C_6$ alkoxy optionally substituted with one or more —$NR^{Y1}R^{Y2}$, $C_1$~$C_3$ alkoxy optionally substituted with one or more hydroxyl, $C_1$~$C_3$ alkoxy optionally substituted with one or more $C_1$~$C_3$ alkoxy, $C_1$~$C_3$ haloalkoxy optionally substituted with one or more $C_1$~$C_3$ alkoxy, —$NR^{Y1}R^{Y2}$, —O—$(CH_2)_{0-1}$—$R^{Y3}$;

or $R^X$, $R^Y$ and the carbon atoms to which they are attached together form a fused heterocyclyl, which is unsubstituted or optionally substituted by one or more $C_1$~$C_3$ alkyl; wherein, the fused heterocyclyl contains one or two heteroatoms selected from N, O or S.

The structure of $R^1$, $R^{Y1}$, $R^{Y2}$, $R^{Y3}$, $R^4$ are defined as above.

In one embodiment, the compound of formula (I) may have the following structure:

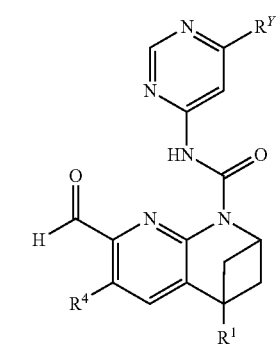

(Ic)

wherein, $R^X$ is selected from the group consisting of hydrogen, halogen, cyano, and $C_1$~$C_3$ haloalkyl;

$R^1$, $R^4$ are defined as above.

In one embodiment, the compound of formula (I) may have the following structure:

(Id)

wherein, $R^Y$ is selected from the group consisting of hydrogen, halogen, cyano, $C_1$~$C_3$ alkyl, $C_3$~$C_6$ cycloalkyl, $C_1$~$C_6$ alkoxy, $C_1$~$C_6$ alkyl optionally substituted with one or more hydroxyl, $C_1$~$C_6$ alkyl optionally substituted with one or more —$NR^{Y1}R^{Y2}$, $C_1$~$C_3$ alkyl optionally substituted with one or more hydroxyl, $C_1$~$C_3$ alkyl optionally substituted with one or more $C_1$~$C_3$ alkyl, $C_1$~$C_3$ haloalkyl optionally substituted with one or more $C_1$~$C_3$ alkyl, —$NR^{Y1}R^{Y2}$, —O—$(CH_2)_{0-1}$—$R^{Y3}$;

$R^{Y1}$, $R^{Y2}$, $R^{Y3}$, $R^4$ are defined as above.

In one embodiment, Y is $C(R^Y)$ $R^Y$ is selected from the group consisting of —$NHCH_2CH_2OCH_3$, —$NHCH(CH_3)CH_2OCH_3$, —$OCH_2CH_2OCH_3$, —$OCH_3$, —$OCH_2CH_3$, —$OCH(CH_3)CH_3$, —$NHCH_2CH_2F$, —$NHCH(CH_3)CH_3$, —$NHCH_2CH_2OCF_3$, —$OCH(CH_3)CH_2OCH_3$, —$SCH(CH_3)CH_3$, —$NHCH_2CH_2S(=O)_2CH_3$, —$NHCH_2CH_2N(CH_3)_2$, —$NHCH_2CH_2NHCH_3$, —$NHCH_2CH_2OCH_2CH_2OCH_3$, and any one of the following structures, wherein " ---- " represents that the bond is connected to other atoms in the structure of formula (I).

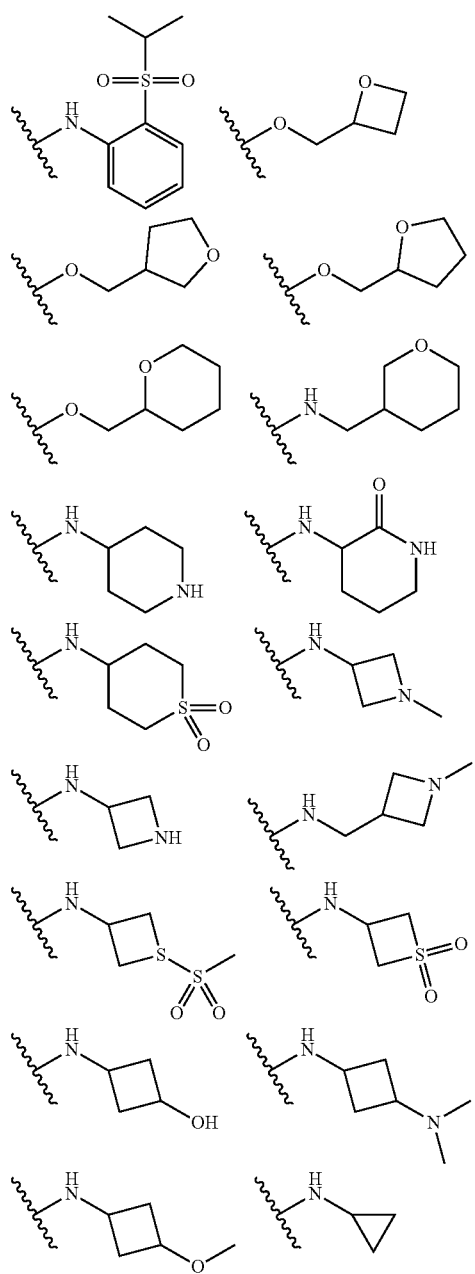

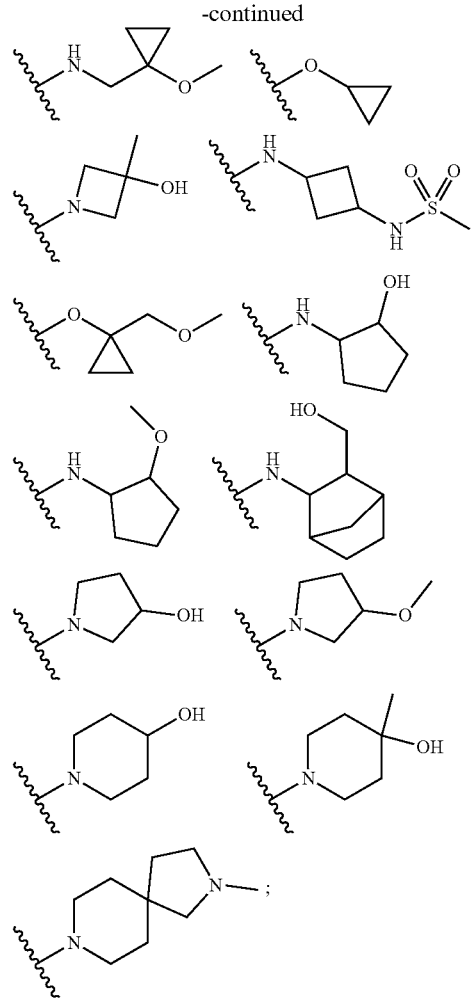

$R^1$ is selected from the group consisting of —F, —OH, —$OCH_3$, —$CH_2OH$, —$N_3$, —$NH_2$, —CN, —H, —$N(CH_3)C(=O)CH_2N(CH_3)_2$, —$NHC(=O)CH_2N(CH_3)_2$, —$NHCH_2CH_2N(CH_3)_2$, —CCH, —$CH_3$, —COOH, —$NHCH_2CH_2OCH_3$, —$C(=O)N(CH_3)CH_2CH_2N(CH_3)_2$, —$C(=O)NHCH_2$—$C(=O)N(CH_3)_2$, —$C(=O)NHCH_2CH_2N(CH_3)_2$, —$CH_2NHCH_2CH_2N(CH_3)_2$, —$CH_2NHC(=O)CH_2N(CH_3)_2$, —$N(CH_3)CH_2C(=O)N(CH_3)_2$, —$OCH_2CH_2N(CH_3)_2$, —$OCH_2CH_2OCH_3$, —$NHCH_2C(=O)N(CH_3)_2$, and any one of the following structures:

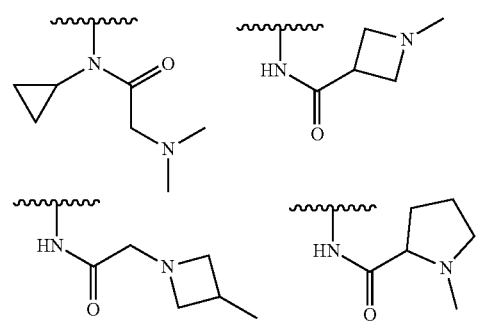

17
-continued
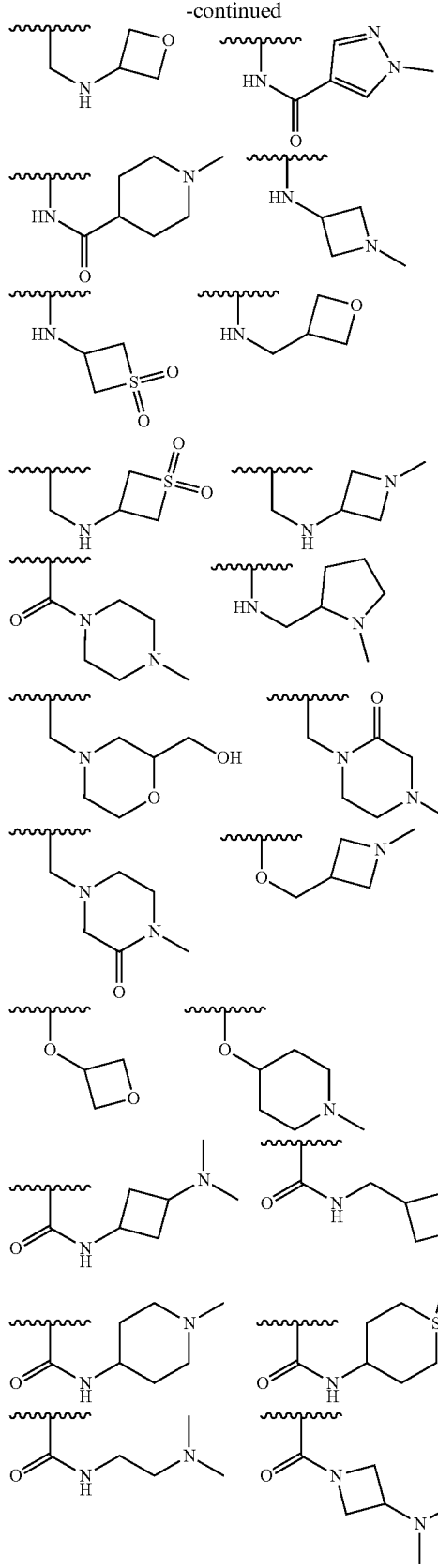
R[4] is selected from the group consisting of —H, —N(CH$_3$)C(=O)CH$_2$N(CH$_3$)$_2$, —CH$_2$N(CH$_3$)C(=O)
18
CH$_3$, —CH$_2$N(CH$_3$)C(=O)CH$_2$OH, —CH$_2$N(CH$_3$)C(=O)CH$_2$OCH$_3$, and any one of the following structures:
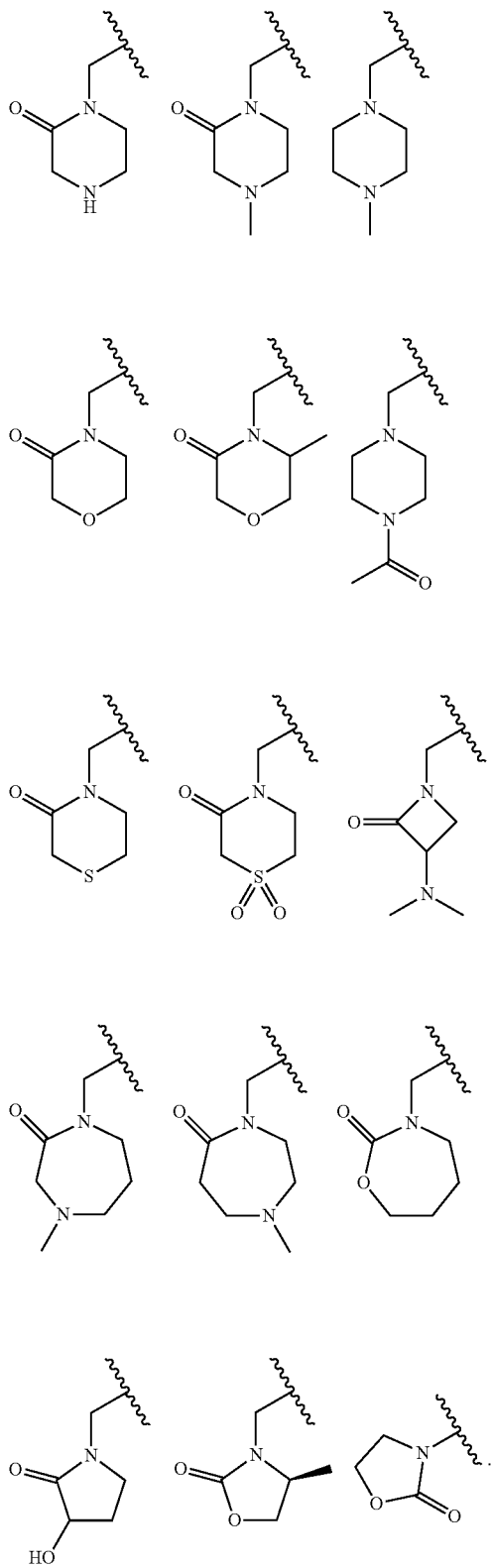

In one embodiment, the compound represented by formula (I) may be:
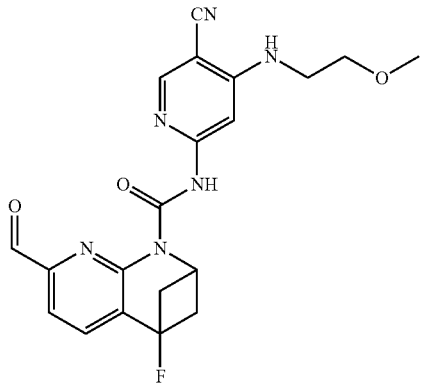
1
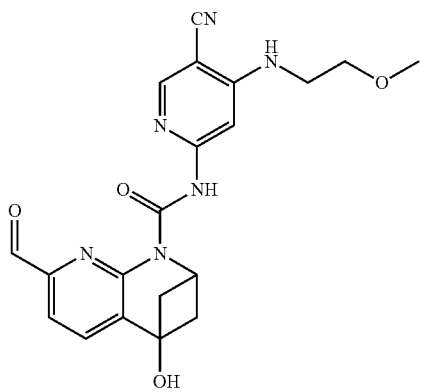
2
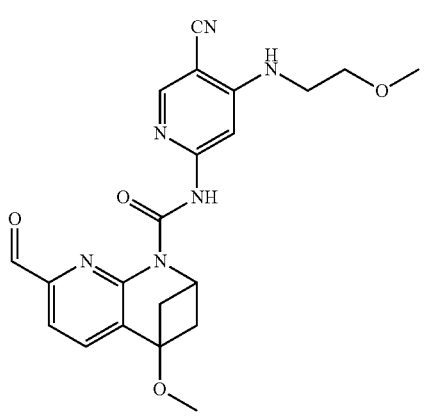
3
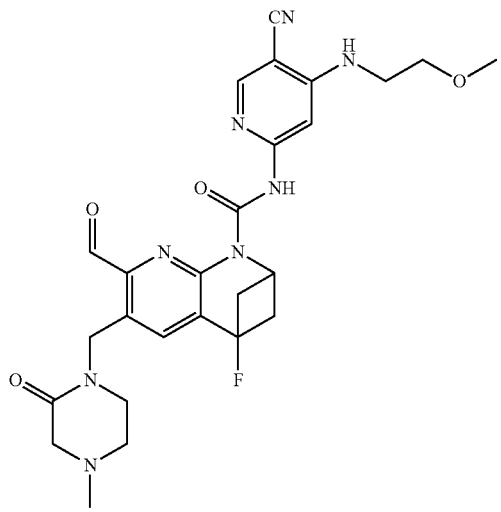
4
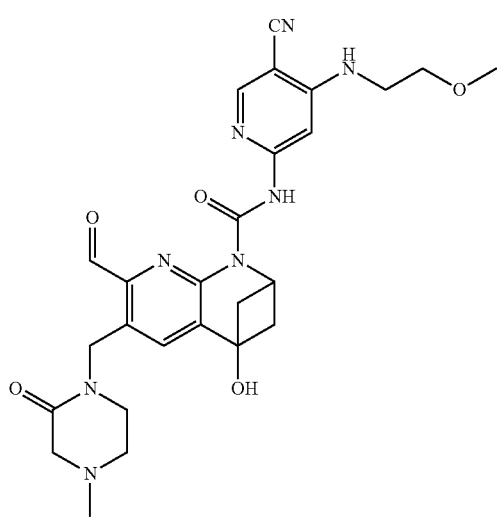
5
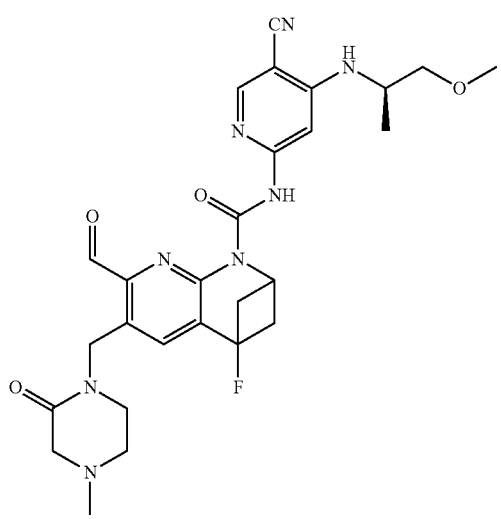
6

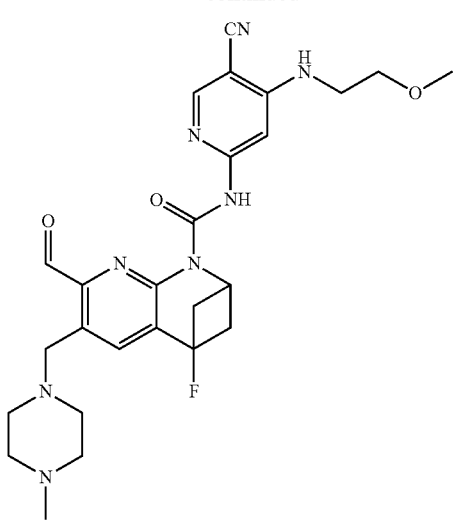
7
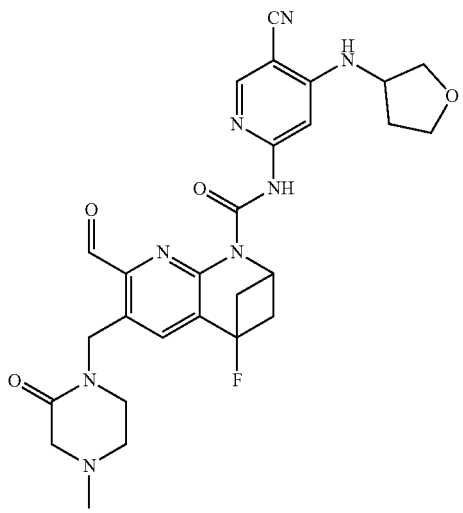
10
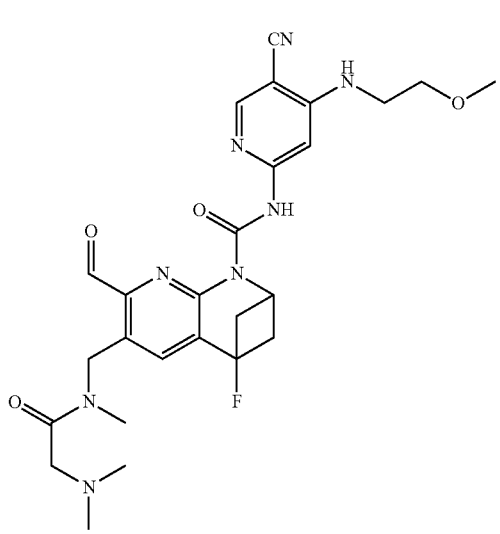
8
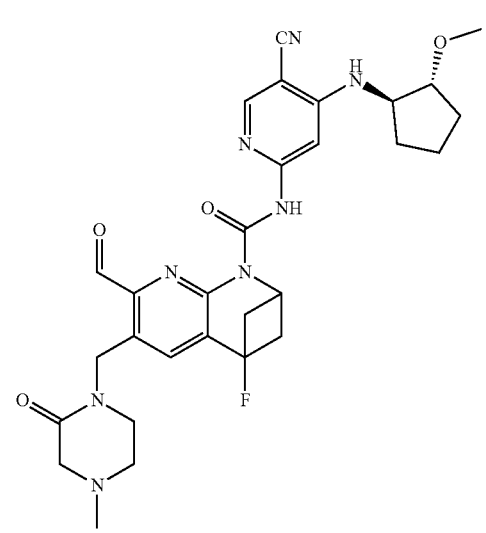
11A
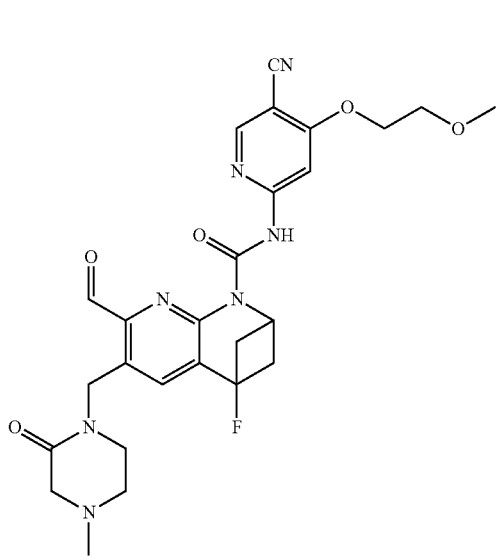
9
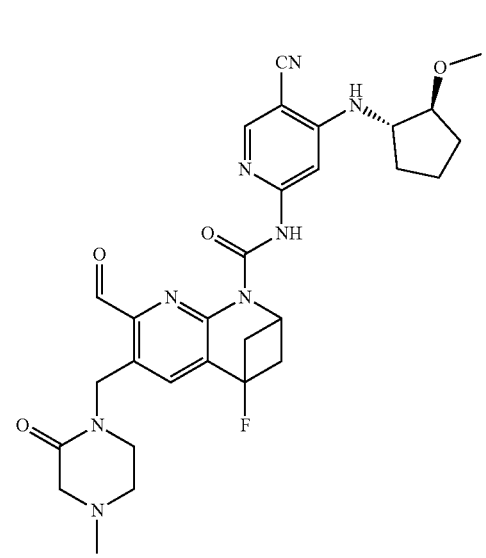
11B 23
-continued
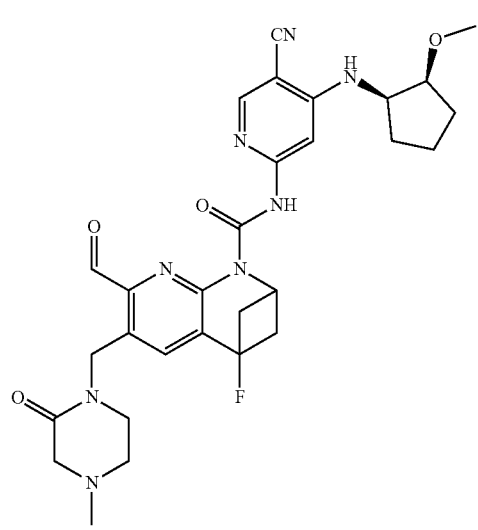
12A
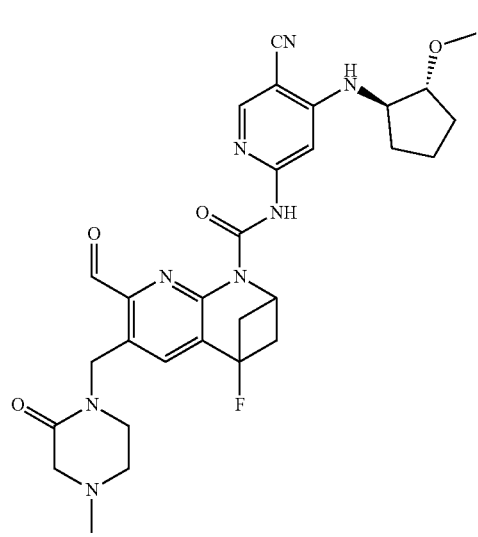
12B
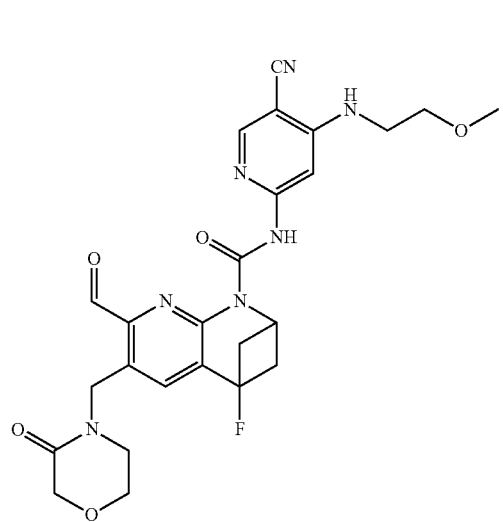
13
24
-continued
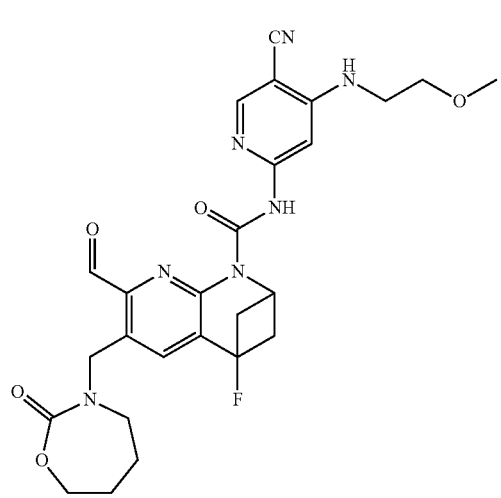
14
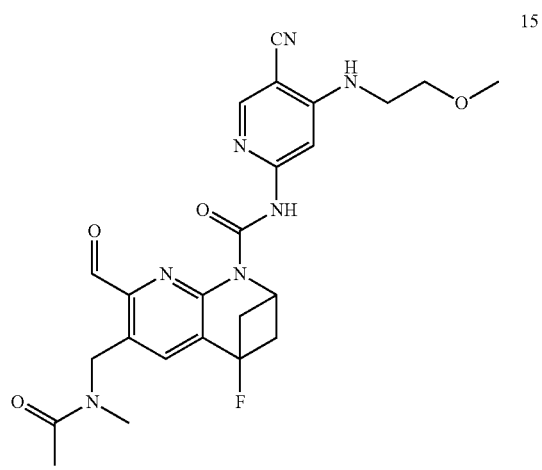
15
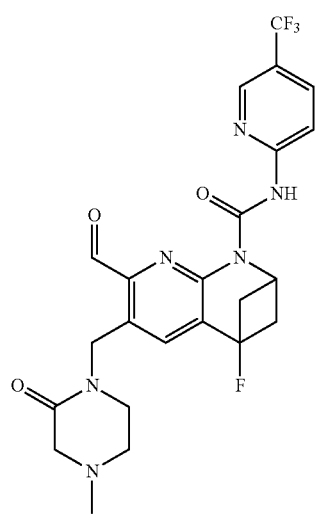
16

-continued
17
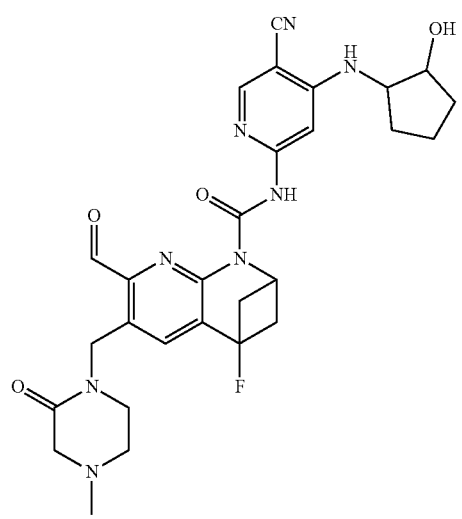
18
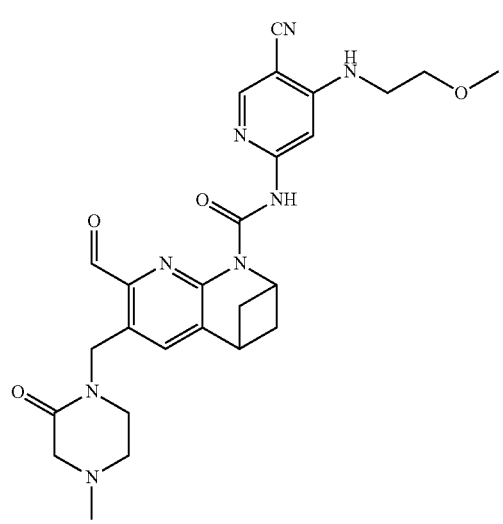
19
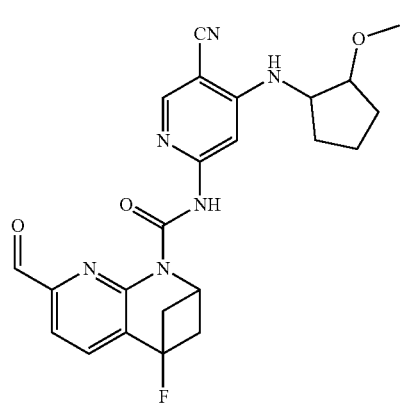
20
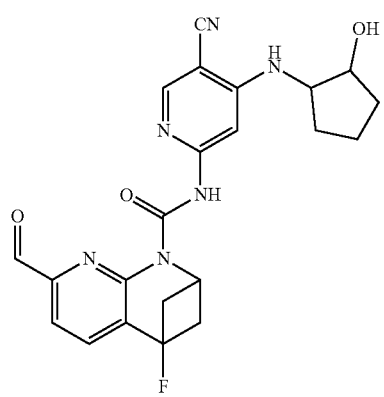
21
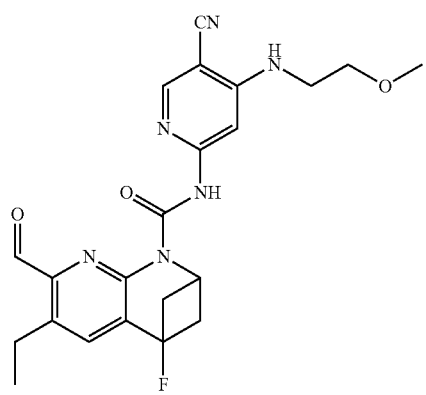
22
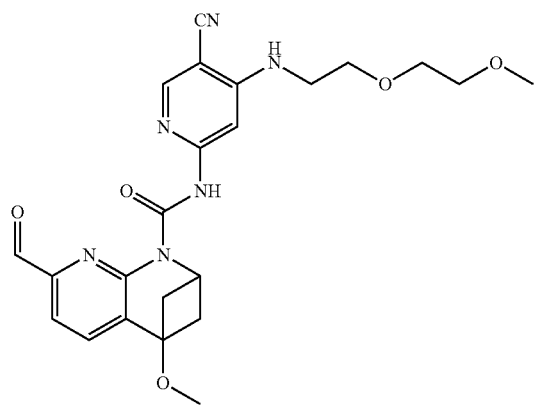
23
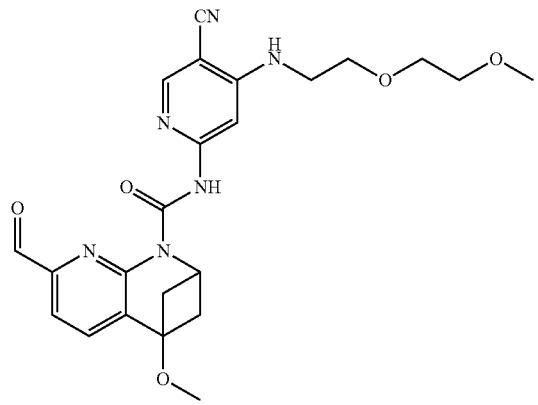

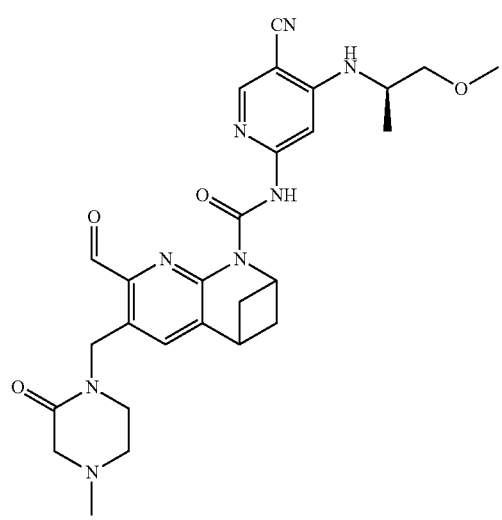
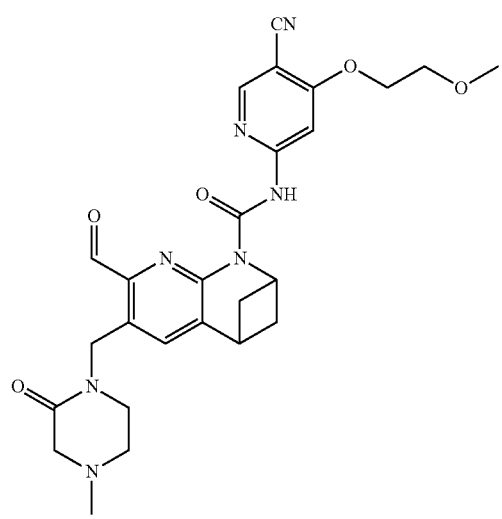
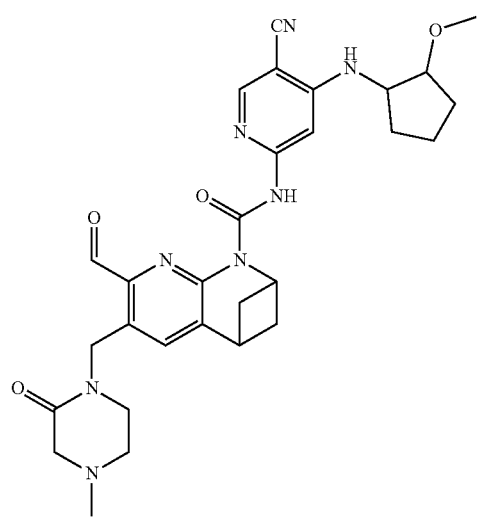
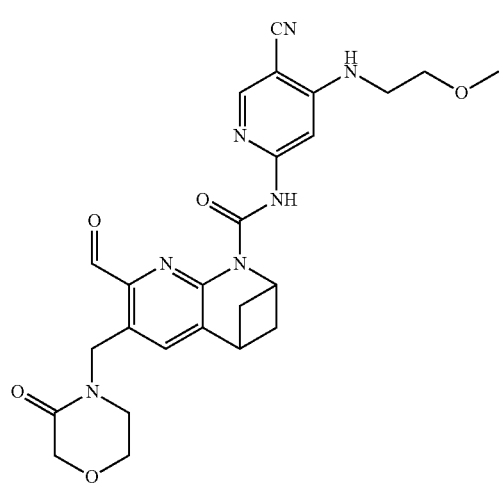
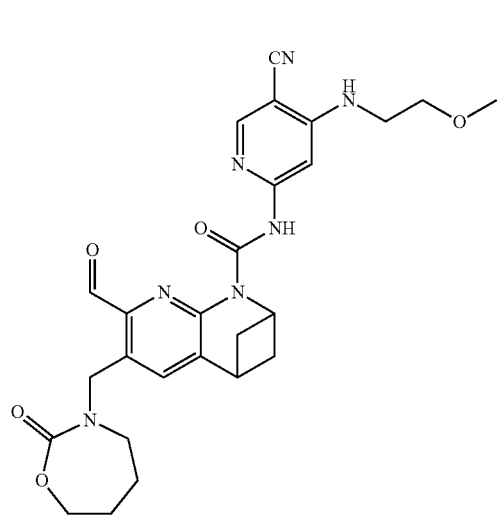

29 -continued
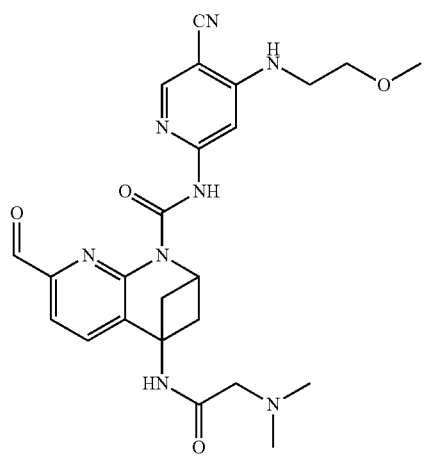
30
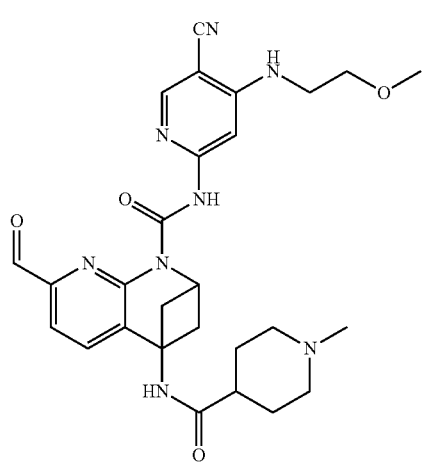
31
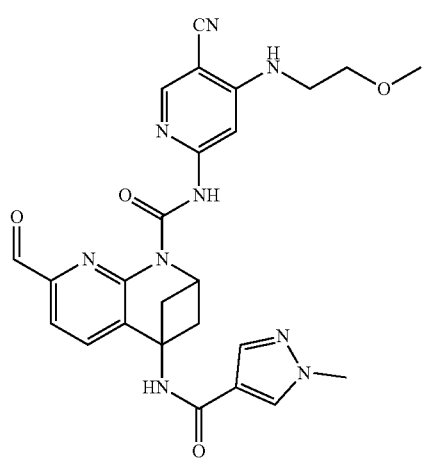
32
30 -continued
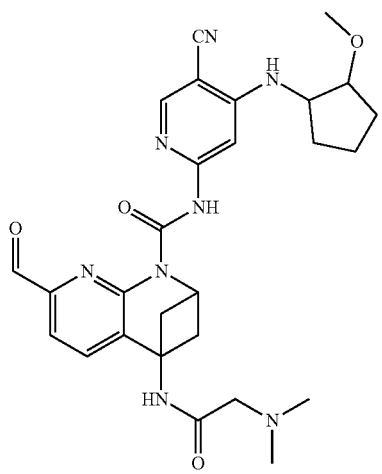
33
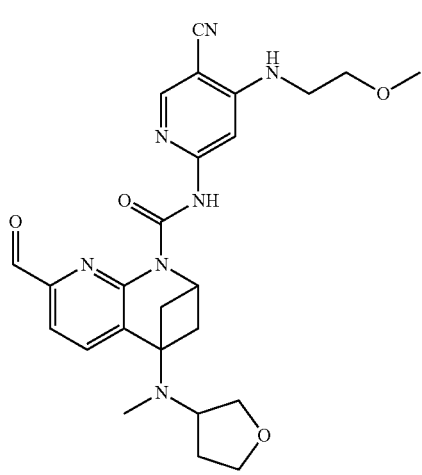
34
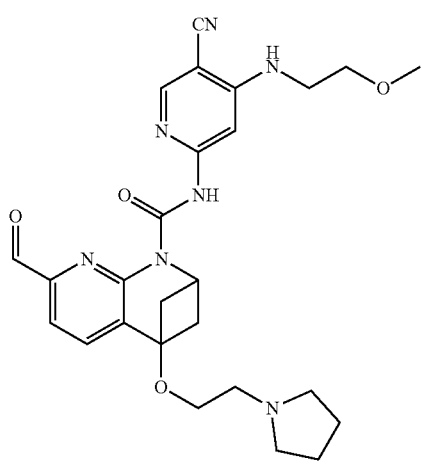
35

| 36 | 39 |
|---|---|
| 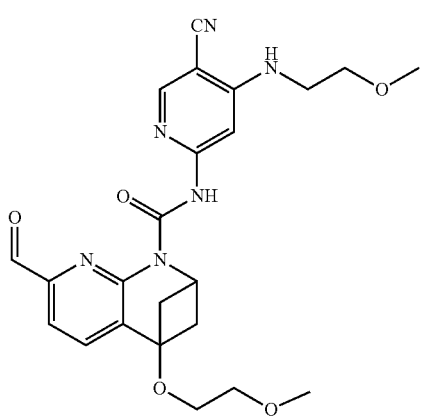 | 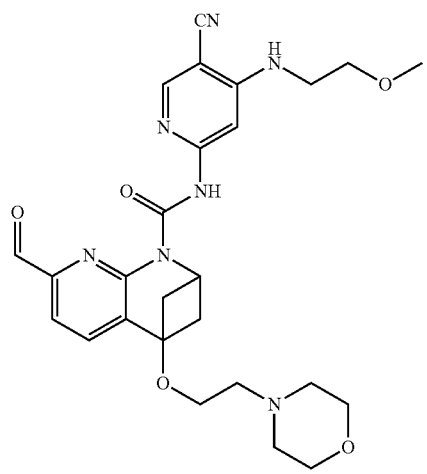 |
| 37 | 40 |
| 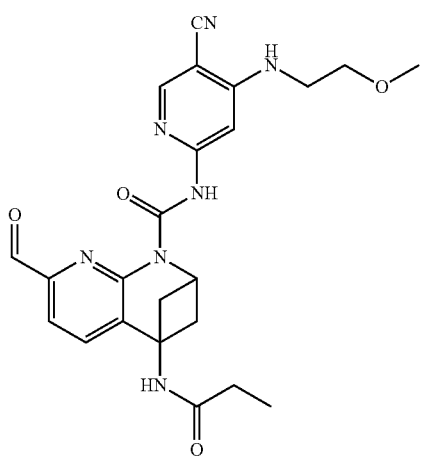 | 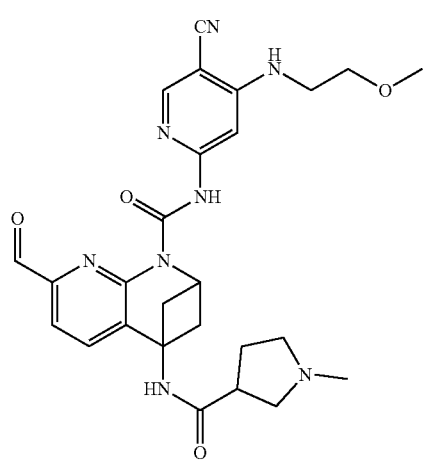 |
| 38 | 41 |
| 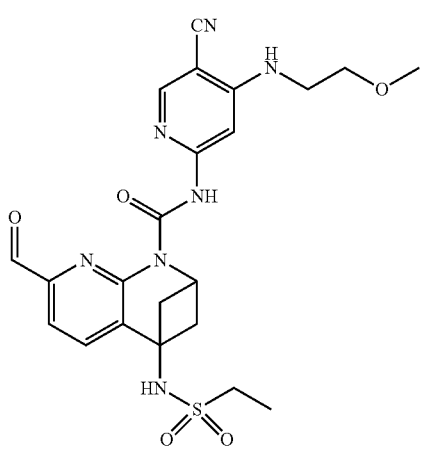 | 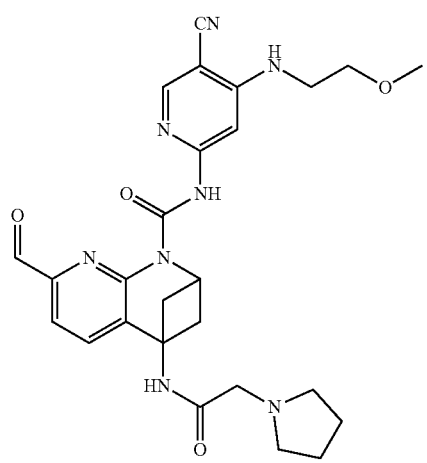 |

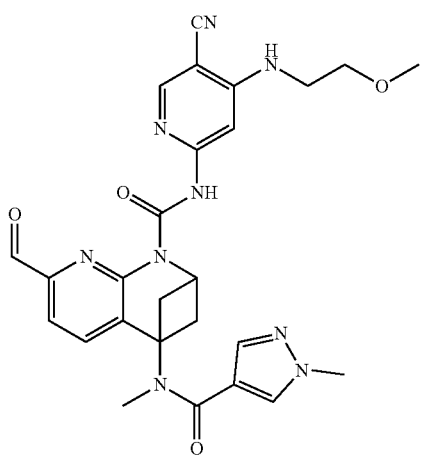
42
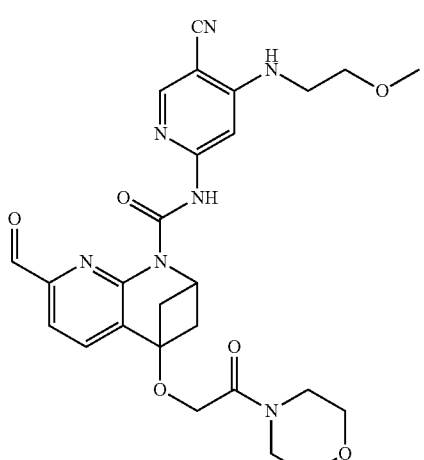
43
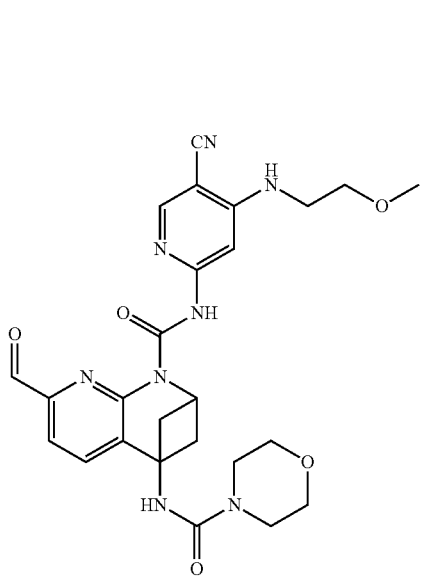
44
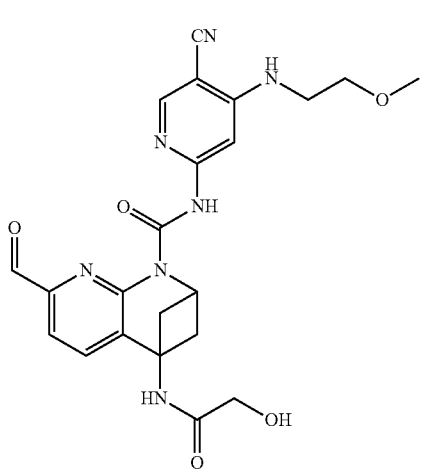

48 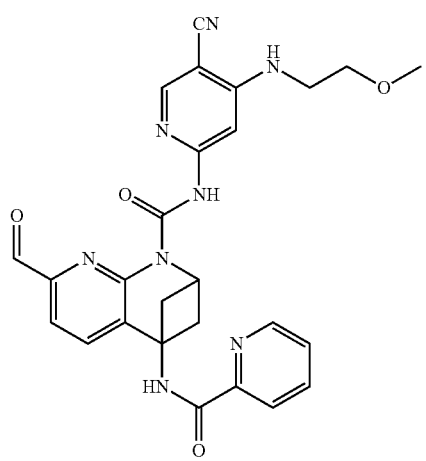
49 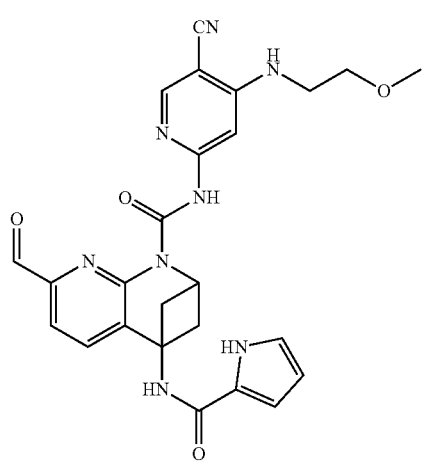
50 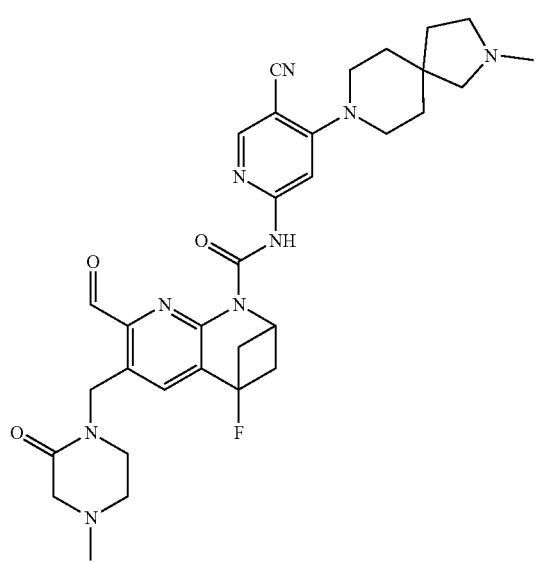
51 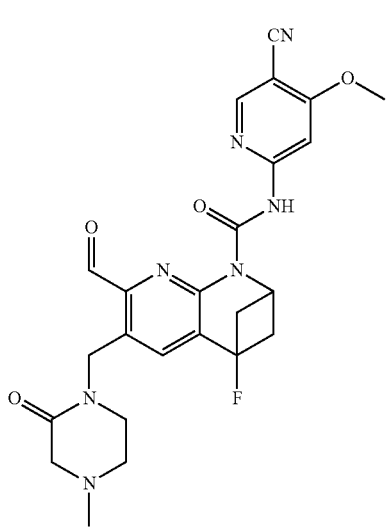
52 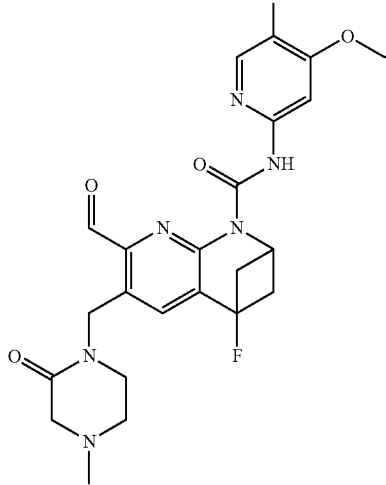
53

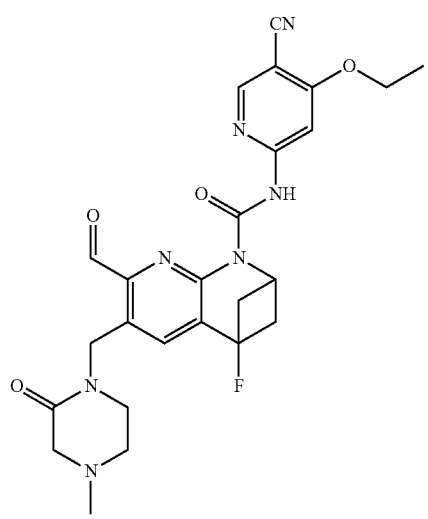
54
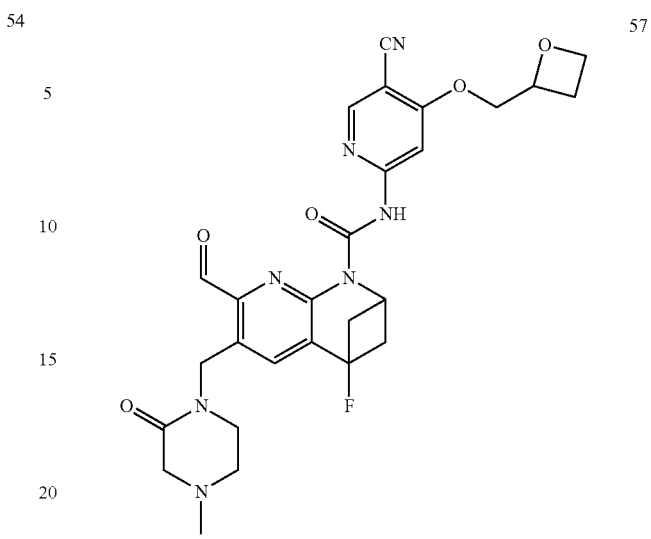
57
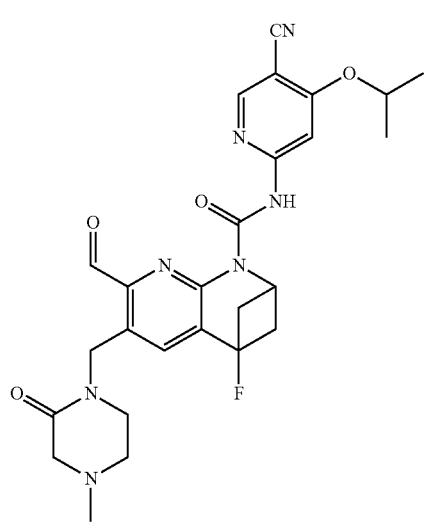
55
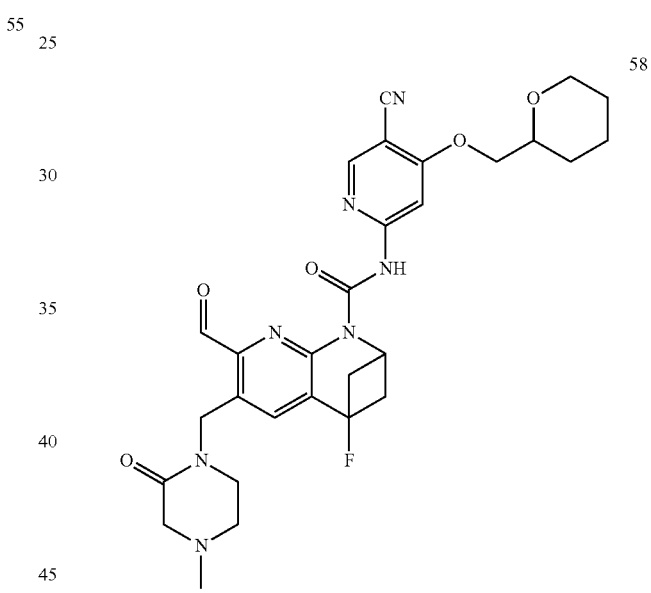
58
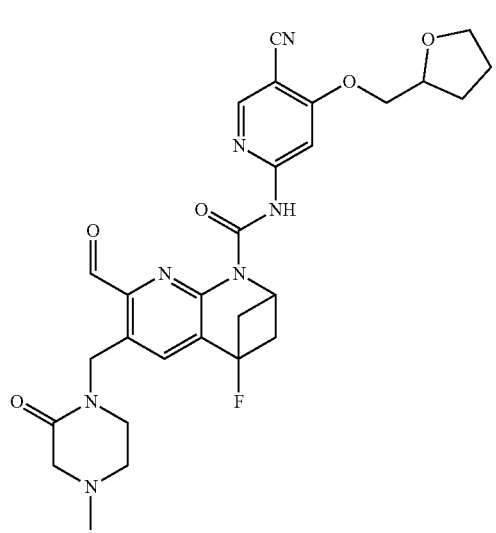
56
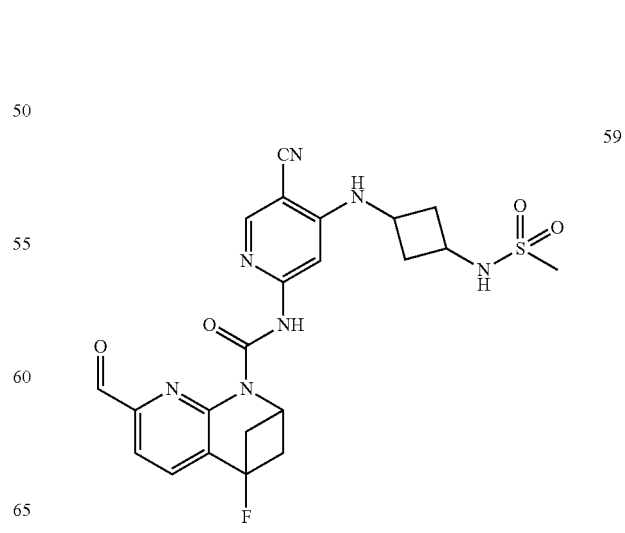
59

60
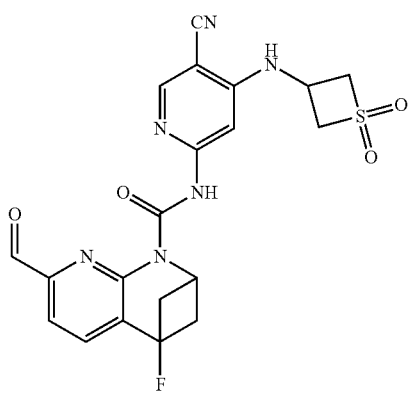
61
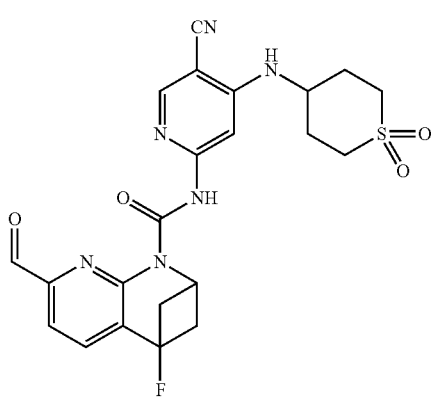
62
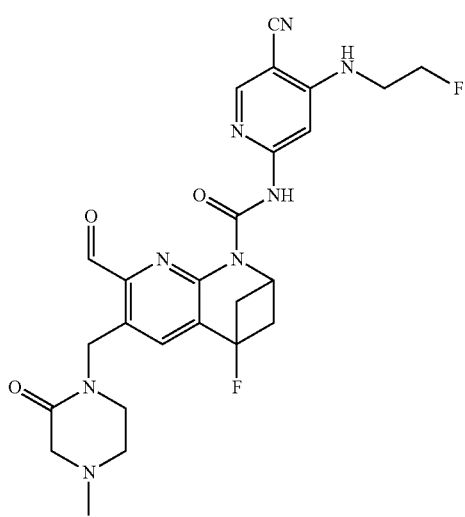
63
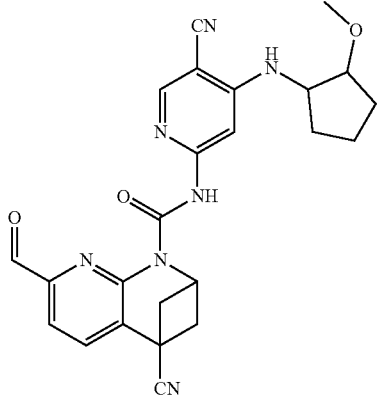
64
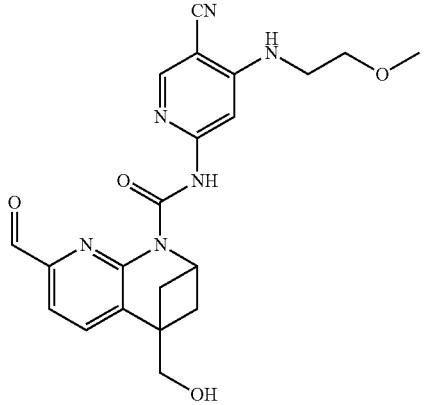
65
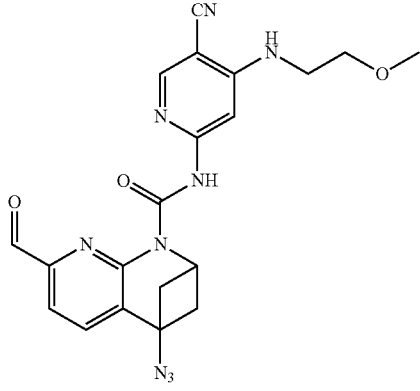
66
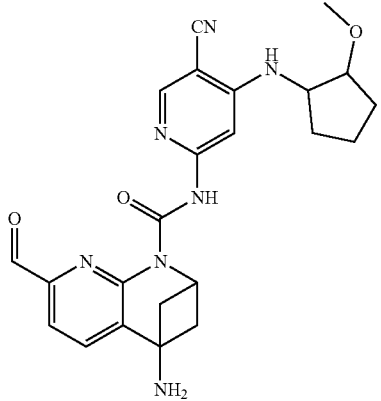

67
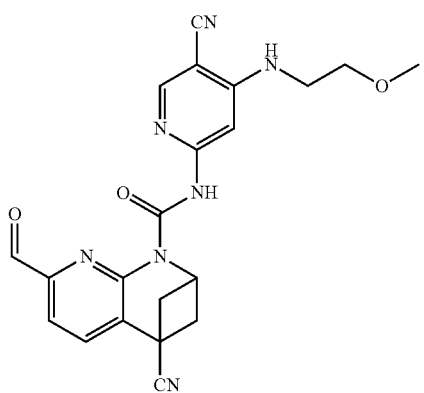
68
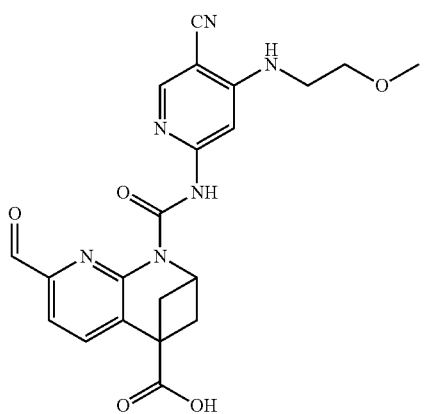
69
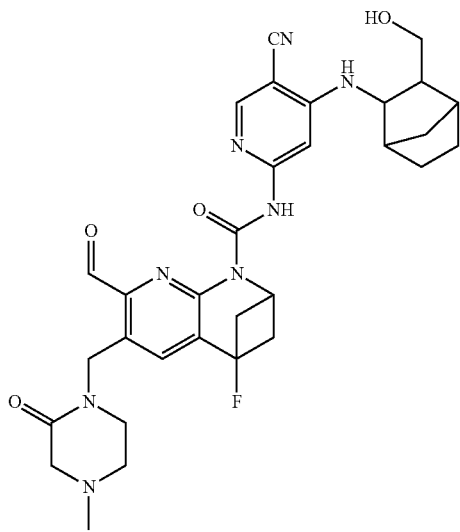
70
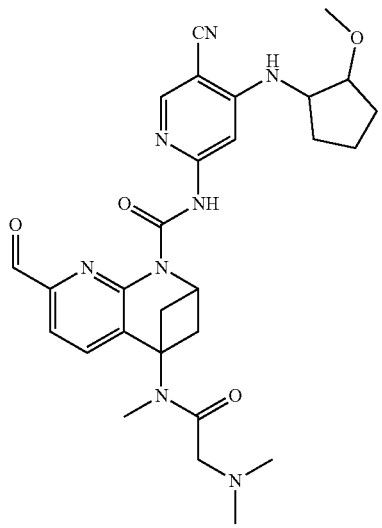
71
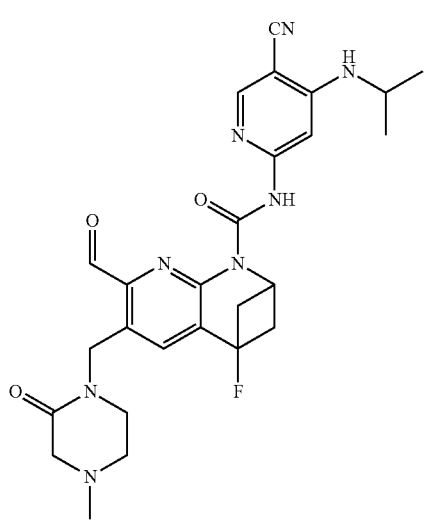
72
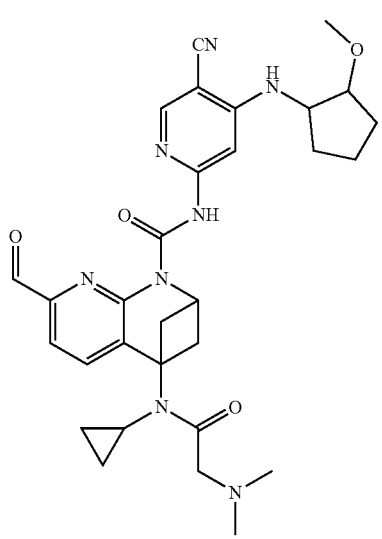

73
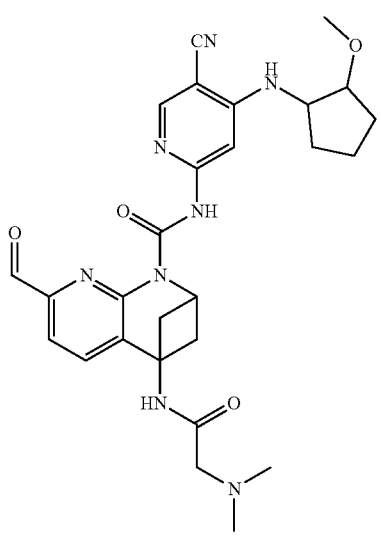
74
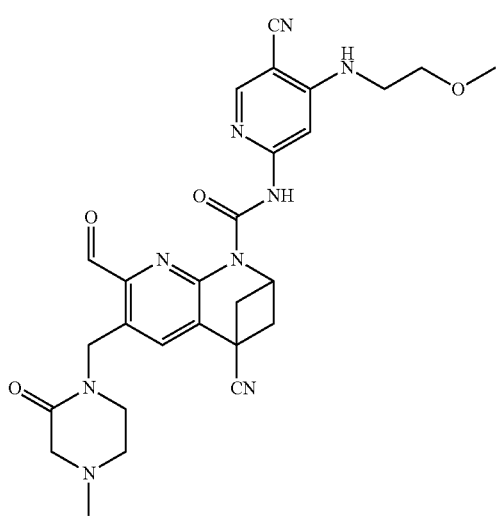
75
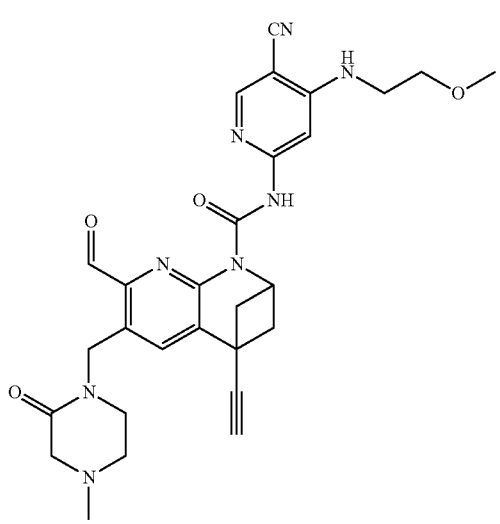
76
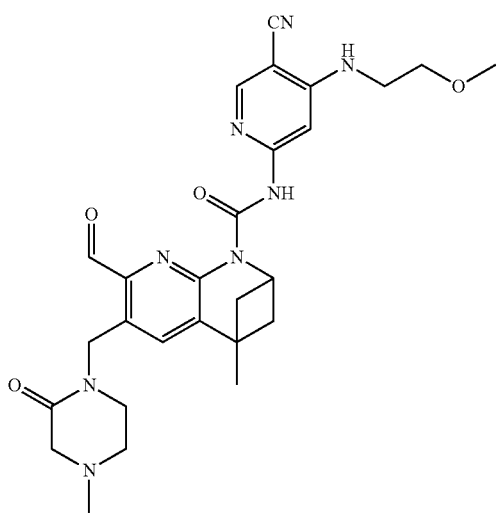
77
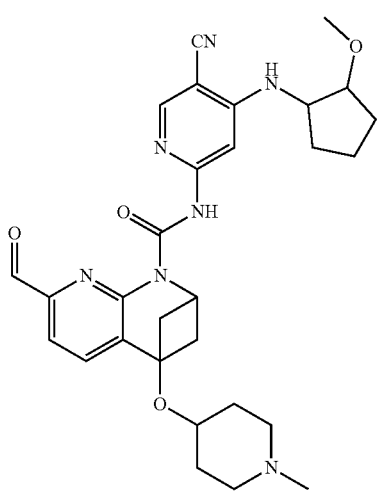
78
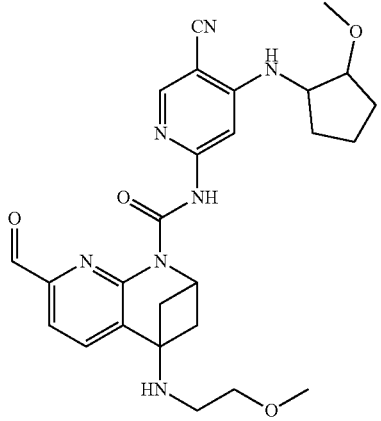

79
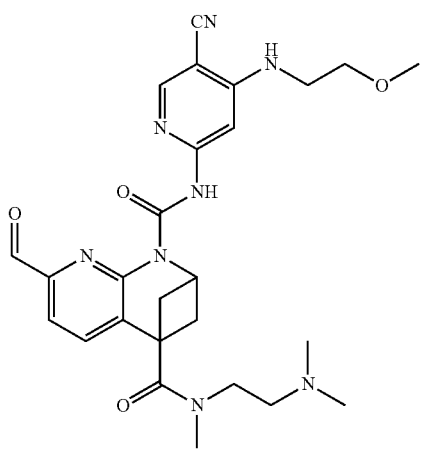
80
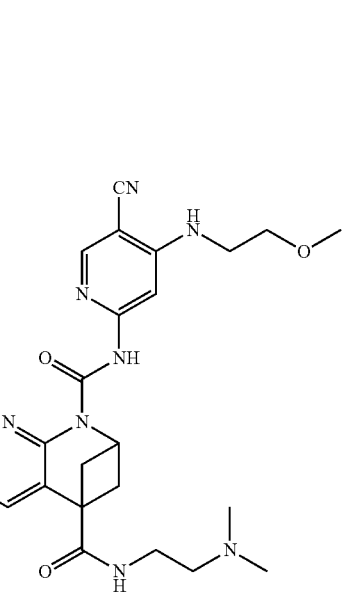
81
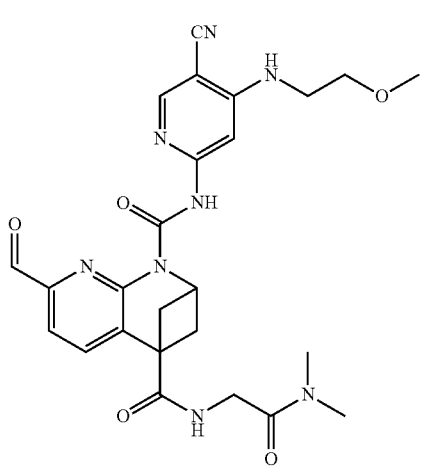
82
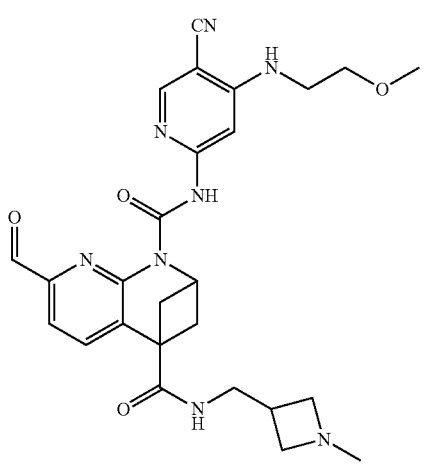
83
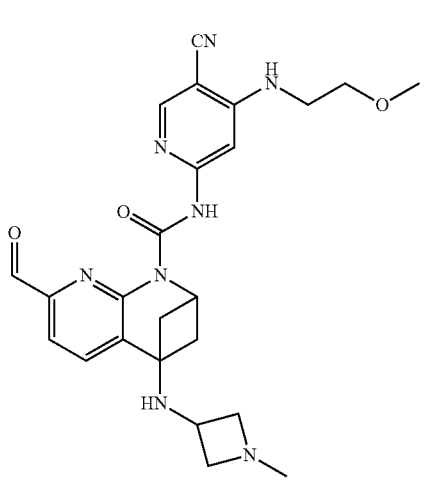
84

85
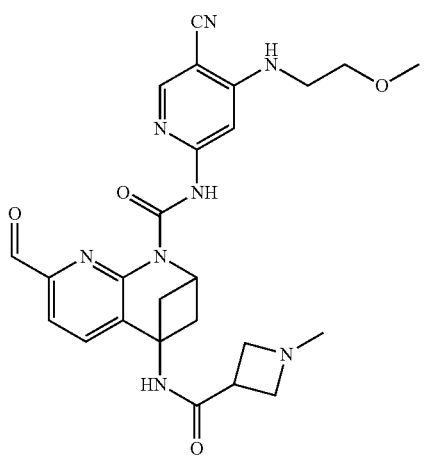
86
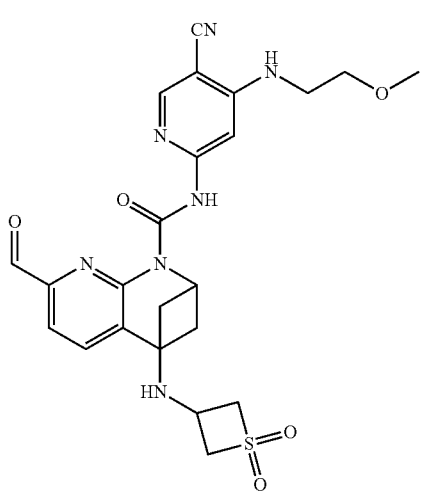
87
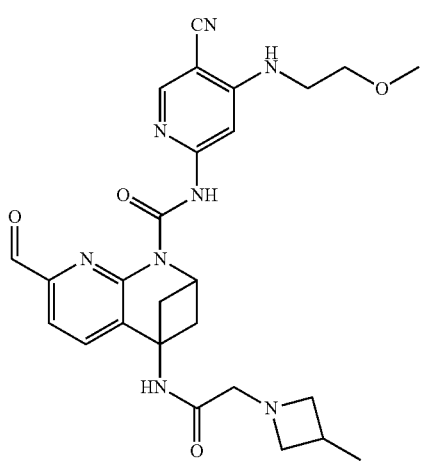
88
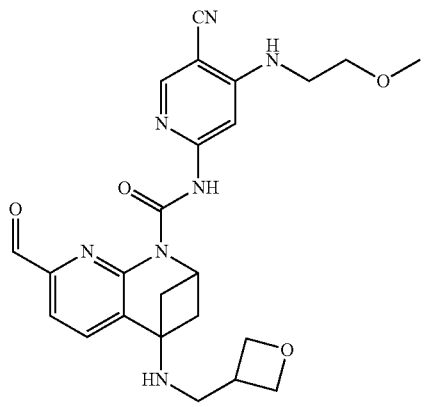
89
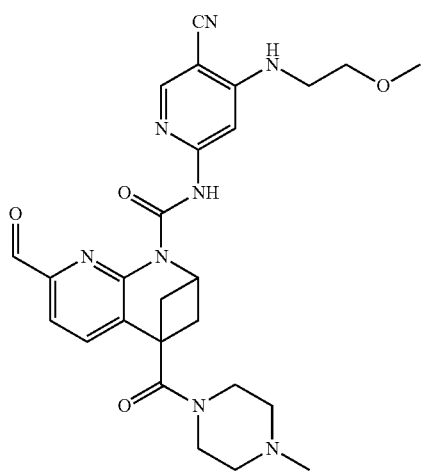
90
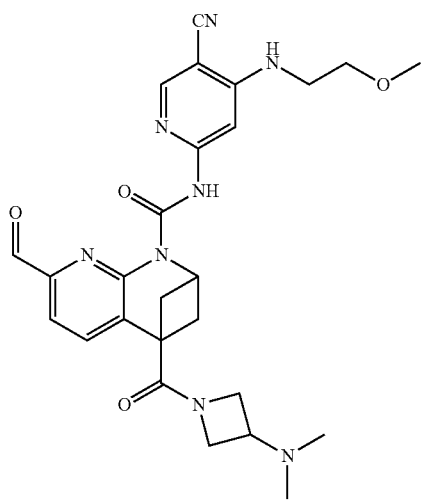

-continued
91
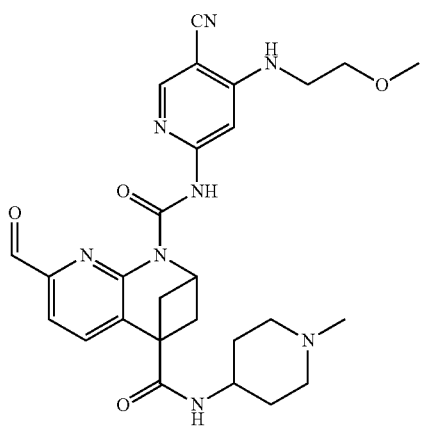
92
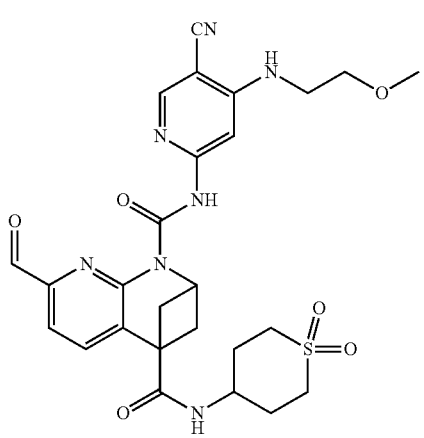
93
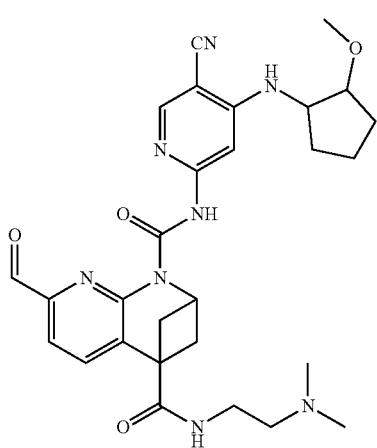
-continued
94
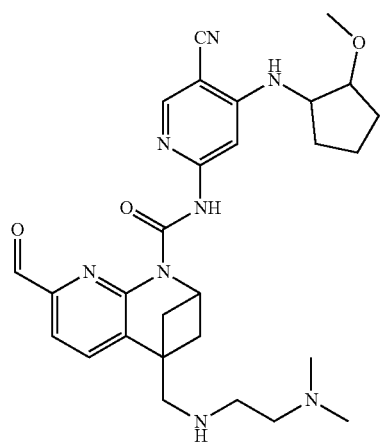
95
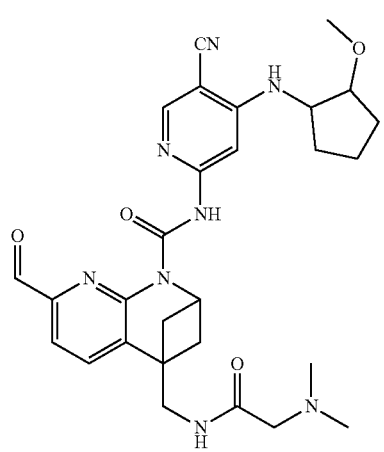
96
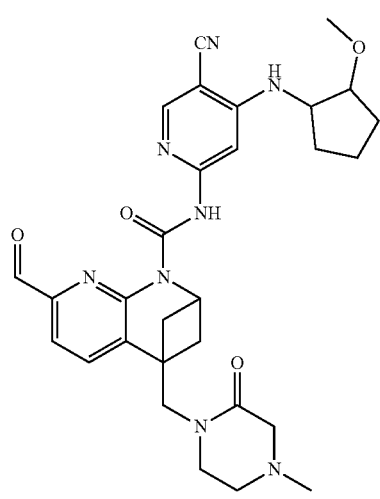

-continued
97
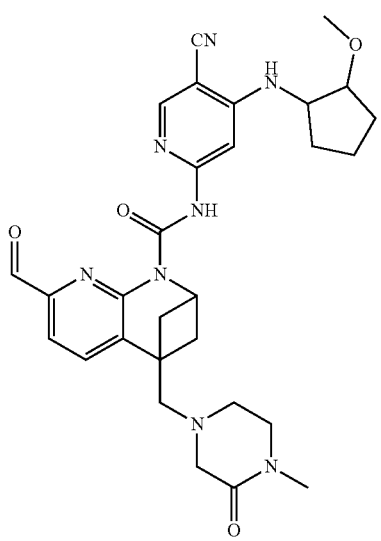
98
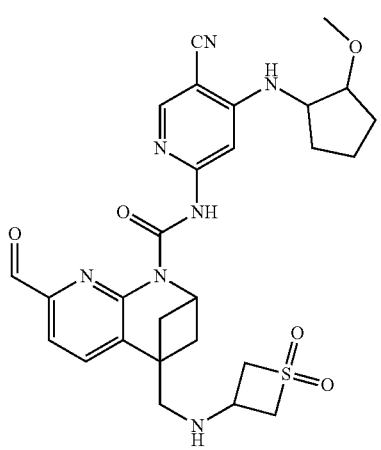
99
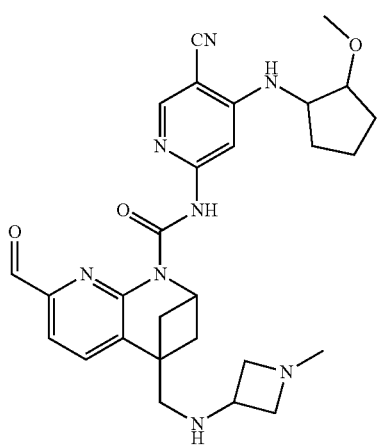
100
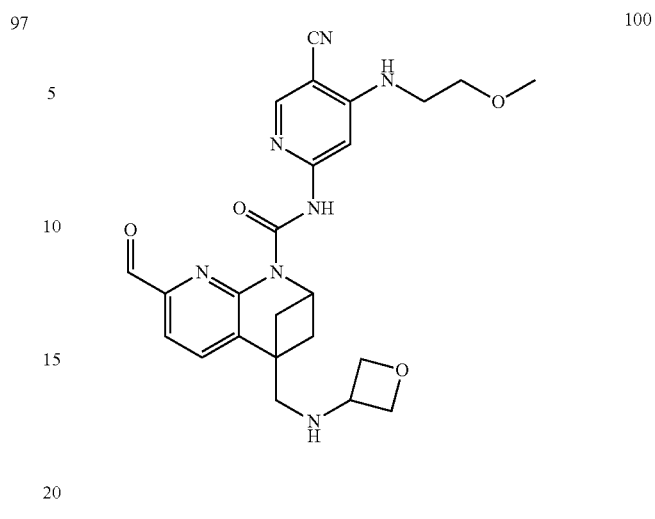
101
102

103
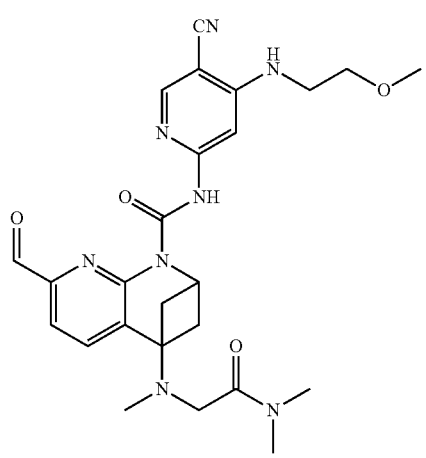
104
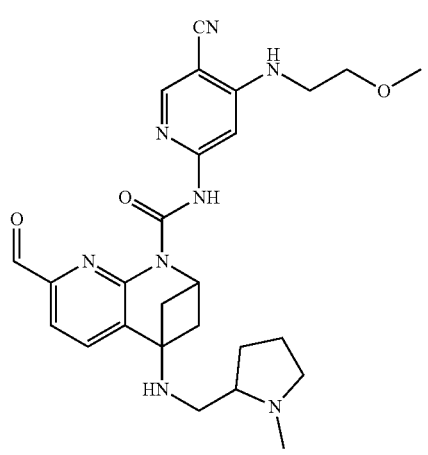
105
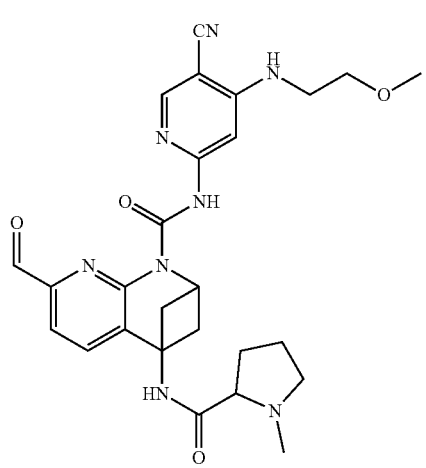
106
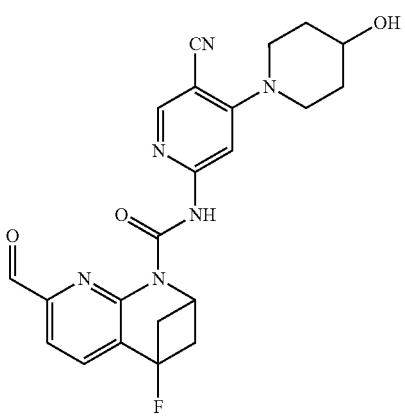
107
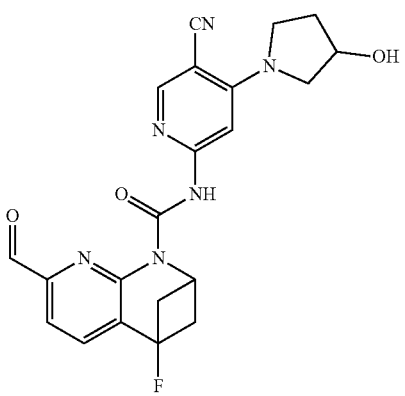
108
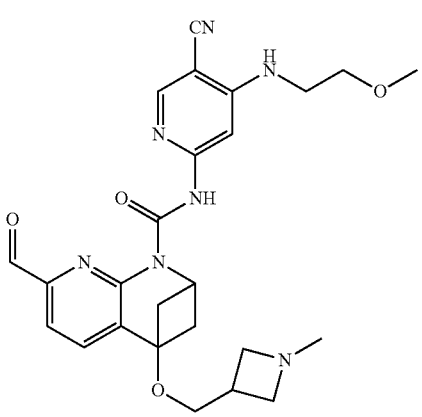

55
-continued
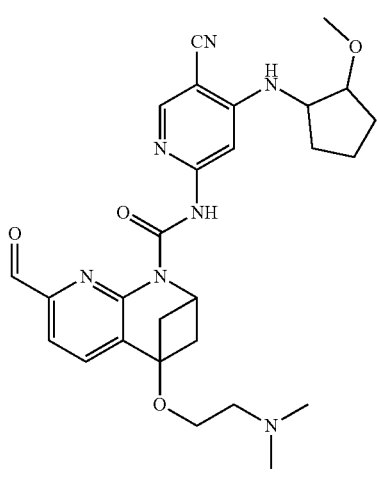
109
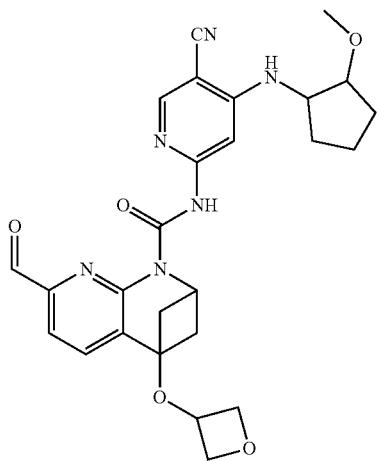
110
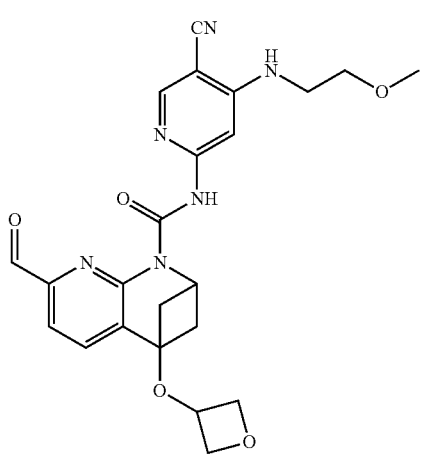
111
56
-continued
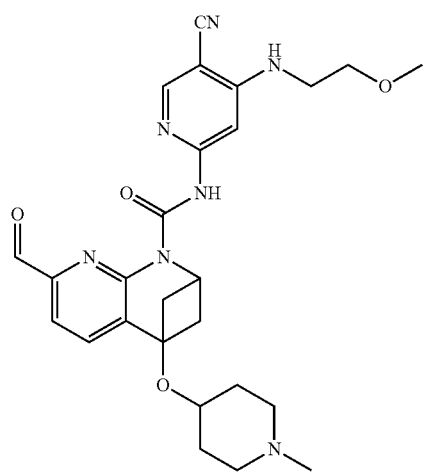
112
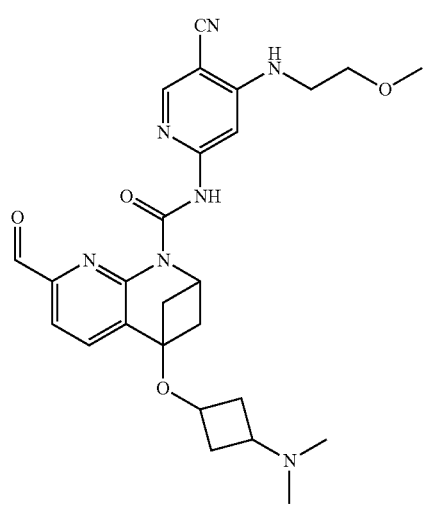
113
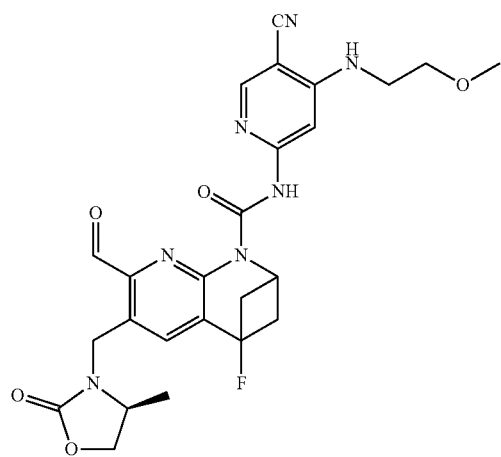
114

115
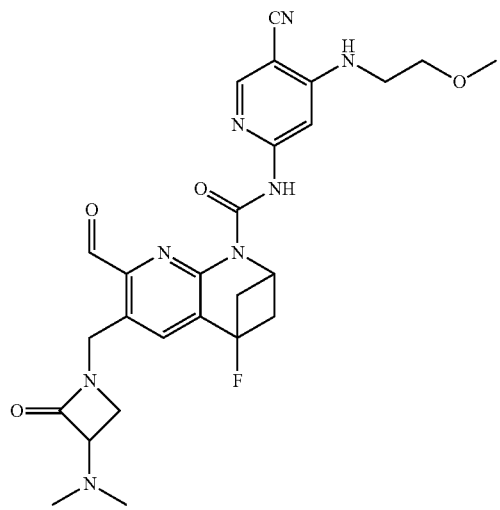
116
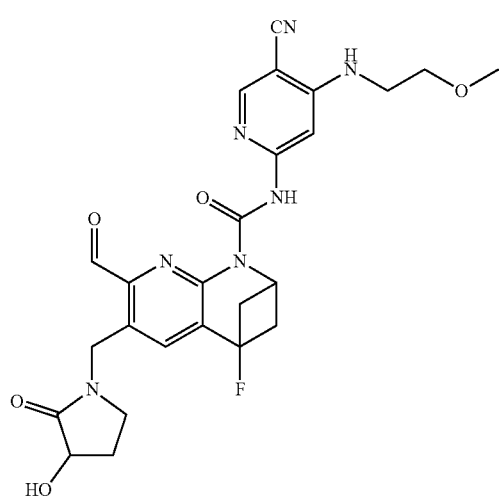
117
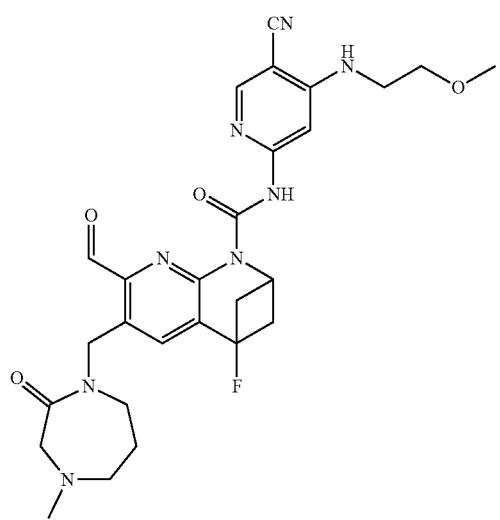
118
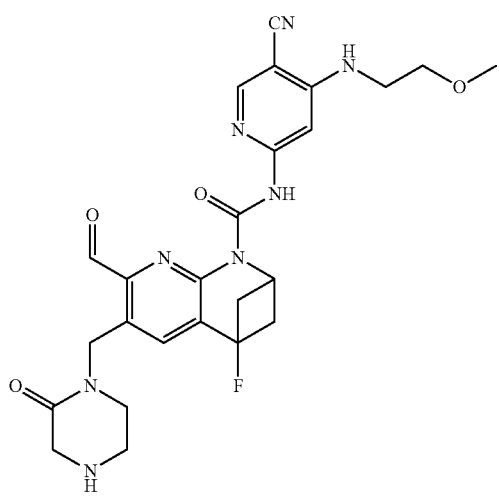
119
120
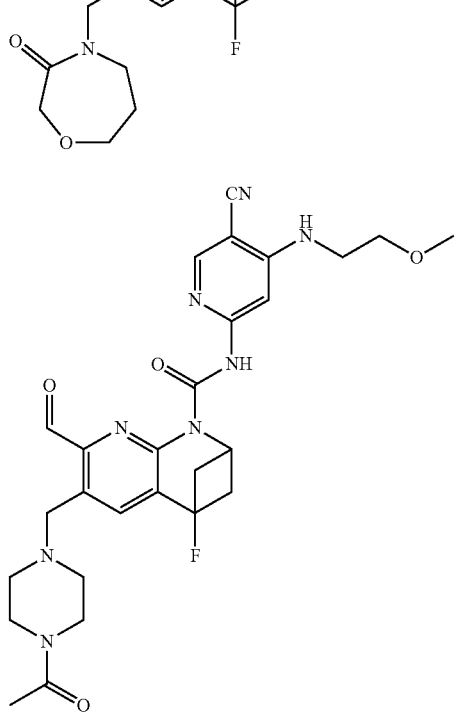

121
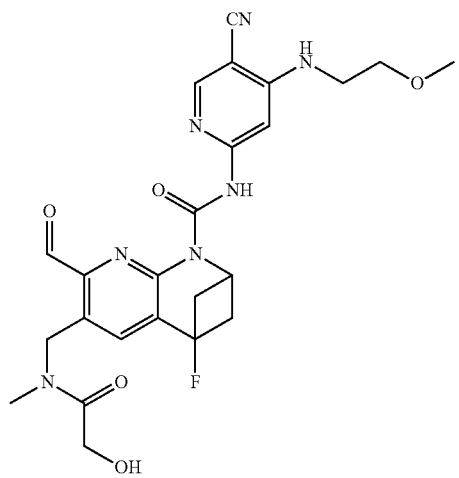
122
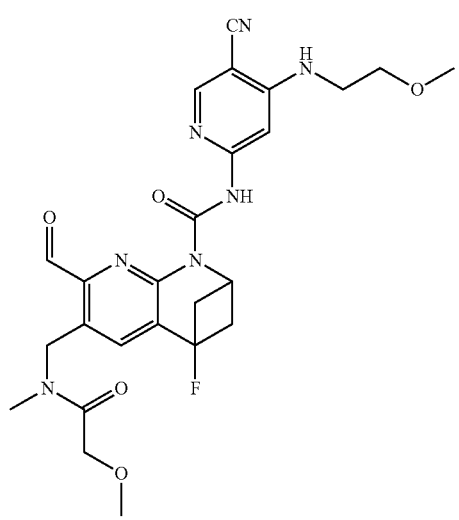
123
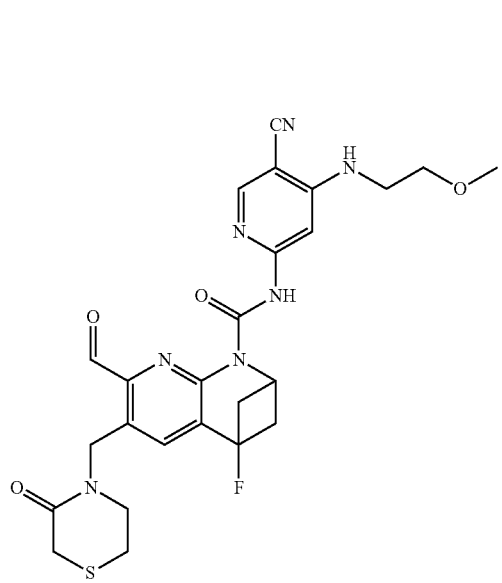
124
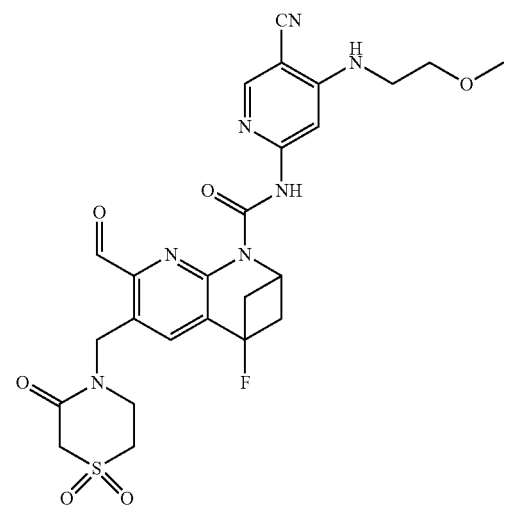
125
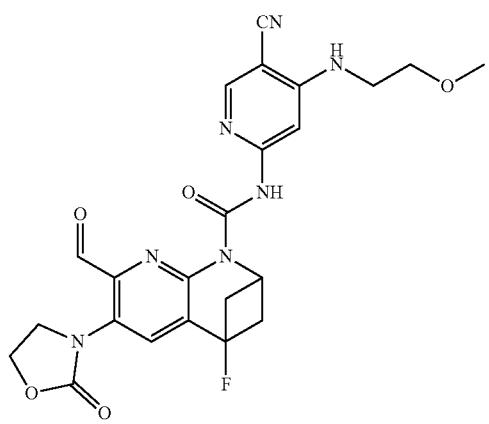
126
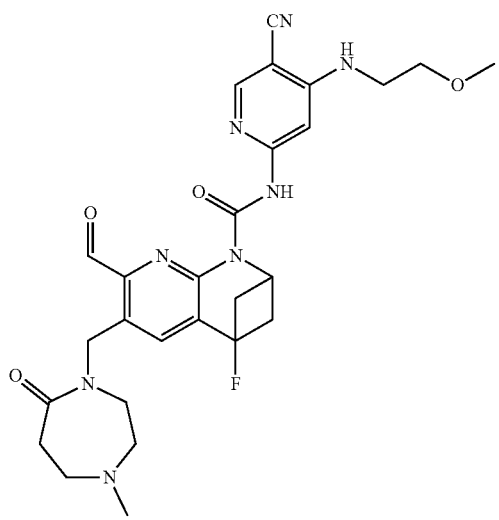

127 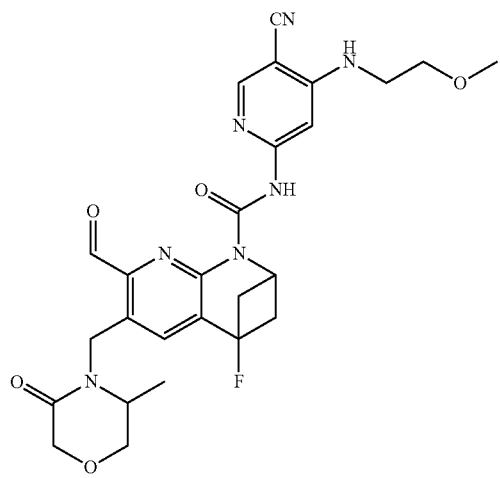
128 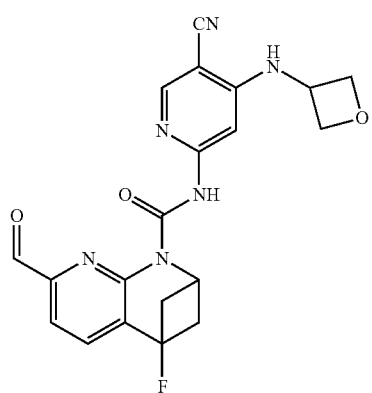
129 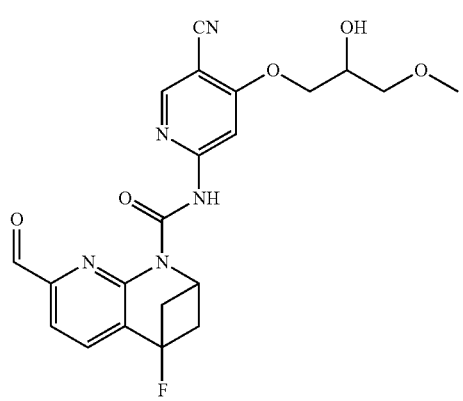
130 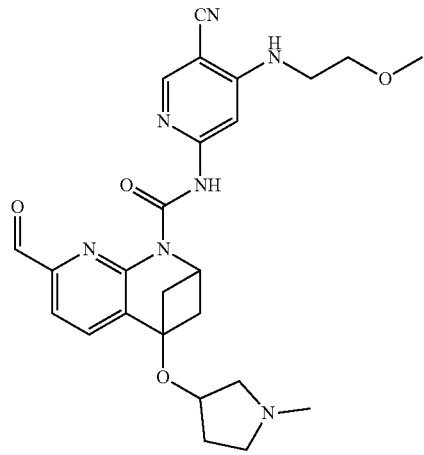
131 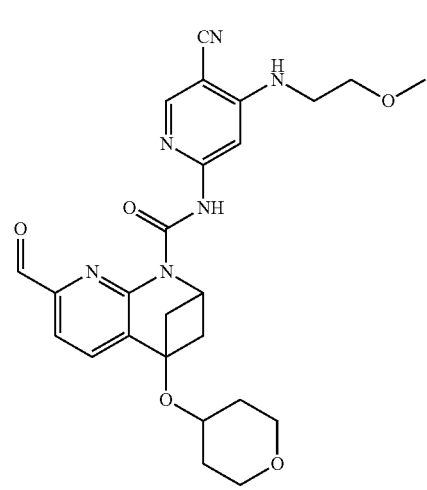
132 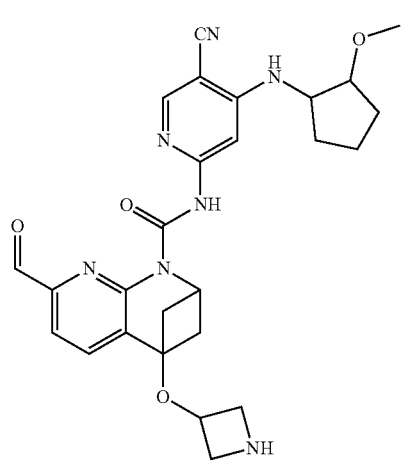

133 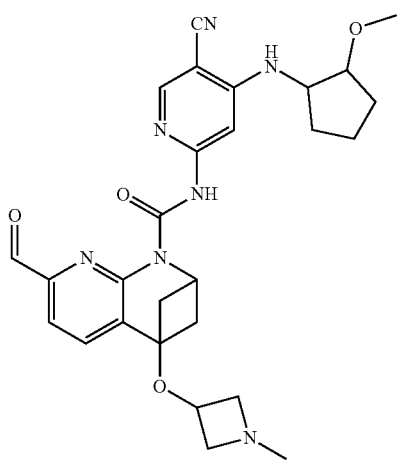
136 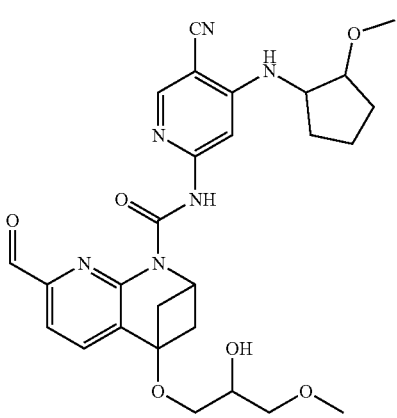
134 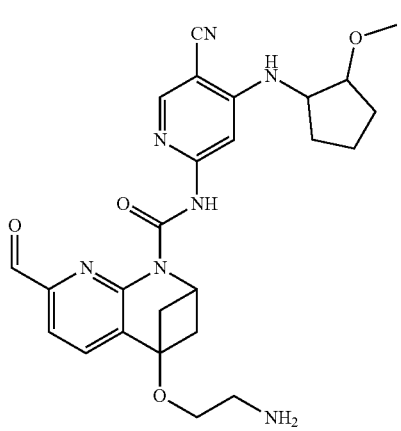
137 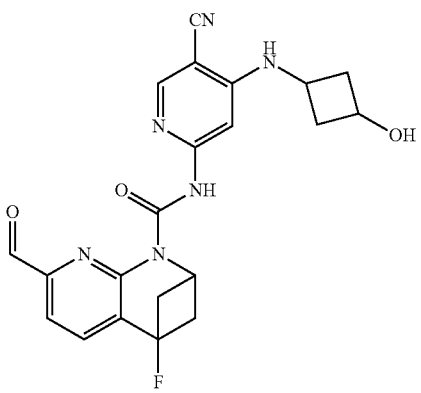
135 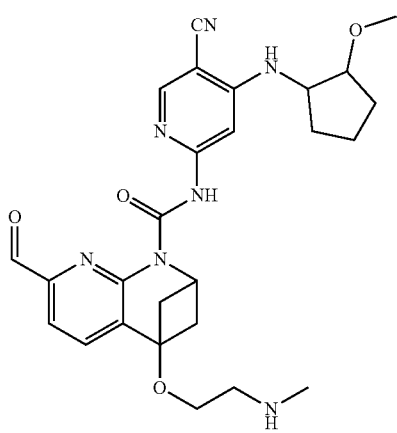
138 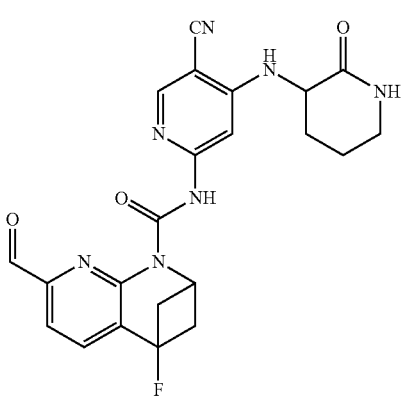

139
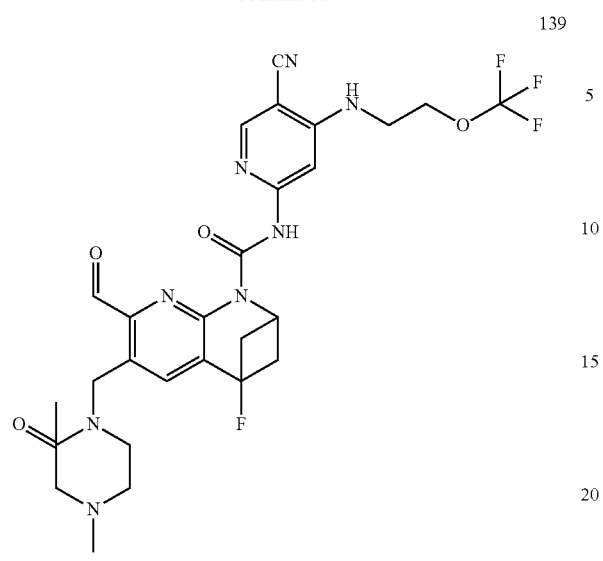
140
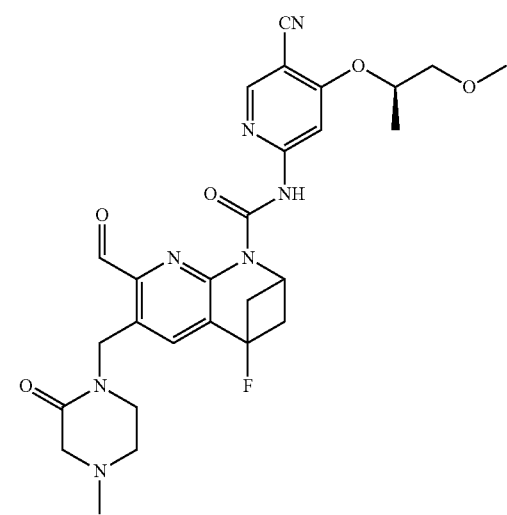
141
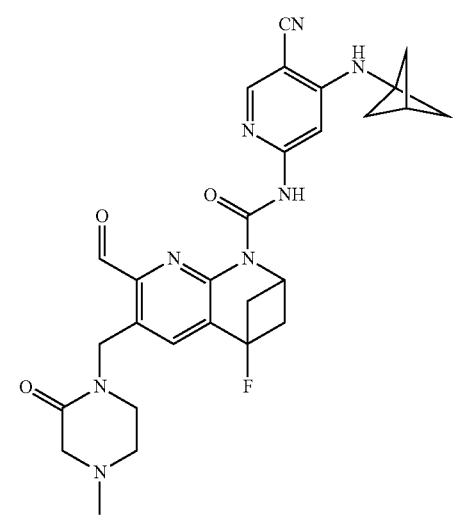
142
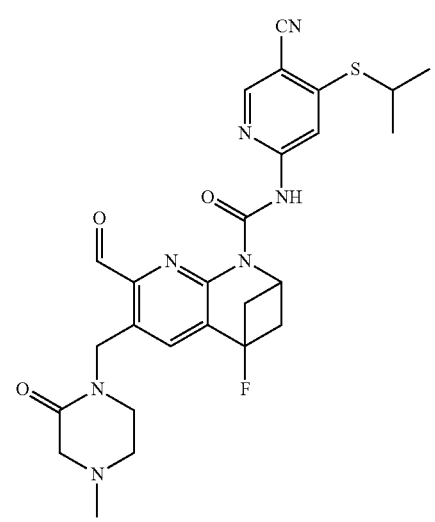
143
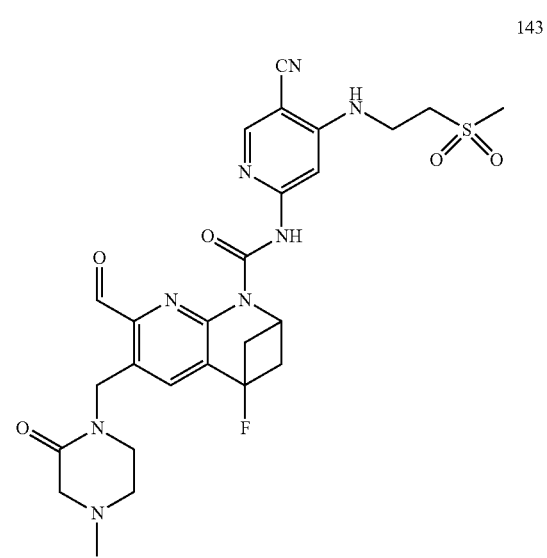
144
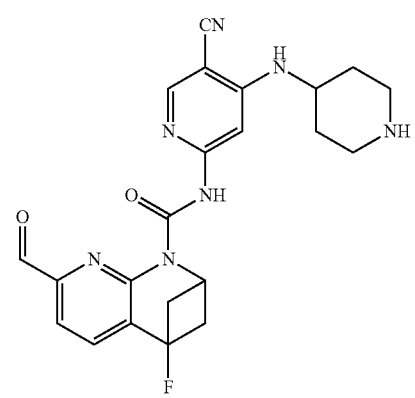

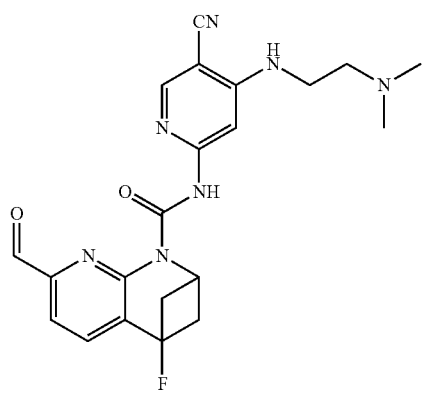
145
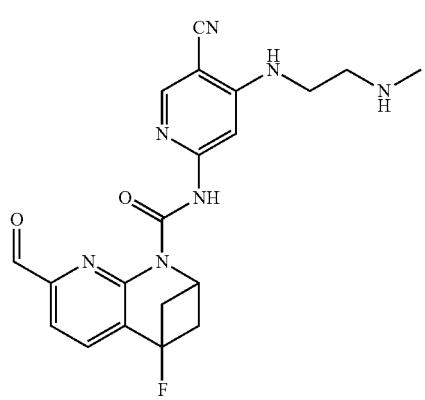
146
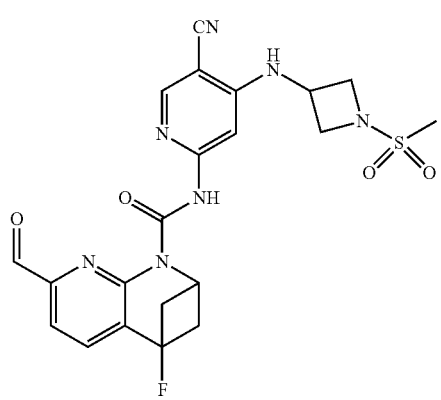
147
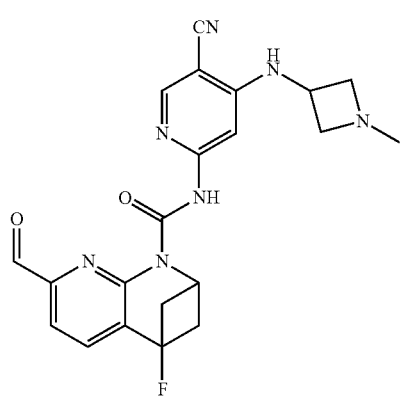
148
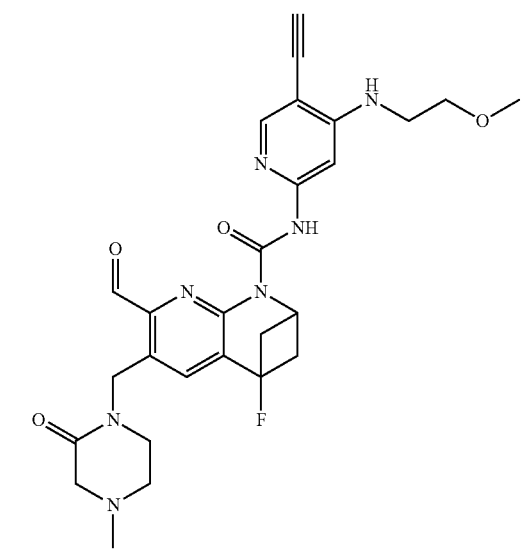
149
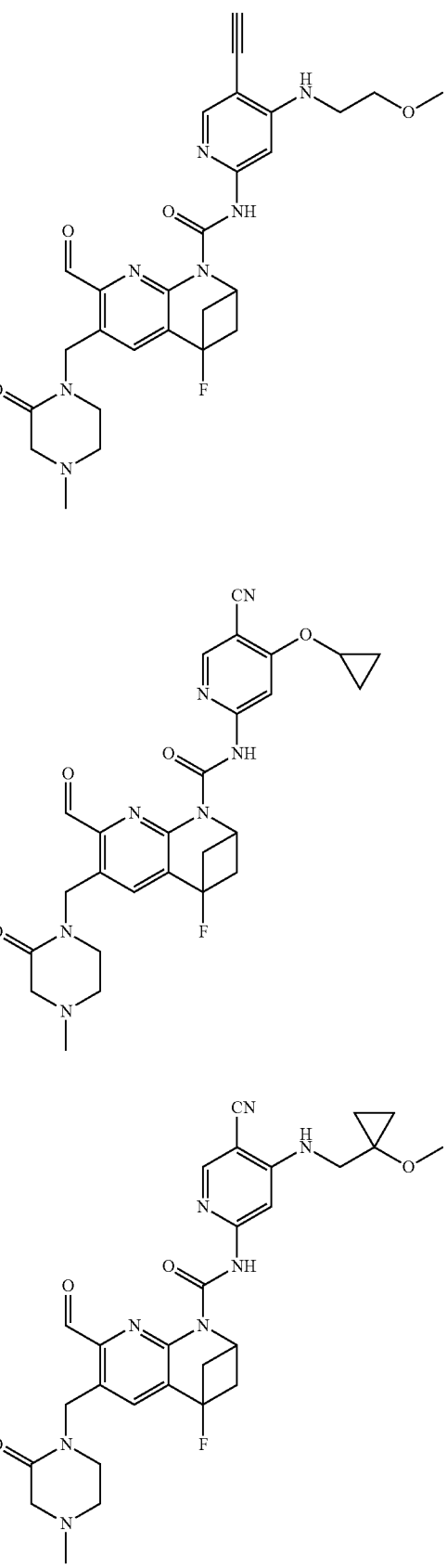
150
151

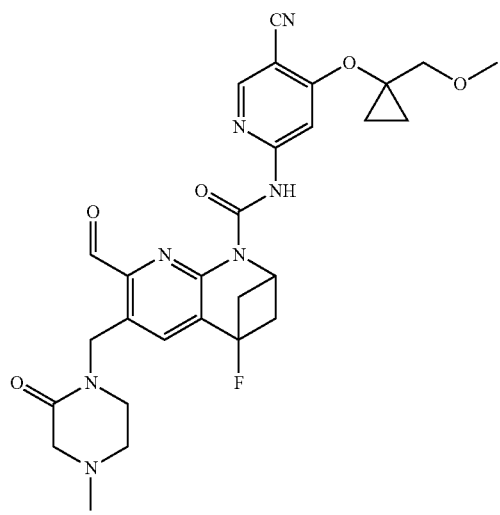
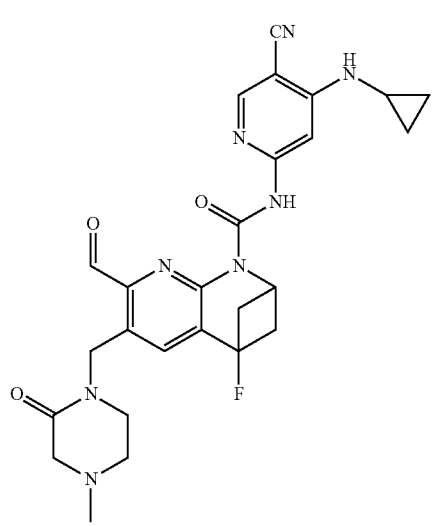
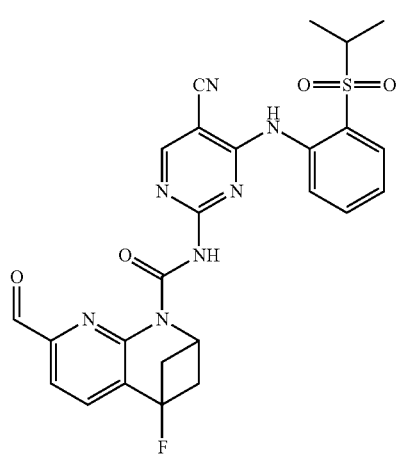
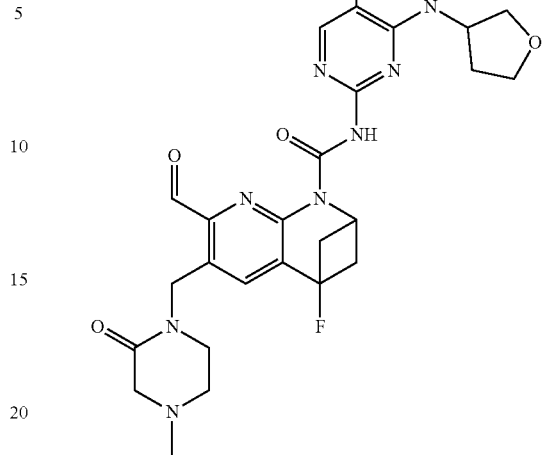
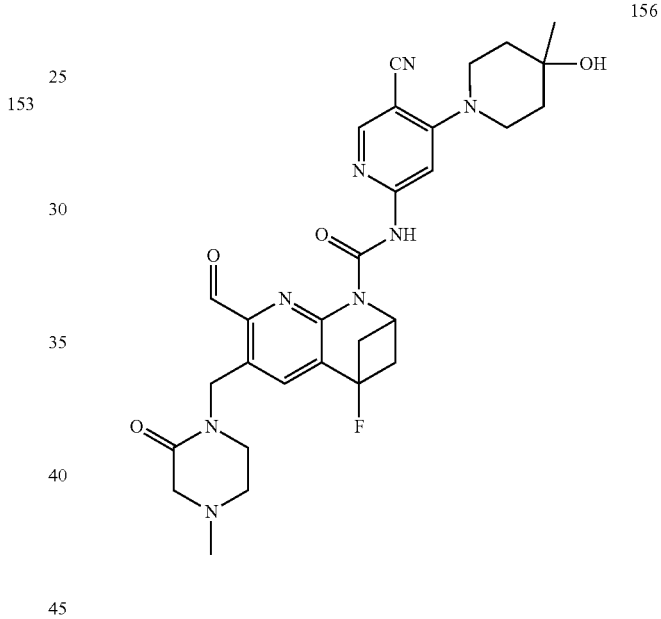
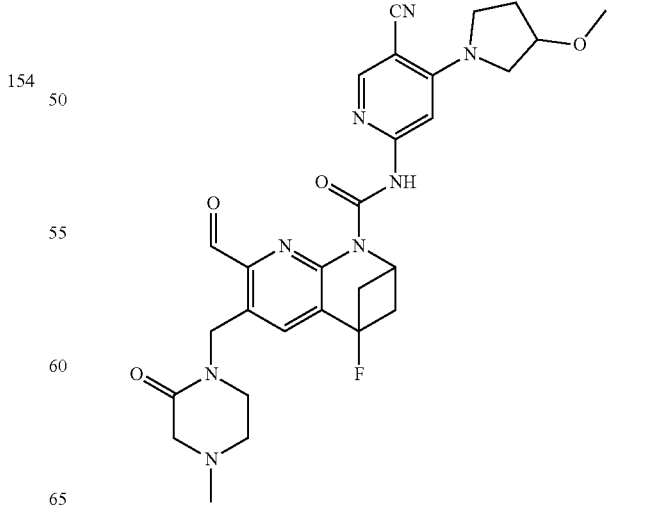

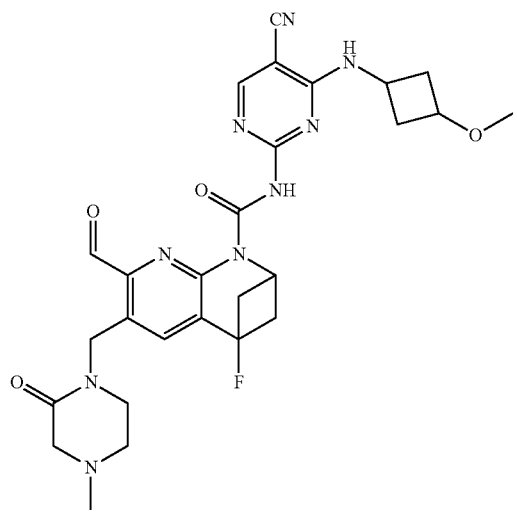
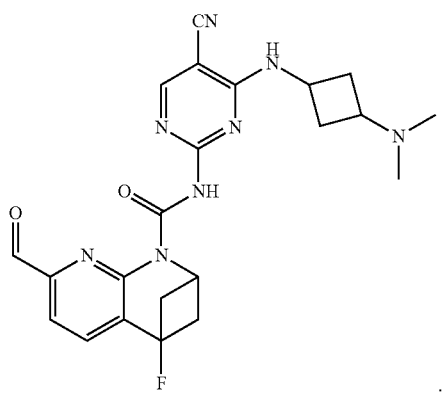
In one embodiment, the compound of formula (I) is selected from the following compound:
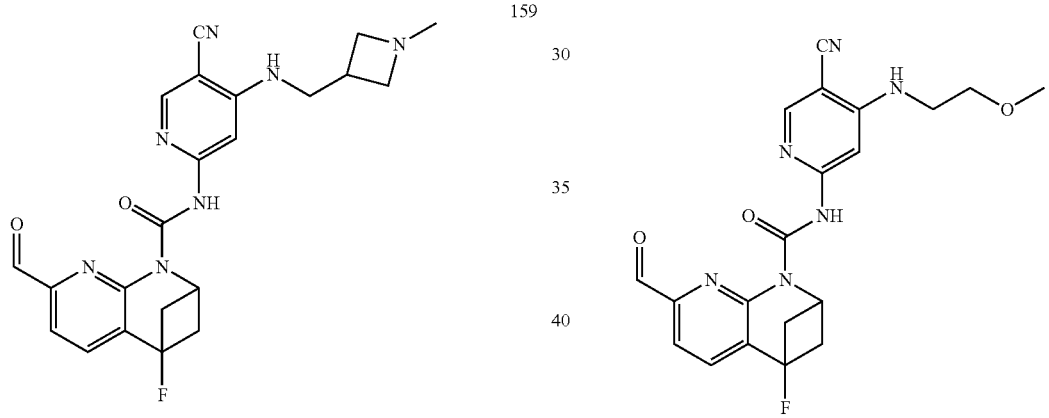
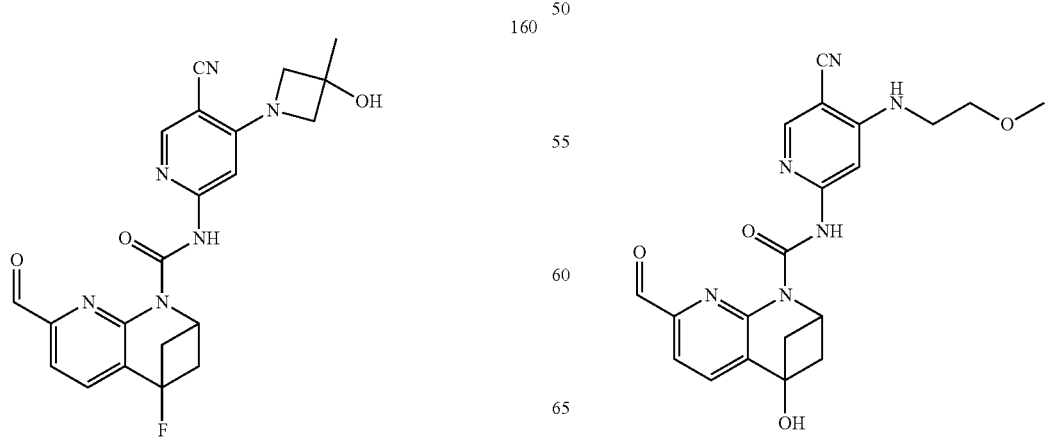

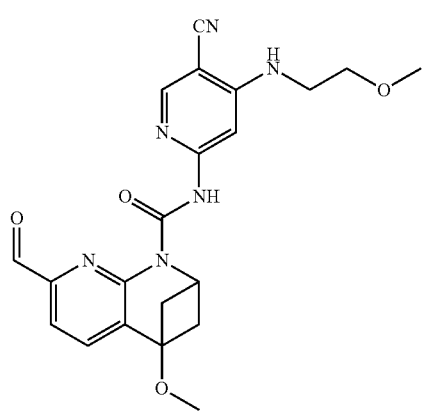
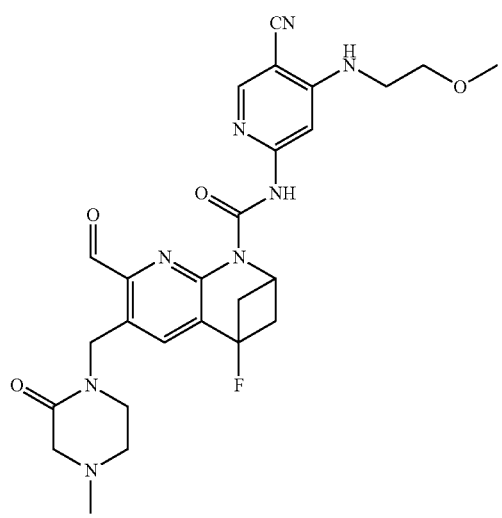
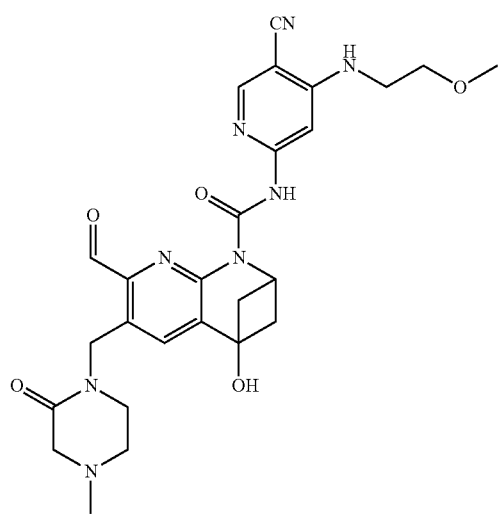
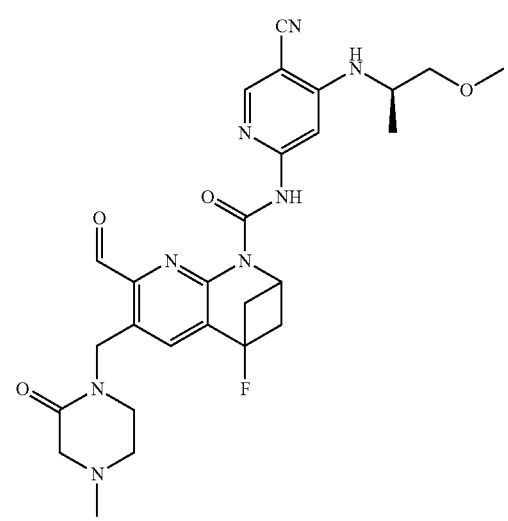
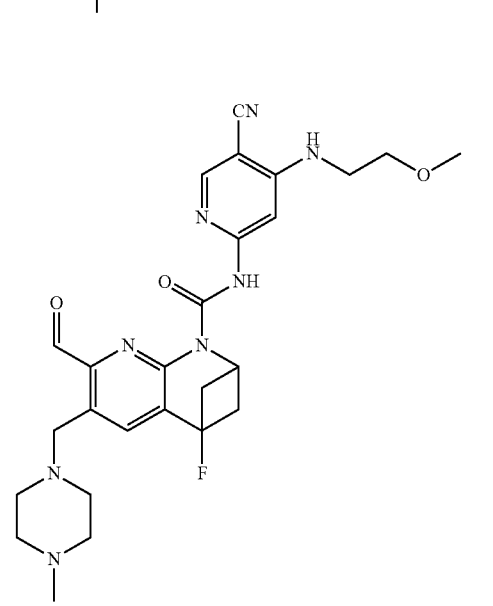
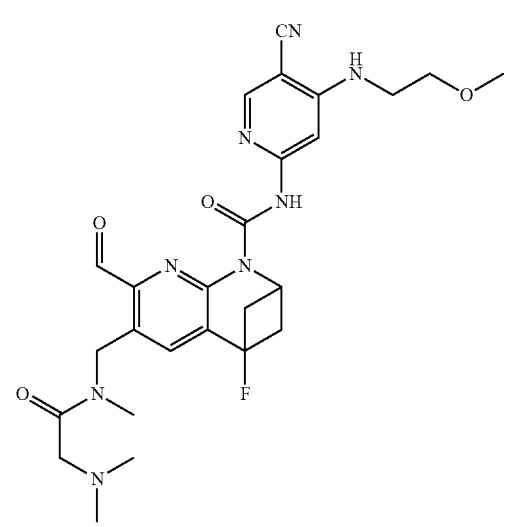

75
-continued
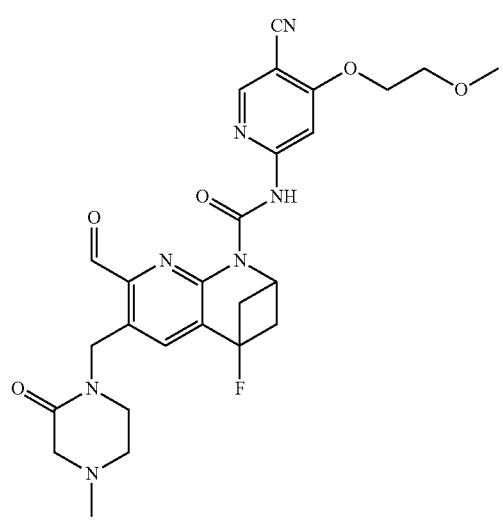
76
-continued
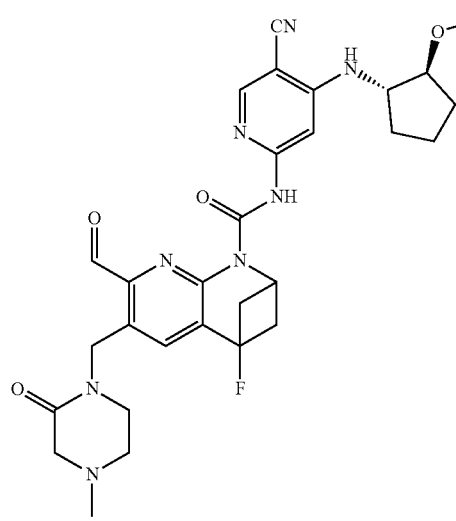

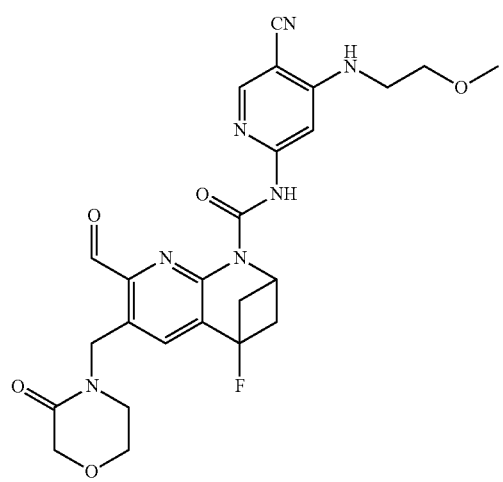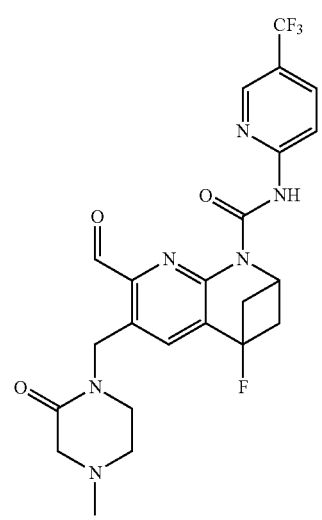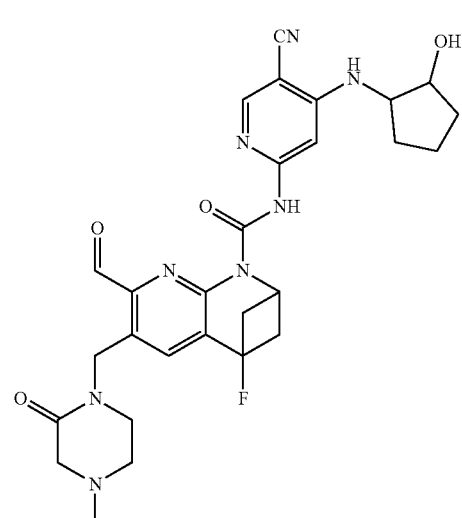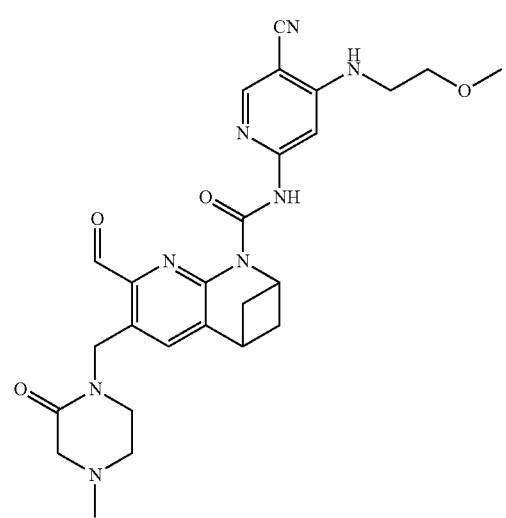

-continued
19
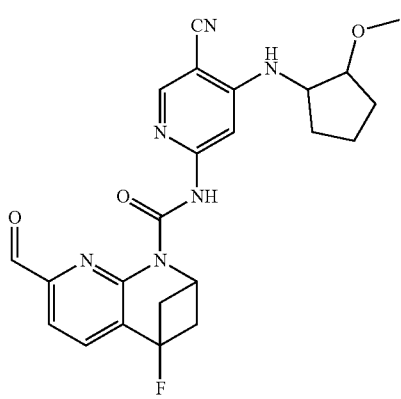
20
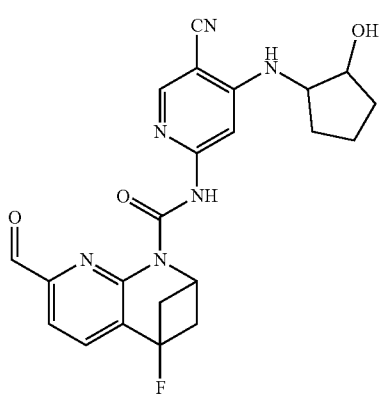
21
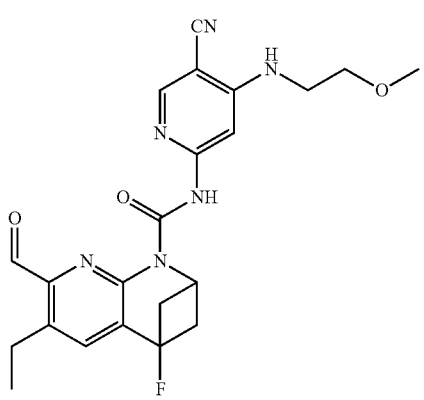
22
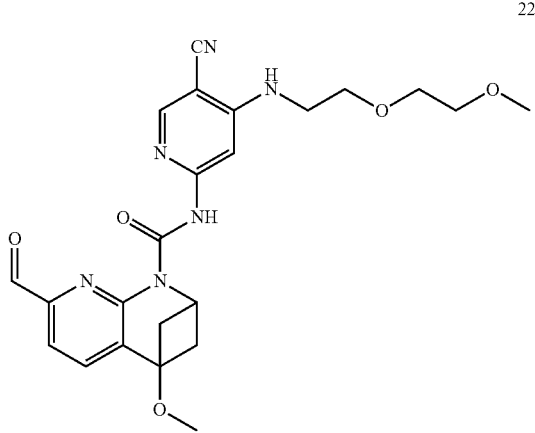
-continued
23
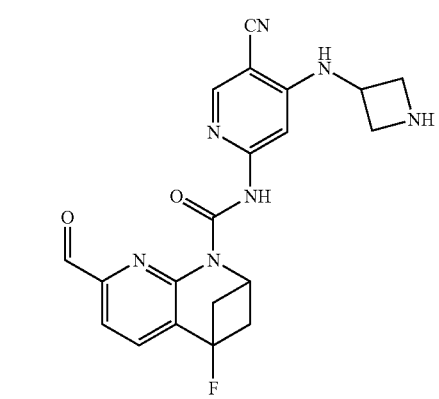
24
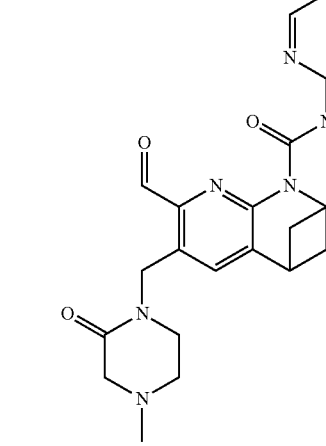
25
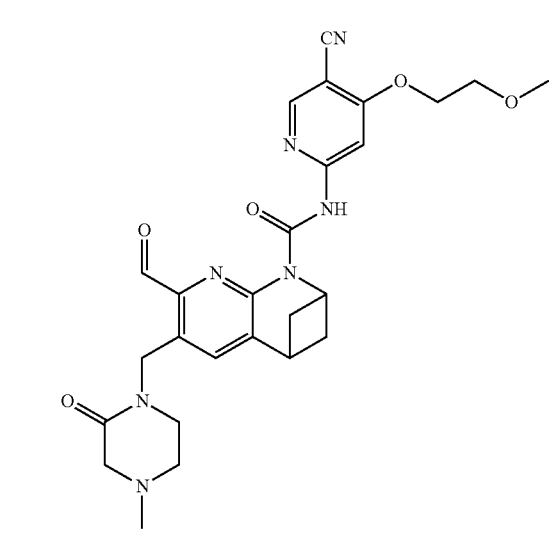

26
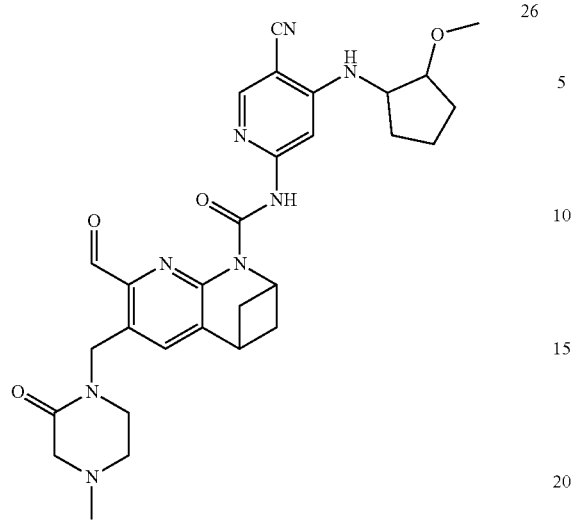
29
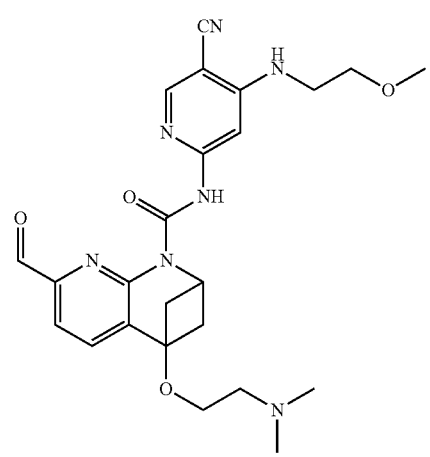
27
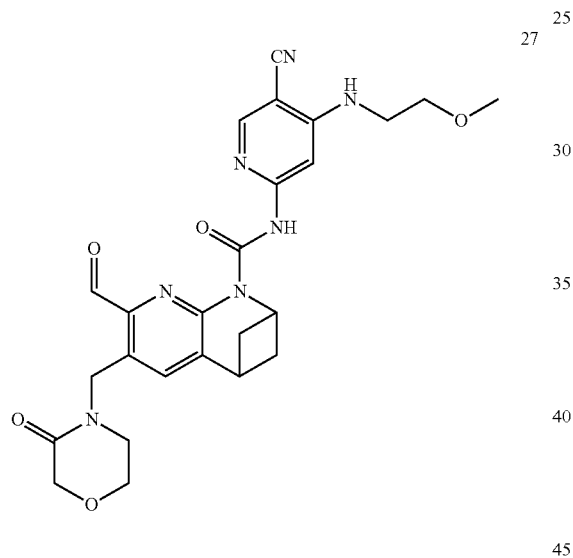
30
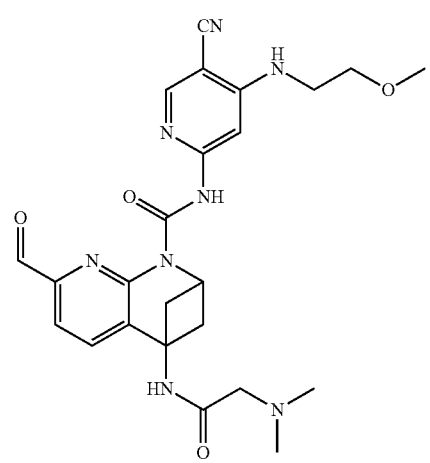
28
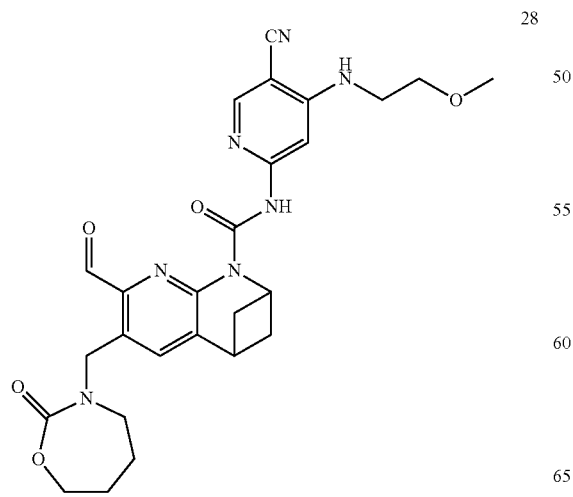
31
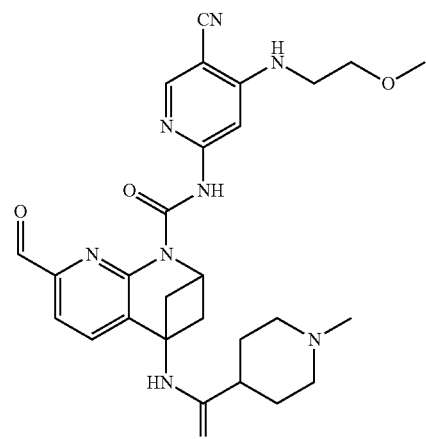

32
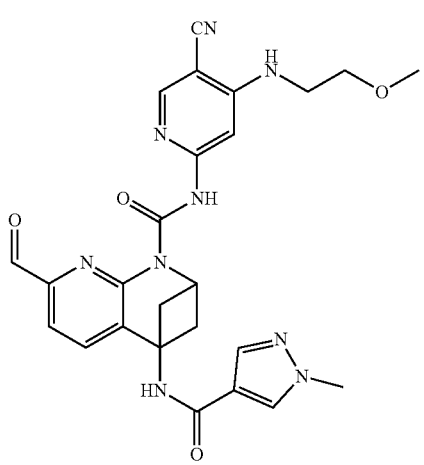
33
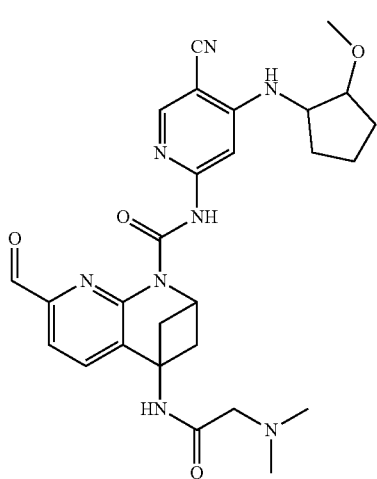
34
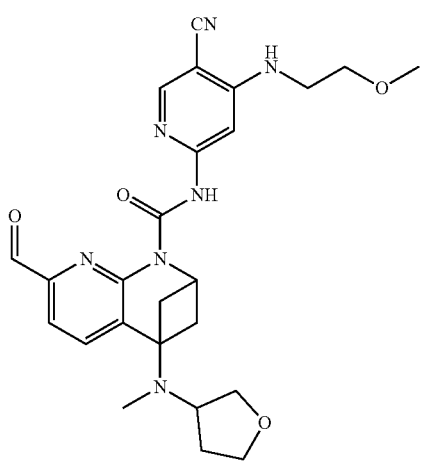
35
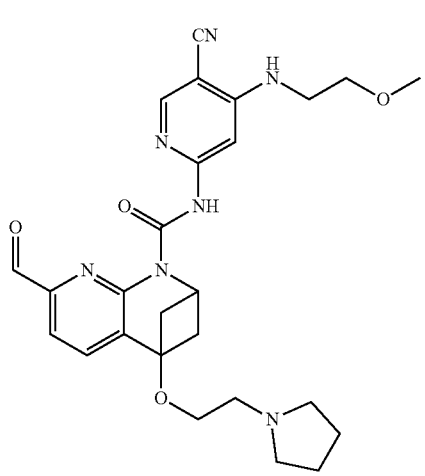
36
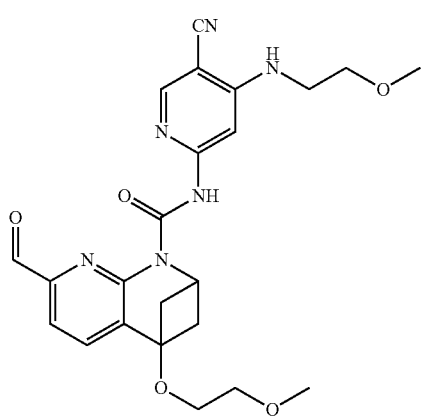
37
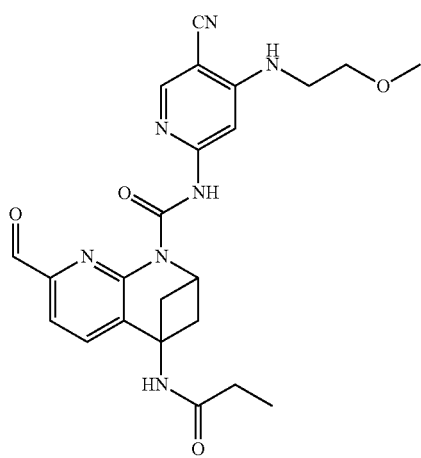

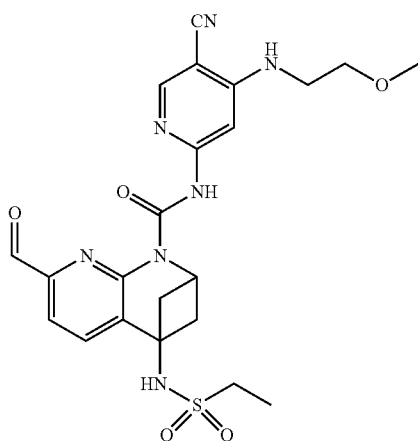
38
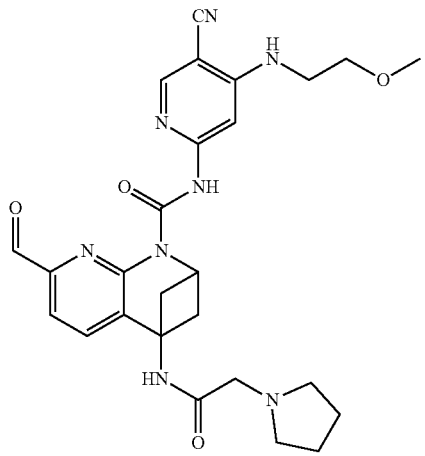
41
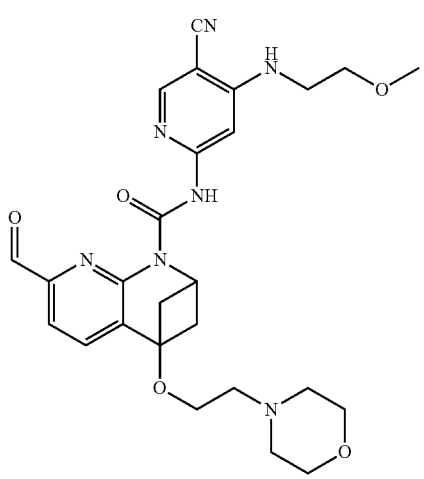
39
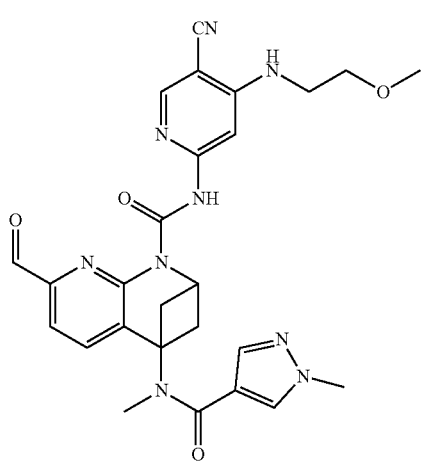
42
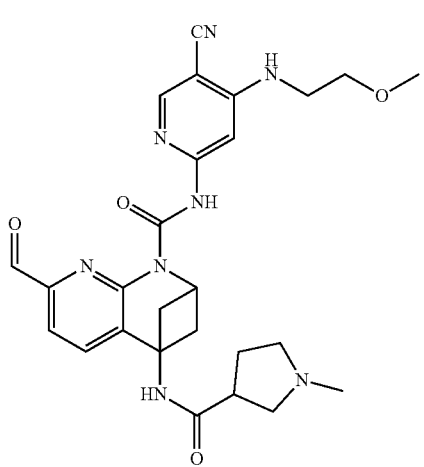
40
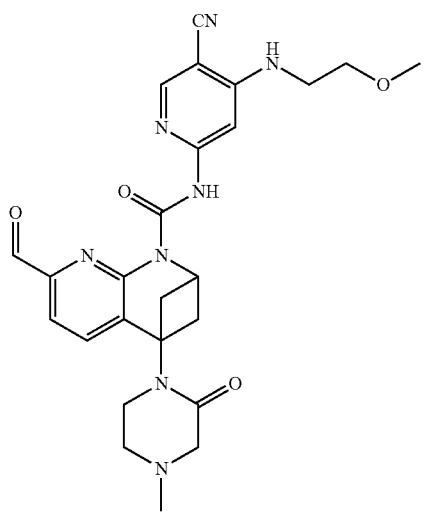
43

44
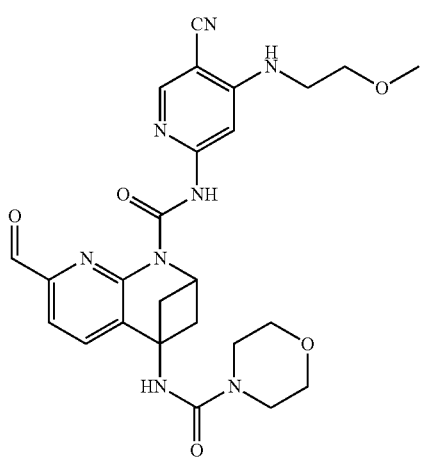
45
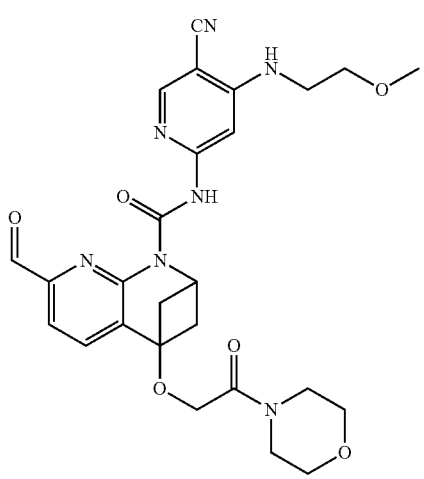
46
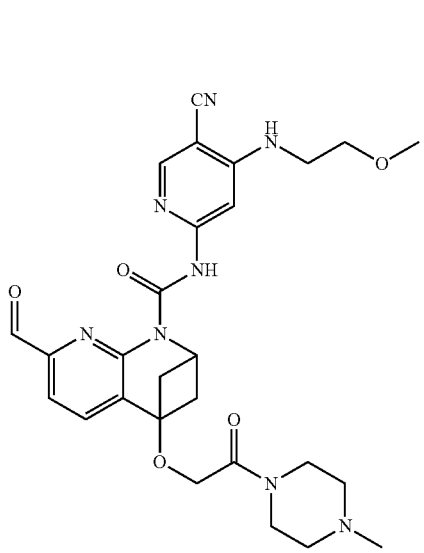
47
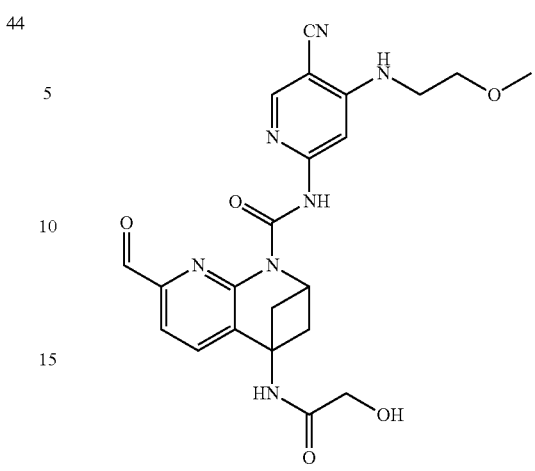
48
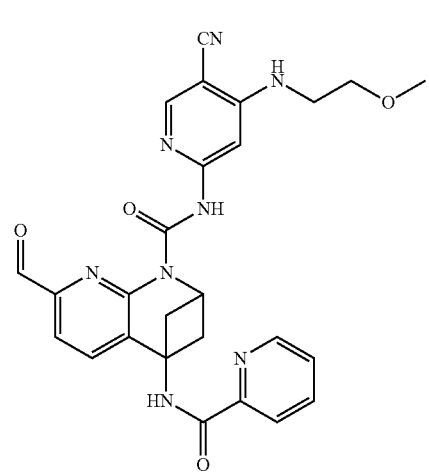
49
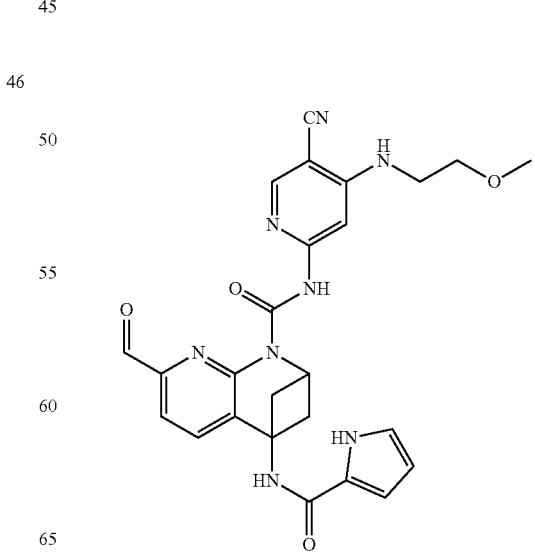

In one embodiment, the compound of formula (I) is selected from the following compound:
1
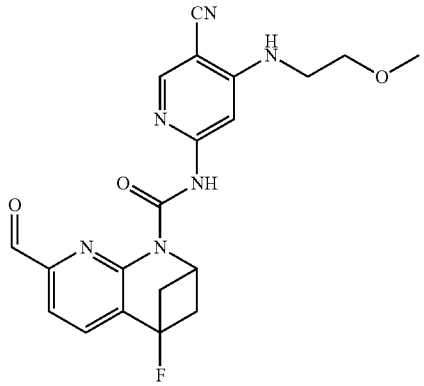
2
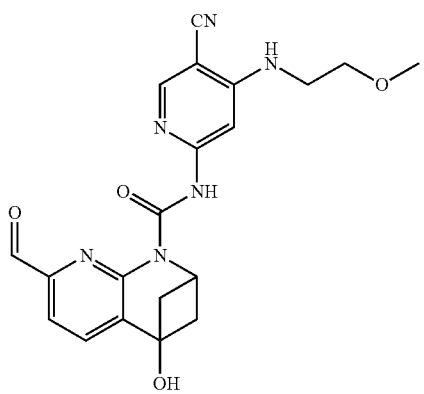
3
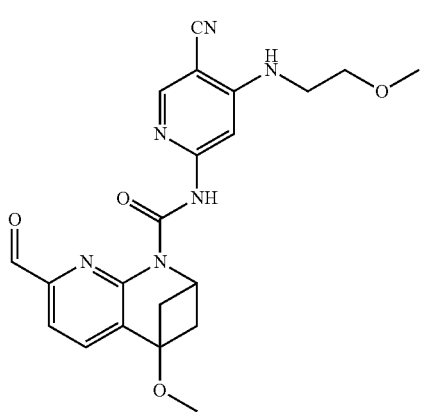
4
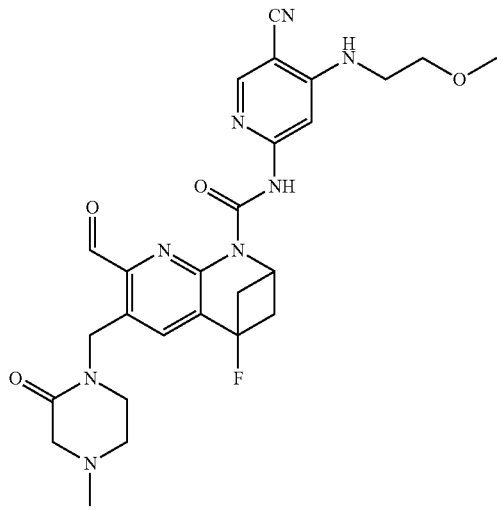
5
6

91
-continued
7
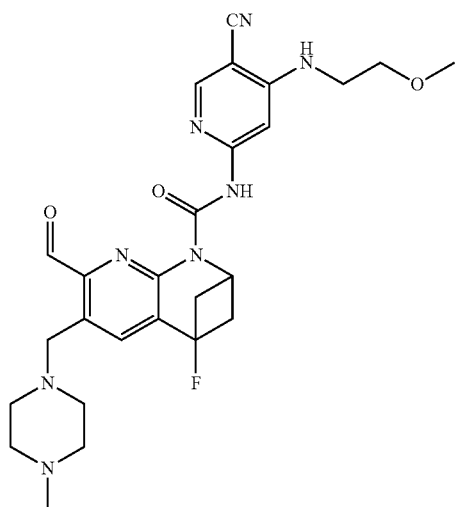
8
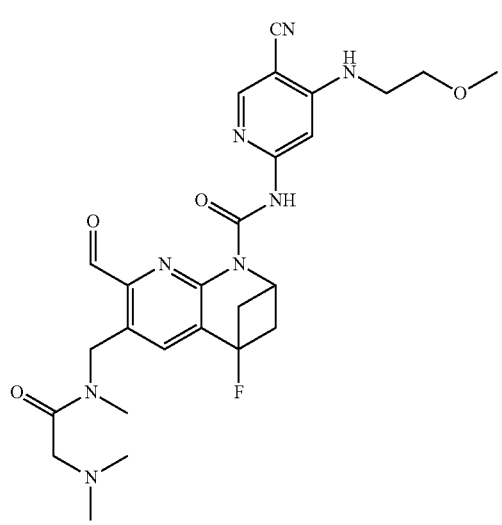
9
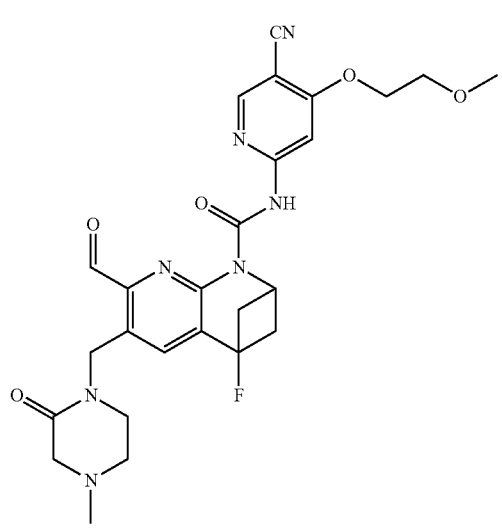
92
-continued
10
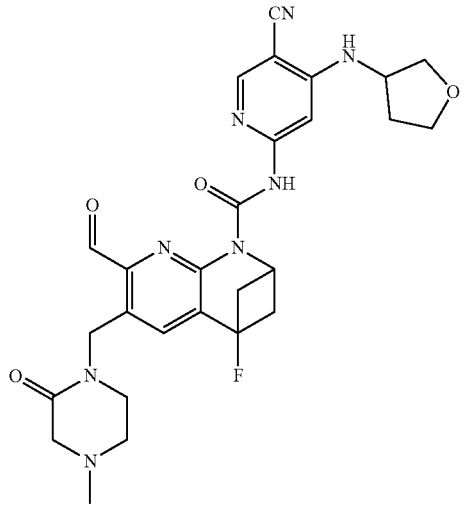
11A
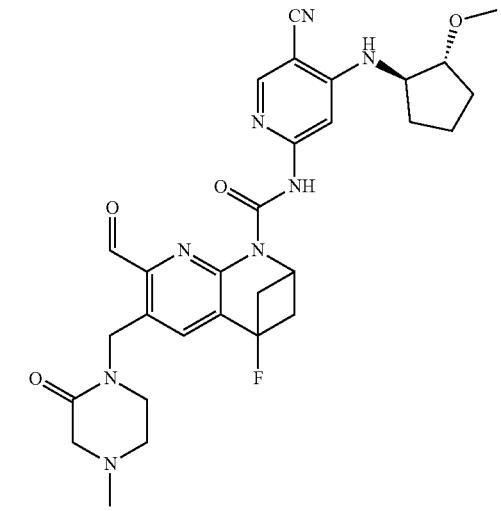
11B
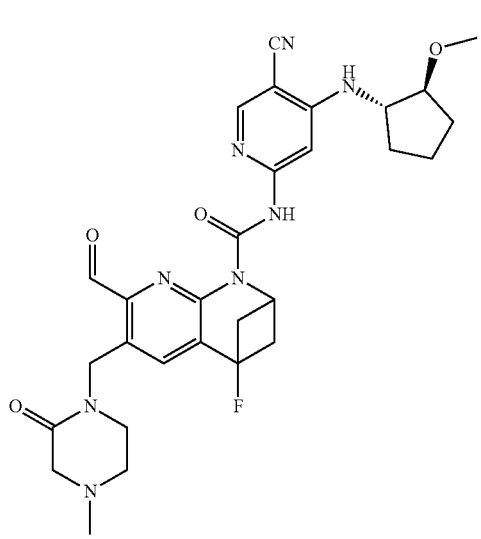

93
-continued
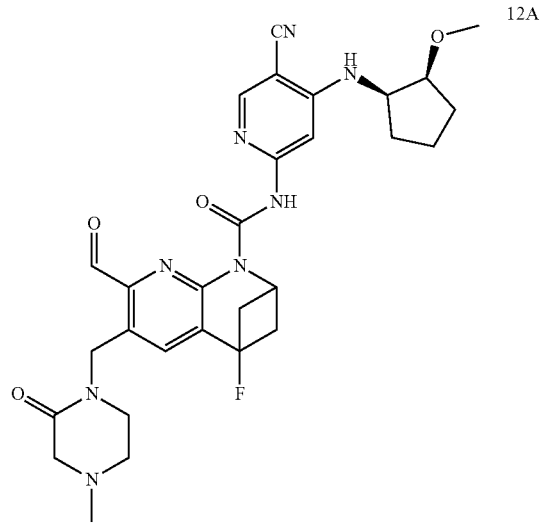
12A
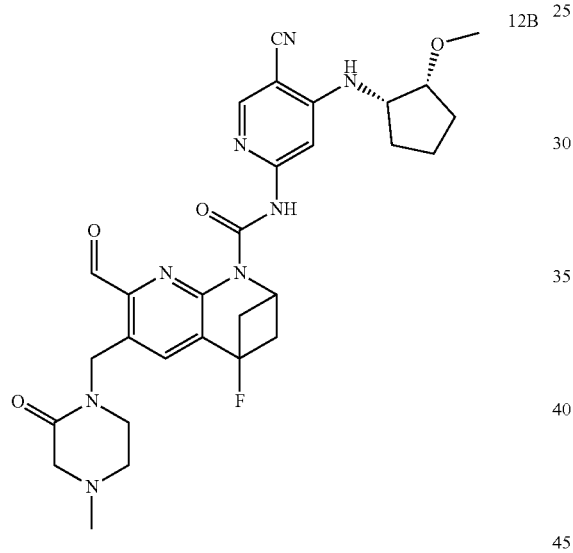
12B
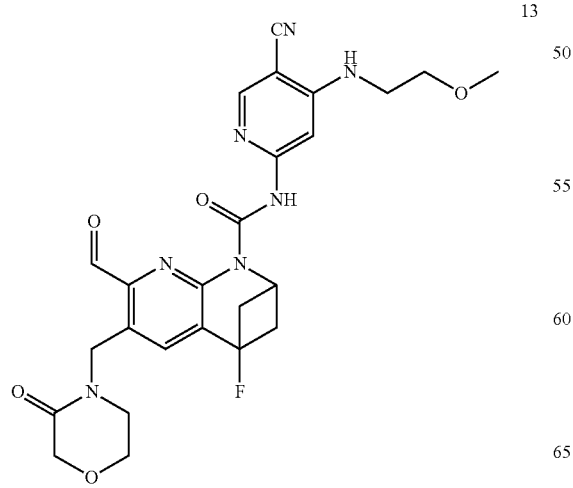
13
94
-continued
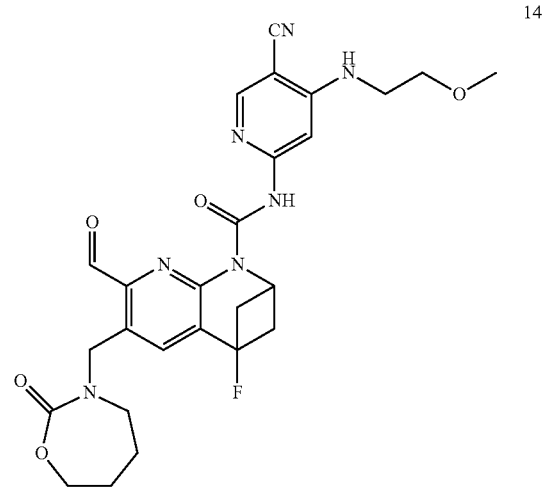
14
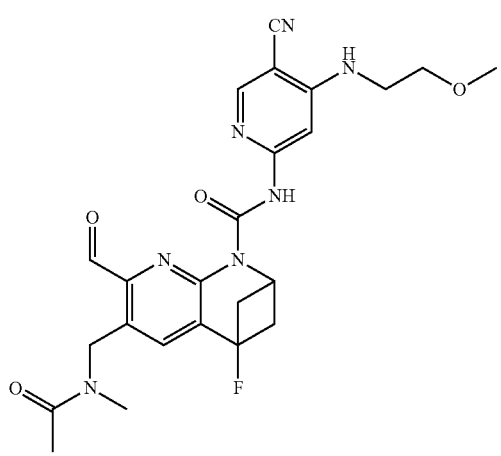
15
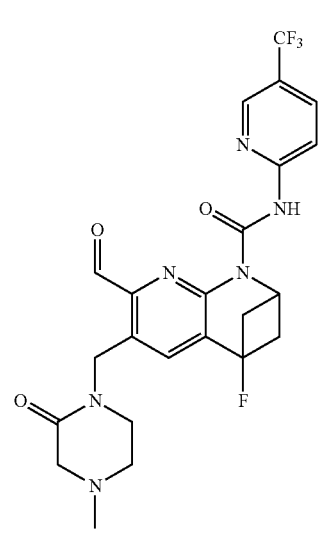
16

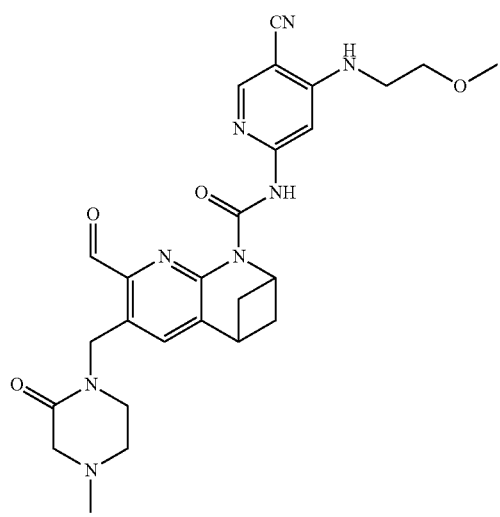
18
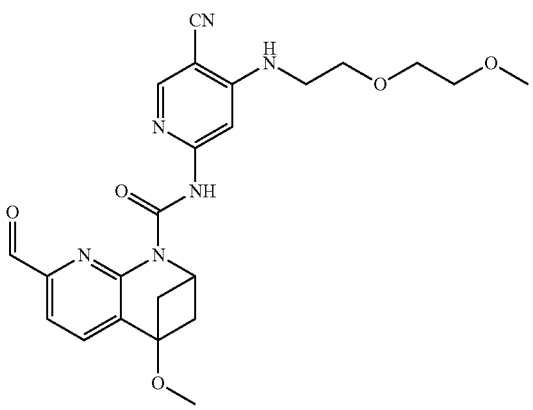
22
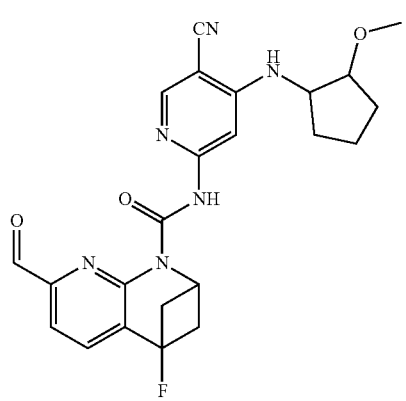
19
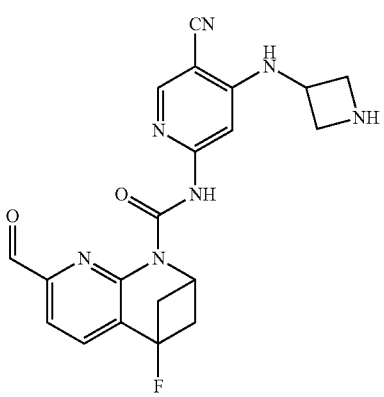
23
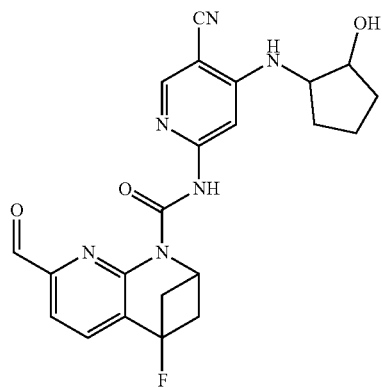
20
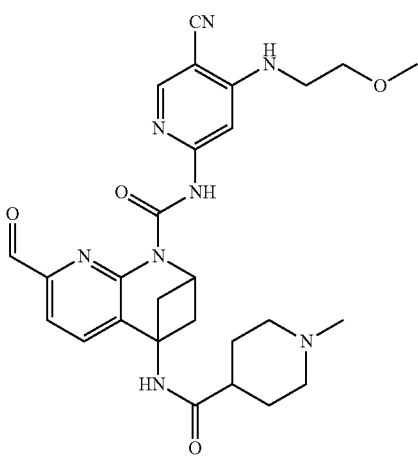
31

-continued
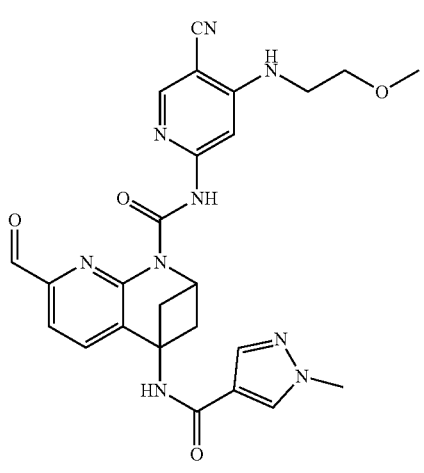
32
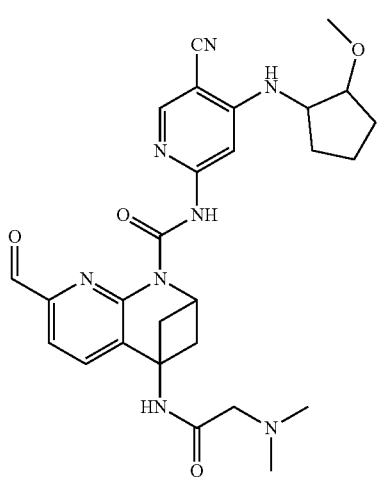
33
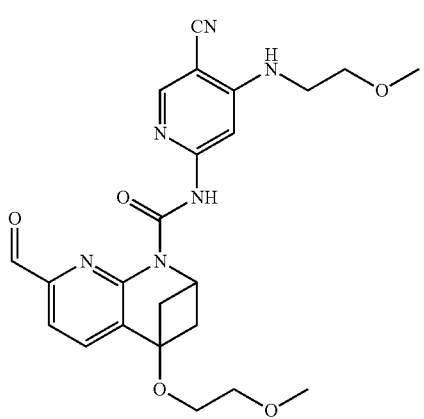
36
In one embodiment, the compound of formula (I) is selected from the following compound:
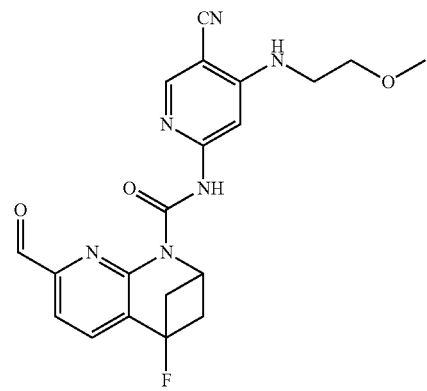
1
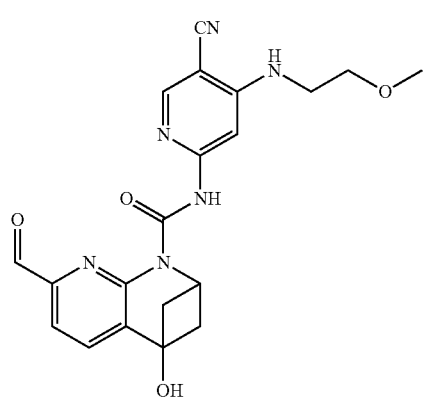
2
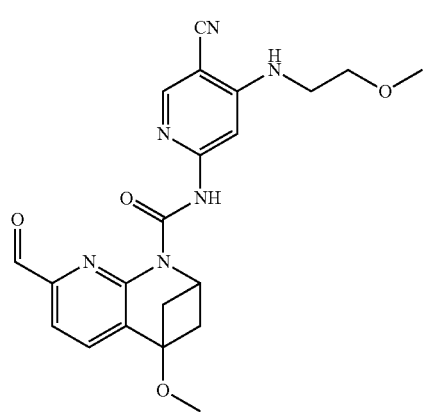
3

4
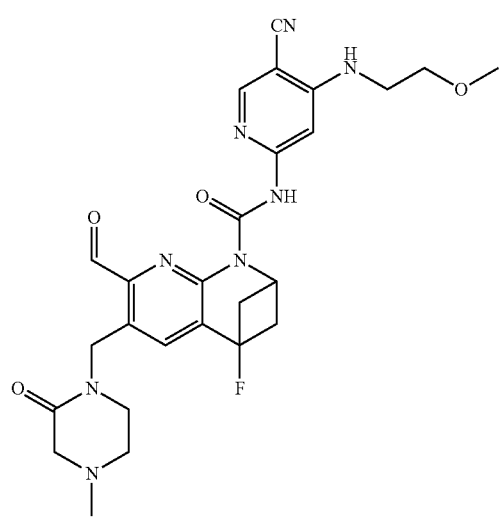
5
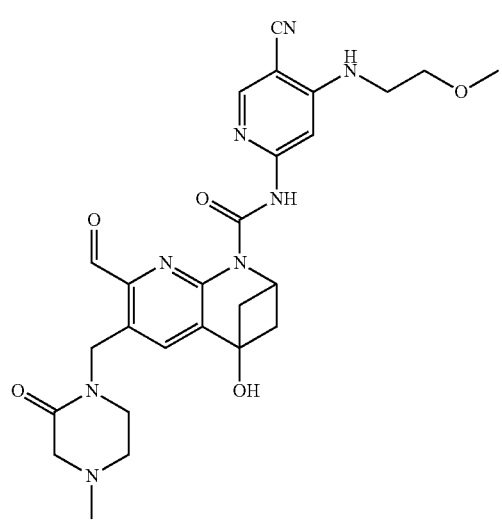
6
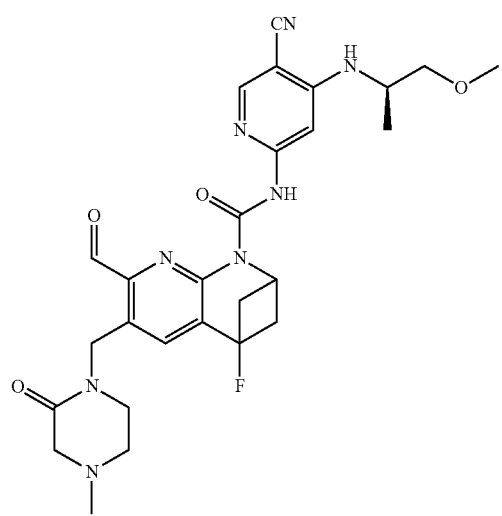
8
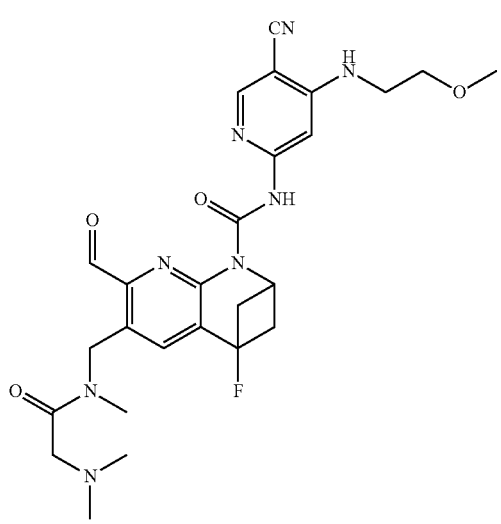
10
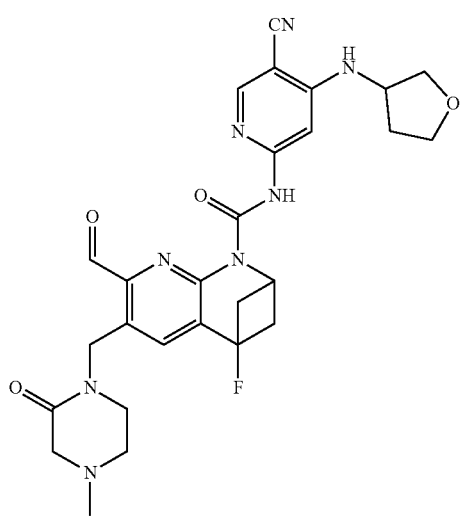
11A
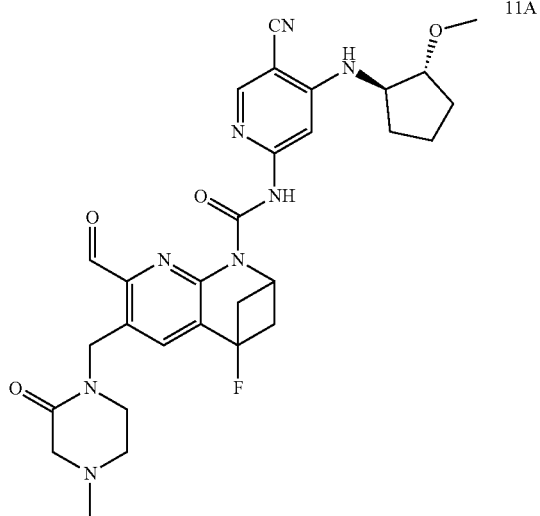 [SMILES: CN1CCN(Cc2cc3c(nc2C=O)N(C(=O)Nc2cc(NC4CCCC4O)c(C#N)cn2)C2CC3(F)C2)C(=O)C1]

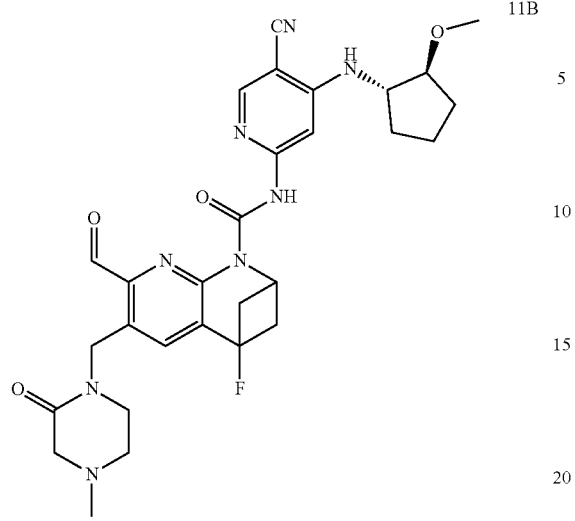
11B
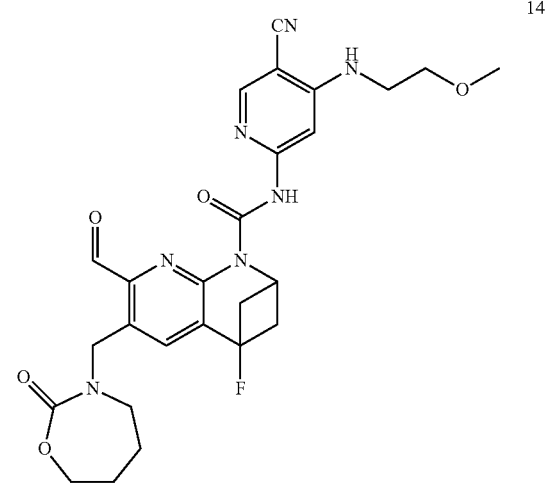
14
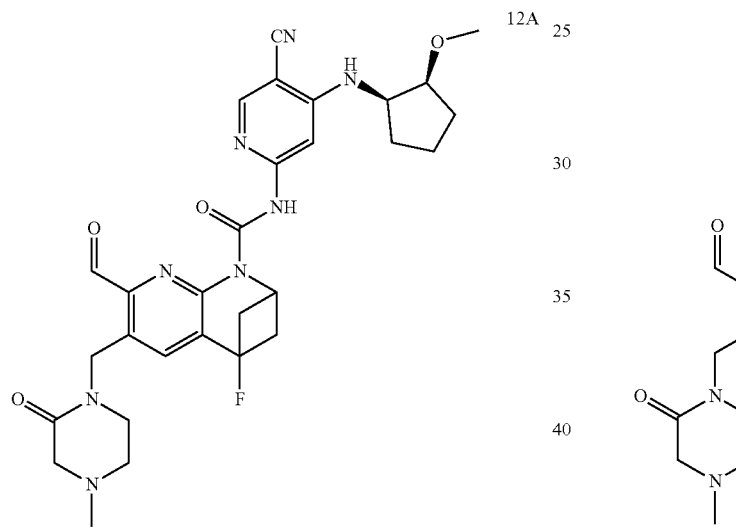
12A
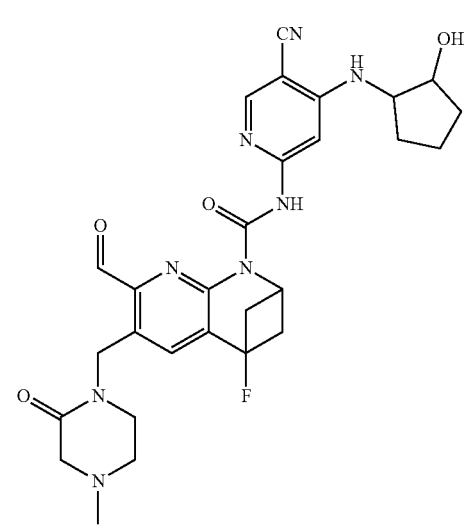
17
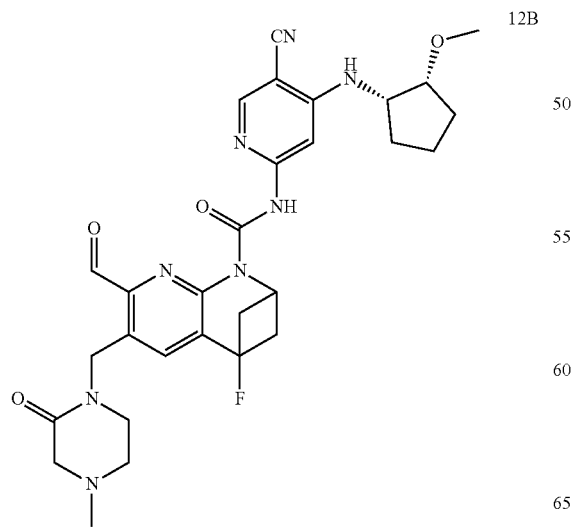
12B
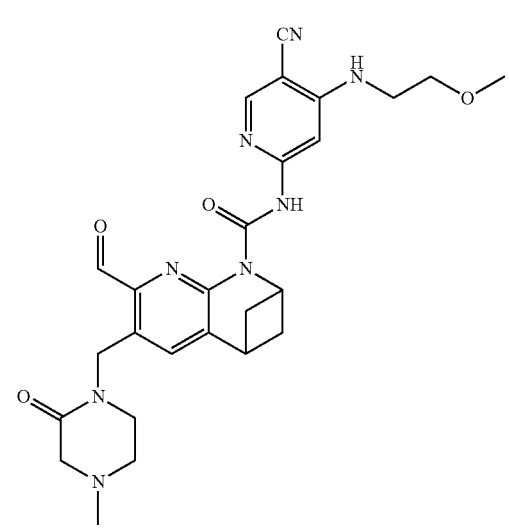
18

103
-continued
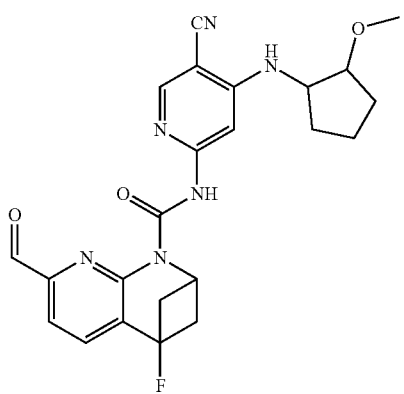
19
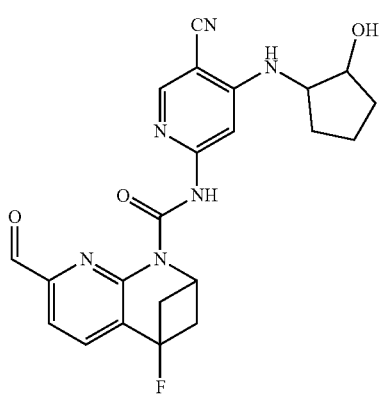
20
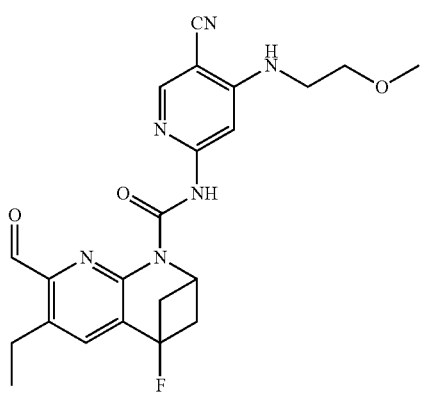
21
104
-continued
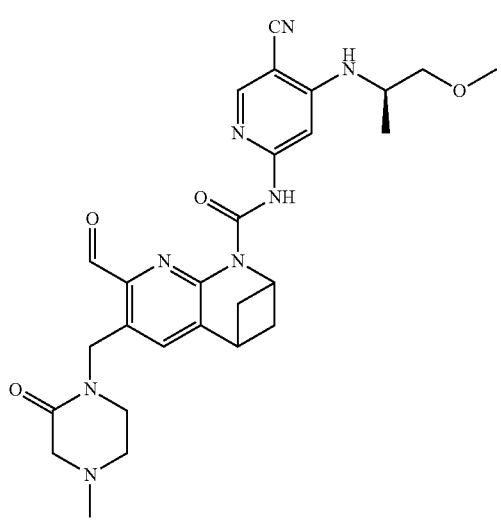
24
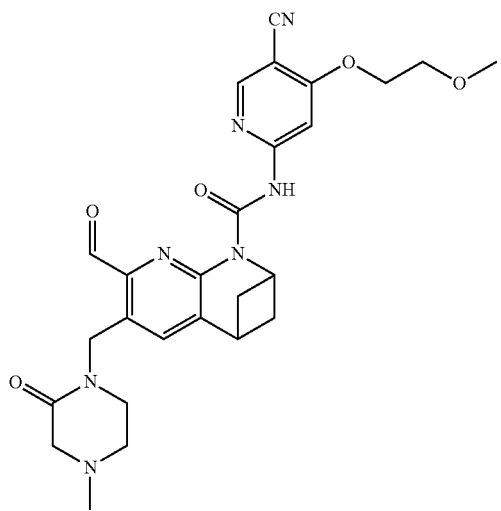
25
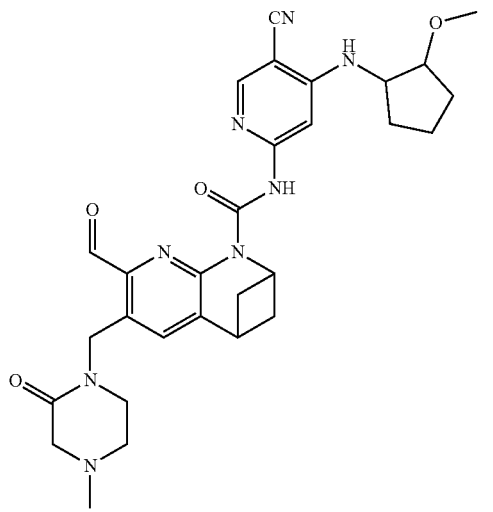
26

-continued
27
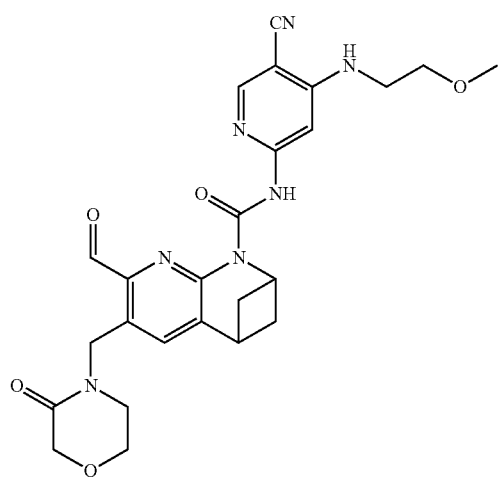
28
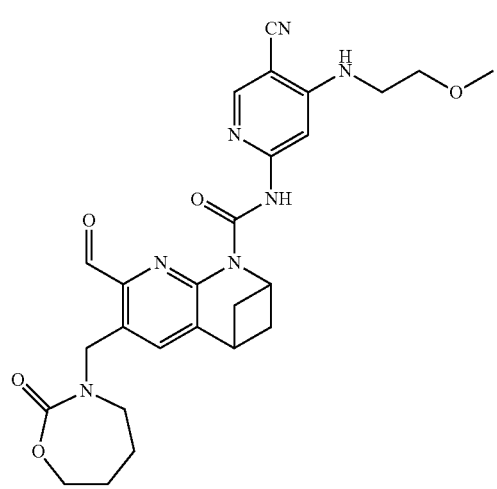
29
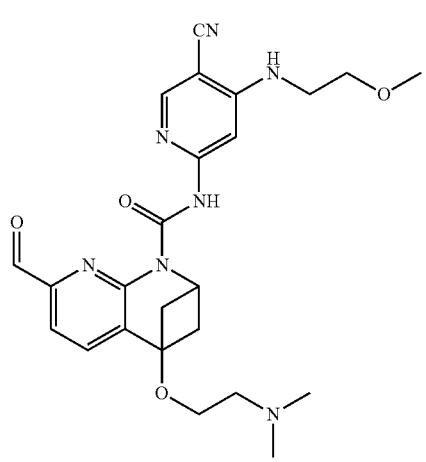
-continued
30
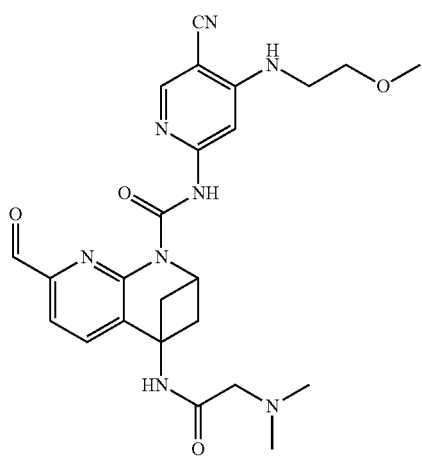
31
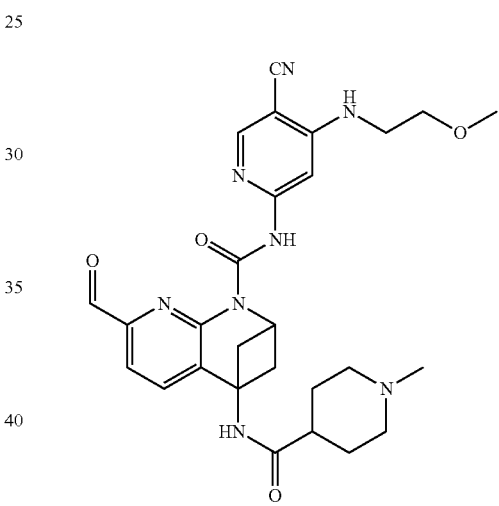
32
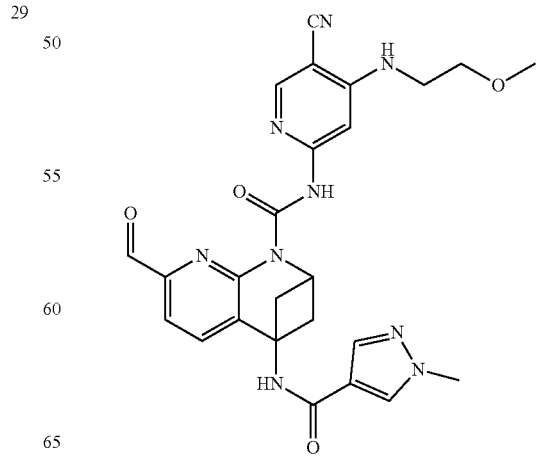

-continued
33
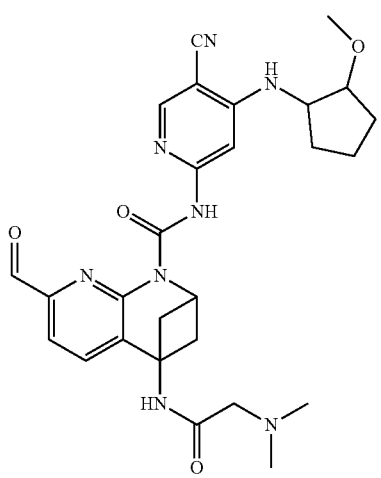
34
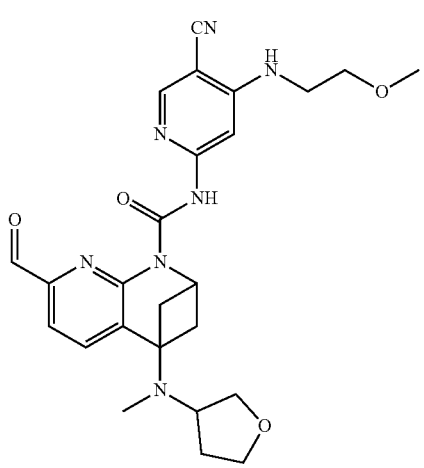
35
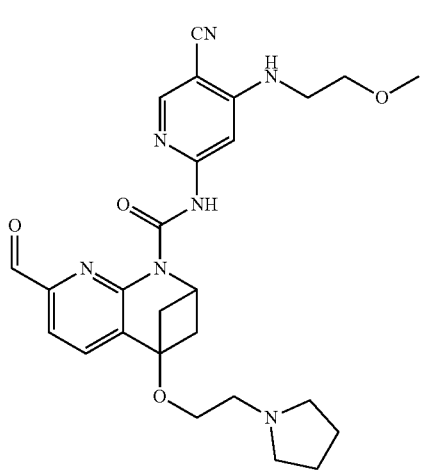
-continued
36
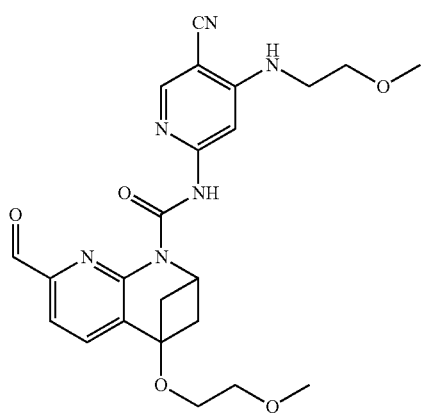
37
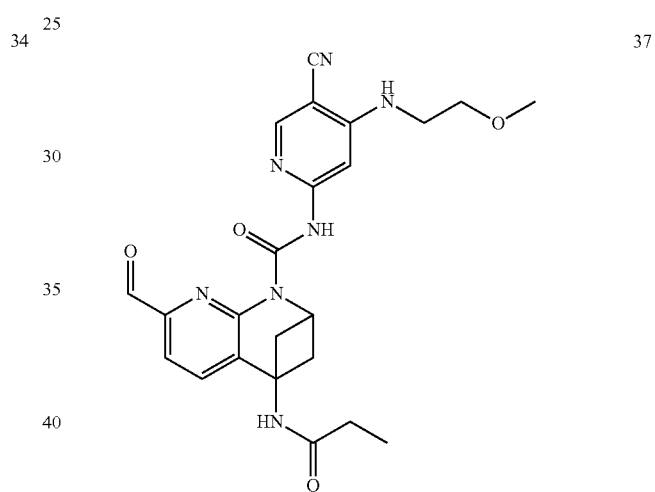
38
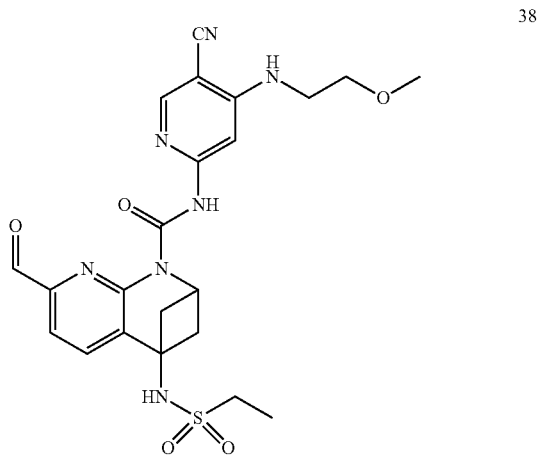

39
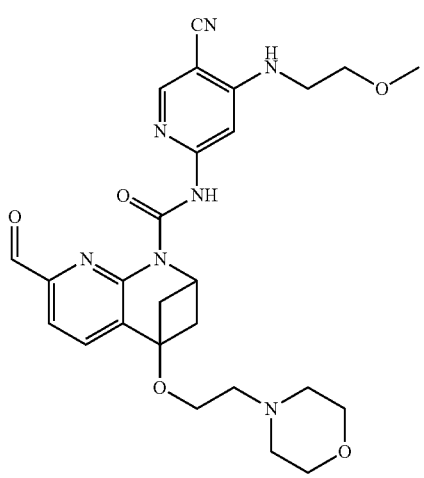
40
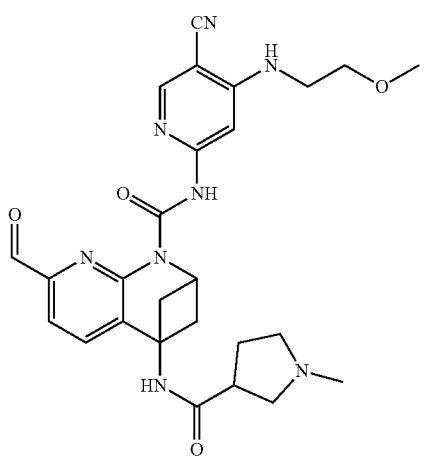
41
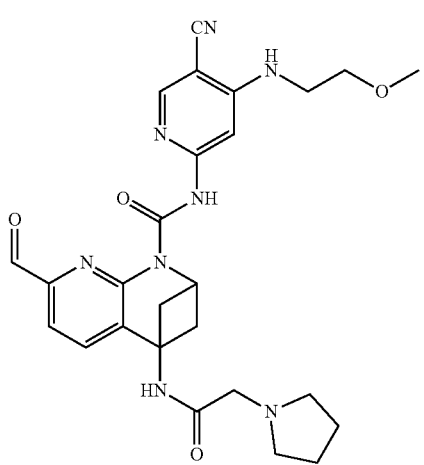
42
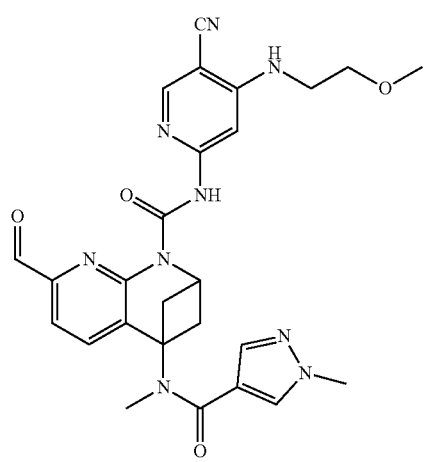
43
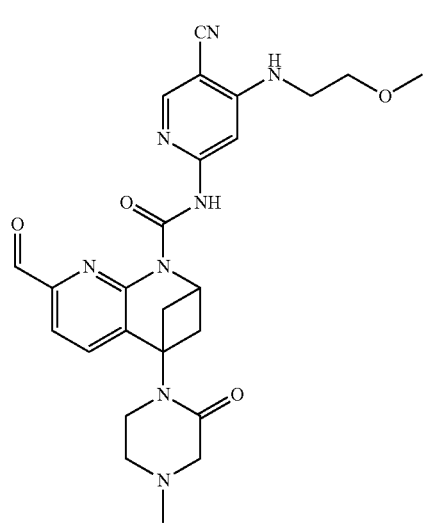
44
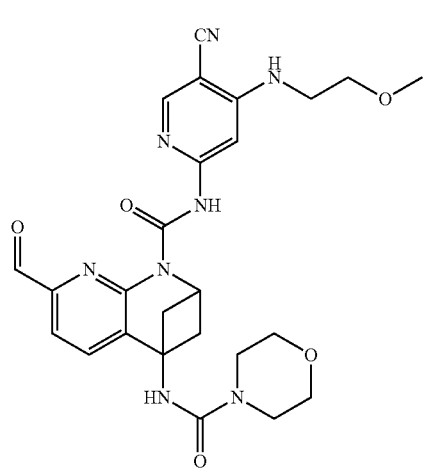

-continued
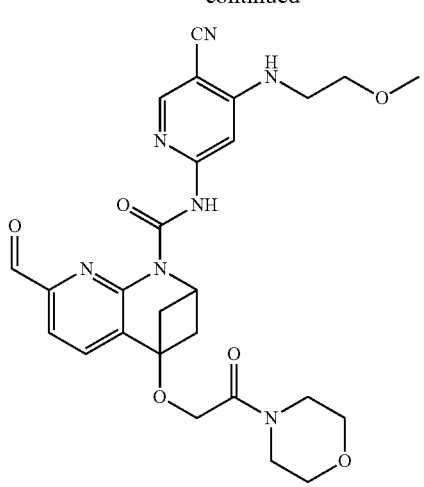
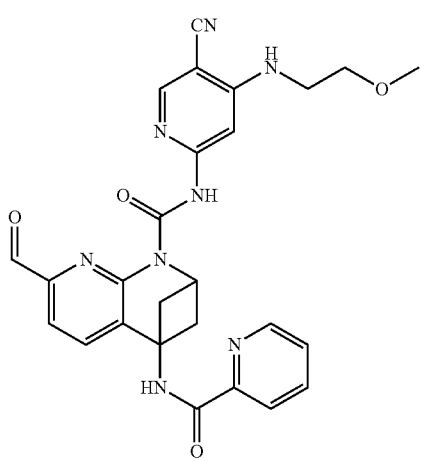
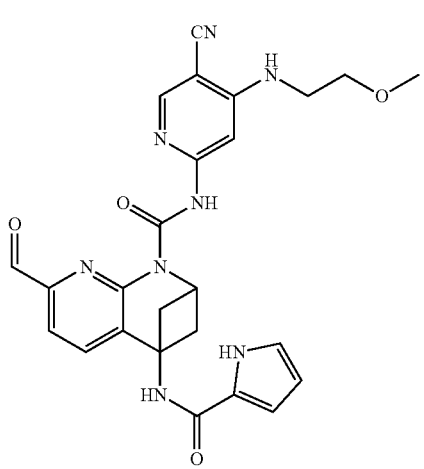
One embodiment of the present disclosure provides a method for preparing a compound represented by formula (I), the reaction scheme is as follows:
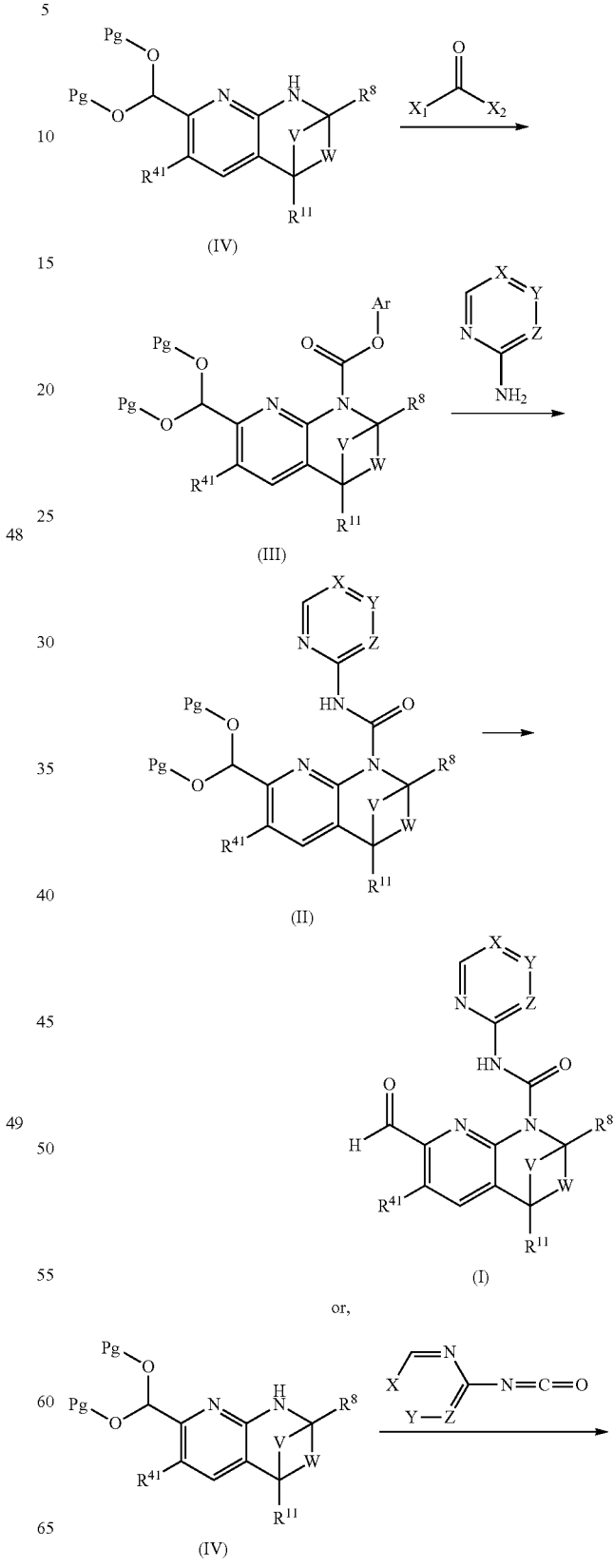

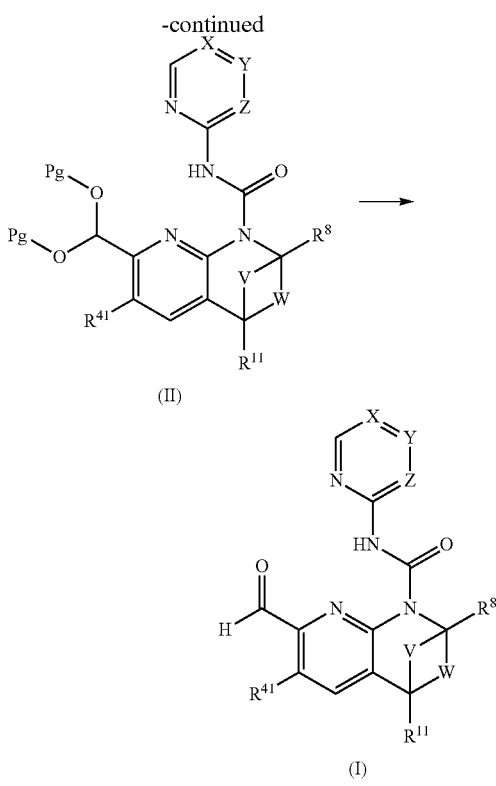

wherein, V, W, X, Y, Z, R$^8$ are defined as those in the compound of formula (I);

R$^{11}$ is selected from hydrogen, halogen, cyano, —N$_3$, —OR$^2$, —OP$_g^1$, —NHP$_g^2$, —NR$^2$P$_g^2$, —NR$^3$P$_g^2$ or —CO$_2$P$_g^3$;

R$^2$ is selected from:
1) C$_3$~C$_6$ cycloalkyl; or
2) C$_1$~C$_3$ alkyl, which is unsubstituted or substituted with one or more groups selected from the group consisting of halogen, C$_1$~C$_3$ alkoxy, C$_1$~C$_3$ haloalkoxy, and —NR$^{Y1}$R$^{Y2}$;

R$^3$ is selected from:
1) C$_1$~C$_3$ alkyl; or
2) C$_1$~C$_4$ acyl, which is unsubstituted or substituted with one or more groups selected from the group consisting of C$_3$~C$_6$ cycloalkyl, C$_1$~C$_3$ alkoxy, and —NR$^{Y1}$R$^{Y2}$;
3) —S(=O)$_2$R$^{Y5}$;

Pg$^1$ is a hydroxyl protecting group, which may be trimethylsilyl, tert-butyldimethylsilyl, tert-butyldiphenylsilyl, benzyl;

Pg$^2$ is an amino protecting group, which may be selected from benzyloxycarbonyl, tert-butoxycarbonyl, 9-fluorenemethoxycarbonyl, phthaloyl, trifluoroacetyl, benzyl, p-methoxybenzyl, 2,4-dimethoxybenzyl, 3,4-dimethoxybenzyl, p-nitrobenzyl;

Pg$^3$ is a carboxyl protecting group, which may be selected from C$_1$~C$_6$ alkyl, allyl, benzyl, phenyl, p-nitrobenzyl;

R$^{41}$ is selected from:
1) hydrogen, halogen;
2) C$_1$~C$_3$ alkyl, which is unsubstituted or substituted with one or more groups selected from the group consisting of —OPg$^1$, halogen, C$_1$~C$_3$ alkoxy, C$_1$~C$_3$ haloalkoxy;
3) C$_3$~C$_6$ cycloalkyl, which is unsubstituted or substituted with one or more groups selected from the group consisting of —OPg$^1$, halogen, C$_1$~C$_3$ alkoxy, C$_1$~C$_3$ haloalkoxy;

4) 5- or 6-membered heterocyclyl, which is unsubstituted or substituted with one or more groups selected from the group consisting of C$_1$~C$_3$ alkyl, C$_1$~C$_3$ haloalkyl, oxetanyl or oxo; or
5) —CH$_2$NR$^5$R$^6$, —CH(CH$_3$)NR$^5$R$^6$, —C(CH$_3$)$_2$NR$^5$R$^6$, R$^5$ is selected from C$_3$~C$_6$ cycloalkyl, which is unsubstituted or substituted with one or more groups selected from —NR$^{Y1}$R$^{Y2}$ substituted C$_1$~C$_3$ alkyl;

R$^6$ is selected from:
1) C$_1$~C$_3$ alkyl, C$_4$~C$_7$ cycloalkyl formyl, —S(=O)$_2$R$^{Y5}$; or
2) C$_1$~C$_4$ acyl, which is unsubstituted or substituted with one or more groups selected from —OPg$^1$, C$_1$~C$_3$ alkoxy, or —NR$^{Y1}$R$^{Y2}$;
or
R$^5$, R$^6$ and the N atom to which they are attached together form a 5-, 6- or 7-membered saturated heterocyclyl that is unsubstituted or substituted by one or more R$^7$;

R$^7$ is selected from C$_1$~C$_3$ alkyl, C$_1$~C$_4$ acyl, —OPg$^1$, or oxo;
or
Two R$^7$ attached to the same carbon atom together with the carbon atom to which they are attached form a 4-6 membered saturated heterocyclyl.

Pg is hydroxyl protecting group, which may be selected from C$_1$~C$_6$ alkyl, benzyl, or two Pg together with —O—CH—O— to which the two Pg attached to form a 5- to 7-membered 1,3-dioxa-cycloalkyl.

Definition of Terms

In this disclosure, unless otherwise specified, a definition of a certain group applies to all groups containing this group. For example, the definition of alkyl is applicable to C$_1$~C$_6$ alkyl, C$_1$~C$_3$ alkyl, etc.; the definition of C$_1$~C$_6$ alkyl is applicable to "C$_1$~C$_6$ alkoxy", etc., and the following definitions are applicable to the claims and the description.

"halogen" includes fluorine, chlorine, bromine, and iodine.

C$_m$~C$_n$ represent corresponding groups containing m-n carbon atoms, for example, C$_1$~C$_6$ alkyl represents an alkyl containing 1-6 carbon atoms.

"alkyl" may be linear or branched alkyl. C$_1$~C$_6$ linear alkyl may be, for example, methyl, ethyl, n-propyl, n-butyl, n-pentyl, n-hexyl. In branched alkyl, the substituent may be a methyl, for example, isopropyl; or may be two methyl groups, for example, tert-butyl; or may be an ethyl group, for example, 1-ethylpropyl; or may be three methyl groups; or may be one methyl group and one ethyl group. The position of the branch chain may be located at the 1-position carbon, the 2-position carbon, the 3-position carbon, the 4-position carbon, and the 5-position carbon, wherein the carbon atom to be bonded (C) represents the 1-position carbon.

C$_1$~C$_6$ alkyl may be linear or branched alkyl containing 1-6 carbon atoms. In C$_1$~C$_6$ alkyl, the number of carbon atoms may be 1, 2, 3, 4, 5 or 6.

C$_1$~C$_6$ alkyl may further be C$_1$~C$_3$ alkyl, and C$_1$~C$_3$ alkyl may be methyl, ethyl, n-propyl or isopropyl.

"Alkylene" refers to a divalent group formed by losing two hydrogen atoms on the carbon atom of alkane at the same time, wherein the two valents may be connected to the same atom, or connected to two atoms respectively, for example, methylene (—CH$_2$—), ethylene (—CH$_2$CH$_2$—).

"alkoxy" may be represented by —O—R$_a$, where R$_a$ is alkyl, and R$_a$ is defined as the above definition of alkyl. "C$_1$~C$_6$ alkoxy" refers to an alkoxy having 1 to 6 carbon atoms. The number of carbon atoms in $C_1 \sim C_6$ alkoxy may be 1, 2, 3, 4, 5 or 6. For example, $C_1 \sim C_6$ alkoxy may be methoxy, ethoxy, n-propoxy, isopropoxy, n-butoxy, isobutoxy, n-pentoxy and n-hexyloxy, etc.

$C_1 \sim C_3$ alkoxy may be methoxy, ethoxy, n-propoxy or isopropoxy.

"Alkylthio" can be represented by $—S—R_a$, where $R_a$ is alkyl, and $R_a$ is defined as the above definition of alkyl. $C_1 \sim C_3$ group may be methylthio ($—SCH_3$), ethylthio ($—SCH_2CH_3$), n-propylthio ($—SCH_2CH_2CH_3$) or isopropylthio ($—SCH(CH_3)_2$).

"Substituted alkyl" means that one or more hydrogen atoms in the alkyl group are replaced by a substituent. The number of substituents may be one or more, eg, 2, 3, 4, 5, 6, etc. Substituents may be attached to any carbon, such as 1-position (the carbon atom to be bonded (C) represents the 1-position carbon), 2-position, 3-position, 4-position, 5-position, and the last carbon. The kinds of the plurality of substituents may be the same, such as 1-fluoromethyl-2-fluoroethyl, or different, such as $—CH_2CHClCH_2OH$.

In "substituted $C_1 \sim C_6$ alkyl", the $C_1 \sim C_6$ alkyl is defined as above, and the substituents are defined as above in "substituted alkyl". The substituted $C_1 \sim C_6$ alkyl may be a substituted $C_1 \sim C_3$ alkyl.

"Haloalkyl" means a substituted alkyl in which one or more hydrogen atoms in the alkyl group are substituted with halogen atoms, ie, the substituents are halogen atoms.

"Alkoxy-substituted alkyl" may be represented by $—R_{a1}O—R_{a2}$, wherein $R_{a1}$ and $R_{a2}$ are both alkyl and are as defined above. "$C_1 \sim C_3$ alkoxy-substituted $C_1 \sim C_6$ alkyl" means that one or more hydrogen atoms in the $C_1 \sim C_6$ alkyl are substituted with $C_1 \sim C_3$ alkoxy.

"Hydroxy-substituted $—NR^{Y1}R^{Y2}$" means that one or more hydrogen atoms in the alkyl group of $R^{Y1}$ and/or $R^{Y2}$ are substituted with hydroxyl, and the number of hydroxyl may be 1, 2, 3, 4, 5, 6 and so on. For example, hydroxy substituted $—NR^{Y1}R^{Y2}$ may be $—N(CH_2OH)_2$, $—NCH_3(CH_2OH)$, and $—N(CH_2CH_3)(CH_2CH_2OH)$.

"Substituted alkoxy" means that one or more hydrogen atoms in the alkoxy group are substituted with a substituent, and the alkoxy group is defined as above. The number of substituents may be one or more, eg, 2, 3, 4, 5, 6, and so on. Substituents can be attached to any carbon, such as 1-position (1-position carbon is represented by the carbon atom attached to the oxygen atom ($C^-$)), 2-position, 3-position, 4-position, 5-position, and the last carbon. The kind of the plurality of substituents may be the same, for example, trifluoromethoxy ($OCF_3$), or may be different, for example, methoxytrifluoropropoxy.

"Substituted $C_1 \sim C_6$ alkoxy" means that one or more hydrogen atoms in the $C_1 \sim C_6$ alkoxy are substituted by a substituent, wherein the $C_1 \sim C_6$ alkoxy is defined as $C_1 \sim C_6$ alkoxy mentioned above.

"Haloalkoxy" means that the hydrogen atom in the alkyl is substituted with one or more halogen atoms. The number of substituents may be one or more, eg, 2, 3, 4, 5, 6, and so on. Substituents may be attached to any carbon, eg, 1-position, 2-position, 3-position, 4-position, 5-position, and the last carbon. For example, $C_1 \sim C_3$ haloalkoxy may be trifluoromethoxy ($—OCF_3$), difluoromethoxy ($—OCHF_2$), trifluoroethoxy (eg, $—OCH_2CF_3$).

A cyclic group refers to a group formed by the loss of one or more hydrogen atoms from a carbon atom or heteroatom in the ring of a cyclic compound. According to the types of atoms in the ring, cyclic group includes carbocyclic group and heterocyclyl. Carbocyclic group refers to a group formed by the loss of one or more hydrogen atoms attached to a carbon atom in the ring of a carbocyclic compound. The ring of a cyclic group contains n atoms (carbon atoms and heteroatoms), and the ring is called a "n-membered ring". For example, cyclopropyl is a carbocyclic group, a three-membered ring. Cyclic groups include monocyclic groups and polycyclic groups, depending on the number of rings contained, and the polycyclic groups may be, for example, bicyclic groups, such as bicycloalkyl.

"Cycloalkyl" refers to a saturated monocyclic group formed by the loss of one or more hydrogen atoms from a ring carbon atom of a cycloalkane. "$C_3 \sim C_6$ cycloalkyl" means a cycloalkyl containing 3 to 6 carbon atoms. The number of carbon atoms in the $C_3 \sim C_6$ cycloalkyl group may be 3, 4, 5 or 6. The $C_3 \sim C_6$ cycloalkyl may be a 3-6 membered ring, such as cyclopropyl, cyclobutyl, cyclopentyl, cyclohexyl.

"Cycloalkoxy" may be represented by $—O—R_b$, and the definition of Rb is as described above for cycloalkyl, wherein an oxygen atom is attached to a carbon atom on the ring. $C_3 \sim C_6$ cycloalkoxy may be, for example, a cyclopropyloxy, a cyclobutyloxy, a cyclopentyloxy, or a cyclohexyloxy.

"Substituted cycloalkyl" means that one or more hydrogen atoms in cycloalkyl are substituted with a substituent. "Substituted $C_3 \sim C_6$ cycloalkyl" means that one or more hydrogen atoms in $C_3 \sim C_6$ cycloalkyl are substituted with a substituent.

"Substituted cycloalkoxy" means that one or more hydrogen atoms in cycloalkoxy are substituted with a substituent. "Substituted $C_3 \sim C_6$ cycloalkoxy" means that one or more hydrogen atoms in $C_3 \sim C_6$ cycloalkoxy are substituted with a substituent.

$C_3 \sim C_6$ cycloalkyl in "$C_3 \sim C_6$ cycloalkoxy", "substituted $C_3 \sim C_6$ cycloalkyl" and "substituted $C_3 \sim C_6$ cycloalkoxy" is defined as the above-mentioned $C_3 \sim C_6$ cycloalkyl.

Substituents in "substituted $C_3 \sim C_6$ cycloalkyl" and "substituted $C_3 \sim C_6$ cycloalkoxy" may be connected to carbon atoms on the ring, and the number of substituents may be one or more, such as 2, 3, 4, 5, 6, etc. Substituents may be attached to any carbon, such as 1-position (the carbon atom to be bonded (C) represents the 1-position carbon), 2-position, 3-position, 4-position, 5-position, and the last carbon. Multiple substituents may be the same or different.

"Bicycloalkyl" means a monovalent hydrocarbon group formed by the loss of a hydrogen atom from a carbon atom located in the ring of a bicycloalkane. $C_5 \sim C_8$ bicycloalkyl refers to bicycloalkyl containing 5-8 carbon atoms; $C_5 \sim C_8$ bicycloalkyl may be 5-8 membered bicycloalkyl, that is, the carbon atoms contained are all located on the ring; $C_5 \sim C_8$ bicycloalkyl may be a bridged ring system, for example, may be bicyclo[2.1.1]hexyl, bicyclo[1.1.1]pentyl, bicyclo[2.2.1] Heptyl, bicyclo[2.2.2]octyl.

"Substituted bicycloalkyl" means that one or more hydrogen atoms in bicycloalkyl are substituted with a substituent. Substituents may be attached to carbon atoms on the ring, and the number of substituents may be one or more, such as 2, 3, 4, 5, 6, and so on. Substituents may be attached to any carbon, such as 1-position, 2-position, 3-position, 4-position, 5-position, and the last carbons, and the types of multiple substituents may be the same or different. $C_5 \sim C_8$ bicycloalkyl in "substituted $C_5 \sim C_8$ bicycloalkyl" is defined as above.

"Heterocyclyl" refers to a group formed by the loss of one or more hydrogen atoms from a carbon atom or heteroatom in a ring of a heterocyclic compound. Heterocyclyl includes aliphatic heterocyclyl (without aromatic character) and aromatic heterocyclyl. According to the degree of saturation, heterocyclyl includes saturated heterocyclyl and unsaturated heterocyclyl. Aromatic heterocyclyl belongs to unsaturated heterocyclyl, and aliphatic heterocyclyl includes both saturated heterocyclyl and unsaturated heterocyclyl. The heteroatoms contained in the heterocyclyl may be one or more, for example, 2, 3, 4, 5, etc.; and the heteroatoms may be selected from N, O, and S.

"Substituted heterocyclyl" means that one or more hydrogen atoms in the heterocyclyl are substituted with a substituent. Substituents may be attached to carbon atoms or heteroatoms on the ring, and the number of substituents may be one or more, such as 2, 3, 4, 5, 6, etc. Substituents may be attached to any atom, such as 1-position, 2-position, 3-position, 4-position, 5-position, and the last carbon, and the types of multiple substituents may be the same or different. Substituted heterocyclyl may include substituted saturated heterocyclyl, substituted aromatic heterocyclyl.

The "aromatic heterocyclyl" includes a single heterocyclyl and a fused heterocyclyl, and the fused heterocyclyl may be a fused phenyl ring and a single heterocyclic ring, or a fused heterocyclic ring and a heterocyclic ring.

"Acyl" may be represented by —C(=O)H 或 —C(=O)$R_a$, wherein $R_a$ represents a alkyl group which is defined as above for alkyl.

"Cycloalkylformyl" is represented by —C(=O)—$R_b$, wherein $R_b$ represents cycloalkyl, which is defined as above for cycloalkyl.

"Oxo" refers to a divalent oxygen atom, which may form a carbonyl group (>C=O) when connected to a carbon atom, and form a sulfinyl group (>S=O) when connected to a sulfur atom. A sulfur atom is attached to form a sulfuryl group (—S(=O)$_2$—). Two oxo groups are attached to a sulfur atom to form a sulfuryl (—S(=O)$_2$—).

In the present disclosure, the term "pharmaceutically acceptable" refers to those compounds, materials, compositions and/or dosage forms, which are within the scope of sound medical judgment, suitable for use in contact with human and animal tissues, without excessive toxicity, irritation, allergic reactions or other problems or complications, commensurate with a reasonable benefit/risk ratio.

The term "pharmaceutical composition" refers to a biologically active compound optionally in admixture with at least one pharmaceutically acceptable chemical component or agent, which is a "carrier" that facilitates for introducing compounds into cells or tissues, include but are not limited to stabilizers, diluents, suspending agents, thickening agents and/or excipients. Pharmaceutical compositions include, but are not limited to, the following forms: tablets, pills, powders, lozenges, sachets, cachets, elixirs, suspensions, emulsions, solutions, syrups, aerosols (solid or dissolved in liquid vehicles), ointments, soft and hard gelatin capsules, suppositories, sterile injectable solutions and sterile packaged powders, etc.

The term "pharmaceutically acceptable carrier" includes any and all solvents, dispersion media, coatings, surfactants, antioxidants, preservatives (eg, antibacterial, antifungal), isotonic agents, absorption delaying agents, salts, preservatives, pharmaceutical stabilizers, binders, excipients, disintegrants, lubricants, sweeteners, flavoring agents, dyes, and the like, as known to those skilled in the art, and combinations thereof. Unless any conventional carrier is incompatible with the active ingredient, its use in therapeutic or pharmaceutical compositions is contemplated.

A "therapeutically effective amount" refers to an amount of a compound of the present disclosure that induces a biological or medical response in a subject, such as reducing or inhibiting enzyme or protein activity or ameliorating symptoms, alleviating a condition, slowing or delaying disease progression, or preventing disease, etc.

"Patient" refers to an individual, including mammals and non-mammals, suffering from a disease, disorder, condition, or the like. Examples of mammals include, but are not limited to, any member of the mammal class: humans, non-human primates (eg, chimpanzees and other apes and monkeys); livestock, such as cattle, horses, sheep, goats, pigs; domestic animals, such as rabbits, dogs, and cats; laboratory animals, including rodents, such as rats, mice, and guinea pigs, and the like. Examples of non-human mammals include, but are not limited to, birds, fish, and the like. In one embodiment of the related methods and compositions provided herein, the mammal is a human.

"Pharmaceutically acceptable salts" refers to salts that retain the biological activity and properties of the compounds of the present disclosure and generally have no biological or otherwise undesirable effects. In many cases, the compounds of the present disclosure are capable of forming acid and/or base addition salts via the presence of amino and/or carboxyl groups or the like.

Pharmaceutically acceptable acid addition salts may be formed with inorganic and organic acids. Inorganic acids include, for example, hydrochloric acid, hydrobromic acid, sulfuric acid, nitric acid, phosphoric acid, and the like. Organic acids include, for example, but not limited to, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, etc.

Pharmaceutically acceptable base addition salts may be formed with inorganic and organic bases. Inorganic bases include basic compounds such as, but not limited to, sodium, potassium, ammonium, calcium, magnesium, iron, silver, zinc, and copper; particularly suitable salts include ammonium, potassium, sodium, calcium, and magnesium salts. Organic bases include primary, secondary and tertiary amines; substituted amines include naturally occurring substituted amines; cyclic amines; base ion exchange resins, and the like. Organic bases include, for example, but not limited to, isopropylamine, benzylamine, choline, diethanolamine, diethylamine, lysine, meglumine, piperazine, and tromethamine.

"Pharmaceutically acceptable prodrug" refers to any pharmaceutically acceptable salt, ester, salt of ester or other derivative of a compound of the present disclosure which, upon administration to a recipient, is capable of providing, directly or indirectly, a compound of the present disclosure or its pharmacologically active metabolite or residue. Particularly preferred prodrugs are those that increase the bioavailability of the compounds of the present disclosure when administered to a patient (eg, make orally administered compounds more readily absorbed into the bloodstream), or those promote the delivery of the parent compound to biological organs or the site of action.

The term "solvate" refers to a physical aggregate of a compound of the present disclosure formed with one or more solvent molecules. The physical aggregate includes various degrees of ions and covalent bonds, such as hydrogen bonds. It has been demonstrated that this solvate can be isolated, for example, when one or more solvent molecules are incorporated in the crystal lattice. "Solvate" includes two parts, a solvent phase and an isolatable solvate. There are many examples of solvates, including ethanol solvate, methanol solvate, and the like. "Hydrate" is a solvate with water ($H_2O$) molecules as the solvent. One or more of the compounds of this disclosure may optionally be prepared as solvates.

In the present disclosure, compounds of formula (I) in which $R^4$ is an aldehyde group and trifluoromethyl such as compounds (I-4) and (I-5) form solvates with water (compounds (I-4a) and (I-5a))) are as follows.

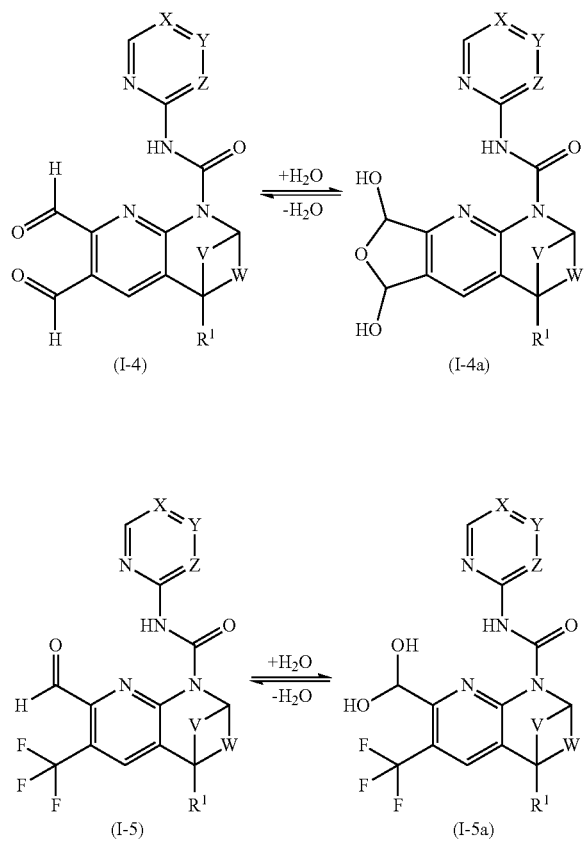

(I-4)   (I-4a)

(I-5)   (I-5a)

wherein V, W, X, Y, Z and $R^1$ are as defined for compounds of formula (I). Accordingly, the present disclosure is intended to include compounds (I-4), (I-5) and solvates (I-4a), (I-5a) thereof. The presence of solvates can be identified by those skilled in the art using tools such as NMR.

Pharmaceutically acceptable solvates of the present disclosure include those in which the crystallized solvent may be isotopically substituted, eg, $D_2O$, $d_6$-acetone, $d_6$-DMSO.

The term "active metabolite" refers to an active derivative of a compound that is formed when the compound is metabolized.

The term "polymorph" refers to compounds of the present disclosure that exist in different crystal lattice forms.

The term "isotopic label" refers to an isotopically labeled compound of the present disclosure.

For example, isotopes in the compounds of the present disclosure may include various isotopes of elements H, C, N, O, P, F, S, Cl, and I, such as $^2H$, $^3H$, $^{13}C$, $^{14}C$, $^{15}N$, $^{18}O$, $^{17}O$, $^{31}P$, $^{32}P$, $^{35}S$, $^{18}F$, $^{36}S$, $^{123}I$, $^{124}I$ and $^{125}I$. The present disclosure includes various isotopically-labeled compounds as defined, such as those compounds in which radioactive isotopes such as $^3H$ and $^{14}C$ are present, or those compounds in which non-radioactive isotopes such as $^2H$ and $^{13}C$ are present. Such isotopically labeled compounds are suitable for metabolic studies (using $^{14}C$); reaction kinetic studies (using eg $^2H$ or $^3H$); detection or imaging techniques such as positron emission tomography (PET) or single photon emission computed tomography (SPECT), including drug or substrate tissue distribution analysis; or radiotherapy for patients.

Specifically, $^{18}F$ compounds may be particularly desirable for PET or SPECT studies. Isotopically-labeled compounds of formula (I) can generally be substituted by conventional techniques known to those skilled in the art or by methods analogous to those described in the accompanying examples and preparations, using an appropriate isotopically-labeled reagent in place of the previous prepared using unlabeled reagents.

In addition, substitution with heavier isotopes, especially deuterium (ie, $^2H$ or D), may yield certain therapeutic advantages resulting from greater metabolic stability, such as increased in vivo half-life or reduced dose requirements or improved therapeutic index. It should be understood that in this context, deuterium is considered as a substituent for the compounds of formula (I), and the present disclosure is also intended to include compounds in which any one or more hydrogen atoms in the compounds of formula (I) are replaced by deuterium.

The term "isomer" refers to an isomer resulting from different arrangements of atoms in a molecule in space. The compounds of the present disclosure may be in the form of one of optically active isomers, geometric isomers, rotamers, tautomers, internal addition products of isomers, or mixtures thereof, eg, in the form of substantially pure geometric isomers (cis or trans), diastereomers, optical isomers (enantiomers), racemates or mixtures thereof. For example, for optical isomers, optically active (R)- and (S)-isomers as well as D and L isomers may be prepared by chiral resolution, chiral synthesis or chiral reagents, or other conventional techniques; as another example, may be converted to diastereomers by reaction with an appropriate optically active species (such as a chiral alcohol or Mosher's acid chloride), which may be separated and converted (such as hydrolyzed) to the corresponding single isomeric species. For another example, separation may also be carried out by means of a chromatographic column.

The compounds of the present disclosure may contain structures such as asymmetric or chiral centers, double bonds, etc.; if the compound contains a double bond, the substituent may be in cis or trans configuration; if the compound contains a disubstituted cycloalkyl, the cycloalkyl substituents may also have a cis or trans configuration; if the compound contains a hindered single bond that does not rotate freely, conformers that do not readily interconvert may arise.

In the present disclosure, compounds of formula (I) may readily form tautomers and internal addition products of isomer as shown below. For example, compounds of formula (I) wherein $R^4$ is hydroxymethyl, —$CH_2CO_2H$, (methylamino)methyl (eg compounds (I-1), (I-2) and (I-3)) may be in the forms shown below (compounds (I-1a), (I-2a) and (I-3a)).

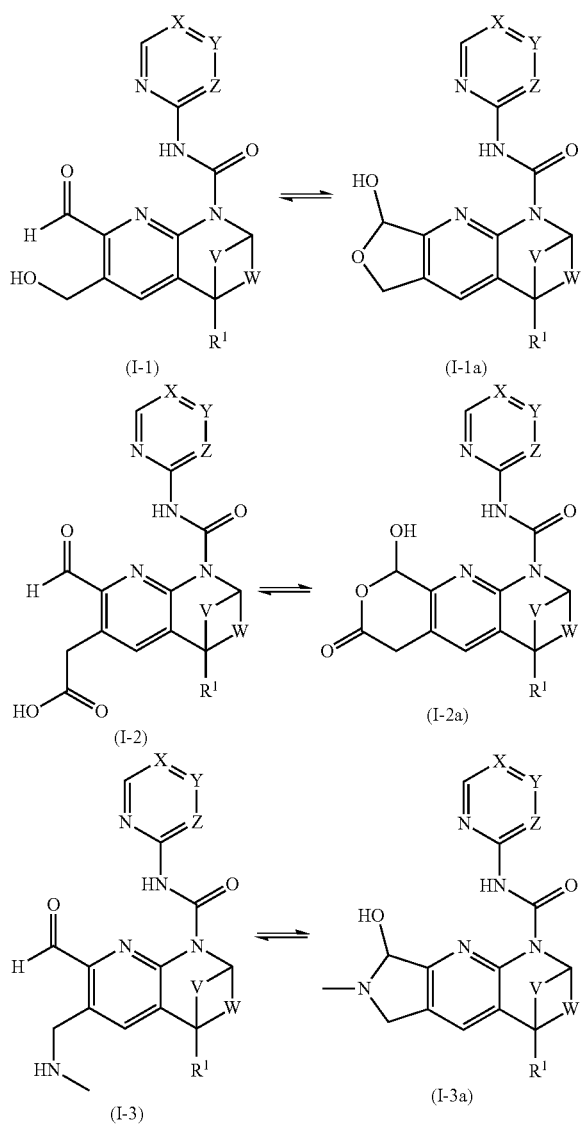

(I-1)  (I-1a)  (I-2)  (I-2a)  (I-3)  (I-3a)

wherein, V, W, X, Y, Z and R¹ are as defined above for the compound of formula (I). Therefore, the compounds of formula (I) of the present disclosure include compounds (I-1), (I-2), (I-3) and all tautomers or internal addition products of isomers including the isomers (I-1a), (I-2a), (I-3a). The presence of tautomers or internal addition products of isomers may be identified by those skilled in the art using tools such as NMR.

All methods described in this specification can be performed in any suitable order unless otherwise indicated or clearly contradicted by context. Any and all examples or exemplary language (eg, "such as") provided in this specification are used only to better clarify the disclosure, and are not intended to limit the scope of the disclosure as otherwise claimed.

The preparation and properties of the compound of formula (I) according to an embodiment of the present disclosure will be described hereinafter with reference to specific examples. In the preparation, the starting materials used are known and commercially available, or may be synthesized using or according to methods known in the art. "Pd₂(dba)₃" in the examples refers to tris(dibenzylideneacetone)dipalladium; "Pd(dppf)Cl₂" refers to (1,1'-bis(diphenylphosphino)ferrocene) palladium dichloride; "dppf" refers to 1,1'-bis(diphenylphosphino)ferrocene; "NaHMDS" refers to sodium bis(trimethylsilyl)amide; "LiHMDS" refers to lithium bis(trimethylsilyl)amide; "HATU" refers to 2-(7-azabenzotriazole)-N,N,N',N'-tetramethylurea hexafluorophosphate.

Unless otherwise specified, all reactions in the examples were carried out under continuous magnetic stirring, in a dry nitrogen or argon atmosphere, the solvent was a dry solvent, and the reaction temperature was in degrees Celsius.

Compound structures of the examples were determined by nuclear magnetic resonance (NMR) or/and liquid chromatography-mass spectrometry (LC-MS). NMR chemical shifts (δ) are given in parts per million (ppm). NMR was measured with a Bruker AVANCE-400 nuclear magnetic resonance instrument, the solvent was deuterated dimethyl sulfoxide (DMSO-d₆) or deuterated chloroform (CDCl₃), and the internal standard was tetramethylsilane (TMS). Agilent 1100 Infinity Series mass spectrometer was used for LC-MS measurements.

The thin-layer chromatography (TLC) used Silica gel 60 F₂₅₄ silica gel plate of Merck Company, and the thin-layer chromatography separation and purification (pre-TLC) product used Anhui Liangchen silicon source GF254 silica gel plate with a size of 1.0 mm. Column chromatography generally uses Qingdao Ocean 100-200 mesh silica gel as the carrier.

Example 0-1

Intermediate 1: Preparation of 6-amino-4-fluoronicotinonitrile

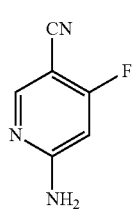

First Step: Preparation of 2-amino-4-fluoro-5-iodopyridine

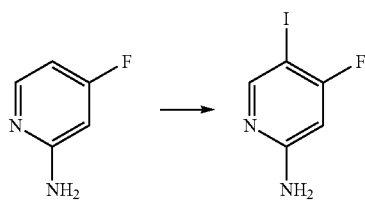

To a solution of 2-amino-4-fluoropyridine (11.2 g, 100 mmol) and N-iodosuccinimide (24.8 g, 110 mmol) in acetonitrile (400 mL) was added trifluoroacetic acid (3.0 mL, 40 mmol) at room temperature and then stirred at room temperature for 3 hours.

Then, ethyl acetate (400 mL) was added to the obtained mixed solution for dilution, and the mixture was washed with saturated sodium thiosulfate solution (500 mL) and saturated sodium carbonate solution (500 mL) successively, and the liquids were separated to obtain an aqueous phase and an organic phase. The obtained aqueous phases were combined, adjusted to pH 10 with saturated sodium carbonate solution, extracted with ethyl acetate (500 mL), and separated to obtain an organic phase. All organic phases were combined, washed with saturated brine (500 mL), and dried over anhydrous sodium sulfate, filtered with suction and evaporate to dryness. The residue was purified by column chromatography, eluting with a gradient of petroleum ether/ethyl acetate=4:1 to 2:1, and the fractions containing the product were concentrated to render the product 2-amino-4-fluoro-5-iodopyridine, and the relevant test data are as follows:

$^1$H NMR (CDCl$_3$, 400 MHz), δ 8.24 (d, J=9.2 Hz, 1H), 6.25 (d, J=9.2 Hz, 1H), 4.70 (s, 2H).

Second Step: Preparation of 6-amino-4-fluoronicotinonitrile

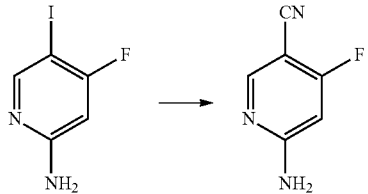 [SMILES: Nc1cc(F)c(I)cn1 ; N#Cc1cnc(N)cc1F]

Under nitrogen protection, a mixture of 2-amino-4-fluoro-5-iodopyridine (15.6 g, 65.5 mmol), zinc cyanide (8.1 g, 69.0 mmol), Pd$_2$(dba)$_3$ (1.5 g, 1.64 mmol), dppf (3.0 g, 5.4 mmol), zinc powder (860 mg, 13.1 mmol) and N,N-dimethylacetamide (100 mL) was stirred at 100° C. for 4 hours. Then it was cooled to room temperature, and saturated sodium bicarbonate solution (500 mL) was added to the obtained mixed solution for dilution and extracted with ethyl acetate (500 mL). The organic phase was obtained by separation, and then was washed with saturated brine (500 mL), dried over anhydrous sodium sulfate, filter with suction, and evaporated to dryness. The residue was purified by column chromatography, eluted with a gradient of petroleum ether/ethyl acetate=5:1 to 1:1, and the fraction containing the product was concentrated to obtain Intermediate 1. The relevant test data are as follows:

$^1$H NMR (DMSO-d$_6$, 400 MHz), δ 8.12 (d, J=10.0 Hz, 1H), 6.45 (s, 2H), 6.30 (d, J=10.8 Hz, 1H).

Example 0-2

Intermediate 2: Preparation of 6-amino-4-((2-methoxyethyl)amino)nicotinonitrile

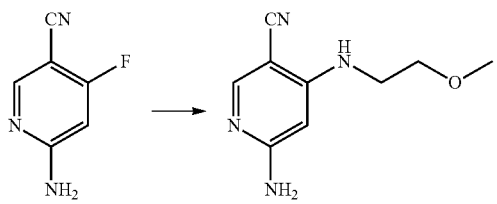

Under nitrogen protection, a solution of 6-amino-4-fluoronicotinonitrile (Intermediate 1, 6.868 g, 50 mmol), 2-methoxyethylamine (13.0 mL, 150 mmol), N,N-diisopropylethylamine (25.0 mL, 152 mmol) in N,N-dimethylacetamide (120 mL) was stirred at 50° C. for 16 hours. After that, it was cooled to room temperature, and the obtained mixture was purified by column chromatography, eluted with a gradient of petroleum ether/ethyl acetate=1:1 to ethyl acetate, and the fraction containing the product was concentrated to obtain Intermediate 2. The relevant test data are as follows:

$^1$H NMR (CDCl$_3$, 400 MHz), δ 8.03 (s, 1H), 5.59 (s, 1H), 5.05 (s, 1H), 4.79 (s, 2H), 3.58 (t, J=5.2 Hz, 2H), 3.39 (s, 3H), 3.30-3.34 (m, 2H).

Example 0-3

Intermediate 3: Preparation of (R)-6-amino-4-((1-methoxyprop-2-yl)amino)nicotinonitrile

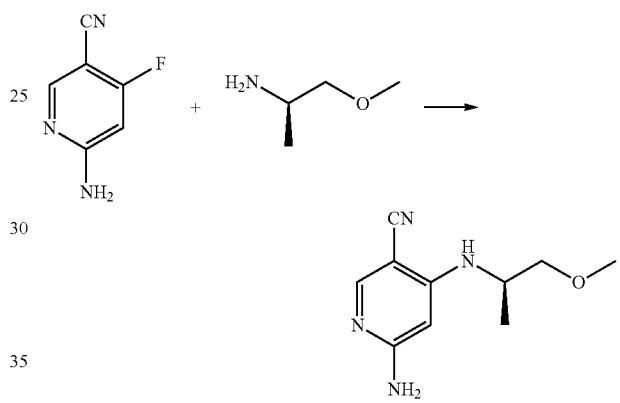

Taking intermediate 1 and (R)-1-methoxy-2-propylamine as starting materials, the reaction was carried out in a manner similar to that for preparing intermediate 2 to obtain intermediate 3, and the relevant test data were as follows:
ESI-MS: 207.1 [M+H]$^+$.

Example 0-4

Intermediate 4: Preparation of 6-amino-4-((tetrahydrofuran-3-yl)amino)nicotinonitrile

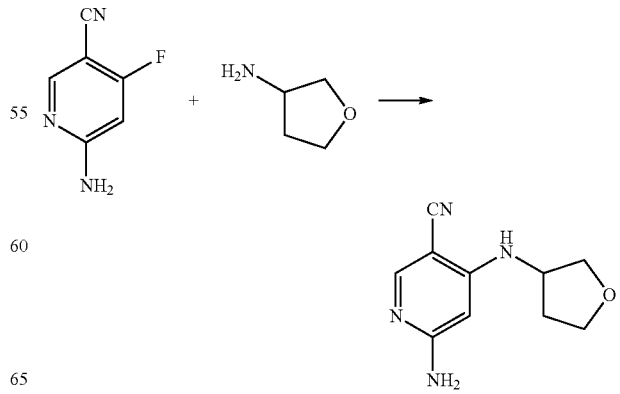

Taking intermediate 1 and 3-aminotetrahydrofuran as starting materials, and reacting in a manner similar to the preparation of intermediate 2 to obtain intermediate 4, and its relevant test data are as follows:

ESI-MS: 205.1 [M+H]$^+$.

Example 0-5

Intermediate 5: Preparation of 6-amino-4-(trans-(2-methoxycyclopentyl)amino)nicotinonitrile

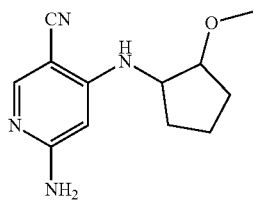 [SMILES: COC1CCCC1Nc1cc(N)ncc1C#N]

The First Step: Preparation of benzyl trans-(2-hydroxycyclopentyl)carbamate

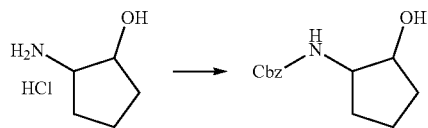 [SMILES: Cl ; NC1CCCC1O ; O=C(NC1CCCC1O)OCc1ccccc1]

To a solution of trans-2-aminocyclopentanol hydrochloride (1.37 g, 10 mmol) and sodium carbonate (3.4 g, 32 mmol) in water (20 mL) was added dropwise benzyl chloroformate (3.4 g, 20 mmol), and then stirred at room temperature for 16 hours. Then, water (40 mL) was added to the obtained mixture for dilution, and extraction was performed with ethyl acetate (100 mL), and the organic phase was obtained by liquid separation. The organic phase was washed with saturated brine (50 mL), dried over anhydrous sodium sulfate, and filtered with suction, and evaporated to dryness. The residue was purified by column chromatography eluting with a gradient of petroleum ether/ethyl acetate=5:1 to 1:1, and the fractions containing the product were concentrated to give benzyl trans-(2-hydroxycyclopentyl)carbamate, and its relevant test data are as follows:

ESI-MS: 236.1 [M+H]$^+$.

The Second Step: Preparation of benzyl trans-(2-methoxycyclopentyl) carbamate

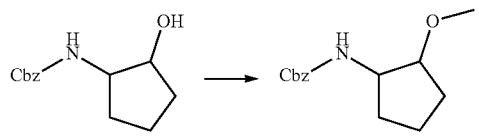 [SMILES: O=C(NC1CCCC1O)OCc1ccccc1 ; COC1CCCC1NC(=O)OCc1ccccc1]

To a solution of benzyl trans-(2-hydroxycyclopentyl) carbamate (1.658 g, 7.055 mmol) in tetrahydrofuran (50 mL) at 0° C. was added sodium hydride (338 mg, 8.466 mmol), and stirred under nitrogen protection for 30 minutes. Then, iodomethane (1 g, 7.055 mmol) was slowly added dropwise to the system and stirring was continued for 4 hours.

After that, the reaction solution was poured into saturated ammonium chloride solution (120 mL) to quench the reaction and extracted with ethyl acetate (120 mL). The organic phase was obtained by separation and was then sequentially washed with water (50 mL) and saturated brine (50 mL), dried over anhydrous sodium sulfate, suction filtered, and evaporated to dryness. The residue was purified by column chromatography, eluting with a gradient of petroleum ether/ethyl acetate=10:1 to 1:1, and the product-containing fraction was concentrated to obtain benzyl trans-(2-methoxycyclopentyl)carbamate, and the relevant test data are as follows:

ESI-MS: 250.1 [M+H]$^+$.

The Third Step: Preparation of trans-2-methoxycyclopentylamine

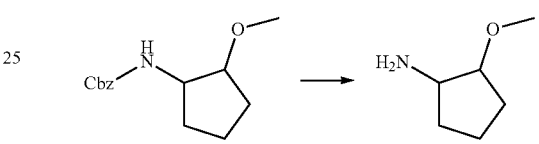

To a solution of benzyl trans-(2-methoxycyclopentyl) carbamate (900 mg, 3.614 mmol) in anhydrous methanol (30 mL) was added 10% palladium on carbon (195 mg) at room temperature, under a hydrogen atmosphere stirring for 2 hours. Then suction filtration, and the filtrate was evaporated to dryness to obtain trans-2-methoxycyclopentylamine. The relevant test data are as follows:

ESI-MS: 116.1 [M+H]$^+$.

The Fourth Step: Preparation of 6-amino-4-(trans-(2-methoxycyclopentyl)amino) nicotinonitrile

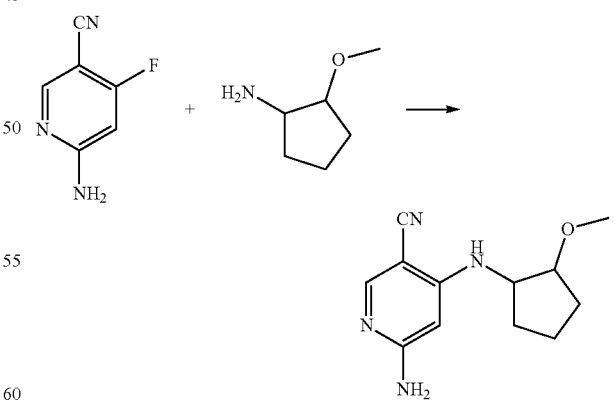

Taking intermediate 1 and trans-2-methoxycyclopentylamine as starting materials, and reacting in a manner similar to the preparation of intermediate 2, intermediate 5 was obtained, and its relevant test data are as follows:

ESI-MS: 233.1 [M+H]$^+$.

Example 0-6

Intermediate 6: Preparation of 6-amino-4-(2-methoxyethoxy) nicotinonitrile

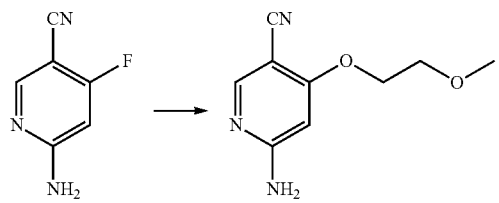

Under nitrogen protection, ethylene glycol methyl ether (152 mg, 2 mmol) was dissolved in dry tetrahydrofuran (4 mL), cooled to 0° C., and a solution of NaHMDS (2 M, 2.5 mL, 5 mmol) in tetrahydrofuran was added dropwise at this temperature. Then, 6-amino-4-fluoronicotinonitrile (Intermediate 2, 127 mg, 1 mmol) was added and the reaction was continued with stirring for 16 hours.

After that, the reaction was quenched with saturated aqueous ammonium chloride solution (50 mL), extracted with ethyl acetate (50 mL), and the organic phase was obtained by separation. The organic phase was washed with saturated brine (50 mL), dried over anhydrous sodium sulfate, suction filtered, and evaporated to dryness. The residue was purified by column chromatography eluting with a gradient of petroleum ether/ethyl acetate=5:1 to 1:1 and the product containing fractions were concentrated to give intermediate 6, which related test data is as follows:

ESI-MS: 194.1 [M+H]$^+$.

Example 0-7

Intermediate 7: Preparation of 6-amino-4-((2-(2-methoxyethoxy)ethyl)amino)nicotinonitrile

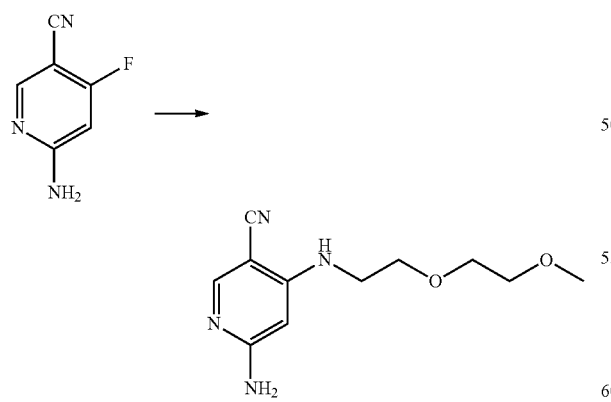

Taking intermediate 1 and 2-(2-methoxyethoxy) ethylamine as starting materials, the reaction was performed in a manner similar to that for preparing intermediate 2 to obtain intermediate 7, and the relevant test data are as follows:

ESI-MS: 236.9 [M+H]$^+$.

Example 0-8

Intermediate 8: Preparation of tert-butyl 3-((2-amino-5-cyanopyridin-4-yl)amino)azetidine-1-carboxylate

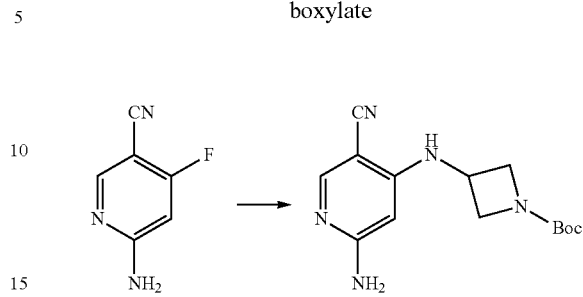

Taking intermediate 1 and tert-butyl 3-aminoazetidine-1-carboxylate as starting materials, and reacting in a manner similar to the preparation of intermediate 2, intermediate 8 was obtained, and its relevant test data are as follows:

ESI-MS: 290.2 [M+H]$^+$.

Example 0-9

Intermediate 9: Preparation of 6-amino-4-(trans-(2-((tert-butyldimethylsilyl)oxy)cyclopentyl)amino) nicotinonitrile

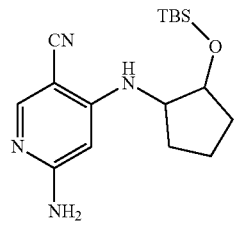

The First Step: Preparation of 6-amino-4-(trans-(2-hydroxycyclopentyl)amino)nicotinonitrile

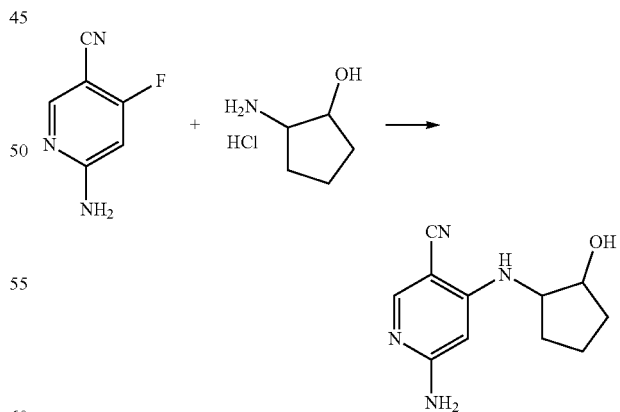

Using intermediate 1 and trans-2-aminocyclopentanol hydrochloride as starting materials, react in a similar manner to the preparation of intermediate 2 to render 6-amino-4-(trans-(2-hydroxycyclopentyl) amino) nicotinonitrile, and its relevant test data are as follows:

ESI-MS: 219.1 [M+H]$^+$.

The Second Step: Preparation of 6-amino-4-(trans-(2-((tert-butyldimethylsilyl)oxy)cyclopentyl)amino)nicotinonitrile

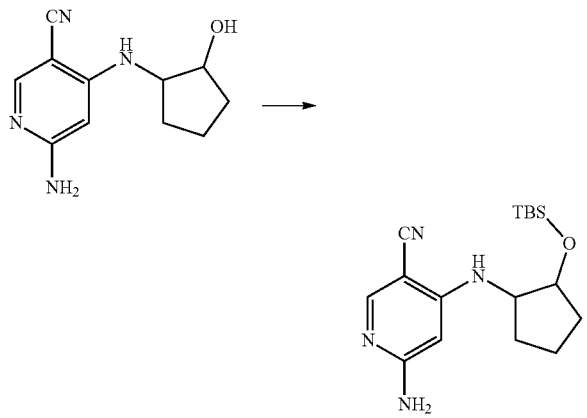

6-amino-4-(trans-(2-hydroxycyclopentyl)amino)nicotinonitrile (2.200 g, 10.09 mmol), imidazole (2.479 g, 36.45 mmol) and tert-butylchlorodimethylsilane (2.197 g, 14.58 mmol) were dissolved in N,N-dimethylformamide (20 mL) and stirred at room temperature for 16 hours.

After that, the reaction solution was poured into water (100 mL) to quench the reaction, and extracted with ethyl acetate (30 mL*3). The organic phase was washed with water (100 mL) and saturated brine (100 mL) successively, and dried over anhydrous sodium sulfate, filtered with suction, and evaporated to dryness. The residue was purified by column chromatography, eluted with petroleum ether/ethyl acetate=4:1, to obtain Intermediate 9, the relevant test data of which are as follows:

ESI-MS: 332.2 [M+H]$^+$.

Example 0-10

Intermediate 10: Preparation of ethyl 2-((2-aminoethyl)(methyl)amino) acetate dihydrochloride

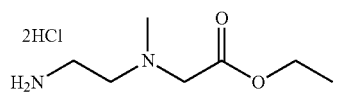

The First Step: Preparation of ethyl 2-((2-((tert-butoxycarbonyl)amino)ethyl)(methyl)amino) acetate

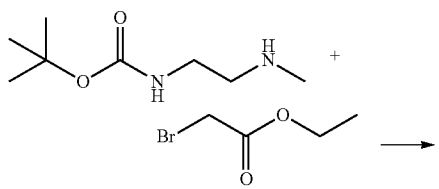

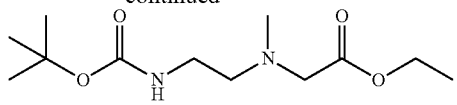

To a solution of tert-butyl (2-(methylamino)ethyl)carbamate (5.0 g, 28.9 mmol) and triethylamine (12 mL) in tetrahydrofuran (58 mL) was added ethyl bromoacetate (3.2 mL 28.9 mmol) at 0° C., and stirred at room temperature for 24 h.

Then, saturated sodium bicarbonate solution (200 mL) and dichloromethane solution (200 mL) were added to the obtained mixture, and the organic phase was obtained by separation. The organic phase was washed with saturated brine (200 mL) and dried over anhydrous sodium sulfate, suction filtered, and evaporated to dryness to obtain ethyl 2-((2-((tert-butoxycarbonyl)amino)ethyl)(methyl)amino) acetate, and the relevant test data of which are as follows:

$^1$H NMR (CDCl$_3$, 400 MHz), δ 5.16 (brs, 1H), 4.16 (q, J=7.2 Hz, 2H), 3.25 (s, 2H), 3.19 (q, J=5.2 Hz, 2H), 2.62 (t, J=6.0 Hz, 2H), 2.36 (s, 3H), 1.43 (s, 9H), 1.26 (t, J=7.2 Hz, 3H).

ESI-MS: 261.2 [M+H]$^+$.

The Second Step: Preparation of ethyl 2-((2-aminoethyl)(methyl)amino) acetate dihydrochloride

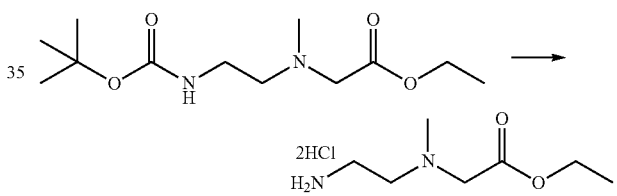

To a solution of ethyl 2-((2-((tert-butoxycarbonyl)amino)ethyl)(methyl)amino)acetate (10.3 g, 28.9 mmol) in tetrahydrofuran (48 mL) and ethanol (240 mL) was added concentrated hydrochloric acid (32 mL) at room temperature. After stirring at room temperature for 3 hours, the reaction mixture was evaporated, ethanol (100 mL) was added, and evaporated to dryness to obtain Intermediate 10. The relevant test data were as follows:

$^1$H NMR (CDCl$_3$, 400 MHz), δ 11.22-11.07 (brs, 1H), 8.61 (s, 2H), 4.31 (s, 2H), 4.21 (q, J=7.2 Hz, 2H), 3.52-3.47 (m, 2H), 3.30-3.23 (m, 2H), 2.91 (s, 3H), 1.24 (t, J=7.2 Hz, 3H).

ESI-MS: 161.2 [M+H]$^+$.

Example 0-11

Intermediate 11: Preparation of ethyl 2-(2-aminoethoxy) acetate hydrochloride

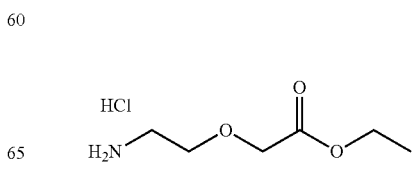

The First Step: Preparation of ethyl 2-((2-((tert-butoxycarbonyl)amino)ethoxy) acetate

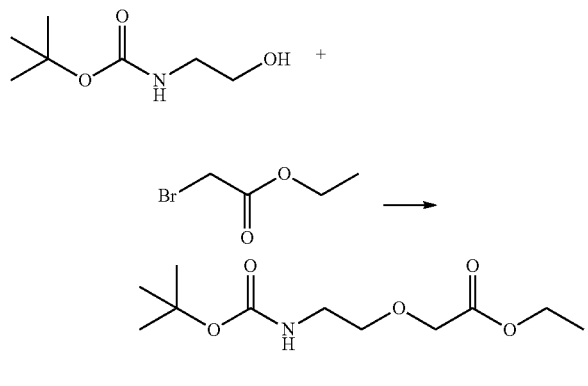

Under nitrogen protection, a solution of tert-butyl (2-hydroxyethyl)carbamate (997 mg, 6.2 mmol) in tetrahydrofuran (5 mL) was added to a mixture of sodium hydride (520 mg, 13.02 mmol), sodium iodide (465 mg, 3.1 mmol) and tetrahydrofuran (30 mL) at 0° C. and stirred at room temperature for 1 hour. Then at 0° C., a solution of ethyl bromoacetate (2.028 g, 12.4 mmol) in tetrahydrofuran (10 mL) was slowly added dropwise to the above mixture, and then the reaction was stirred at room temperature for 16 hours.

After that, saturated ammonium chloride solution (80 mL) was added to the reaction mixture to quench the reaction, extracted three times with ethyl acetate (25 mL×3). Combined the organic phases, washed twice with saturated brine (40 mL×2), and dried over anhydrous sodium sulfate, suction filtered, then evaporated to dryness. The residue was purified by column chromatography, eluted with PE/EtOAc=5:1, and the product-containing fraction was concentrated to obtain ethyl 2-((2-((tert-butoxycarbonyl)amino)ethoxy)acetate, the relevant test data of which are as follows:

ESI-MS: 270.1 [M+Na]$^+$.

The Second Step: Preparation of ethyl 2-(2-aminoethoxy) acetate hydrochloride

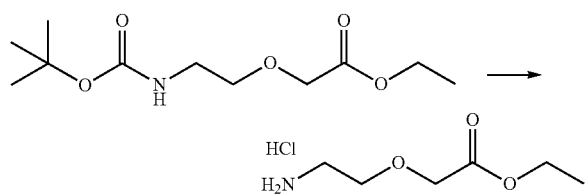

At 0° C., ethyl 2-((2-((tert-butoxycarbonyl)amino)ethoxy)acetate (323 mg, 1.3 mmol) was dissolved in a solution of hydrogen chloride in dioxane (4M, 2.5 mL, 10.0 mmol), stirring at room temperature for 1.5 hours. The obtained solution was evaporated to dryness to obtain Intermediate 11, and its relevant test data were as follows:

ESI-MS: 148.1 [M+H]$^+$.

Example O-12

Intermediate 12: Preparation of 4-fluoro-7-bromo-1,2,3,4-tetrahydro-2,4-methylene-1,8-naphthyridine

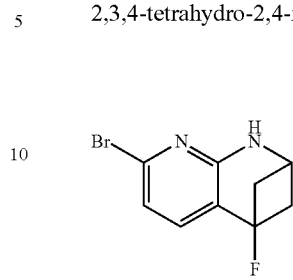

The First Step: Preparation of tert-butyl ((1r, 3s)-3-(6-bromo-2-fluoropyridin-3-yl)-3-hydroxycyclobutyl) carbamate

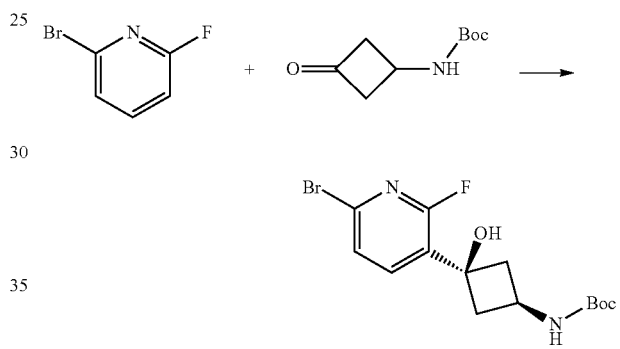

To a solution of 2-bromo-6-fluoropyridine (185.3 g, 1.05 mol) in tetrahydrofuran (1 L) was slowly added dropwise a solution of lithium diisopropylamide in tetrahydrofuran (2 M, 526 mL, 1.05 mol) at −65° C., and stirring was continued at this temperature for 1 hour. Then, a solution of tert-butyl (3-oxocyclobutyl)carbamate (65.0 g, 0.35 mol) in tetrahydrofuran (500 mL) was added dropwise to the reaction solution at −65° C., and continue stirring at this temperature for 2 hours.

Water (1 L) was added to the reaction mixture at 0° C. to quench the reaction and extracted with ethyl acetate (1 L). The organic phase was obtained by separation. The organic phase was washed with saturated brine (1 L) and dried over anhydrous sodium sulfate, filtered with suction, and evaporated to dryness. The residue was purified by column chromatography, eluting with a gradient of petroleum ether/ethyl acetate=50:1 to 5:1, and the product-containing fractions were concentrated to render tert-butyl ((1r, 3s)-3-(6-bromo-2-fluoropyridin-3-yl)-3-hydroxycyclobutyl) carbamate, and its relevant test data are as follows:

$^1$H NMR (CDCl$_3$, 400 MHz), δ 7.83 (t, J=8.8 Hz, 1H), 7.37 (d, J=8.0 Hz, 1H), 5.15 (d, J=7.2 Hz, 1H), 4.81 (s, 1H), 3.78-3.84 (m, 1H), 3.00-3.12 (m, 2H), 2.57-2.60 (m, 2H), 1.44 (s, 9H).

ESI-MS: 361.1 [M+H]$^+$.

The Second Step: Preparation of tert-butyl (3-(6-bromo-2-fluoropyridin-3-yl)-3-fluorocyclobutyl)carbamate

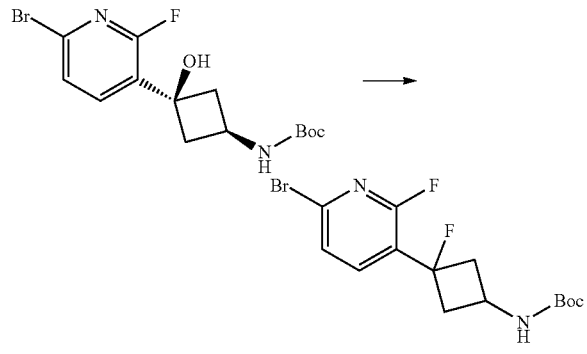

To a solution of tert-butyl ((1r,3s)-3-(6-bromo-2-fluoropyridin-3-yl)-3-hydroxycyclobutyl)carbamate (15.3 g, 42.4 mmol) in dichloromethane (200 mL) was slowly added dropwise diethylaminosulfur trifluoride (7.0 mL, 52.2 mmol) at −78° C., and then the temperature was naturally raised to room temperature. The reaction solution was continued to stir for 16 hours at room temperature.

Saturated sodium bicarbonate solution (500 mL) was added to the reaction mixture to quench the reaction and extracted with dichloromethane (500 mL). The organic phase was obtained by separation, and then washed with saturated brine (500 mL), dried over anhydrous sodium sulfate, filtered with suction, and evaporated to dryness. The residue was purified by column chromatography, eluting with petroleum ether/ethyl acetate=5:1, and the fractions containing the product were concentrated and purified by recrystallization with petroleum ether/methyl tert-butyl ether to obtain tert-butyl (3-(6-bromo-2-fluoropyridin-3-yl)-3-fluorocyclobutyl)carbamate, and its relevant test data are as follows:

ESI-MS: 385.0 [M+Na]+.

The Third Step: Preparation of 3-(6-bromo-2-fluoropyridin-3-yl)-3-fluorocyclobutylamine trifluoroacetate

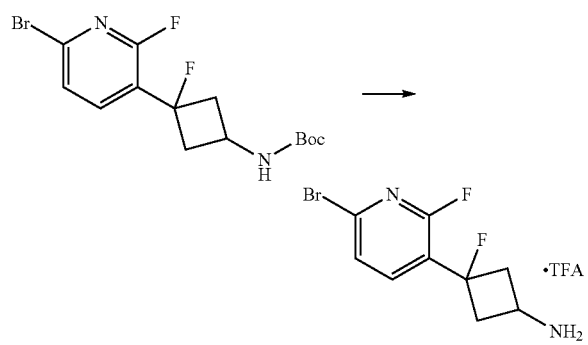

To a solution of tert-butyl (3-(6-bromo-2-fluoropyridin-3-yl)-3-fluorocyclobutyl)carbamate (9.0 g, 24.8 mmol) in dichloromethane (50 mL) at room temperature trifluoroacetic acid (10 mL) was added. The mixture was stirred at room temperature for 6 hours, and then evaporated to dryness to obtain Intermediate 15, the relevant test data of which are as follows:

ESI-MS: 263.1 [M+H]+.

The Fourth Step: Preparation of 4-fluoro-7-bromo-1,2,3,4-tetrahydro-2,4-methylene-1,8-naphthyridine

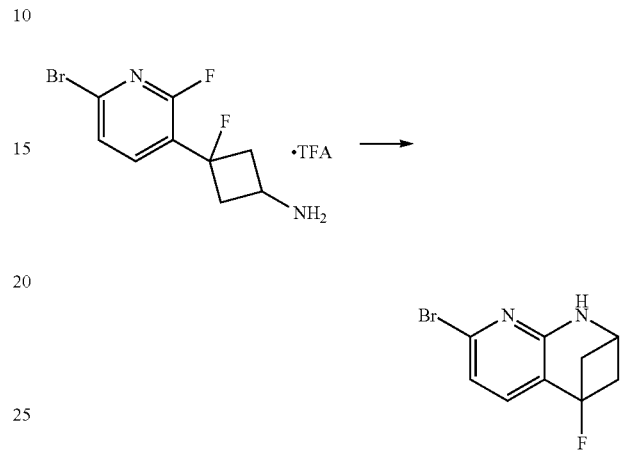

At 140° C., to a solution of N,N-diisopropylethylamine (25.0 mL, 151.2 mmol) in N-methylpyrrolidone (400 mL) was slowly added dropwise 3-(6-bromo-2-fluoropyrid-3-yl)-3-fluorocyclobutylamine trifluoroacetate (6.0 g, 16.0 mmol) in N-methylpyrrolidone (100 mL), and stirring was continued at this temperature for 6 h.

Then it was cooled to room temperature, ethyl acetate (2 L) was added to the obtained mixture for dilution, washed with water (1 L×3) and saturated brine (1 L) successively, dried over anhydrous sodium sulfate, filtered with suction, and evaporated to dryness. The residue was purified by column chromatography, eluting with a gradient of petroleum ether/ethyl acetate=5:1 to 3:1, and the fractions containing the product were concentrated to obtain Intermediate 12, the relevant test data of which are as follows:

1H NMR (CDCl3, 400 MHz), δ 7.27 (d, J=8.0 Hz, 1H), 6.80 (d, J=7.6 Hz, 1H), 6.03 (s, 1H), 4.19-4.10 (m, 1H), 2.51-2.46 (m, 2H), 1.86-1.80 (m, 2H).

ESI-MS: 243.0 [M+H]+.

Example O-13

Intermediate 13: 4-((tert-butyldiphenylsilyl)oxy)-7-bromo-1,2,3,4-tetrahydro-2,4-methylene-1,8-naphthyridine

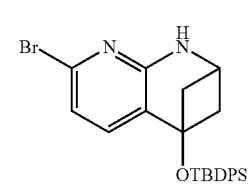

The First Step: Preparation of tert-butyl ((1r, 3r)-3-(6-bromo-2-fluoropyridin-3-yl)-3-hydroxycyclobutyl)carbamate

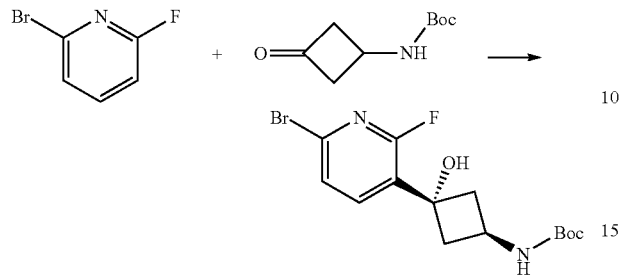

To a solution of 2-bromo-6-fluoropyridine (185.3 g, 1.05 mol) in tetrahydrofuran (1 L) was slowly added dropwise a solution of lithium diisopropylamide in tetrahydrofuran (2 M, 526 mL, 1.05 mol) at −65° C., and stirring was continued at this temperature for 1 hour. Then, a solution of tert-butyl (3-oxocyclobutyl) carbamate (65.0 g, 0.35 mol) in tetrahydrofuran (500 mL) was added dropwise to the reaction solution at −65° C. and continue to stir the reaction solution at this temperature for 2 hours.

Water (1 L) was added to the reaction mixture at 0° C. to quench the reaction and extracted with ethyl acetate (1 L). The organic phase was obtained by separation and was then washed with saturated brine (1 L), dried over anhydrous sodium sulfate, filtered with suction, and evaporated to dryness. The residue was purified by column chromatography, eluting with a gradient of petroleum ether/ethyl acetate=50:1 to 5:1, and the product-containing fractions were concentrated to render tert-butyl ((1r, 3r)-3-(6-bromo-2-fluoropyridin-3-yl)-3-hydroxycyclobutyl) carbamate, its relevant test data are as follows:

$^1$H NMR (CDCl$_3$, 400 MHz), δ 7.68 (t, J=8.6 Hz, 1H), 7.38 (d, J=7.6 Hz, 1H), 4.83 (s, 1H), 4.60 (d, J=7.6 Hz, 1H), 3.27 (s, 1H), 2.75-2.80 (m, 2H), 2.38-2.48 (m, 2H), 1.42 (s, 9H).

The Second Step: Preparation of (1r, 3r)-3-(6-bromo-2-fluoropyridin-3-yl)-3-hydroxycyclobutylamine trifluoroacetate

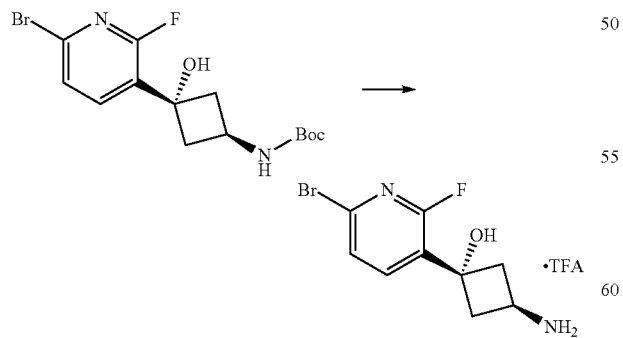

To a solution of tert-butyl ((1r,3r)-3-(6-bromo-2-fluoropyridin-3-yl)-3-hydroxycyclobutyl) carbamate (40.0 g, 110.7 mmol) in chloromethane (200 mL) was added trifluoroacetic acid (50 mL) at room temperature. The mixture was stirred at room temperature for 2 hours and then evaporated to dryness to give (1r,3r)-3-(6-bromo-2-fluoropyridin-3-yl)-3-hydroxycyclobutylamine trifluoroacetate, and its relevant test data are as follows:

ESI-MS: 261.1 [M+H]$^+$.

The Third Step: Preparation of 4-hydroxy-7-bromo-1,2,3,4-tetrahydro-2,4-methylene-1,8-naphthyridine

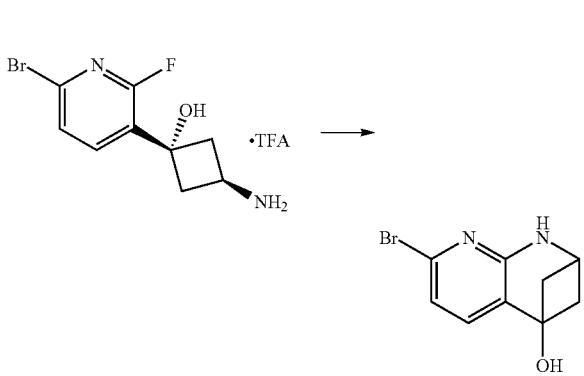

To a solution of N,N-diisopropylethylamine (232.2 mL, 1.33 mol) in N-methylpyrrolidone (1200 mL) was slowly added dropwise a solution of (1r,3r)-3-(6-bromo-2-fluoropyridin-3-yl)-3-hydroxycyclobutylamine trifluoroacetate (50.0 g, 133.3 mmol) in N-methylpyrrolidone (500 mL) at 140° C. and stirring was continued at this temperature for 12 h. Then it was concentrated under reduced pressure at 120° C., and the residue was cooled to room temperature and diluted with water (500 mL), extracted with ethyl acetate (500 mL×3). The organic phase was washed with saturated brine (1 L), dried over anhydrous sodium sulfate, filtered with suction, and evaporated to dryness. The residue was purified by column chromatography, eluting with a gradient of petroleum ether/ethyl acetate=20:1 to 2:1, and the product-containing fractions were concentrated to give 4-hydroxyl-7-bromo-1,2,3,4-tetrahydro-2,4-methylene-1,8-naphthyridine. The relevant test data are as follows:

ESI-MS: 241.3 [M+H]$^+$.

The Fourth Step: Preparation of 4-((tert-butyldiphenylsilyl)oxy)-7-bromo-1,2,3,4-tetrahydro-2,4-methylene-1,8-naphthyridine

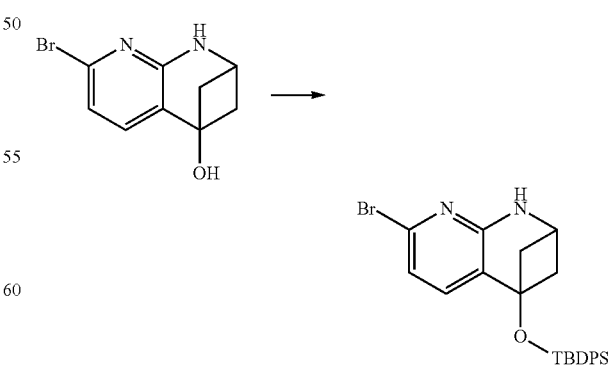

To a solution of 4-hydroxy-7-bromo-1,2,3,4-tetrahydro-2,4-methylene-1,8-naphthyridine (18.0 g, 74.7 mmol) and imidazole (15.3 g, 225.0 mmol) in N,N-dimethylformamide (100 mL) was added tert-butyldiphenylchlorosilane (38.4 mL, 149.3 mmol)) at room temperature, and the reaction was continued to stir at room temperature for 10 hours.

Then, water (400 mL) was added to the mixture for dilution, extracted three times with ethyl acetate (300 mL×3), and three parts of organic phase were obtained by separation and combined together, and then washed with saturated brine (500 mL), dried over anhydrous sodium sulfate, filtered with suction, and evaporated to dryness. The residue was rinsed with methanol (200 mL), filtered with suction. The filter cake was washed with methanol (100 mL×2), and dried to obtain Intermediate 13, of which the relevant test data are as follows:

$^1$H NMR (CDCl$_3$, 400 MHz), δ 7.70-7.72 (m, 4H), 7.54-7.57 (m, 1H), 7.26-7.44 (m, 6H), 6.80-6.82 (m, 1H), 5.71 (d, J=4.4 Hz, 1H), 3.70 (dd, J=10.8 Hz, J=6.0 Hz, 1H), 1.96-2.00 (m, 2H), 1.45-1.47 (m, 1H), 1.09 (s, 9H).

ESI-MS: 478.9 [M+H]$^+$.

Example 0-14

Intermediate 14: Preparation of 7-chloro-1,2,3,4-tetrahydro-2,4-methylene-1,8-naphthyridine

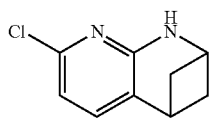 [SMILES: Clc1ccc2c(n1)NC1CC2C1]

The First Step: Preparation of tert-butyl (methoxymethyl) (3-oxocyclobutyl) carbamate

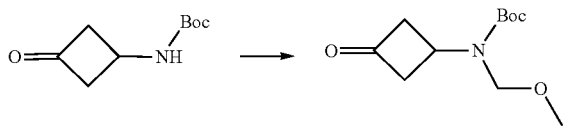 [SMILES: CC(C)(C)OC(=O)NC1CC(=O)C1 ; COCN(C(=O)OC(C)(C)C)C1CC(=O)C1]

To a solution of tert-butyl (3-oxocyclobutyl)carbamate (50.0 g, 270 mmol) in dichloromethane (400 mL) was added paraformaldehyde (12.7 g, 423 mmol) at 0° C. Subsequently, chlorotrimethylsilane (77 mL, 603 mmol) was slowly added dropwise and stirring was continued at 0° C. for 2 hours. The reaction solution was then added dropwise to a solution of triethylamine (95 mL, 687 mmol) in methanol (450 mL) at 0° C., and was continued to be stirred at room temperature for 2 hours.

The reaction solution was poured into saturated sodium bicarbonate solution (1 L) to quench the reaction, and extracted with dichloromethane (1 L). The organic phase was obtained by separation and was then washed with saturated brine (1 L), dried over anhydrous sodium sulfate, suction filtered, and evaporated to dryness. The residue was purified by column chromatography, eluting with petroleum ether/ethyl acetate=5:1, and the fractions containing the product were concentrated to give tert-butyl (methoxymethyl)(3-oxocyclobutyl) carbamate. The relevant test data of the product are as follows:

$^1$H NMR (CDCl$_3$, 400 MHz), δ 4.78 (s, 2H), 4.41-4.25 (m, 1H), 3.45-3.35 (m, 2H), 3.29 (s, 3H), 3.28-3.21 (m, 2H), 1.48 (s, 9H).

The Second Step: Preparation of tert-butyl ((1r, 3r)-3-(6-chloro-2-fluoropyridin-3-yl)-3-hydroxycyclobutyl)(methoxymethyl)carbamate

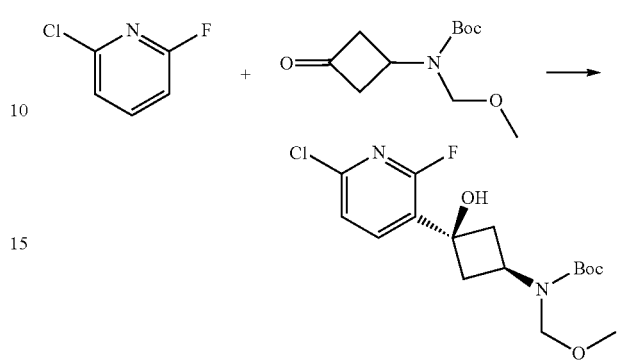

To a solution of 2-chloro-6-fluoropyridine (9.0 g, 68.4 mmol) in tetrahydrofuran (120 mL) was slowly added dropwise a solution of lithium diisopropylamide in tetrahydrofuran (2M, 54.7 mL, 109.4 mol) at −70° C., and continued stirring at this temperature for 1 hour. Then, at −70° C., a solution of tert-butyl (methoxymethyl)(3-oxocyclobutyl) carbamate (15.7 g, 68.6 g) in tetrahydrofuran (20 mL) was added dropwise to the reaction solution, and the reaction was continued to stir at this temperature for 2 hours.

The reaction mixture was poured into water (500 mL) to quench the reaction, and extracted with ethyl acetate (500 mL), and the organic phase was obtained by separation. The organic phase was washed with saturated brine (500 mL), dried over anhydrous sodium sulfate, filtered with suction, and evaporated to dryness. The residue was purified by column chromatography, eluting with petroleum ether/ethyl acetate=10:1, and the fractions containing the product were concentrated to give tert-butyl ((1r, 3r)-3-(6-chloro-2-fluoropyridin-3-yl)-3-hydroxycyclobutyl)(methoxymethyl)carbamate. The relevant test data of the product are as follows:

ESI-MS: 383.1 [M+Na]$^+$.

The Third Step: Preparation of (1r, 3r)-3-((tert-butoxycarbonyl)(methoxymethyl)amino)-1-(6-chloro-2-fluoropyridin-3-yl)cyclobutyl ethyl oxalate

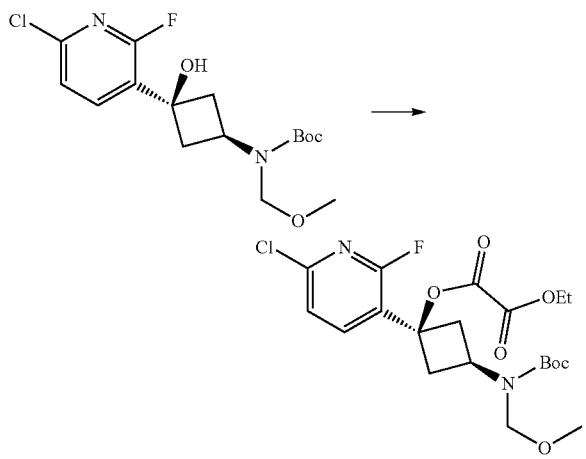

To a solution of tert-butyl ((1r,3r)-3-(6-chloro-2-fluoropyridin-3-yl)-3-hydroxycyclobutyl)(methoxymethyl)carbamate (19.431 g, 53.8 mmol) and 4-dimethylaminopyridine (9.750 g, 79.9 mmol) in dichloromethane (450 mL) was added dropwise a solution of oxalyl chloride monoethyl ester (8.5 mL, 79.7 mmol) in dichloromethane (50 mL) at 0° C. The solution was naturally warmed to room temperature after addition and continued to stir for 1 hour at room temperature.

Dichloromethane (500 mL) was added to the reaction solution for dilution, followed by washing with water (500 mL), 0.5% citric acid solution (500 mL), saturated sodium bicarbonate solution (500 mL) and saturated brine (500 mL), successively, and then dried over anhydrous sodium sulfate, filtered with suction, and evaporated to dryness. The residue was purified by column chromatography, eluting with petroleum ether/ethyl acetate=2:1, and the product-containing fractions were concentrated to give (1r, 3r)-3-((tert-butoxycarbonyl)(methoxymethyl)amino)-1-(6-chloro-2-fluoropyridin-3-yl)cyclobutyl ethyl oxalate. The relevant test data of the product are as follows:

ESI-MS: 460.9 [M+H]$^+$.

The Fourth Step: Preparation of tert-butyl (3-(6-chloro-2-fluoropyridin-3-yl) cyclobutyl)(methoxymethyl) carbamate

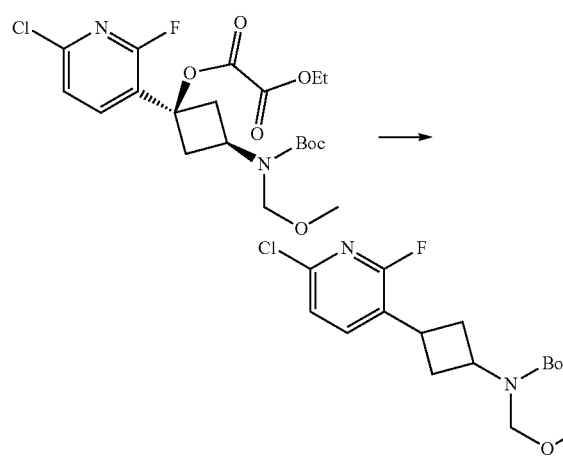

To a solution of (1r,3 r)-3-((tert-butoxycarbonyl)(methoxymethyl)amino)-1-(6-chloro-2-fluoropyridin-3-yl) cyclobutyl ethyl oxalate (18.896 g, 41.0 mmol) in toluene (300 mL) was slowly added dropwise a solution of tri-n-butyltin hydride (7.0 mL, 26.0 mmol) and azobisisobutyronitrile (1.200 g, 7.3 mmol) in toluene (25 mL) at reflux temperature. After the mixture was stirred at this temperature for 30 minutes, a solution of tri-n-butyltin hydride (7.0 mL, 26.0 mmol) and azobisisobutyronitrile (1.200 g, 7.3 mmol) in toluene (25 mL) was slowly added dropwise and continued stirring for 2 hours.

After the reaction solution was cooled to room temperature, saturated sodium sulfite solution (500 mL) was added and extracted with ethyl acetate (500 mL). The organic phase was obtained by separation and was washed successively with 5% sodium hydroxide solution (500 mL) and saturated brine (500 mL), and then dried over anhydrous sodium sulfate, suction filtered, and evaporated to dryness. The residue was purified by column chromatography, eluting with petroleum ether/ethyl acetate=8:1, and the fractions containing the product were concentrated to render tert-butyl (3-(6-chloro-2-fluoropyridin-3-yl)cyclobutyl)(methoxymethyl)carbamate. The relevant test data of the product are as follows:

ESI-MS: 213.0 [M+H-Boc-MeOH]$^+$.

The Fifth Step: Preparation of 3-(6-chloro-2-fluoropyridin-3-yl)cyclobutanamine hydrochloride

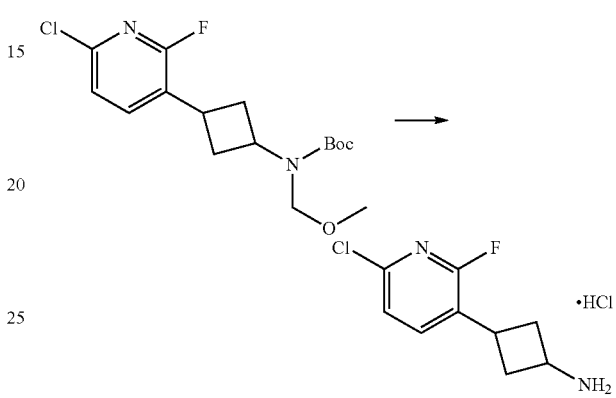

To a solution of tert-butyl (3-(6-chloro-2-fluoropyridin-3-yl)cyclobutyl)(methoxymethyl)carbamate (6.2 g, 17.98 mmol) in ethyl acetate (40 mL) was added a solution of hydrogen chloride in ethyl acetate (3M, 40 mL), and stirred at room temperature for 6 hours. The precipitated white solid was filtered off with suction, and the filter cake was washed with ethyl acetate to obtain 3-(6-chloro-2-fluoropyridin-3-yl)cyclobutylamine hydrochloride. The relevant test data of the product are as follows:

ESI-MS: 201.0 [M+H]$^+$.

The Sixth Step: Preparation of 7-chloro-1,2,3,4-tetrahydro-2,4-methylene-1,8-naphthyridine

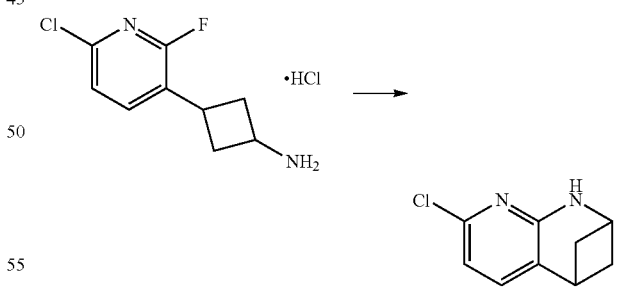

To a solution of sodium bicarbonate (2.820 g, 33.5 mmol) in N-methylpyrrolidone (200 mL) was slowly added dropwise 3-(6-chloro-2-fluoropyridin-3-yl)cyclobutanamine hydrochloride (2.650 g, 11.2 mmol) in N-methylpyrrolidone (50 mL) at 140° C. and stirring was continued at this temperature for 6 h.

Then it was cooled to room temperature, ethyl acetate (500 mL) was added to the obtained mixture. The organic phase was washed with water (500 mL×3) and saturated brine (500 mL) successively, dried with anhydrous sodium sulfate, filtered with suction, and evaporated to dryness. The residue was purified by column chromatography, eluted with a gradient of petroleum ether/ethyl acetate=10:1 to 3:1, and the fractions containing the product were concentrated to obtain Intermediate 14. The relevant test data are as follows:

ESI-MS: 181.0 [M+H]$^+$.

Example 0-15

Intermediate 15: Preparation of tert-butyl (7-bromo-1,2,3,4-tetrahydro-2,4-methylene-1,8-naphthyridin-4-yl)carbamate

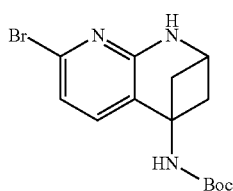

The First Step: Preparation of tert-butyl ((1r, 3r)-3-(6-bromo-2-fluoropyridin-3-yl)-3-azidocyclobutyl) carbamate

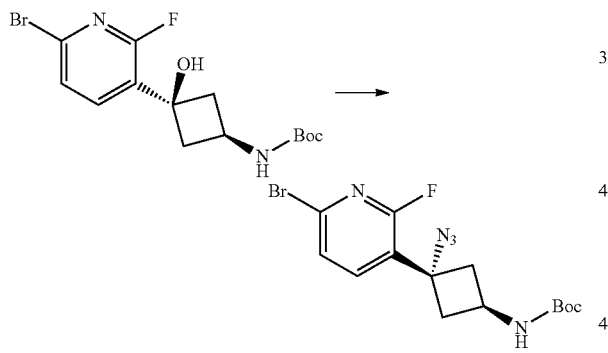

To a solution of tert-butyl ((1r,3s)-3-(6-bromo-2-fluoropyridin-3-yl)-3-hydroxycyclobutyl)carbamate (12.6 g, 35.0 mmol) in N,N-dimethylformamide (80 mL) and toluene (40 mL) were added diphenylphosphoryl azide (14.5 mL, 67.3 mmol) and 1,8-diazabicycloundec-7-ene (10.2 mL, 68.3 mmol) in turn at 0° C., then the temperature was raised to 40° C. and the reaction was continued to stir for 16 hours.

Water (500 mL) was added to the reaction mixture to quench the reaction, and the mixture was extracted with ethyl acetate (500 mL). The organic phase was obtained by separation and was washed with saturated brine (500 mL), dried over anhydrous sodium sulfate, filtered with suction and evaporated to dryness. The residue was purified by column chromatography, eluting with petroleum ether/ethyl acetate=8:1, and the fractions containing the product were concentrated to give tert-butyl ((1r, 3r)-3-(6-bromo-2-fluoropyridin-3-yl)-3-azidocyclobutyl) carbamate. The relevant test data of the product are as follows:

ESI-MS: 330.1 [M+H]$^+$.

The Second Step: Preparation of (1r, 3r)-1-(6-bromo-2-fluoropyridin-3-yl)cyclobutane-1,3-diamine hydrochloride

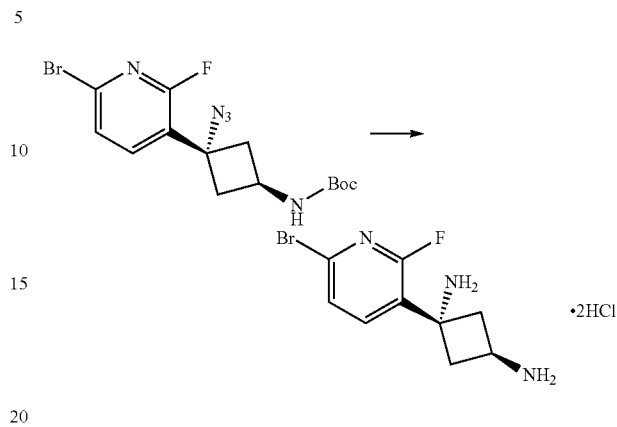

At room temperature, tert-butyl ((1r,3r)-3-(6-bromo-2-fluoropyridin-3-yl)-3-azidocyclobutyl)carbamate (8.990 g, 23.3 mmol) was dissolved in a solution of hydrogen chloride in dioxane (4M, 60 mL), and the mixture was stirred at room temperature for 2 hours. Then at 0° C., to the reaction solution was added triphenylphosphine (7.300 g, 27.9 mmol), and stirring was continued for 5 hours. The precipitated white solid was filtered off with suction, and the filter cake was washed with ethyl acetate to obtain (1r, 3r)-1-(6-bromo-2-fluoropyridin-3-yl)cyclobutane-1,3-diamine hydrochloride. The relevant test data of the product are as follows:

ESI-MS: 260.0 [M+H]$^+$.

The Third Step: Preparation of tert-butyl (7-bromo-1,2,3,4-tetrahydro-2,4-methylene-1,8-naphthyridin-4-yl)carbamate

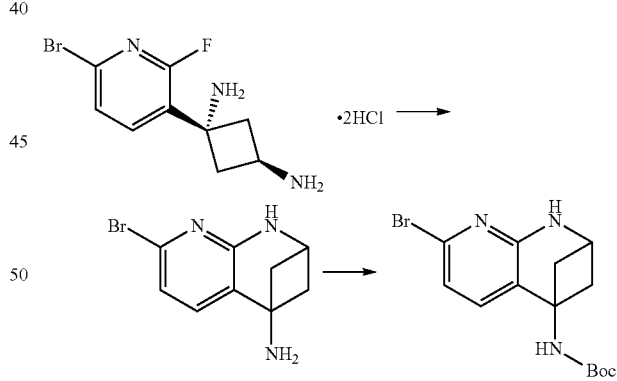

To a solution of N,N-diisopropylethylamine (40.0 mL, 242.5 mmol) in N-methylpyrrolidone (300 mL) was slowly added dropwise a solution of (1r,3r)-1-(6-bromo-2-fluoropyridin-3-yl)cyclobutane-1,3-diamine hydrochloride (7.651 g, 25.8 mmol) and N,N-diisopropylethylamine (5.0 mL, 30.3 mmol) in N-methylpyrrolidone (100 mL) at 150° C., and stirring was continued at this temperature for 4 hours. After cooling to room temperature, di-tert-butyl carbonate (25.0 mL, 108.9 mmol) was added to the reaction solution, and stirring was continued for 16 hours.

Ethyl acetate (2 L) was added to the obtained mixture for dilution, washed with water (1 L×3) and saturated brine (1

L) sequentially, dried over anhydrous sodium sulfate, filtered with suction, and evaporated to dryness. The residue was purified by column chromatography, eluting with petroleum ether/ethyl acetate=2:1, and the fractions containing the product was concentrated to obtain Intermediate 15. The relevant test data of the product are as follows:

ESI-MS: 340.0 [M+H]+.

Example 0-16

Intermediate 16: Preparation of 7-(dimethoxymethyl)-4-fluoro-1,2,3,4-tetrahydro-2,4-methylene-1,8-naphthyridine

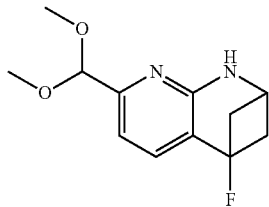 [SMILES: COC(OC)c1ccc2c(n1)NC1CC2(F)C1]

The First Step: Preparation of 4-fluoro-7-vinyl-1,2,3,4-tetrahydro-2,4-methylene-1,8-naphthyridine

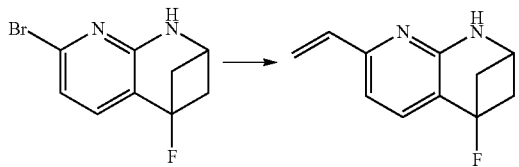

Under nitrogen protection, a mixture of 4-fluoro-7-bromo-1,2,3,4-tetrahydro-2,4-methylene-1,8-naphthyridine (Intermediate 9, 5.310 g, 21.9 mmol), vinyl pinacol borate (4.5 mL, 26.6 mmol), Pd(dppf)Cl$_2$ (0.640 g, 0.87 mmol), potassium phosphate (9.300 g, 43.9 mmol), 1,4-dioxane (75 mL) and water (25 mL) was stirred at 100° C. for 14 hours.

Then, the mixture was cooled to room temperature, diluted with water (200 mL), extracted with ethyl acetate (200 mL), and separated to obtain an organic phase. The organic phase was washed with saturated brine (200 mL), dried over anhydrous sodium sulfate, filtered with suction, and evaporated to dryness. The residue was purified by column chromatography, eluting with a gradient of petroleum ether/ethyl acetate=5:1 to 3:1, and the fractions containing the product were concentrated to give 4-fluoro-7-vinyl-1,2,3,4-tetrahydro-2,4-methylene-1,8-naphthyridine. The relevant test data of the product are as follows:

$^1$H NMR (CDCl$_3$, 400 MHz), δ 7.42 (d, J=7.6 Hz, 1H), 6.68-6.61 (m, 2H), 6.13-6.09 (m, 1H), 5.35-5.29 (m, 1H), 4.10-4.03 (m, 1H), 2.51-2.46 (m, 2H), 1.87-1.85 (m, 2H).

ESI-MS: 191.1 [M+H]+.

The Second Step: Preparation of tert-butyl 4-fluoro-7-vinyl-3,4-dihydro-2,4-methylene-1,8-naphthyridine-1(2H)-carboxylate

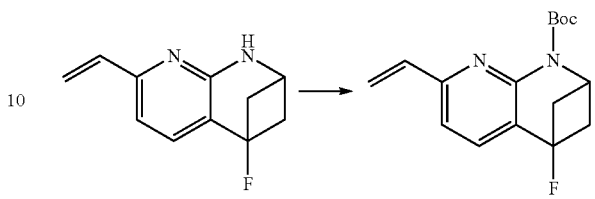

To a solution of 4-fluoro-7-vinyl-1,2,3,4-tetrahydro-2,4-methylene-1,8-naphthyridine (3.117 g, 16.4 mmol), triethylamine (20.0 mL, 144.6 mmol), 4-dimethylaminopyridine (0.400 g, 3.3 mmol) in tetrahydrofuran (100 mL) was added di-tert-butyl carbonate (12.0 mL, 52.3 mmol) at room temperature, and the reaction was continued to stir for 14 hours.

The reaction solution was then evaporated to dryness, and the residue was purified by column chromatography, eluting with a gradient of petroleum ether/ethyl acetate=20:1 to 10:1, and the product-containing fractions were concentrated to give tert-butyl 4-fluoro-7-vinyl-3,4-dihydro-2,4-methylene-1,8-naphthyridine-1(2H)-carboxylate. The relevant test data of the product are as follows:

$^1$H NMR (CDCl$_3$, 400 MHz), δ 7.59 (d, J=7.6 Hz, 1H), 6.97 (d, J=7.6 Hz, 1H), 6.79-6.72 (m, 1H), 6.34-6.29 (m, 1H), 5.42 (dd, J=1.6, 10.4 Hz, 1H), 5.33-5.25 (m, 1H), 2.61-2.56 (m, 2H), 1.96-1.91 (m, 2H), 1.60 (s, 9H).

ESI-MS: 291.1 [M+H]+.

The Third Step: Preparation of tert-butyl 4-fluoro-7-formyl-3,4-dihydro-2,4-methylene-1,8-naphthyridine-1(2H)-carboxylate

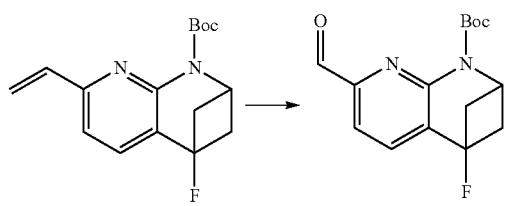 [SMILES: C=Cc1ccc2c(n1)N(C(=O)OC(C)(C)C)C1CC2(F)C1 ; CC(C)(C)OC(=O)N1c2nc(C=O)ccc2C2(F)CC1C2]

To a mixed solution of tert-butyl 4-fluoro-7-vinyl-3,4-dihydro-2,4-methylene-1,8-naphthyridine-1(2H)-carboxylate (4.430 g, 15.3 mmol), potassium osmate (110 mg, 0.30 mmol), 2,6-lutidine (3.6 mL, 31.0 mmol) in 1,4-dioxane (120 mL) and water (40 mL) was added sodium periodate (13.100 g, 61.2 mmol) and continued to stir for 14 hours.

Saturated sodium thiosulfate solution (500 mL) was added to the reaction mixture to quench the reaction and extracted with ethyl acetate (500 mL). The organic phase was obtained by separation and was then washed with saturated brine (500 mL), dried over anhydrous sodium sulfate, filtered with suction, and evaporated to dryness. The residue was purified by column chromatography, eluting with petroleum ether/ethyl acetate=8:1, and the product-containing fractions were concentrated to give tert-butyl 4-fluoro-7-formyl-3,4-dihydro-2,4-methylene-1,8-naphthyridine-1(2H)-carboxylate. The relevant test data of the product are as follows:

¹H NMR (CDCl₃, 400 MHz), δ 10.01 (s, 1H), 7.82 (d, J=7.6 Hz, 1H), 7.70 (d, J=7.6 Hz, 1H), 5.35-5.27 (m, 1H), 2.68-2.63 (m, 2H), 1.97-1.95 (m, 2H), 1.61 (s, 9H).
ESI-MS: 293.1 [M+H]⁺.

The Fourth Step: Preparation of 7-(dimethoxymethyl)-4-fluoro-1,2,3,4-tetrahydro-2,4-methylene-1,8-naphthyridine

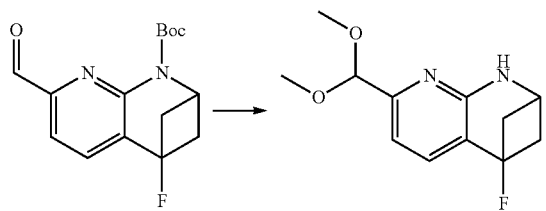 [SMILES: CC(C)(C)OC(=O)N1c2nc(C=O)ccc2C2(F)CC1C2 ; COC(OC)c1ccc2c(n1)NC1CC2(F)C1]

A solution of tert-butyl 4-fluoro-7-formyl-3,4-dihydro-2,4-methylene-1,8-naphthyridine-1(2H)-carboxylate (3.226 g, 11.0 mmol) and pyridine p-toluenesulfonate (4.200 g, 16.7 mmol) in methanol (100 mL) was heated to reflux for 16 hours.

After that, the obtained solution was concentrated and poured into saturated sodium carbonate solution (200 mL), extracted with ethyl acetate (200 mL×2), and the organic phase was obtained by separation. The organic phase was washed with saturated brine (500 mL), dried over anhydrous sodium sulfate, filtered with suction, and evaporated to dryness. The residue was purified by column chromatography, eluting with petroleum ether/ethyl acetate=1:1, and the fractions containing the product were concentrated to give intermediate 16. The relevant test data of the product are as follows:

¹H NMR (CDCl₃, 400 MHz), δ 7.47 (d, J=7.6 Hz, 1H), 6.89 (d, J=7.6 Hz, 1H), 5.34 (s, 1H), 5.19 (s, 1H), 4.12-4.06 (m, 1H), 3.40 (s, 6H), 2.49-2.45 (m, 2H), 1.86-1.84 (m, 2H).
ESI-MS: 239.1 [M+H]⁺.

Example 0-17

Intermediate 17: 7-(dimethoxymethyl)-4-((tert-butyldiphenylsilyl)oxy)-1,2,3,4-tetrahydro-2,4-methylene-1,8-naphthyridine

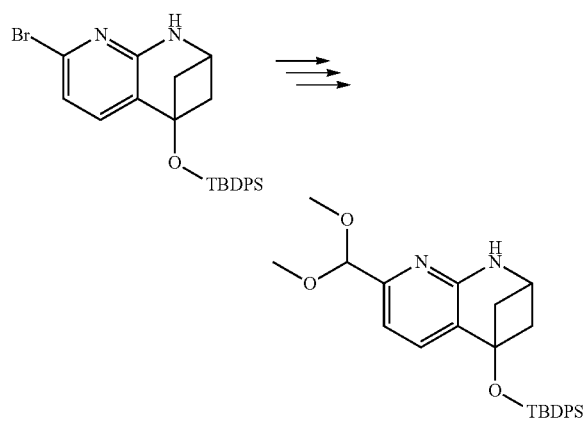

Taking Intermediate 13 as a starting material, using a manner similar to Intermediate 16, Intermediate 17 was prepared. The relevant test data of Intermediate 17 are as follows:
ESI-MS: 475.1 [M+H]⁺.

Example 0-18

Intermediate 18: 7-(dimethoxymethyl)-1,2,3,4-tetrahydro-2,4-methylene-1,8-naphthyridine

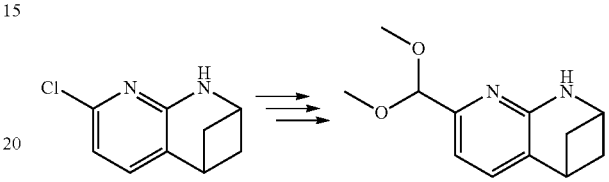

Taking Intermediate 14 as a starting material, using a manner similar to Intermediate 16, Intermediate 18 was prepared. The relevant test data of Intermediate 18 are as follows:
ESI-MS: 221.0 [M+H]⁺.

Example 0-19

Intermediate 19: tert-butyl ((7-(dimethoxymethyl)-1,2,3,4-tetrahydro-2,4-methylene-1,8-naphthyridin-4-yl)amino)biscarboxylate

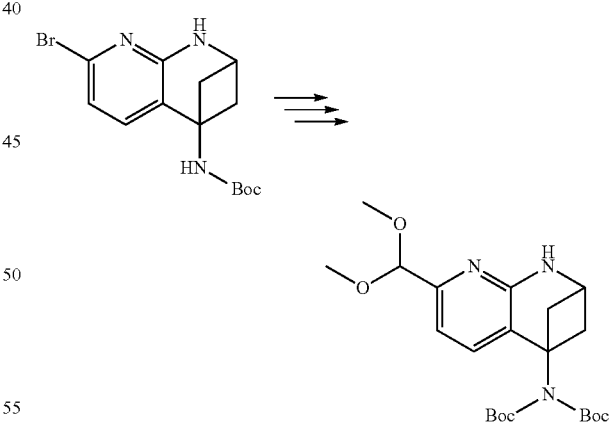

Taking Intermediate 15 as a starting material, using a manner similar to Intermediate 16, Intermediate 19 was prepared. The relevant test data of Intermediate 19 are as follows:

¹H NMR (DMSO-d₆, 400 MHz), δ 7.19 (d, J=4.4 Hz, 1H), 6.94 (d, J=7.2 Hz, 1H), 6.66 (d, J=7.2 Hz, 1H), 5.06 (s, 1H), 3.95 (dd, J=10.2, 5.0 Hz, 1H), 3.26 (s, 6H), 2.29 (d, J=5.6 Hz, 1H), 1.66 (d, J=6.4 Hz, 1H), 1.39 (s, 18H).
ESI-MS: 436.2 [M+H]⁺.

Example 0-20

Intermediate 20: 7-(dimethoxymethyl)-4-amino-1,2,3,4-tetrahydro-2,4-methylene-1,8-naphthyridine

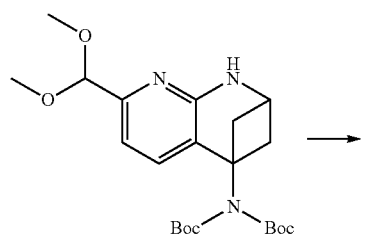

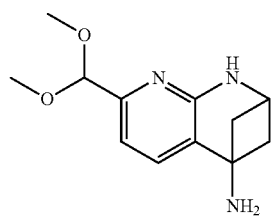

At room temperature, tert-butyl ((7-(dimethoxymethyl)-1,2,3,4-tetrahydro-2,4-methylene-1,8-naphthyridin-4-yl)amino) bisformate (Intermediate 19, 7.128 g, 14.6 mmol) was dissolved in a solution of hydrogen chloride in methanol (3 M, 20 mL) and stirred for 2 hours.

After that, the obtained solution was poured into saturated sodium carbonate solution (200 mL) and extracted with dichloromethane/isopropanol mixed solvent (200 mL×2). The organic phase was obtained by separation, washed with saturated brine (500 mL), dried over anhydrous sodium sulfate, suction filtered, and evaporated to dryness to obtain Intermediate 20. The relevant test data of Intermediate 20 are as follows:

ESI-MS: 236.1 [M+H]⁺.

Example 0-21

Intermediate 21: 7-(dimethoxymethyl)-4-methoxy-1,2,3,4-tetrahydro-2,4-methylene-1,8-naphthyridine

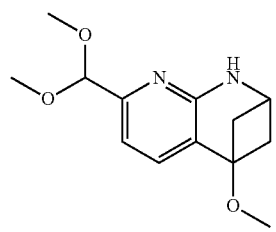

The First Step: Preparation of tert-butyl 4-((tert-butyldiphenylsilyl)oxy)-7-(dimethoxymethyl)-3,4-dihydro-2,4-methylene-1,8-naphthyridine-1(2H)-carboxylate

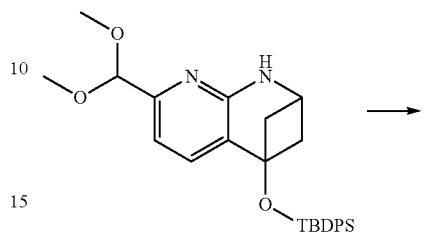

At room temperature, to a solution of 7-(dimethoxymethyl)-4-((tert-butyldiphenylsilyl)oxy)-1,2,3,4-tetrahydro-2,4-methylene-1,8-naphthyridine (Intermediate 17, 1.0 g, 2.11 mmol), triethylamine (1.07 g, 10.55 mmol), 4-dimethylaminopyridine (39 mg, 0.32 mmol) in tetrahydrofuran (10 mL) di-tert-butyl carbonate (1.84 g, 8.44 mmol) was added and the reaction continued to stir for 3 hours.

Water (50 mL) was added to the reaction mixture to quench the reaction, extracted with ethyl acetate (50 mL), and the organic phase was obtained by separation. The organic phase was washed with saturated brine (50 mL), dried over anhydrous sodium sulfate, and filtered with suction, and evaporated to dryness. The residue was purified by column chromatography, eluting with petroleum ether/ethyl acetate=5:1, and the fractions containing the product were concentrated to give tert-butyl 4-((tert-butyldiphenylsilyl)oxy)-7-(dimethoxymethyl)-3,4-dihydro-2,4-methylene-1,8-naphthyridine-1(2H)-carboxylate. The relevant test data are as follows:

ESI-MS: 575.1 [M+H]⁺.

The Second Step: Preparation of tert-butyl 7-(dimethoxymethyl)-4-hydroxy-3,4-dihydro-2,4-methylene-1,8-naphthyridine-1(2H)-carboxylate

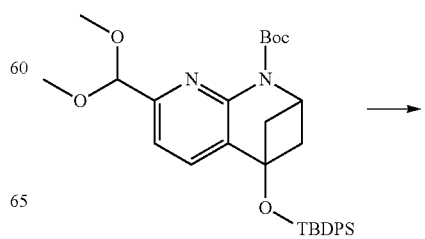

-continued

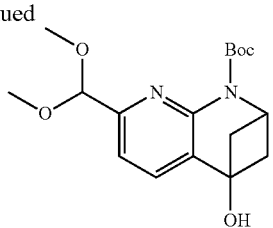

To a solution of tert-butyl 4-((tert-butyldiphenylsilyl)oxy)-7-(dimethoxymethyl)-3,4-dihydro-2,4-methylene-1,8-naphthyridine-1(2H)-carboxylate (1.21 g, 2.11 mmol) in tetrahydrofuran (12 mL) was added dropwise a solution of tetrabutylammonium fluoride in tetrahydrofuran (1M, 4.22 mL, 4.22 mmol) at 0° C., and continued to stir at room temperature for 1 hour.

Water (50 mL) was added to the reaction mixture to quench the reaction, extracted with ethyl acetate (50 mL), and the organic phase was obtained by separation. The organic phase was washed with saturated brine (50 mL), dried over anhydrous sodium sulfate, filtered and evaporated to dryness. The residue was purified by column chromatography, eluting with ethyl acetate, and the fractions containing the product were concentrated to give tert-butyl 7-(dimethoxymethyl)-4-hydroxy-3,4-dihydro-2,4-methylene-1,8-naphthyridine-1(2H)-carboxylate. The relevant test data are as follows:
ESI-MS: 337.2 [M+H]$^+$.

The Third Step: Preparation of tert-butyl 7-(dimethoxymethyl)-4-methoxy-3,4-dihydro-2,4-methylene-1,8-naphthyridine-1(2H)-carboxylate

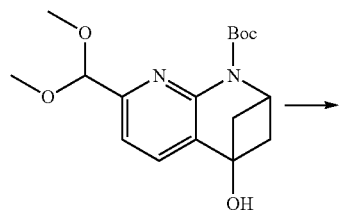

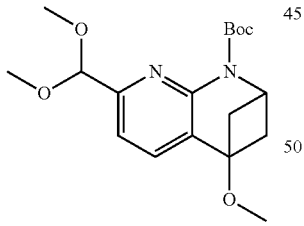

To a solution of tert-butyl 7-(dimethoxymethyl)-4-hydroxy-3,4-dihydro-2,4-methylene-1,8-naphthyridine-1(2H)-carboxylate (653 mg, 1.94 mmol) in N,N-dimethylformamide (1 mL) sodium hydride (194 mg, 4.96 mmol) was added at 0° C., and iodomethane (745 mg, 5.25 mmol) was slowly added dropwise to the system after stirring for 30 minutes under nitrogen protection, then continued stirring for 4 hours.

The reaction solution was poured into saturated ammonium chloride solution (60 mL) to quench the reaction and extracted with ethyl acetate (60 mL), and the organic phase was obtained by separation. The organic phase was washed with water (50 mL) and saturated brine (50 mL) in turn, dried over anhydrous sodium sulfate, filtered with suction, and evaporated to dryness. The residue was purified by column chromatography, eluting with petroleum ether/ethyl acetate=5:1, and the fractions containing the product were concentrated to give tert-butyl 7-(dimethoxymethyl)-4-methoxy-3,4-dihydro-2,4-methylene-1,8-naphthyridine-1(2H)-carboxylate. The relevant test data are as follows:
ESI-MS: 351.1 [M+H]$^+$.

The Fourth Step: Preparation of 7-(dimethoxymethyl)-4-methoxy-1,2,3,4-tetrahydro-2,4-methylene-1,8-naphthyridine

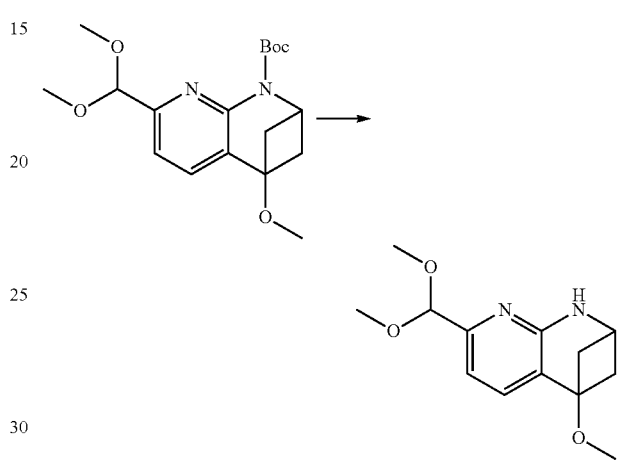

A solution of tert-butyl 7-(dimethoxymethyl)-4-methoxy-3,4-dihydro-2,4-methylene-1,8-naphthyridine-1(2H)-carboxylate (415 mg, 1.18 mmol) and pyridine p-toluenesulfonate (447 mg, 1.78 mmol) in methanol (15 mL) was heated to reflux for 6 hours.

After that, the obtained solution was poured into saturated sodium carbonate solution (200 mL), extracted with ethyl acetate (50 mL×2), and the organic phase was obtained by separation. The organic phase was washed with saturated brine (80 mL), dried over anhydrous sulfuric acid, filtered with suction, and evaporated to dryness. The residue was purified by column chromatography eluting with a gradient of petroleum ether/ethyl acetate=20:1 to 3:1, and the product-containing fractions were concentrated to give Intermediate 21. The relevant test data are as follows:
ESI-MS: 251.2 [M+H]$^+$.

Example 0-22

Intermediate 22: 7-(dimethoxymethyl)-4-(2-methoxyethoxy)-1,2,3,4-tetrahydro-2,4-methylene-1,8-naphthyridine

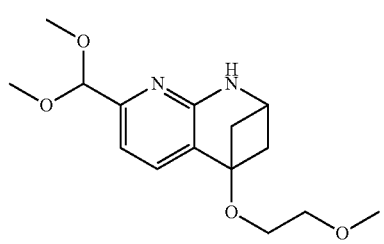

The First Step: Preparation of 7-(dimethoxymethyl)-4-((tert-butyldiphenylsilyl)oxy)-1-((2-(trimethylsilyl)ethoxy)methyl)-1,2,3,4-tetrahydro-2,4-methylene-1,8-naphthyridine

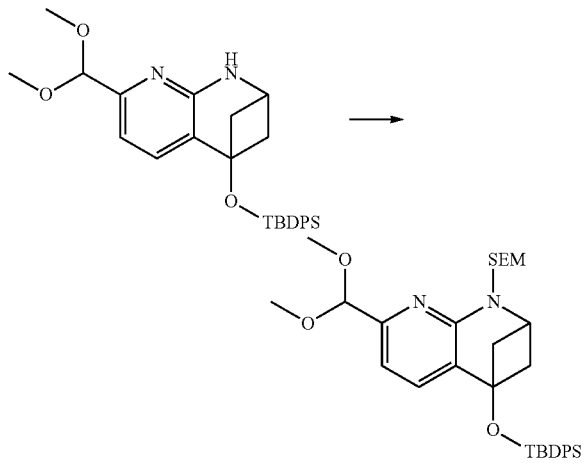

To a solution of 7-(dimethoxymethyl)-4-((tert-butyldiphenylsilyl)oxy)-1,2,3,4-tetrahydro-2,4-methylene-1,8-naphthyridine (Intermediate 17, 1.500 g, 3.16 mmol) in N,N-dimethylformamide (15 mL) was added a solution of sodium bis(trimethylsilyl)amide in tetrahydrofuran (2 M, 3.0 mL, 6.00 mmol) at 0° C., and stirred at room temperature for 1 hour under nitrogen protection. Then sodium iodide (0.600 g, 4.00 mmol) and 2-(trimethylsilyl)ethoxymethyl chloride (0.9 mL, 5.09 mmol) were added, and the reaction solution was stirred at 40° C. for 3 h.

Water (100 mL) was added to the reaction mixture to quench the reaction, extracted with ethyl acetate (100 mL), and the organic phase was obtained by separation. The organic phase was washed with saturated brine (100 mL), dried over anhydrous sodium sulfate, and filtered with suction, and evaporated to dryness to give 7-(dimethoxymethyl)-4-((tert-butyldiphenylsilyl)oxy)-1-((2-(trimethylsilyl)ethoxy)methyl)-1,2,3,4-tetrahydro-2,4-methylene-1,8-naphthyridine crude product. The relevant test data of the product are as follows:

ESI-MS: 605.2 [M+H]⁺.

The Second Step: Preparation of 7-(dimethoxymethyl)-4-hydroxy-1-((2-(trimethylsilyl)ethoxy)methyl)-1,2,3,4-tetrahydro-2,4-methylene-1,8-naphthyridine

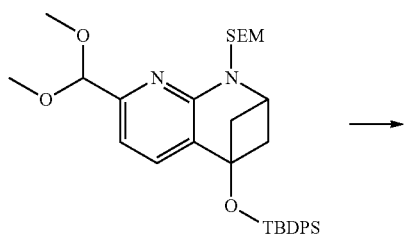

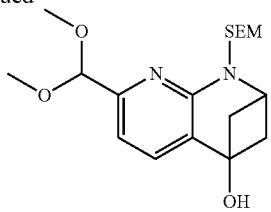

A solution of 7-(dimethoxymethyl)-4-((tert-butyldiphenylsilyl)oxy)-1-((2-(trimethylsilyl)ethoxy)methyl)-1,2,3,4-tetrahydro-2,4-methylene-1,8-naphthyridine (1.909 g, 3.16 mmol) in tetrahydrofuran (30 mL) was added dropwise tetrabutylammonium fluoride in tetrahydrofuran (1 M, 4.5 mL, 4.50 mmol) at 0° C. and continued to stir at room temperature for 1 hour.

Water (100 mL) was added to the reaction mixture to quench the reaction, extracted with ethyl acetate (100 mL), and the organic phase was obtained by separation. The organic phase was washed with saturated brine (100 mL), dried over anhydrous sodium sulfate, filtered and evaporated to dryness to render 7-(dimethoxymethyl)-4-hydroxy-1-((2-(trimethylsilyl)ethoxy)methyl)-1,2,3,4-tetrahydro-2,4-methylene-1,8-naphthyridine crude product. The relevant test data of the product are as follows:

ESI-MS: 367.0 [M+H]⁺.

The Third Step: Preparation of 7-(dimethoxymethyl)-4-(2-methoxyethoxy)-1-((2-(trimethylsilyl)ethoxy)methyl)-1,2,3,4-tetrahydro-2,4-methylene-1,8-naphthyridine

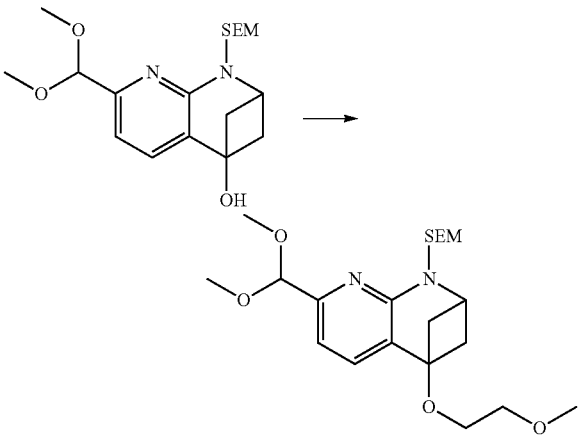

At 0° C., to a solution of 7-(dimethoxymethyl)-4-hydroxy-1-((2-(trimethyl silyl)ethoxy)methyl)-1,2,3,4-tetrahydro-2,4-methylene-1,8-naphthyridine (385 mg, 1.05 mmol) in N,N-dimethylformamide (5 mL) was added sodium hydride (60 mg, 1.50 mmol), and the mixture was stirred under nitrogen protection for 30 minutes. Then sodium iodide (240 mg, 1.60 mmol) and 2-bromoethyl methyl ether (0.2 mL, 2.13 mmol) were added to the system, and reaction solution was stirred at 40° C. for 2 hours.

The reaction solution was poured into saturated ammonium chloride solution (50 mL) to quench the reaction, and extracted with dichloromethane (50 mL), and the organic phase was obtained by separation. The organic phase was washed with saturated brine (50 mL), dried over anhydrous sodium sulfate, filtered and evaporated to dryness to give 7-(dimethoxymethyl)-4-(2-methoxyethoxy)-1-((2-(trimethyl silyl) ethoxy)methyl)-1,2,3,4-tetrahydro-2,4-methylene-1,8-naphthyridine crude product. The relevant test data of the product are as follows:

ESI-MS: 425.2 [M+H]+.

The Fourth Step: Preparation of 7-(dimethoxymethyl)-4-(2-methoxyethoxy)-1,2,3,4-tetrahydro-2,4-methylene-1,8-naphthyridine

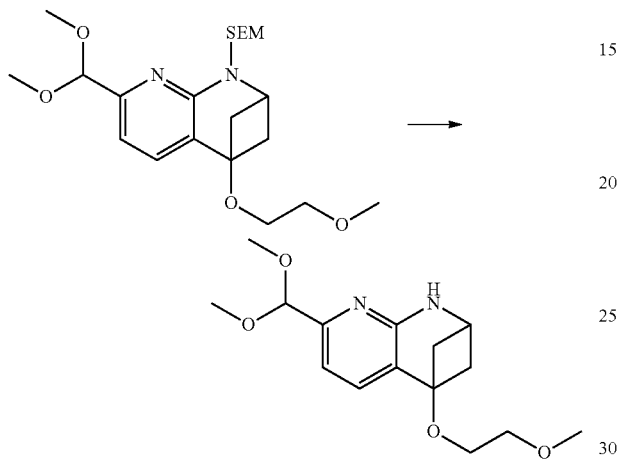

At room temperature, to a solution of 7-(dimethoxymethyl)-4-(2-methoxyethoxy)-1-((2-(trimethyl silyl)ethoxy)methyl)-1,2,3,4-tetrahydro-2,4-methylene-1,8-naphthyridine (445 mg, 1.05 mmol) in dichloromethane (20 mL) was added trifluoroacetic acid (0.5 mL), and stirred for 1 hour.

After that, the obtained solution was poured into saturated sodium carbonate solution (100 mL), extracted with dichloromethane (100 mL), and the organic phase was obtained by separation. The organic phase was washed with saturated brine (100 mL) and dried over anhydrous sodium sulfate, filtered with suction, and evaporated to dryness. The residue was purified by column chromatography, eluting with a gradient of petroleum ether/ethyl acetate=1:1 to pure ethyl acetate, and the product-containing fractions were concentrated to give Intermediate 22. The relevant test data of the product are as follows:

ESI-MS: 295.1 [M+H]+.

Example 0-23

Intermediate 23: 7-(dimethoxymethyl)-4-(2-(N,N-dimethylamino)ethoxy)-1,2,3,4-tetrahydro-2,4-methylene-1,8-naphthyridine

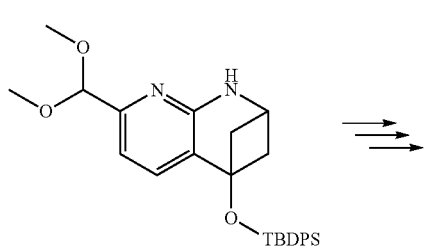

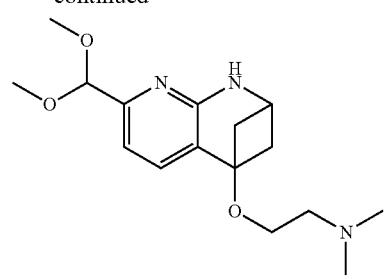

Taking Intermediate 17 as a starting material, using a manner similar to Intermediate 22, Intermediate 23 was prepared. The relevant test data of Intermediate 23 are as follows:

ESI-MS: 307.9 [M+H]+.

Example 0-24

Intermediate 24: N-(2-iodoethyl)pyrrolidine hydroiodide

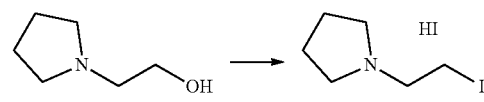

To a solution of triphenylphosphine (4.7 g, 17.9 mmol) and imidazole (1.2 g, 17.6 mmol) in tetrahydrofuran (90 mL) was added iodine (4.5 g, 17.7 mmol) at room temperature, and the mixture was stirred at 30° C. for 10 minutes. After that, N-(2-hydroxyethyl)pyrrolidine (2.0 mL, 17.1 mmol) was added, and stirring was continued for 4 hours. The precipitated white solid was suction filtered, and the filter cake was washed with ethyl acetate to obtain Intermediate 24. The test data of the product are as follows:

ESI-MS: 225.8 [M+H]+.

Example 0-25

Intermediate 25: Preparation of N-(2-iodoethyl)morpholine hydroiodide

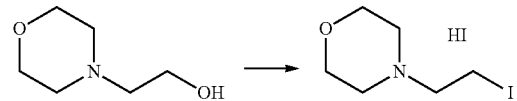

Taking 2-morpholinoethanol as the starting material, Intermediate 25 was obtained by reacting in a manner similar to the preparation of Intermediate 24. The relevant test data are as follows:

ESI-MS: 242.0 [M+H]+.

Example O-26

Intermediate 26: Preparation of 7-(dimethoxymethyl)-4-(2-(pyrrolidin-1-yl)ethoxy)-1,2,3,4-tetrahydro-2,4-methylene-1,8-naphthyridine

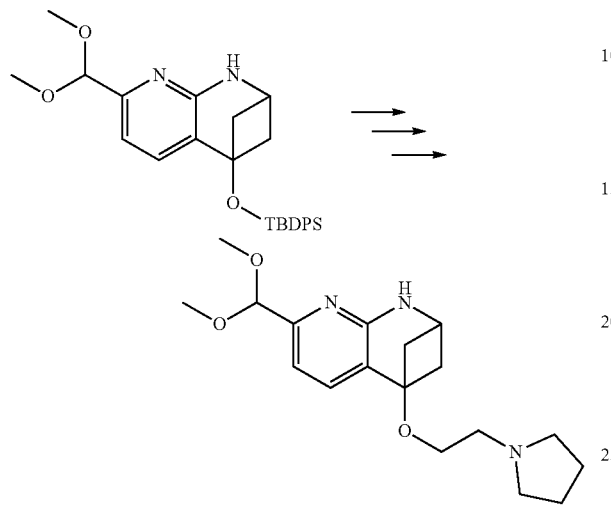

Taking Intermediate 17 and Intermediate 24 as starting materials, Intermediate 26 was obtained by reacting in a manner similar to the preparation of Intermediate 22. The relevant test data of Intermediate 26 are as follows:
ESI-MS: 333.9 [M+H]$^+$.

Example O-27

Intermediate 27: Preparation of 7-(dimethoxymethyl)-4-(2-(morpholin-4-yl)ethoxy)-1,2,3,4-tetrahydro-2,4-methylene-1,8-naphthyridine

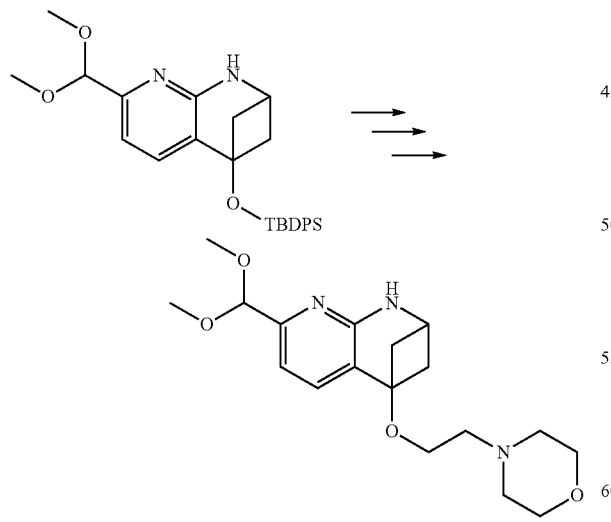

Taking Intermediate 17 and Intermediate 25 as starting materials, Intermediate 27 was obtained by reacting in a manner similar to the preparation of Intermediate 22. The relevant test data of Intermediate 27 are as follows:
ESI-MS: 480.3 [M+H]$^+$.

Example O-28

Intermediate 28: Preparation of methyl 2-((7-(dimethoxymethyl)-1,2,3,4-tetrahydro-2,4-methylene-1,8-naphthyridin-4-yl)oxy)acetate

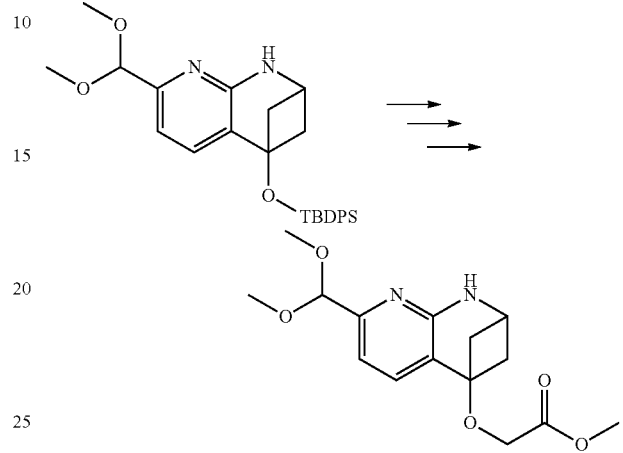

Taking Intermediate 17 as starting material, Intermediate 28 was obtained by reacting in a manner similar to the preparation of Intermediate 22. The relevant test data of Intermediate 28 are as follows:
ESI-MS: 309.1 [M+H]$^+$.

Example O-29

Intermediate 29: Preparation of 7-(dimethoxymethyl)-4-(2-(morpholin-4-yl)-2-oxoethoxy)-1,2,3,4-tetrahydro-2,4-methylene-1,8-naphthyridine

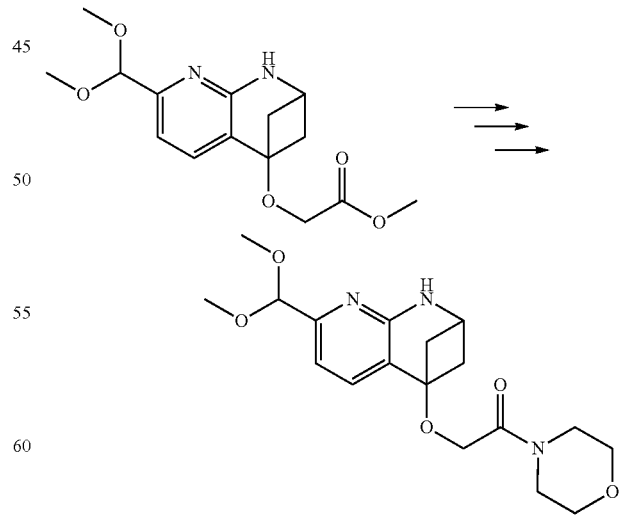

A solution of methyl 24(7-(dimethoxymethyl)-1,2,3,4-tetrahydro-2,4-methylene-1,8-naphthyridin-4-yl)oxy)acetate (Intermediate 28, 37 mg, 0.12 mmol) and morpholine (0.5 mL, 5.75 mmol) in methanol (0.5 mL) was stirred at reflux temperature for 72 hours. The reaction solution was then concentrated and purified by column chromatography with gradient elution by dichloromethane/methanol=20:1 to 10:1, and the fraction containing the product was concentrated to obtain Intermediate 29. The relevant test data of the product are as follows:

ESI-MS: 364.1 [M+H]$^+$.

Example 0-30

Intermediate 30: Preparation of 7-(dimethoxymethyl)-4-(2-(4-methylpiperazin-1-yl)-2-oxoethoxy)-1,2,3,4-tetrahydro-2,4-methylene-1,8-naphthyridine

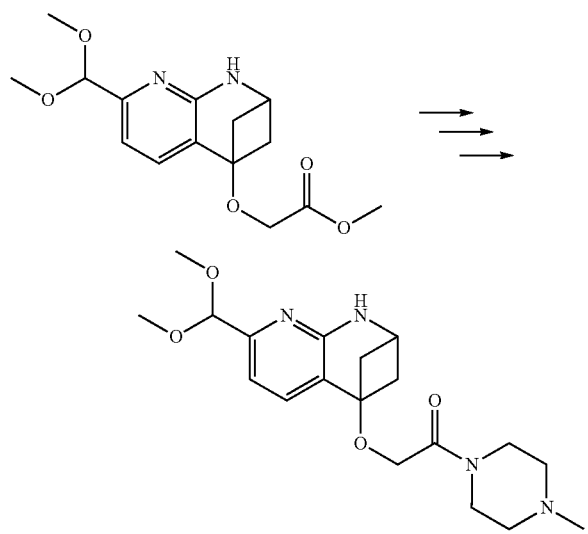

Taking Intermediate 28 as starting material, Intermediate 30 was obtained by reacting in a manner similar to the preparation of Intermediate 29. The relevant test data of Intermediate 30 are as follows:

ESI-MS: 377.1 [M+H]$^+$.

Example 0-31

Intermediate 31: Preparation of N-(7-(dimethoxymethyl)-1,2,3,4-tetrahydro-2,4-methylene-1,8-naphthyridin-4-yl)-2-(dimethyl)amino)acetamide

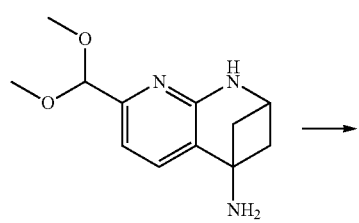

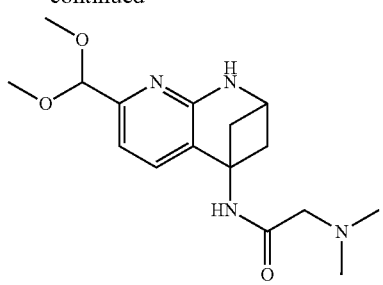

To a solution of 7-(dimethoxymethyl)-4-amino-1,2,3,4-tetrahydro-2,4-methylene-1,8-naphthyridine (Intermediate 20, 100 mg, 0.43 mmol), N,N-dimethylglycine (44 mg, 0.43 mmol) and HATU (194 mg, 0.51 mmol) in N,N-dimethylformamide (2 mL) was added dropwise N,N-diisopropylethylamine (137 mg, 1.06 mmol) at 0° C., and then stirred at room temperature for 2 hours. After the reaction was completed, water (20 mL) was added to quench the reaction, and the reaction solution was extracted with dichloromethane (50 mL). The organic phase was washed with saturated brine (20 mL), dried over anhydrous sodium sulfate, filtered with suction, and evaporated to dryness. The residue was purified by column chromatography, eluting with dichloromethane/methanol=10:1, to obtain Intermediate 31. The relevant test data of the product are as follows:

ESI-MS: 321.1 [M+H]$^+$.

Example 0-32

Intermediate 32: Preparation of N-(7-(dimethoxymethyl)-1,2,3,4-tetrahydro-2,4-methylene-1,8-naphthyridin-4-yl)-1-methylpiperidine-4-carboxamide

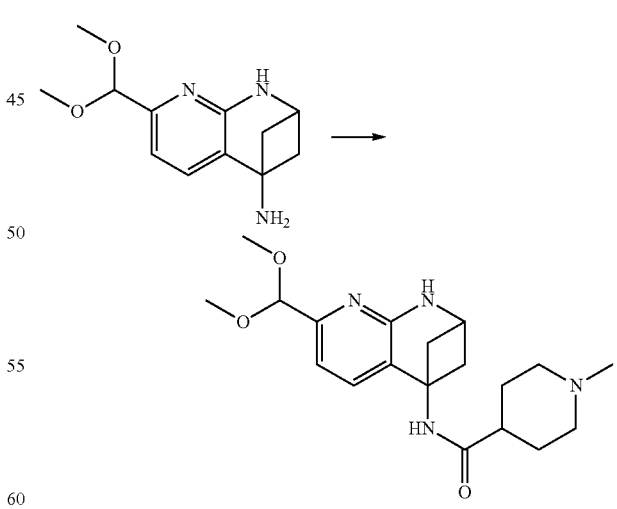

Taking Intermediate 20 as starting material, Intermediate 32 was obtained by reacting in a manner similar to the preparation of Intermediate 31. The relevant test data of Intermediate 32 are as follows:

ESI-MS: 361.1 [M+H]$^+$.

Example O-33

Intermediate 33: Preparation of N-(7-(dimethoxymethyl)-1,2,3,4-tetrahydro-2,4-methylene-1,8-naphthyridin-4-yl)-1-methyl-1H-pyrazole-4-carboxamide

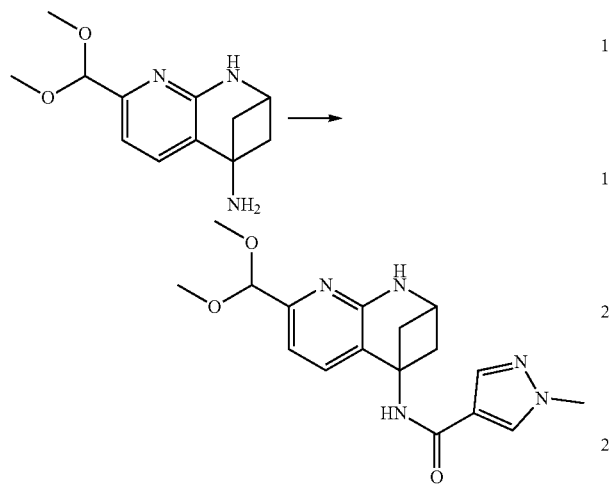

Taking Intermediate 20 as starting material, Intermediate 33 was obtained by reacting in a manner similar to the preparation of Intermediate 31. The relevant test data of Intermediate 33 are as follows:

ESI-MS: 344.1 [M+H]$^+$.

Example O-34

Intermediate 34: Preparation of N-(7-(dimethoxymethyl)-1,2,3,4-tetrahydro-2,4-methylene-1,8-naphthyridin-4-yl) propionamide

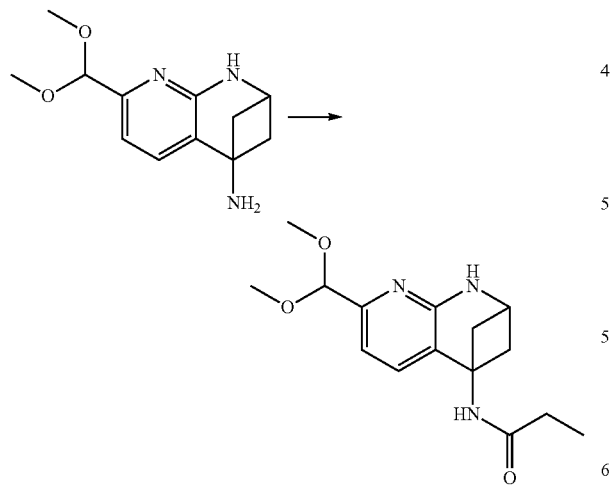

Taking Intermediate 20 as starting material, Intermediate 34 was obtained by reacting in a manner similar to the preparation of Intermediate 31. The relevant test data of Intermediate 34 are as follows:

ESI-MS: 292.2 [M+H]$^+$.

Example O-35

Intermediate 35: Preparation of N-(7-(dimethoxymethyl)-1,2,3,4-tetrahydro-2,4-methylene-1,8-naphthyridin-4-yl)-1-methylpyrrolidine-3-carboxamide

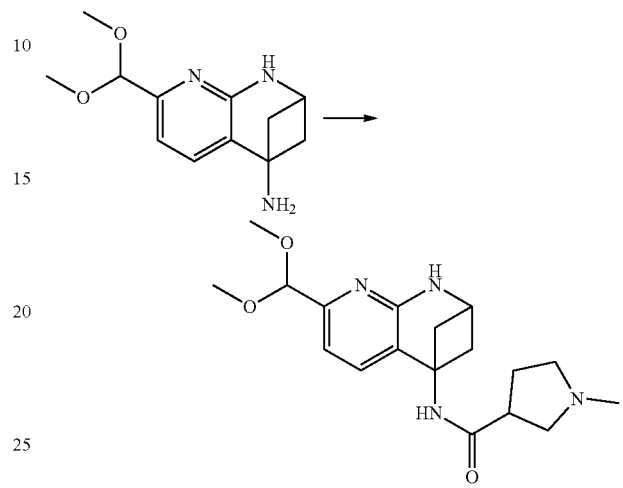

Taking Intermediate 20 as starting material, Intermediate 35 was obtained by reacting in a manner similar to the preparation of Intermediate 31. The relevant test data of Intermediate 35 are as follows:

ESI-MS: 347.1 [M+H]$^+$.

Example O-36

Intermediate 36: Preparation of N-(7-(dimethoxymethyl)-1,2,3,4-tetrahydro-2,4-methylene-1,8-naphthyridin-4-yl)-2-(pyrrolidine-1-yl)acetamide

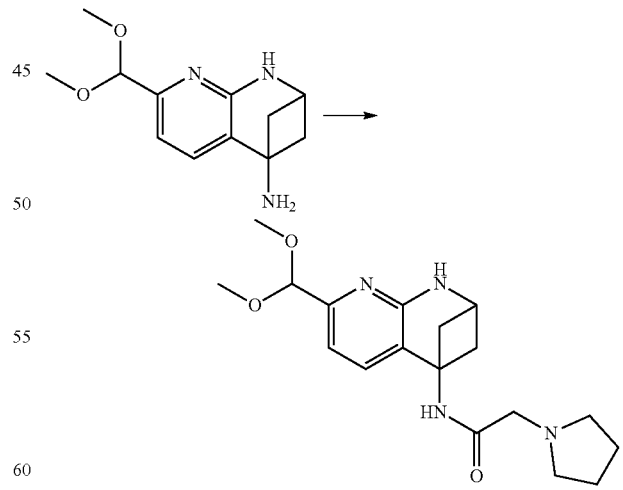

Taking Intermediate 20 as starting material, Intermediate 36 was obtained by reacting in a manner similar to the preparation of Intermediate 31. The relevant test data of Intermediate 36 are as follows:

ESI-MS: 347.1 [M+H]$^+$.

Example 0-37

Intermediate 37: Preparation of N-(7-(dimethoxymethyl)-1,2,3,4-tetrahydro-2,4-methylene-1,8-naphthyridin-4-yl)-2-(tert-butyl) dimethylsilyloxy)acetamide

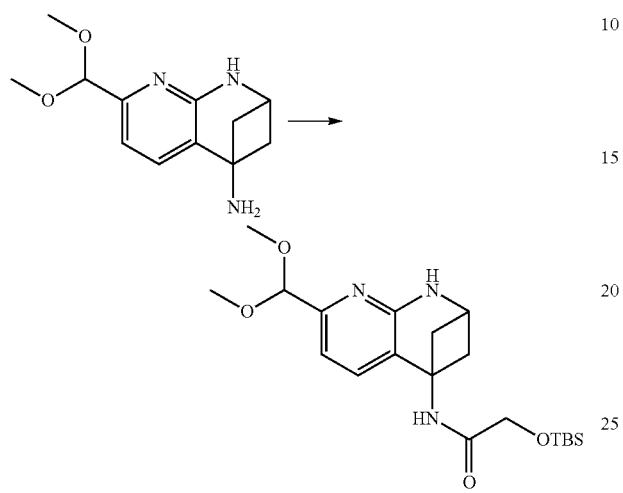

Taking Intermediate 20 as starting material, Intermediate 37 was obtained by reacting in a manner similar to the preparation of Intermediate 31. The relevant test data of Intermediate 37 are as follows:
ESI-MS: 408.2 [M+H]$^+$.

Example 0-38

Intermediate 38: Preparation of N-(7-(dimethoxymethyl)-1,2,3,4-tetrahydro-2,4-methylene-1,8-naphthyridin-4-yl)-pyridine-2-carboxamide

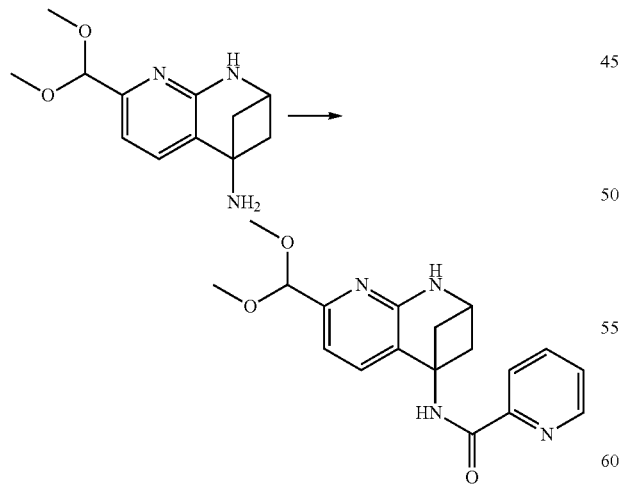

Taking Intermediate 20 as starting material, Intermediate 38 was obtained by reacting in a manner similar to the preparation of Intermediate 31. The relevant test data of Intermediate 38 are as follows:
ESI-MS: 341.1 [M+H]$^+$.

Example 0-39

Intermediate 39: Preparation of N-(7-(dimethoxymethyl)-1,2,3,4-tetrahydro-2,4-methylene-1,8-naphthyridin-4-yl)-1H-pyrazole-2-carboxamide

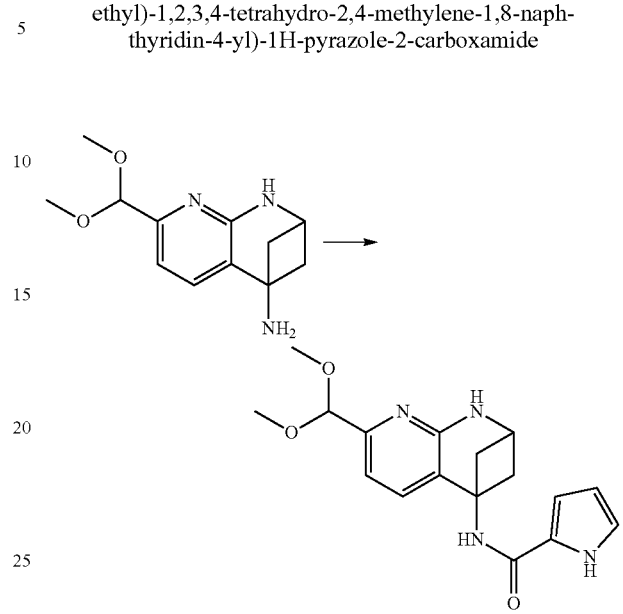

Taking Intermediate 20 as starting material, Intermediate 39 was obtained by reacting in a manner similar to the preparation of Intermediate 31. The relevant test data of Intermediate 39 are as follows:
ESI-MS: 329.1 [M+H]$^+$.

Example 0-40

Intermediate 40: Preparation of N-(7-(dimethoxymethyl)-1,2,3,4-tetrahydro-2,4-methylene-1,8-naphthyridin-4-yl)ethanesulfonamide

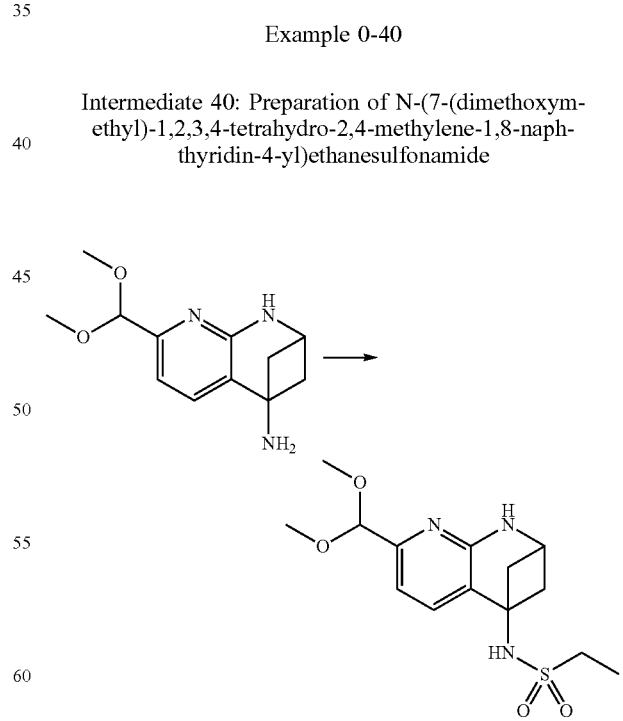

To a solution of 7-(dimethoxymethyl)-4-amino-1,2,3,4-tetrahydro-2,4-methylene-1,8-naphthyridine (Intermediate 20, 50 mg, 0.21 mmol) and triethylamine (70 µL, 0.50 mmol) in dichloromethane (2 mL) was added dropwise a solution of ethylsulfonyl chloride (27 mg, 0.21 mmol) in dichloromethane (0.5 mL), followed by stirring at room temperature for 3 hours.

After the reaction was completed, water (20 mL) was added to quench the reaction, and the mixture was extracted with dichloromethane (30 mL). The organic phase was washed with saturated sodium bicarbonate solution (30 mL) and saturated brine (30 mL) in turn, dried with anhydrous sodium sulfate, filtered and evaporated to dryness. The residue was purified by column chromatography, eluting with dichloromethane/methanol=20:1, to give Intermediate 40. the relevant test data of the product are as follows:

ESI-MS: 328.1 [M+H]+.

Example 0-41

Intermediate 41: Preparation of 7-(dimethoxymethyl)-4-(N-methyl-N-(tetrahydrofuran-3-yl)amino)-1,2,3,4-tetrahydro-2,4-methylene-1,8-naphthyridine

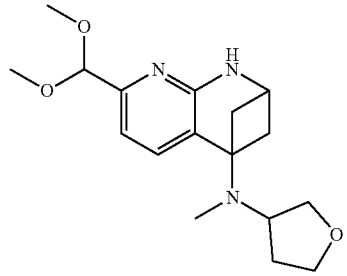

The First Step: Preparation of 7-(dimethoxymethyl)-4-((tetrahydrofuran-3-yl)amino)-1,2,3,4-tetrahydro-2,4-methylene-1,8-naphthyridine

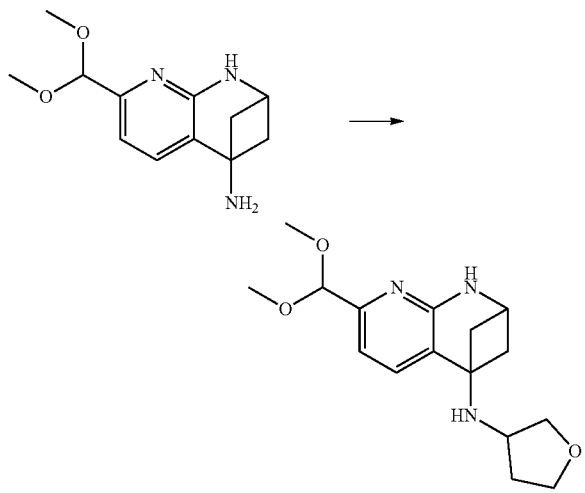

To a solution of 7-(dimethoxymethyl)-4-amino-1,2,3,4-tetrahydro-2,4-methylene-1,8-naphthyridine (Intermediate 20, 300 mg, 1.275 mmol) and dihydro-3(2H)-furanone (220 mg, 2.550 mmol) in dichloromethane (15 mL) was added sodium triacetoxyborohydride (568 mg, 2.678 mmol)) at room temperature and continued stirring at room temperature for 3 hours.

After the reaction was completed, the reaction solution was poured into saturated sodium carbonate solution (50 mL) to quench the reaction and extracted with dichloromethane (15 mL*3). The organic phase was washed with saturated brine (50 mL), dried over anhydrous sodium sulfate, filtered with suction and evaporated to dryness. The residue was purified by column chromatography eluting with a gradient of dichloromethane and dichloromethane/methanol=80:1 to give 7-(dimethoxymethyl)-4-(N-(tetrahydrofuran-3-yl)amino)-1,2,3,4-tetrahydro-2,4-methylene-1,8-naphthyridine. The relevant test data of the product are as follows:

ESI-MS: 306.1 [M+H]+

The Second Step: Preparation of tert-butyl 7-(dimethoxymethyl)-4-((tetrahydrofuran-3-yl)amino)-3,4-dihydro-2,4-methylene-1,8-naphthyridine-1(2H)-carboxylate

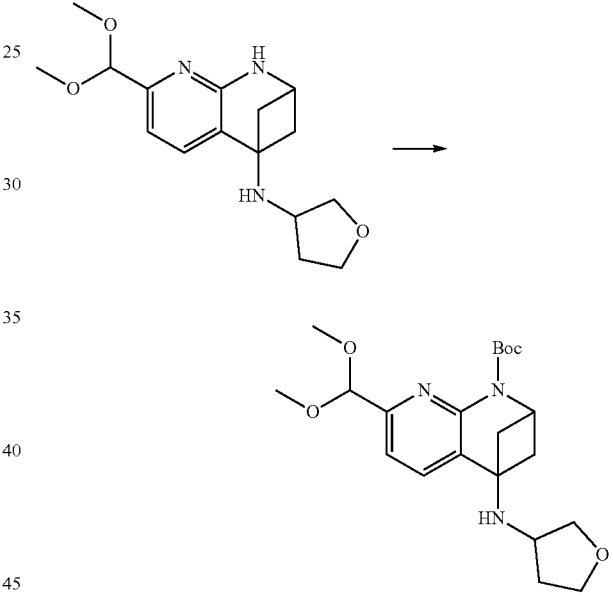

At room temperature, to a solution of 7-(dimethoxymethyl)-4-(N-(tetrahydrofuran-3-yl)amino)-1,2,3,4-tetrahydro-2,4-methylene-1,8-naphthyridine (280 mg, 0.917 mmol), 4-dimethylaminopyridine (45 mg, 0.367 mmol) and triethylamine (557 mg, 5.500 mmol) in tetrahydrofuran (10 mL) was added di-tert-butyl dicarbonate (600 mg, 2.750 mmol) and stirred at 30° C. for 16 h.

After the reaction was completed, the reaction solution was poured into water (50 mL) to quench the reaction and extracted with ethyl acetate (15 mL*3). The organic phase was washed with saturated brine (50 mL*2), dried over anhydrous sodium sulfate, filtered with suction and evaporated to dryness. The residue was purified by column chromatography, eluting with a gradient of petroleum ether/ethyl acetate=50:1 to 1:1 to give tert-butyl 7-(dimethoxymethyl)-4-((tetrahydrofuran-3-yl)amino)-3,4-dihydro-2,4-methylene-1,8-naphthyridine-1(2H)-carboxylate. The relevant test data of the product are as follows:

ESI-MS: 406.4 [M+H]+

The Third Step: Preparation of tert-butyl 7-(dimethoxymethyl)-4-(N-methyl-N-(tetrahydrofuran-3-yl)amino)-3,4-dihydro-2,4-methylene-1,8-naphthyridine-1(2H)-carboxylate

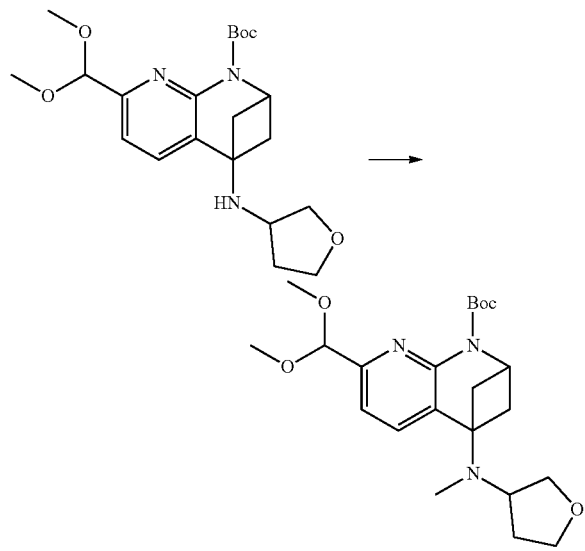

To a solution of tert-butyl 7-(dimethoxymethyl)-4-((tetrahydrofuran-3-yl)amino)-3,4-dihydro-2,4-methylene-1,8-naphthyridine-1(2H)-carboxylate (350 mg, 0.863 mmol) and paraformaldehyde (700 mg) in dichloromethane (12 mL) was added sodium triacetoxyborohydride (700 mg, 3.302 mmol) at room temperature and stirred at 35° C. for 16 hours.

After the reaction, the reaction solution was poured into saturated sodium bicarbonate solution (50 mL) to quench the reaction and extracted with ethyl acetate (15 mL*3). The organic phase was washed with saturated brine (50 mL*2), dried over anhydrous sodium sulfate, filtered with suction and evaporated to dryness. The residue was purified by column chromatography eluting with a gradient of petroleum ether/ethyl acetate=40:1 to 3:1 to give tert-butyl 7-(dimethoxymethyl)-4-(N-methyl-N-(tetrahydrofuran-3-yl)amino)-3,4-dihydro-2,4-methylene-1,8-naphthyridine-1(2H)-carboxylate. The relevant test data of the product are as follows:

ESI-MS: 420.2 [M+H]⁺

The Fourth Step: Preparation of 7-(dimethoxymethyl)-4-(N-methyl-N-(tetrahydrofuran-3-yl)amino)-1,2,3,4-tetrahydro-2,4-methylene-1,8-naphthyridine

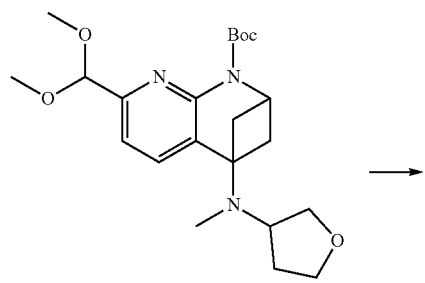

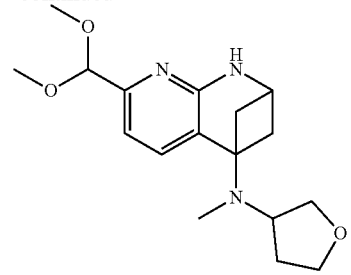 [SMILES: COC(OC)c1ccc2c(n1)NC1CC2(N(C)C2CCOC2)C1]

A solution of tert-butyl 7-(dimethoxymethyl)-4-(N-methyl-N-(tetrahydrofuran-3-yl)amino)-3,4-dihydro-2,4-methylene-1,8-naphthyridine-1(2H)-carboxylate (280 mg, 0.667 mmol) and pyridine p-toluenesulfonate (335 mg, 1.335 mmol) in methanol (5 mL) was stirred at reflux temperature for 2 hours.

After the reaction, the reaction solution was poured into saturated sodium bicarbonate solution (50 mL) to quench the reaction and extracted with ethyl acetate (15 mL*3). The organic phase was washed with saturated brine (50 mL*2), dried over anhydrous sodium sulfate, filtered with suction, and evaporated to dryness to obtain Intermediate 41. The relevant test data of the product are as follows:

ESI-MS: 319.4 [M+H]⁺

Example 0-42

Intermediate 42: Preparation of N-(7-(dimethoxymethyl)-1,2,3,4-tetrahydro-2,4-methylene-1,8-naphthyridin-4-yl)-N,1-di methyl-1H-pyrazole-4-carboxamide

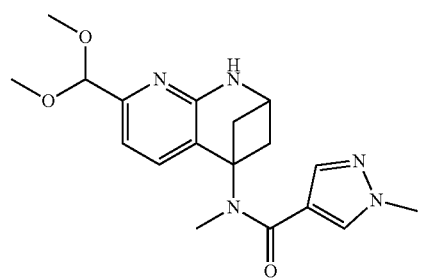

The First Step: Preparation of benzyl 7-(dimethoxymethyl)-4-(1-methyl-1H-pyrazole-4-carboxamido)-3,4-dihydro-2,4-methylene-1,8-naphthyridine-1(2H)-carboxylate

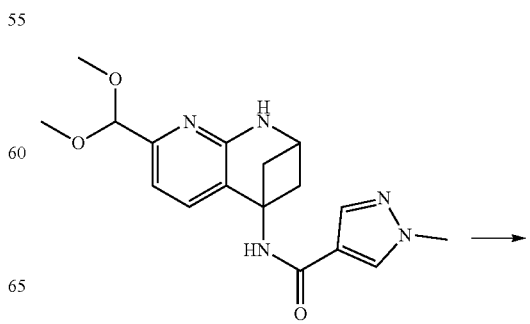

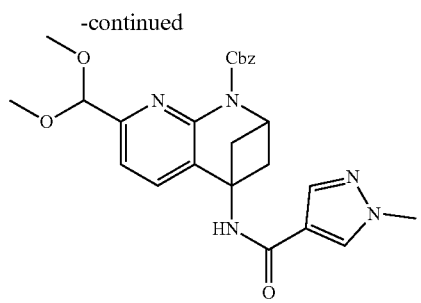

At room temperature, to a solution of N-(7-(dimethoxymethyl)-1,2,3,4-tetrahydro-2,4-methylene-1,8-naphthyridin-4-yl)-1-methyl-1H-pyrazole-4-carboxamide (Intermediate 33, 68 mg, 0.198 mmol) and N,N-diisopropylethylamine (50 mg, 0.388 mmol) in dichloromethane (5 mL) was added benzyl chloroformate (35 mg, 0.205 mmol) and continued stirring at room temperature for 1 hour.

After the reaction, saturated sodium bicarbonate solution (50 mL) was added to the reaction solution to quench the reaction, and extracted with dichloromethane (50 mL). The organic phase was washed with saturated brine (50 mL), dried over anhydrous sodium sulfate, filtered with suction, and evaporated to dryness. The residue was purified by column chromatography eluting with dichloromethane/methanol=20:1 to give benzyl 7-(dimethoxymethyl)-4-(1-methyl-1H-pyrazole-4-carboxamido)-3,4-dihydro-2,4-methylene-1,8-naphthyridine-1(2H)-carboxylate. The relevant test data of the product are as follows:

ESI-MS: 478.2 [M+H]$^+$

The Second Step: Preparation of benzyl 7-(dimethoxymethyl)-4-(N,1-dimethyl-1H-pyrazole-4-carboxamido)-3,4-dihydro-2,4-methylene-1,8-naphthyridine-1(2H)-carboxylate

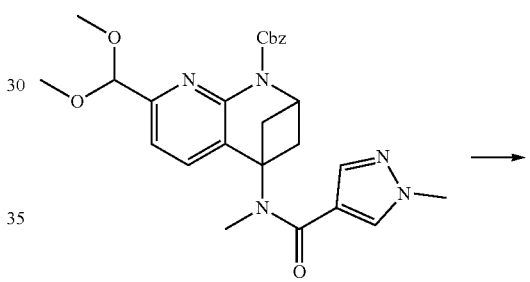

To a solution of benzyl 7-(dimethoxymethyl)-4-(1-methyl-1H-pyrazole-4-carboxamido)-3,4-dihydro-2,4-methylene-1,8-naphthyridine-1(2H)-carboxylate (46 mg, 0.10 mmol) in N,N-dimethylformamide (1 mL) was added sodium hydride (8 mg, 0.18 mmol) at 0° C. After stirring for 30 minutes under nitrogen protection, iodomethane (28 mg, 0.20 mmol) was slowly added dropwise to the system, followed by stirring for 2 hours.

After the reaction, the reaction solution was poured into saturated ammonium chloride solution (60 mL) to quench the reaction and extracted with ethyl acetate (30 mL). The organic phase was washed with saturated brine (30 mL), dried over sodium sulfate, filtered with suction, and evaporated to dryness. The residue was purified by column chromatography, eluting with dichloromethane/methanol=20:1, to give benzyl 7-(dimethoxymethyl)-4-(N,1-dimethyl-1H-pyrazole-4-carboxamido)-3,4-dihydro-2,4-methylene-1,8-naphthyridine-1(2H)-carboxylate. The relevant test data of the product are as follows:

ESI-MS: 492.1 [M+H]$^+$

The Third Step: Preparation of N-(7-(dimethoxymethyl)-1,2,3,4-tetrahydro-2,4-methylene-1,8-naphthyridin-4-yl)-N,1-dimethyl-1H-pyrazole-4-carboxamide

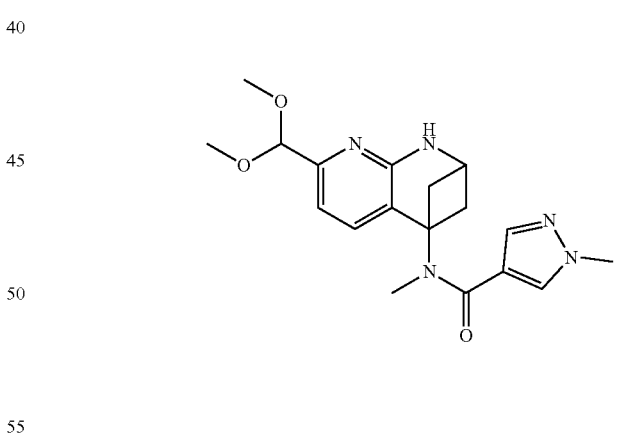

At room temperature, to a solution of benzyl 7-(dimethoxymethyl)-4-(N,1-dimethyl-1H-pyrazole-4-carboxamido)-3,4-dihydro-2,4-methylene-1,8-naphthyridine-1(2H)-carboxylate (38 mg, 0.08 mmol) in methanol (3 mL) was added 10% palladium on carbon (5 mg) and stirred under a hydrogen atmosphere of 1 atm for 14 hours. After the reaction, the insolubles were filtered off with celite suction filtration, and the filtrate was evaporated to dryness to obtain Intermediate 42. The relevant test data of the product are as follows:

ESI-MS: 358.1 [M+H]$^+$

Example 0-43

Intermediate 43: Preparation of N-(7-(dimethoxymethyl)-1,2,3,4-tetrahydro-2,4-methylene-1,8-naphthyridin-4-yl)morpholine-4-carboxamide

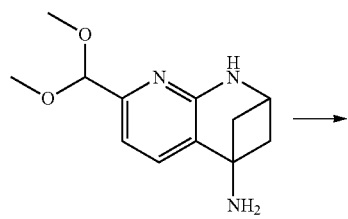

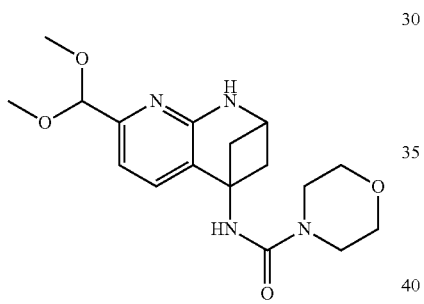

Example 0-44

Intermediate 44: Preparation of 1-(7-(dimethoxymethyl)-1,2,3,4-tetrahydro-2,4-methylene-1,8-naphthyridin-4-yl)-4-methylpiperazin-2-one

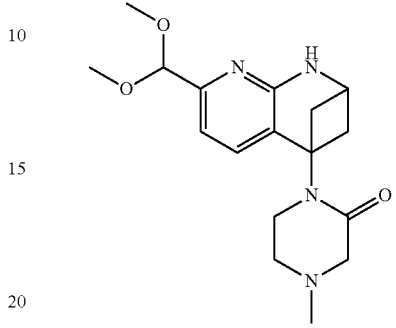

The First Step: Preparation of tert-butyl N-(24(7-(dimethoxymethyl)-1,2,3,4-tetrahydro-2,4-methylene-1,8-naphthyridin-4-yl)amino) ethyl)-N-methylcarbamate

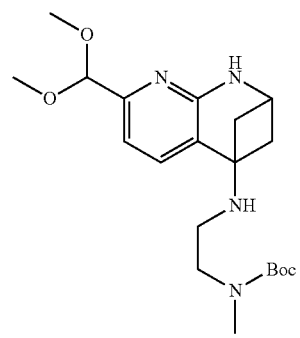

To a solution of bis(trichloromethyl)carbonate (214 mg, 0.72 mmol) in tetrahydrofuran (5 mL) was added dropwise triethylamine (0.89 mL, 6.40 mmol) and morpholine (174 mg, 2.00 mmol) at 0° C. under nitrogen protection and stirred at room temperature for 1 hour. Then 7-(dimethoxymethyl)-4-amino-1,2,3,4-tetrahydro-2,4-methylene-1,8-naphthyridine (Intermediate 20, 50 mg, 0.21 mmol) was added to the reaction system and stirred at room temperature for 14 hours.

After the reaction, saturated sodium bicarbonate solution (30 mL) was added to the reaction solution to quench the reaction and extracted with dichloromethane (50 mL). The organic phase was washed with saturated brine (30 mL), dried over anhydrous sodium sulfate, and filtered with suction, and evaporated to dryness. The residue was purified by column chromatography, eluting with dichloromethane/methanol=20:1, to give Intermediate 43. The relevant test data of the product are as follows:

ESI-MS: 349.2 [M+H]$^+$

To a solution 7-(dimethoxymethyl)-4-amino-1,2,3,4-tetrahydro-2,4-methylene-1,8-naphthyridine (Intermediate 20, 200 mg, 0.85 mmol) and tert-butyl methyl(2-oxoethyl)carbamate (147 mg, 0.85 mmol) in dichloromethane (5 mL) was added 1 drop of glacial acetic acid at room temperature and stirred for 1 hour. To this solution, sodium triacetoxyborohydride (541 mg, 2.55 mmol) was added and stirring was continued at room temperature for 2 hours.

After the reaction was completed, saturated sodium bicarbonate solution (30 mL) was added to the reaction solution to quench the reaction and extracted with dichloromethane (30 mL). The organic phase was washed with saturated brine (30 mL), dried over anhydrous sodium sulfate, and filtered with suction, and evaporated to dryness. The residue was purified by column chromatography eluting with dichloromethane/methanol=20:1 to give tert-butyl N-(2-((7-(dimethoxymethyl)-1,2,3,4-tetrahydro-2,4-methylene-1,8-naphthyridin-4-yl)amino)ethyl)-N-methylcarbamate. The relevant test data of the product are as follows:
ESI-MS: 393.2 [M+H]⁺

The Second Step: Preparation of tert-butyl N-(2-(2-chloro-N-(7-(dimethoxymethyl)-1,2,3,4-tetrahydro-2,4-methylene-1,8-naphthyridine-4-yl)acetamido)ethyl)-N-methylcarbamate

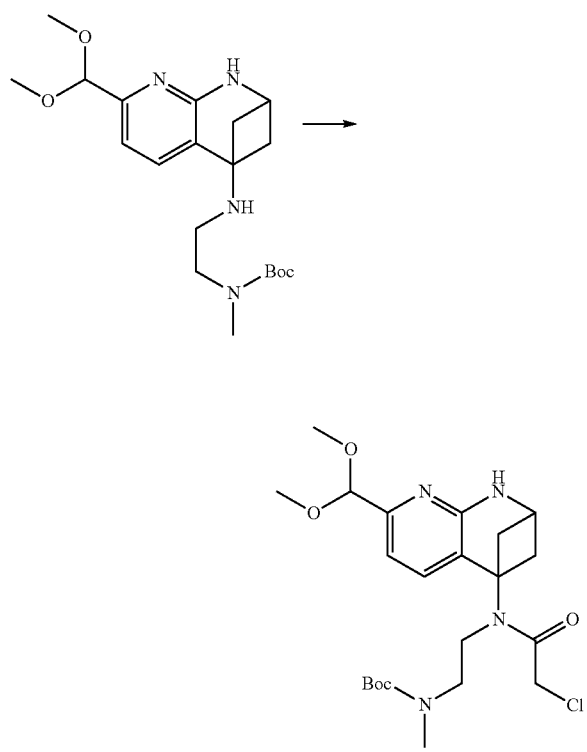

To a solution of tert-butyl N-(2-((7-(dimethoxymethyl)-1,2,3,4-tetrahydro-2,4-methylene-1,8-naphthyridin-4-yl)amino)ethyl)-N-methylcarbamate (180 mg, 0.46 mmol) in dichloromethane (5 mL) was added chloroacetic anhydride (102 mg, 0.60 mmol)) and triethyl amine (0.19 mL, 1.38 mmol) under nitrogen protection at 0° C., then continued stirring under an ice-water bath for 1 hour.

After the reaction, water (30 mL) was added to the reaction solution to quench the reaction and extracted with dichloromethane (30 mL×2). The organic phase was washed with saturated brine (30 mL), dried over anhydrous sodium sulfate, filtered with suction, and evaporated to dryness. The residue was purified by column chromatography eluting with a gradient of petroleum ether/ethyl acetate=2:1 to ethyl acetate to give tert-butyl N-(2-(2-chloro-N-(7-(dimethoxymethyl)-1,2,3,4-tetrahydro-2,4-methylene-1,8-naphthyridin-4-yl)acetamido)ethyl)-N-methylcarbamate. The relevant test data of the product are as follows:
ESI-MS: 469.2 [M+H]⁺

The Third Step: Preparation of 1-(7-(dimethoxymethyl)-1,2,3,4-tetrahydro-2,4-methylene-1,8-naphthyridin-4-yl)-4-methylpiperazin-2-one

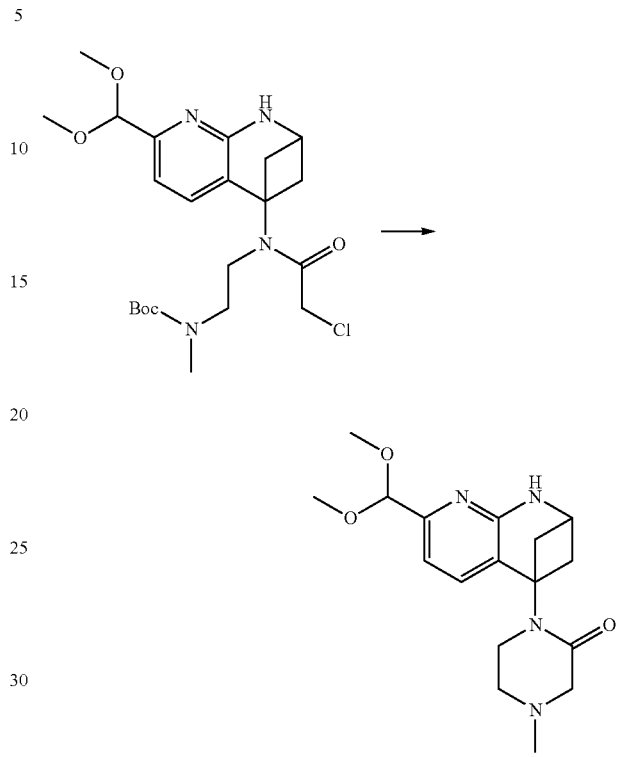

At room temperature, to a solution of tert-butyl N-(2-(2-chloro-N-(7-(dimethoxymethyl)-1,2,3,4-tetrahydro-2,4-methylene-1, 8-naphthyridin-4-yl)acetamido)ethyl)-N-methylcarbamate (100 mg, 0.21 mmol) in dichloromethane (4 mL) was added trifluoroacetic acid (0.8 mL), and stirred for 2 hours.

After the reaction was completed, the reaction solution was poured into saturated sodium carbonate solution (15 mL) and continued to stir for 5 hours. Then, water (20 mL) was added to dilute, extracted with dichloromethane (50 mL). The organic phase was washed with water (30 mL) and saturated brine (30 mL), dried with anhydrous sodium sulfate, filtered with suction, and evaporated to dryness to obtain Intermediate 44. The relevant test data of the product are as follows:
ESI-MS: 333.1 [M+H]⁺

Example 0-45

Intermediate 45: Preparation of tert-butyl 7-(dimethoxymethyl)-4-fluoro-6-formyl-3,4-dihydro-2,4-methylene-1,8-naphthyridine-1(2H)-carboxylate

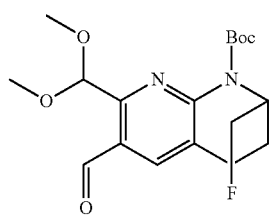 [SMILES: COC(OC)c1nc2c(cc1C=O)CCC(CF)N2C(=O)OC(C)(C)C]

The First Step: Preparation of 7-(dimethoxymethyl)-4-fluoro-6-bromo-1,2,3,4-tetrahydro-2,4-methylene-1,8-naphthyridine

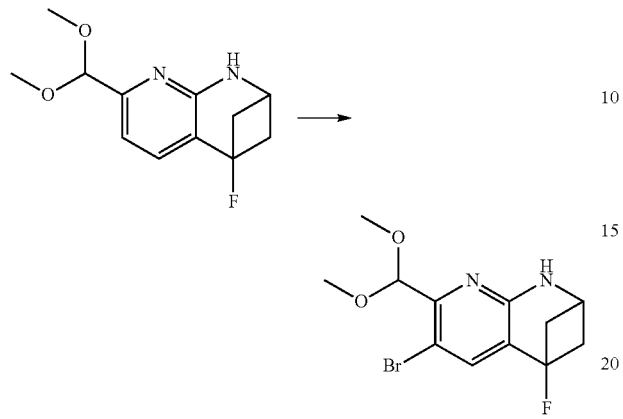

At room temperature, to 7-(dimethoxymethyl)-4-fluoro-1,2,3,4-tetrahydro-2,4-methylene-1,8-naphthyridine (Intermediate 16, 2.395 g, 10.1 mmol) in acetonitrile (40 mL) was added N-bromosuccinimide (1.900 g, 10.7 mmol), and the reaction was continued to stir for 1 hour.

Water (200 mL) was added to the reaction mixture to quench the reaction, extracted with ethyl acetate (200 mL), and the organic phase was obtained by separation. The organic phase was washed with saturated brine (200 mL), dried over anhydrous sodium sulfate, and filtered with suction, and evaporated to dryness. The residue was purified by column chromatography, eluting with a gradient of petroleum ether/ethyl acetate=2:1 and ethyl acetate/dichloromethane=5:1, and the fractions containing the product were concentrated to render 7-(dimethoxymethyl)-4-fluoro-6-bromo-1,2,3,4-tetrahydro-2,4-methylene-1,8-naphthyridine. The relevant test data of the product are as follows:

ESI-MS: 317.1 [M+H]$^+$.

The Second Step: Preparation of 7-(dimethoxymethyl)-4-fluoro-6-vinyl-1,2,3,4-tetrahydro-2,4-methylene-1,8-naphthyridine

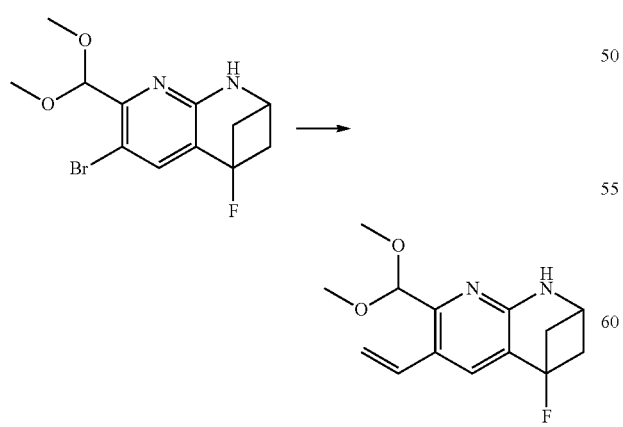

Under nitrogen protection, a mixture of 7-(dimethoxymethyl)-4-fluoro-6-bromo-1,2,3,4-tetrahydro-2,4-methylene-1,8-naphthyridine (3.017 g, 9.5 mmol), vinyl pinacol borate (2.0 mL, 11.8 mmol), Pd(dppf)Cl$_2$ (0.280 g, 0.38 mmol), potassium phosphate (4.028 g, 19.0 mmol), 1,4-dioxane (36 mL) and water (12 mL) was stirred at 100° C. for 14 h.

Then, the mixture was cooled to room temperature, diluted with water (200 mL), extracted with ethyl acetate (200 mL), and separated to obtain an organic phase. The organic phase was washed with saturated brine (200 mL), dried over anhydrous sodium sulfate, suction filtered, and evaporated to dryness. The residue was purified by column chromatography, eluting with a gradient of petroleum ether/ethyl acetate=2:1 and ethyl acetate, and the fractions containing the product were concentrated to give 7-(dimethoxymethyl)-4-fluoro-6-vinyl-1,2,3,4-tetrahydro-2,4-methylene-1,8-naphthyridine. The relevant test data of the product are as follows:

ESI-MS: 265.1 [M+H]$^+$.

The Third Step: Preparation of tert-butyl 7-(dimethoxymethyl)-4-fluoro-6-vinyl-3,4-dihydro-2,4-methylene-1,8-naphthyridine-1(2H)-carboxylate

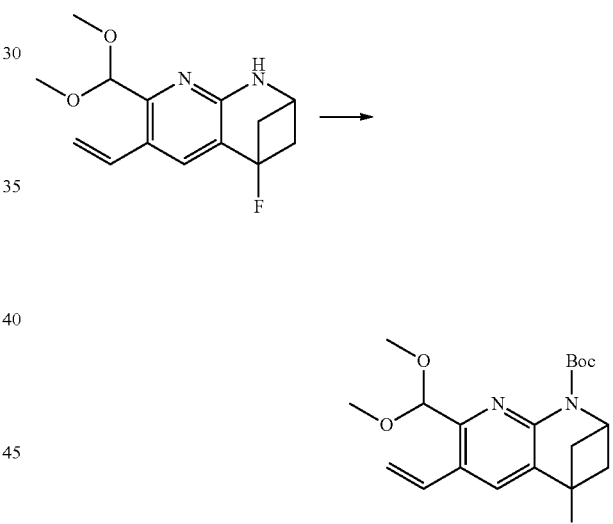

At room temperature, to a solution of 7-(dimethoxymethyl)-4-fluoro-6-vinyl-1,2,3,4-tetrahydro-2,4-methylene-1,8-naphthyridine (2.245 g, 8.5 mmol), triethylamine (7.0 mL, 50.6 mmol), 4-dimethylaminopyridine (0.250 g, 2.0 mmol) in tetrahydrofuran (40 mL) was added di-tert-butyl carbonate (6.0 mL, 26.1 mmol) and continued stirring for 3 hours.

The resulting solution was then evaporated to dryness, the residue was purified by column chromatography, eluting with petroleum ether/ethyl acetate=10:1, and the fractions containing the product were concentrated to give tert-butyl 7-(dimethoxymethyl)-4-fluoro-6-vinyl-3,4-dihydro-2,4-methylene-1,8-naphthyridine-1(2H)-carboxylate. The relevant test data of the product are as follows:

ESI-MS: 365.1 [M+H]$^+$.

The Fourth Step: Preparation of tert-butyl 7-(dimethoxymethyl)-4-fluoro-6-formyl-3,4-dihydro-2,4-methylene-1,8-naphthyridine-1(2H)-carboxylate

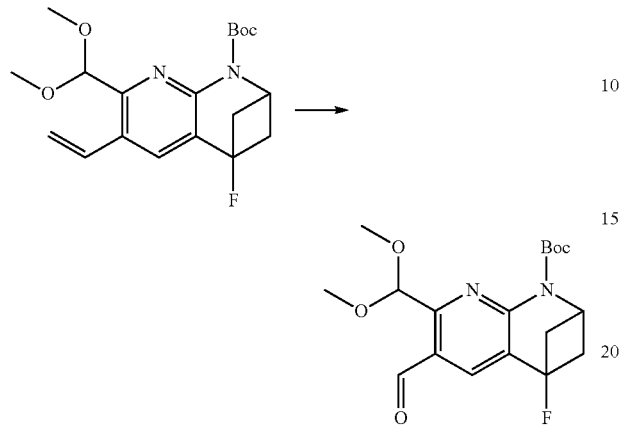

At room temperature, to a mixed solution of tert-butyl 7-(dimethoxymethyl)-4-fluoro-6-vinyl-3,4-dihydro-2,4-methylene-1,8-naphthyridine-1(2H)-carboxylate (2.905 g, 8.0 mmol), potassium osmate (60 mg, 0.16 mmol), 2,6-lutidine (2.0 mL, 17.2 mmol) in 1,4-dioxane (60 mL) and water (20 mL), sodium periodate (6.850 g, 32.0 mmol) was added, and then continued to stir for 14 hours.

Saturated sodium thiosulfate solution (200 mL) was added to the reaction mixture to quench the reaction, and extracted with ethyl acetate (200 mL), and the organic phase was obtained by separation. The organic phase was washed with 1M citric acid solution (200 mL), saturated sodium hydrogen carbonate (200 mL), and saturated brine (200 mL) sequentially, dried over anhydrous sodium sulfate, suction filtered, and evaporated to dryness. The residue was purified by column chromatography, eluting with petroleum ether/ethyl acetate=2:1, and fractions containing the product were concentrated to obtain Intermediate 45. The relevant test data of the product are as follows:

ESI-MS: 367.1 [M+H]$^+$.

Example 0-46

Intermediate 46: Preparation of tert-butyl 7-(dimethoxymethyl)-4-((tert-butyldiphenylsilyl)oxy)-6-formyl-3,4-dihydro-2,4-methylene-1,8-naphthyridine-1(2H)-carboxylate

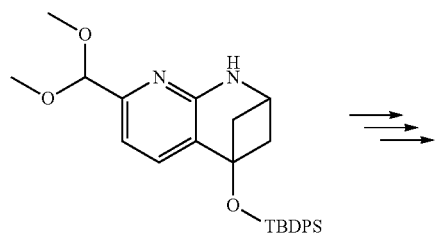

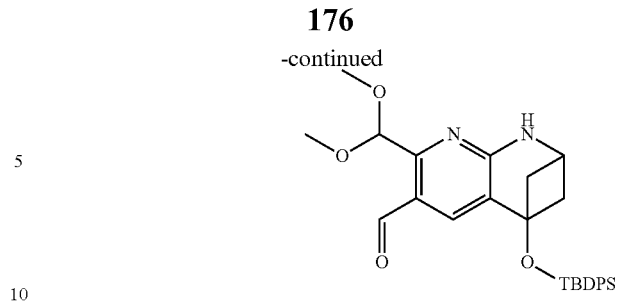

Taking Intermediate 17 as starting material, Intermediate 46 was obtained by reacting in a manner similar to the preparation of Intermediate 45. The relevant test data of Intermediate 46 are as follows:

ESI-MS: 603.1 [M+H]$^+$.

Example 0-47

Intermediate 47: Preparation of tert-butyl 7-(dimethoxymethyl)-6-formyl-3,4-dihydro-2,4-methylene-1,8-naphthyridine-1(2H)-carboxylate

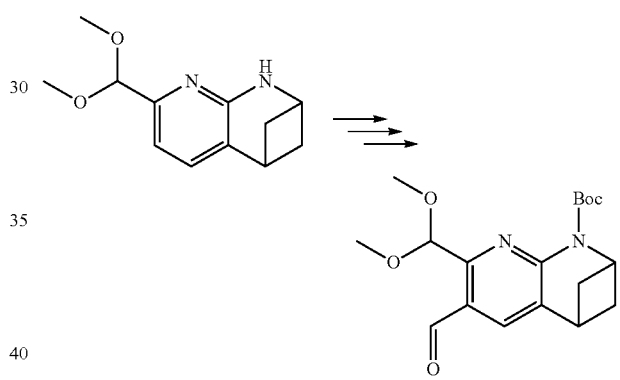

Taking Intermediate 18 as starting material, Intermediate 47 was obtained by reacting in a manner similar to the preparation of Intermediate 45. The relevant test data of Intermediate 47 are as follows:

ESI-MS: 349.1 [M+H]$^+$.

Example 0-48

Intermediate 48: Preparation of 7-(dimethoxymethyl)-4-fluoro-6-ethyl-1,2,3,4-tetrahydro-2,4-methylene-1,8-naphthyridine

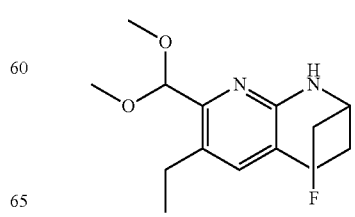

The First Step: Preparation of 7-(dimethoxym-ethyl)-4-fluoro-6-vinyl-1,2,3,4-tetrahydro-2,4-methylene-1,8-naphthyridine

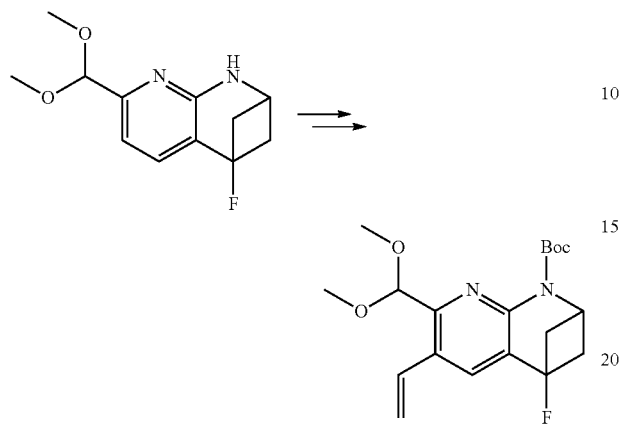

Taking Intermediate 16 as starting material, 7-(dimethoxymethyl)-4-fluoro-6-vinyl-1,2,3,4-tetrahydro-2,4-methylene-1,8-naphthyridine was obtained by reacting in a manner similar to the preparation of Intermediate 45.

The Second Step: Preparation of 7-(dimethoxym-ethyl)-4-fluoro-6-ethyl-1,2,3,4-tetrahydro-2,4-methylene-1,8-naphthyridine

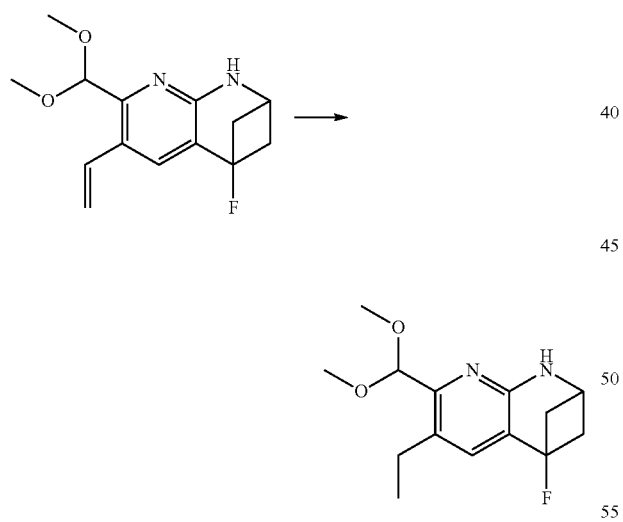

At room temperature, to a solution of 7-(dimethoxymethyl)-4-fluoro-6-vinyl-1,2,3,4-tetrahydro-2,4-methylene-1,8-naphthyridine (112 mg, 0.42 mmol) in methanol (5 mL) was added 10% palladium/carbon (15 mg), and the reaction solution was stirred under a hydrogen atmosphere of 1 atm for 2 hours. After the reaction, the insolubles were filtered off through celite by suction filtration. The filtrate was evaporated to dryness to obtain Intermediate 48. The relevant test data of the product are as follows:

ESI-MS: 267.1 [M+H]+

Example O-49

Intermediate 49: Preparation of 14(7-(dimethoxymethyl)-4-fluoro-1,2,3,4-tetrahydro-2,4-methylene-1,8-naphthyridin-6-yl)methyl)-4-methylpiperazin-2-one

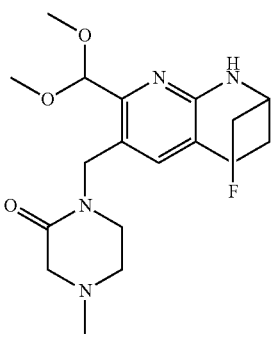 [SMILES: COC(OC)c1nc2c(cc1CN1CCN(C)CC1=O)CCC(CF)N2]

The First Step: Preparation of tert-butyl 7-(dimethoxymethyl)-4-fluoro-6-((4-methyl-2-oxopiperazin-1-yl)methyl)-3,4-dihydro-2,4-methylene-1,8-naphthyridine-1(2H)-carboxylate

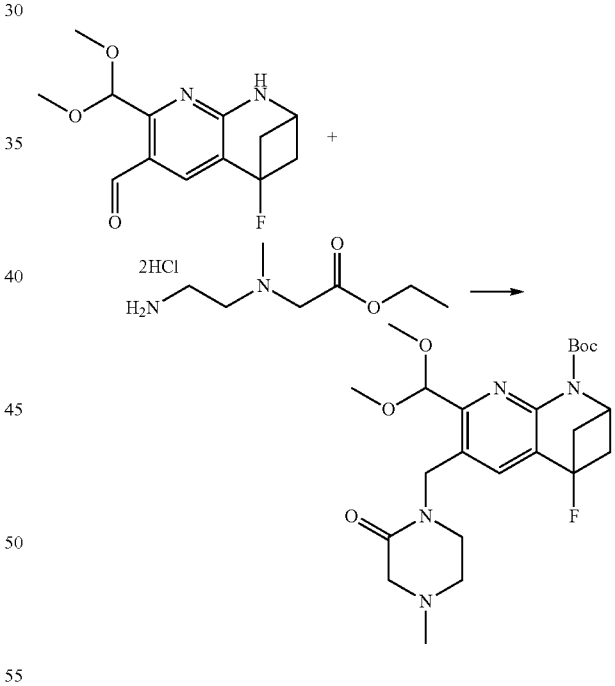

A solution of tert butyl 7-(dimethoxymethyl)-4-fluoro-6-formyl-3,4-dihydro-2,4-methylene-1,8-naphthyridine-1 (2H)-carboxylate (intermediate 45, 1.500 g, 4.1 mmol), ethyl 2-((2-aminoethyl)(methyl)amino)acetate dihydrochloride (intermediate 10, 2.500 g, 10.8 mmol) and triethylamine (7.0 ml, 50.6 mmol) in 1,2-dichloroethane (10 ml) was stirred at room temperature for 1 hour. Then, sodium triacetoxyborohydride (2.600 g, 12.3 mmol) was added to the solution and stirring was continued at room temperature for 16 hours.

Sodium bicarbonate solution (200 mL) was added to the reaction mixture to quench the reaction, extracted with dichloromethane (200 mL), and the organic phase was obtained by separation. The organic phase was washed with saturated brine (200 mL), dried over anhydrous sodium sulfate, filtered with suction, and evaporated to dryness. The residue was purified by column chromatography, eluting with a gradient of ethyl acetate and ethyl acetate/methanol=50:1, and the fractions containing the product were concentrated to give tert-butyl 7-(dimethoxymethyl)-4-fluoro-64(4-methyl-2-oxopiperazin-1-yl)methyl)-3,4-dihydro-2,4-methylene-1,8-naphthyridine-1(2H)-carboxylate. The relevant test data are as follows:

ESI-MS: 464.8 [M+H]⁺.

The Second Step: Preparation of 1-((7-(dimethoxymethyl)-4-fluoro-1,2,3,4-tetrahydro-2,4-methylene-1,8-naphthyridin-6-yl)methyl)-4-methylpiperazin-2-one

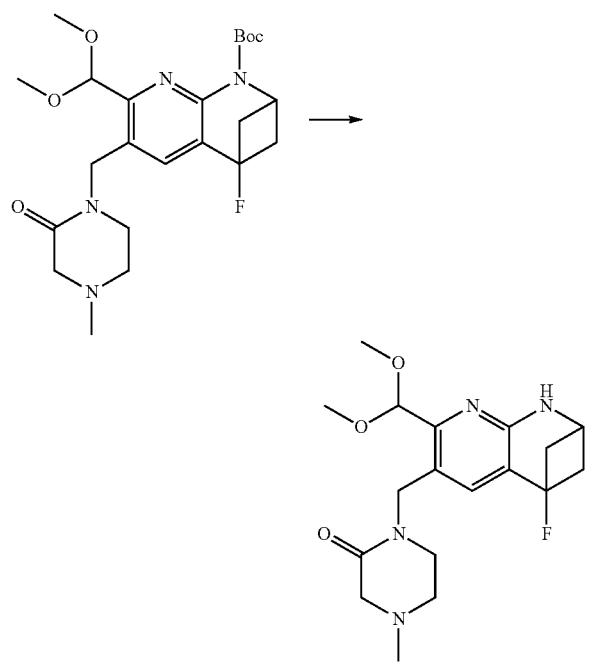

A solution of tert-butyl 7-(dimethoxymethyl)-4-fluoro-6-(4-methyl-2-oxopiperazin-1-yl)methyl)-3,4-dihydro-2,4-methylene-1,8-naphthyridine-1(2H)-carboxylate (1.232 g, 2.7 mmol), pyridine p-toluenesulfonate (1.000 g, 4.0 mmol) in methanol (15 mL) was heated to reflux for 16 hours.

The obtained solution was poured into saturated sodium carbonate solution (200 mL), extracted with dichloromethane (200 mL×2), and the organic phase was obtained by separation. The organic phase was washed with saturated brine (500 mL), dried with anhydrous sodium sulfate, filtered with suction and evaporated to dryness. The residue was purified by column chromatography, eluting with a gradient of dichloromethane/methanol=20:1 to 10:1, and the fractions containing the product were concentrated to give Intermediate 49. The relevant test data are as follows:

ESI-MS: 333.2 [M+H-MeOH]⁺.

Example 0-50

Intermediate 50: Preparation of 14(7-(dimethoxymethyl)-4-((tert-butyldiphenylsilyl)oxy)-1,2,3,4-tetrahydro-2,4-methylene-1,8-naphthyridin-6-yl)methyl)-4-methylpiperazin-2-one

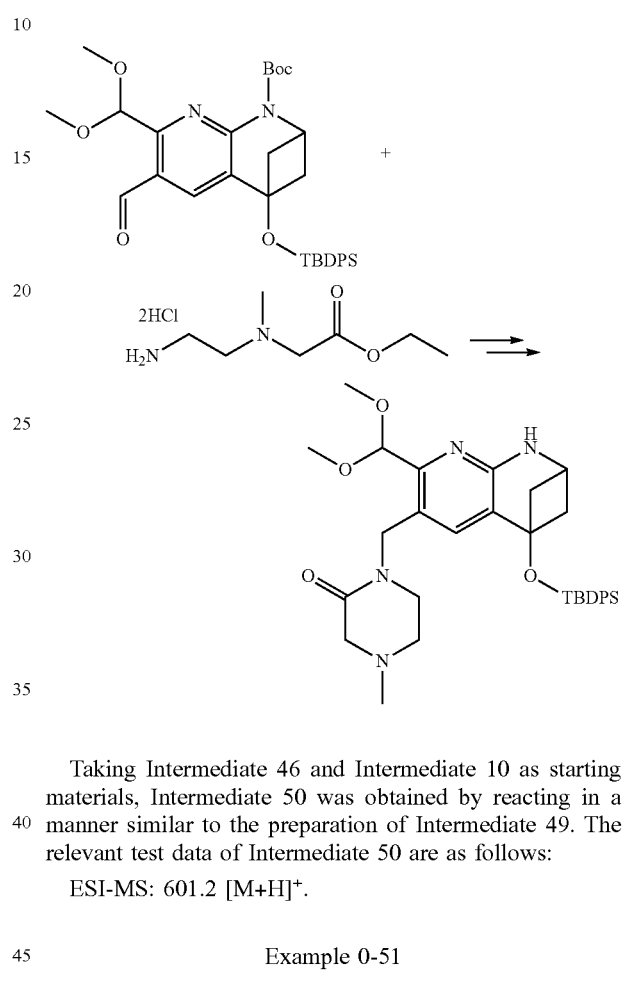

Taking Intermediate 46 and Intermediate 10 as starting materials, Intermediate 50 was obtained by reacting in a manner similar to the preparation of Intermediate 49. The relevant test data of Intermediate 50 are as follows:

ESI-MS: 601.2 [M+H]⁺.

Example 0-51

Intermediate 51: Preparation of 14(7-(dimethoxymethyl)-1,2,3,4-tetrahydro-2,4-methylene-1,8-naphthyridin-6-yl)methyl)-4-methylpiperazin-2-one

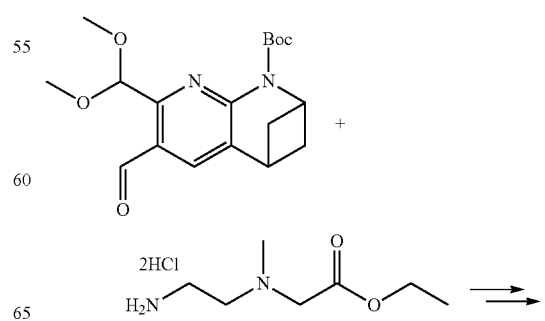

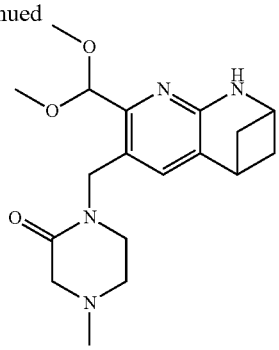

Taking Intermediate 47 and Intermediate 10 as starting materials, Intermediate 51 was obtained by reacting in a manner similar to the preparation of Intermediate 49. The relevant test data of Intermediate 51 are as follows:

ESI-MS: 347.1 [M+H]⁺.

Example O-52

Intermediate 52: Preparation of 14(7-(dimethoxymethyl)-4-fluoro-1,2,3,4-tetrahydro-2,4-methylene-1,8-naphthyridin-6-171)methyl)morpholin-3-one

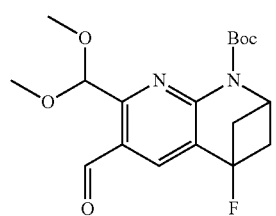

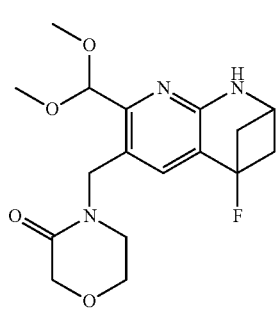

Taking Intermediate 45 and Intermediate 11 as starting materials, Intermediate 52 was obtained by reacting in a manner similar to the preparation of Intermediate 49. The relevant test data are as follows:

ESI-MS: 352.4 [M+H]⁺.

Example O-53

Intermediate 53: Preparation of 1-((7-(dimethoxymethyl)-1,2,3,4-tetrahydro-2,4-methylene-1,8-naphthyridin-6-yl)methyl)morpholin-3-one

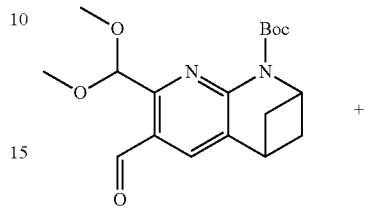

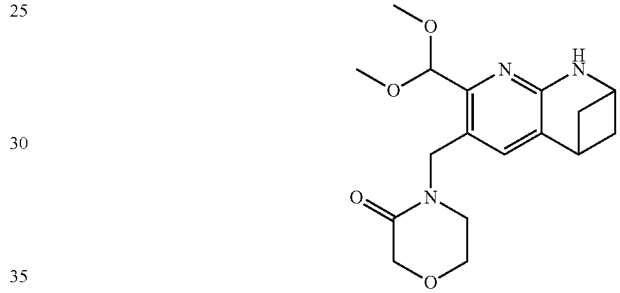

Taking Intermediate 47 and Intermediate 11 as starting materials, Intermediate 53 was obtained by reacting in a manner similar to the preparation of Intermediate 49. The relevant test data are as follows:

ESI-MS: 334.1 [M+H]⁺.

Example O-54

Intermediate 54: Preparation of 7-(dimethoxymethyl)-4-fluoro-64(4-methylpiperazin-1-yl)methyl)-1,2,3,4-tetrahydro-2,4-methylene-1,8-naphthyridine

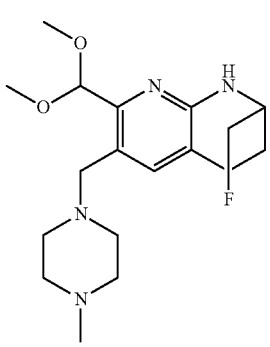 [SMILES: COC(OC)c1nc2c(cc1CN1CCN(C)CC1)CCC(CF)N2]

The First Step: Preparation of tert-butyl 7-(dimethoxymethyl)-4-fluoro-6-((4-methylpiperazin-1-yl)methyl)-3,4-dihydro-2,4-methylene-1,8-naphthyridine-1(2H)-carboxylate

The Second Step: Preparation of 7-(dimethoxymethyl)-4-fluoro-6-((4-methylpiperazin-1-yl)methyl)-1,2,3,4-tetrahydro-2,4-methylene-1,8-naphthyridine

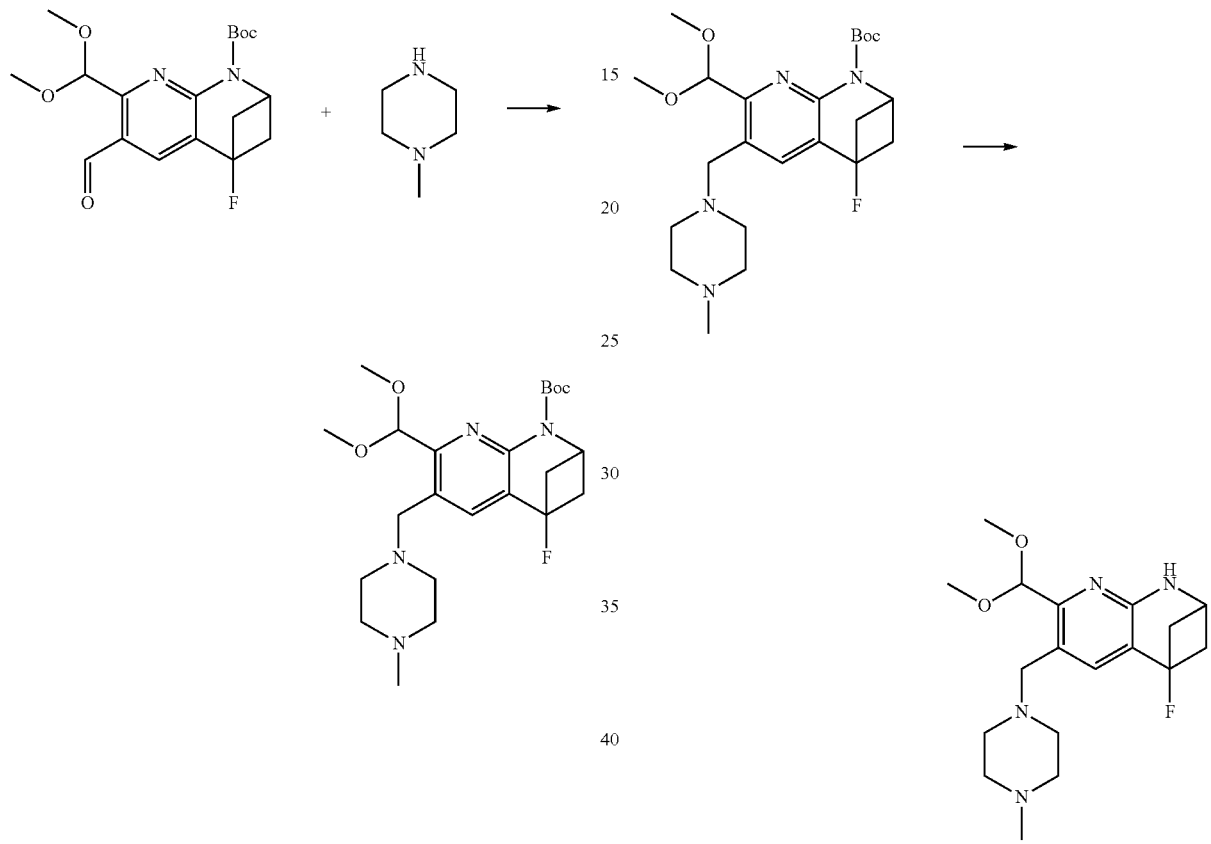

A solution of tert-butyl 7-(dimethoxymethyl)-4-fluoro-6-formyl-3,4-dihydro-2,4-methylene-1,8-naphthyridine-1(2H)-carboxylate (Intermediate 45, 100 mg, 0.27 mmol), 4-methylpiperazine (40 mg, 0.40 mmol) in 1,2-dichloroethane (1 mL) was stirred at room temperature for 1 hour. Sodium triacetoxyborohydride (90 mg, 0.42 mmol) was added and continued to stir at room temperature for 16 hours.

Sodium bicarbonate solution (200 mL) was added to the reaction mixture to quench the reaction, extracted with dichloromethane (200 mL), and the organic phase was obtained by separation. The organic phase was washed with saturated brine (200 mL), dried over anhydrous sodium sulfate, filtered with suction, and evaporated to dryness. The residue was purified by column chromatography eluting with a gradient of ethyl acetate and ethyl acetate/methanol=50:1, and the product-containing fractions were concentrated to give tert-butyl 7-(dimethoxymethyl)-4-fluoro-6-((4-methylpiperazin-1-yl)methyl)-3,4-dihydro-2,4-methylene-1,8-naphthyridine-1(2H)-carboxylate. The relevant test data are as follows:

ESI-MS: 451.2 [M+H]$^+$.

A solution of tert-butyl 7-(dimethoxymethyl)-4-fluoro-6-((4-methylpiperazin-1-yl)methyl)-3,4-dihydro-2,4-methylene-1,8-naphthyridine-1(2H)-carboxylate (112 mg, 0.25 mmol) and pyridine p-toluenesulfonate (100 mg, 0.40 mmol) in methanol (5 mL) was heated to reflux for 3 h.

The obtained solution was poured into saturated sodium carbonate solution (200 mL), extracted with dichloromethane (200 mL×2), and the organic phase was obtained by separation. The organic phase was washed with saturated brine (500 mL), dried over anhydrous sodium sulfate, filtered with suction and evaporated to dryness. The residue was purified by column chromatography eluting with a gradient of dichloromethane/methanol=20:1 to 10:1 and the fractions containing the product were concentrated to give Intermediate 54. The relevant test data are as follows:

ESI-MS: 351.2 [M+H]$^+$.

Example 0-55

Intermediate 55: Preparation of 34(7-(dimethoxymethyl)-4-fluoro-1,2,3,4-tetrahydro-2,4-methylene-1,8-naphthyridin-6-yl)methyl)-1,3-oxazepan-2-one

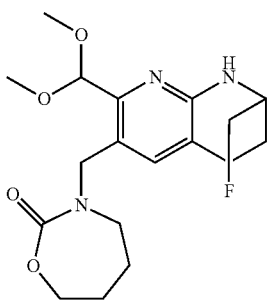 [SMILES: COC(OC)c1nc2c(cc1CN1CCCCOC1=O)CCC(CF)N2]

The First Step: Preparation of tert-butyl 7-(dimethoxymethyl)-4-fluoro-6-(((4-hydroxybutyl)amino)methyl)-3,4-dihydro-2,4-methylene-1,8-naphthyridine-1(2H)-carboxylate

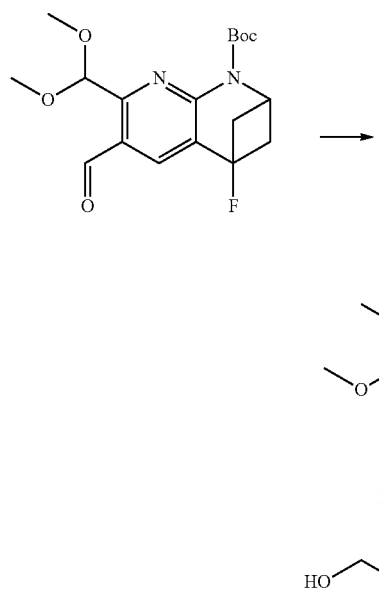

A solution of tert-butyl 7-(dimethoxymethyl)-4-fluoro-6-formyl-3,4-dihydro-2,4-methylene-1,8-naphthyridine-1(2H)-carboxylate (Intermediate 45, 150 mg, 0.41 mmol), 4-amino-1-butanol (65 mg, 0.73 mmol) in 1,2-dichloroethane (3 mL) was stirred at room temperature for 1 hour. To the solution was added sodium triacetoxyborohydride (215 mg, 1.01 mmol) and the reaction mixture was continued to stir at room temperature for 16 hours.

Sodium bicarbonate solution (200 mL) was added to the reaction mixture to quench the reaction, extracted with dichloromethane (200 mL), and the organic phase was obtained by separation. The organic phase was washed with saturated brine (200 mL), dried over anhydrous sodium sulfate, filtered with suction, and evaporated to dryness. The residue was purified by column chromatography, eluting with a gradient of dichloromethane and dichloromethane/methanol=10:1, and the product-containing fractions were concentrated to give tert-butyl 7-(dimethoxymethyl)-4-fluoro-6-(((4-hydroxybutyl)amino)methyl)-3,4-dihydro-2,4-methylene-1,8-naphthyridine-1(2H)-carboxylate. The relevant test data are as follows:

ESI-MS: 440.2 [M+H]$^+$.

The Second Step: Preparation of tert-butyl 7-(dimethoxymethyl)-4-fluoro-64(2-oxo-1,3-oxazepan-3-yl)methyl)-3,4-dihydro-2,4-methylene-1,8-naphthyridine-1(2H)-carboxylate

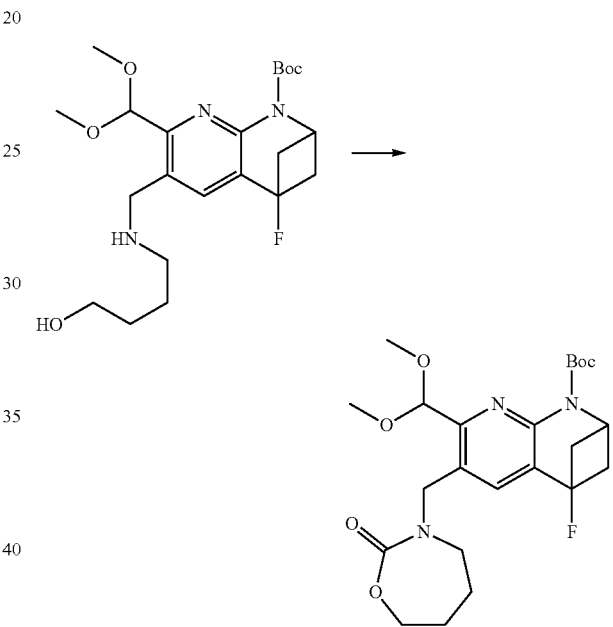

To tert-butyl 7-(dimethoxymethyl)-4-fluoro-64(4-hydroxybutyl)amino)methyl)-3,4-dihydro-2,4-methylene-1,8-naphthyridine-1(2H)-carboxylate (147 mg, 0.33 mmol) and bis(trichloromethyl)carbonate (40 mg, 0.13 mmol) in 1,2-dichloroethane (5 mL) was added dropwise triethylamine (0.2 mL, 1.45 mmol) and stirred at room temperature for 1 hour. Then the reaction mixture was heated to 80° C. for reacting for 5 hours.

Saturated sodium bicarbonate solution (50 mL) was added to the reaction mixture to quench the reaction, extracted with dichloromethane (50 mL), and the organic phase was obtained by separation. The organic phase was washed with saturated brine (50 mL), dried over anhydrous sodium sulfate, filtered with suction, and evaporated to dryness. The residue was purified by column chromatography, eluting with petroleum ether/ethyl acetate=1:1, and the product-containing fractions were concentrated to give tert-butyl 7-(dimethoxy methyl)-4-fluoro-6-((2-oxo-1,3-oxazepan-3-yl)methyl)-3,4-dihydro-2,4-methylene-1,8-naphthyridine-1(2H)-carboxylate. The relevant test data are as follows.

ESI-MS: 466.2 [M+H]$^+$.

The Third Step: Preparation of 34(7-(dimethoxymethyl)-4-fluoro-1,2,3,4-tetrahydro-2,4-methylene-1,8-naphthyridin-6-yl)methyl)-1,3-oxazepan-2-one

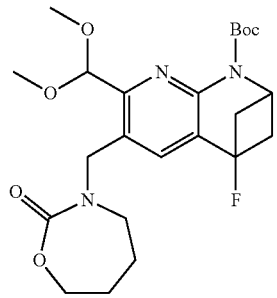

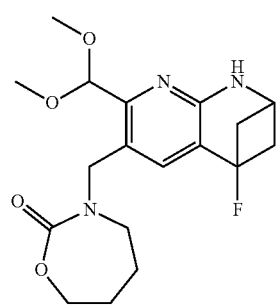

A solution of tert-butyl 7-(dimethoxymethyl)-4-fluoro-64(2-oxo-1,3-oxazepan-3-yl)methyl)-3,4-dihydro-2,4-methylene-1,8-naphthyridine-1(2H)-carboxylate (59 mg, 0.13 mmol), pyridine p-toluenesulfonate (50 mg, 0.20 mmol) in methanol (5 mL) was heated to reflux for 3 hours.

The obtained solution was poured into saturated sodium carbonate solution (100 mL), extracted with dichloromethane (100 mL), and the organic phase was obtained by separation. The organic phase was washed with saturated brine (100 mL), dried over anhydrous sodium sulfate, filtered with suction and evaporated to dryness. The residue was purified by column chromatography, eluting with a gradient of petroleum ether/ethyl acetate=1:1 to ethyl acetate, and the fractions containing the product were concentrated to give Intermediate 55. The test data are as follows:

ESI-MS: 334.2 [M+H-MeOH]$^+$.

Example 0-56

Intermediate 56: Preparation of 34(7-(dimethoxymethyl)-1,2,3,4-tetrahydro-2,4-methylene-1,8-naphthyridin-6-yl)methyl)-1,3-oxazepan-2-one

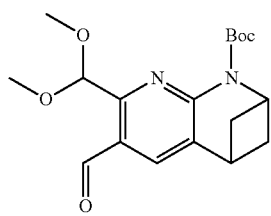

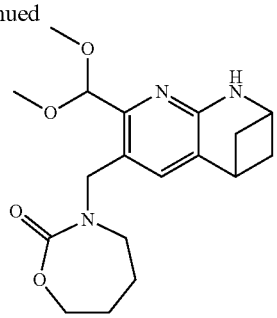

Taking Intermediate 47 as starting material, Intermediate 56 was obtained by reacting in a manner similar to the preparation of Intermediate 55. The relevant test data are as follows:

ESI-MS: 348.1 [M+H]$^+$.

Example 0-57

Intermediate 57: Preparation of N-((7-(dimethoxymethyl)-4-fluoro-1,2,3,4-tetrahydro-2,4-methylene-1,8-naphthyridin-6-yl)methyl)-2-(dimethylamino)-N-methylacetamide

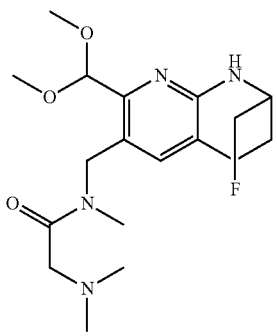 [SMILES: COC(OC)c1nc2c(cc1CN(C)C(=O)CN(C)C)CCC(CF)N2]

The First Step: Preparation of tert-butyl 7-(dimethoxymethyl)-4-fluoro-6-((methylamino)methyl)-3,4-dihydro-2,4-methylene-1,8-naphthyridine-1(2H)-carboxylate

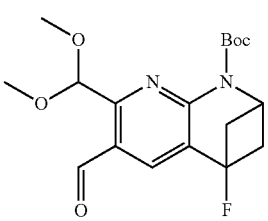

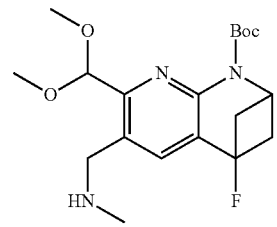

A solution of tert-butyl 7-(dimethoxymethyl)-4-fluoro-6-formyl-3,4-dihydro-2,4-methylene-1,8-naphthyridine-1(2H)-carboxylate (Intermediate 45, 150 mg, 0.41 mmol), methylamine (32% in ethanol, 90 mg, 0.93 mmol) and methylamine hydrochloride (60 mg, 0.89 mmol) in methanol (3 mL) was stirred at room temperature for 2 h. Then sodium cyanoborohydride (105 mg, 1.66 mmol) was added to the solution, and was then heated to 70° C. and stirred for 2 hours.

After cooling to room temperature, saturated sodium bicarbonate solution (50 mL) was added to the reaction mixture to quench the reaction, extracted with dichloromethane (50 mL), the organic phase was obtained by separation. The organic phase was washed with saturated brine (50 mL), dried over anhydrous sodium sulfate, filtered with suction and evaporated to dryness. The residue was purified by column chromatography, eluting with a gradient of dichloromethane and dichloromethane/methanol=10:1, and the fractions containing the product were concentrated to give tert-butyl 7-(dimethoxymethyl)-4-fluoro-6-((methylamino)methyl)-3,4-dihydro-2,4-methylene-1,8-naphthyridine-1(2H)-carboxylate. The relevant test data are as follows:

ESI-MS: 382.1 [M+H]$^+$.

The Second Step: Preparation of tert-butyl 7-(dimethoxymethyl)-4-fluoro-6-((2-(dimethylamino)-N-methylacetamido)methyl)-3,4-dihydro-2,4-methylene-1,8-naphthyridine-1(2H)-carboxylate

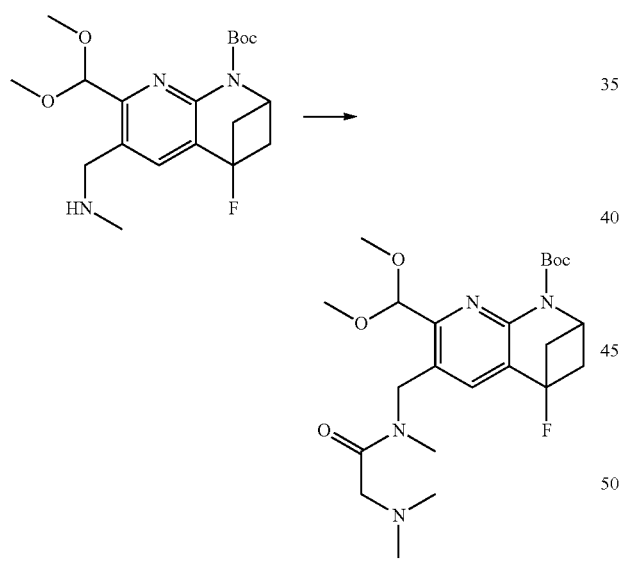

To a solution of tert-butyl 7-(dimethoxymethyl)-4-fluoro-6-((methylamino)methyl)-3,4-dihydro-2,4-methylene-1,8-naphthyridine-1(2H)-carboxylate (100 mg, 0.26 mmol) and triethylamine (0.2 mL, 1.45 mmol) in dichloromethane (2 mL) was added 2-(dimethylamino)acetyl chloride (83 mg, 0.68 mmol) in dichloromethane (1 mL) at 0° C. and stirred at room temperature for 2 hours.

Saturated sodium bicarbonate solution (50 mL) was added to the reaction mixture to quench the reaction, extracted with dichloromethane (50 mL), and the organic phase was obtained by separation. The organic phase was washed with saturated brine (50 mL), dried over anhydrous sodium sulfate, filtered with suction, and evaporated to dryness. The residue was purified by column chromatography, eluting with dichloromethane/methanol=10:1, and the product-containing fractions were concentrated to give tert-butyl 7-(dimethoxymethyl) yl)-4-fluoro-6-((2-(dimethylamino)-N-methylacetamido)methyl)-3,4-dihydro-2,4-methylene-1,8-naphthyridine-1(2H)-carboxylate. The relevant test data are as follows:

ESI-MS: 467.2 [M+H]$^+$.

The Third Step: Preparation of N-((7-(dimethoxymethyl)-4-fluoro-1,2,3,4-tetrahydro-2,4-methylene-1,8-naphthyridin-6-yl)methyl)-2-(dimethylamino)-N-methylacetamide

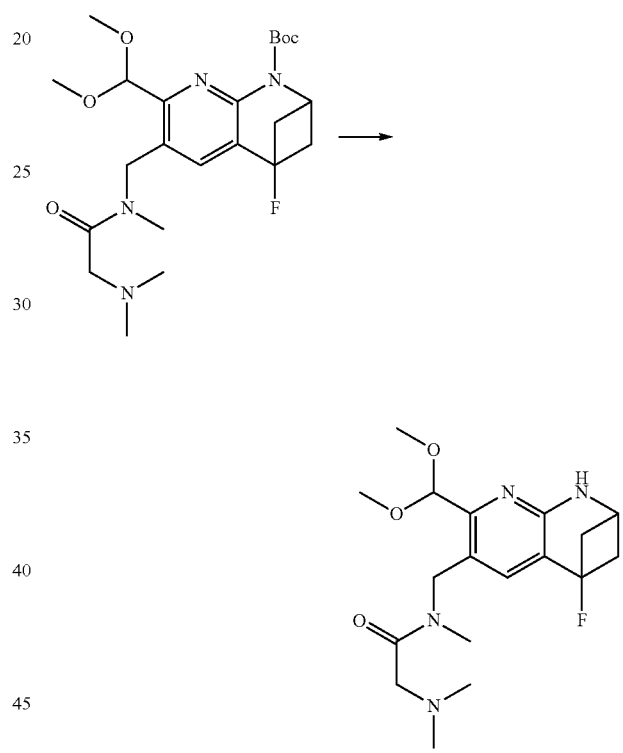

A solution of tert-butyl 7-(dimethoxymethyl)-4-fluoro-6-((2-(dimethylamino)-N-methylacetamido)methyl)-3,4-dihydro-2,4-methylene-1,8-naphthyridine-1(2H)-carboxylate (113 mg, 0.24 mmol) and pyridine p-toluenesulfonate (90 mg, 0.36 mmol) in methanol (5 mL) was heated to reflux for 3 hours.

The obtained solution was poured into saturated sodium carbonate solution (100 mL), extracted with dichloromethane (100 mL), and the organic phase was obtained by separation. The organic phase was washed with saturated brine (100 mL), and then dried over anhydrous sodium sulfate, suction filtration and evaporation to dryness. The residue was purified by column chromatography, eluted with dichloromethane/methanol=10:1, and the fraction containing the product was concentrated to obtain Intermediate 57, The relevant test data of the product are as follows:

ESI-MS: 335.2 [M+H-MeOH]$^+$.

Example 0-58

Intermediate 58: Preparation of N-((7-(dimethoxymethyl)-4-fluoro-1,2,3,4-tetrahydro-2,4-methylene-1,8-naphthyridin-6-yl)methyl)-N-methylacetamide

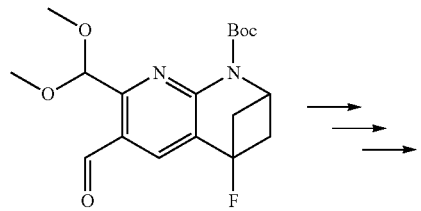

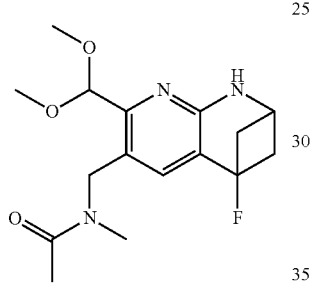

Taking Intermediate 45 as starting material, Intermediate 58 was obtained by reacting in a manner similar to the preparation of Intermediate 57. The relevant test data are as follows:

ESI-MS: 292.1 [M+H-MeOH]⁺.

Example 0-59

Intermediate 59: Preparation of 6-amino-4-(cis-(2-methoxycyclopentyl)amino)nicotinonitrile

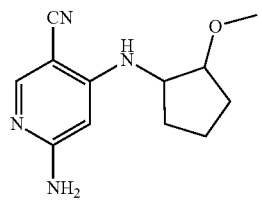 [SMILES: COC1CCCC1Nc1cc(N)ncc1C#N]

Taking cis-2-aminocyclopentanol hydrochloride as starting materials, Intermediate 59 was obtained by reacting in a manner similar to the preparation of Intermediate 5. The relevant test data are as follows:

ESI-MS: 233.1 [M+H]⁺.

Example 1

Compound 1: Preparation of N-(5-cyano-4-((2-methoxyethyl)amino)pyridin-2-yl)-4-fluoro-7-formyl-3,4-dihydro-2,4-methylene-1,8-naphthyridine-1(2H)-carboxamide

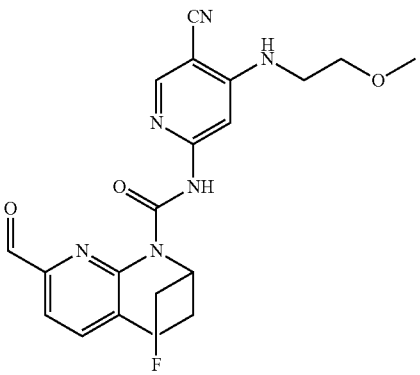 [SMILES: COCCNc1cc(NC(=O)N2c3nc(C=O)ccc3CCC2CF)ncc1C#N]

The First Step: Preparation of N-(5-cyano-4-((2-methoxyethyl)amino)pyridin-2-yl)-7-(dimethoxymethyl)-4-fluoro-3,4-dihydro-2,4-methylene-1,8-naphthyridine-1(2H)-carboxamide To a solution of bis(1H-1,2,4-triazol-1-yl)methanone (340 mg, 2.07 mmol) in N,N-dimethylformamide (3.0 mL) was added 6-amino-4-((2-methoxyethyl)amino)nicotinonitrile (Intermediate 2, 400 mg, 2.07 mmol) at 0° C. and stirred at room temperature for 2 hours. To this solution were then added a solution of 7-(dimethoxymethyl)-4-fluoro-1,2,3,4-tetrahydro-2,4-methylene-1,8-naphthyridine (Intermediate 16, 200 mg, 0.84 mmol) in N,N-dimethylformamide (2 mL) and triethylamine (0.5 mL, 3.61 mmol), and the reaction solution was continued to stir for 16 hours.

Water (50 mL) was added to the reaction mixture to quench the reaction, extracted with dichloromethane (50 mL), and the organic phase was obtained by separation. The organic phase was washed with saturated brine (50 mL), dried over anhydrous sodium sulfate, filtered with suction, and evaporated to dryness. The residue was purified by column chromatography, eluting with petroleum ether/ethyl acetate=1:1, and the fractions containing the product were concentrated to give N-(5-cyano-4-(2-methoxyethyl)amino)pyridin-2-yl)-7-(dimethoxymethyl)-4-fluoro-3,4-dihydro-2,4-methylene-1,8-naphthyridine-1(2H)-carboxamide. The relevant test data are as follows:

ESI-MS: 457.2 [M+H]$^+$.

The Second Step: Preparation of N-(5-cyano-4-((2-methoxyethyl)amino)pyridin-2-yl)-4-fluoro-7-formyl-3,4-dihydro-2,4-methylene-1,8-naphthyridine-1(2H)-carboxamide

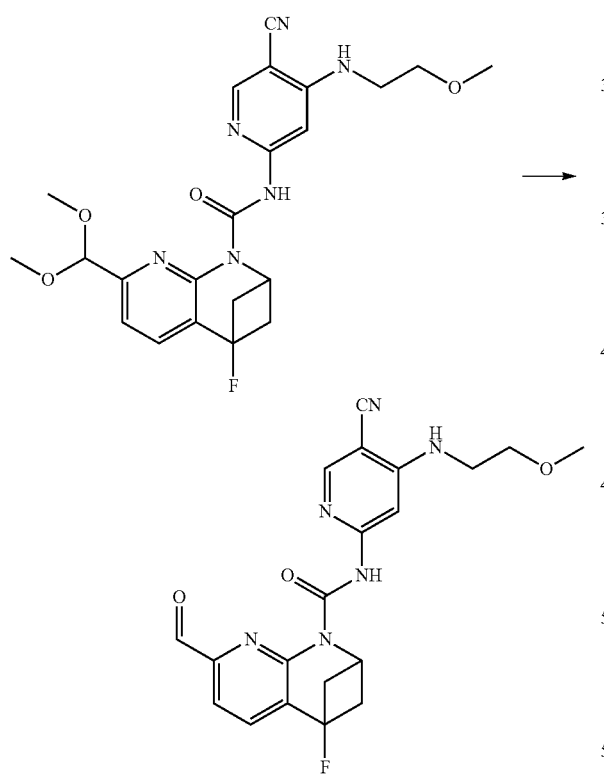

To a solution of N-(5-cyano-4-(2-methoxyethyl)amino)pyridin-2-yl)-7-(dimethoxymethyl)-4-fluoro-3,4-dihydro-2,4-methylene-1,8-naphthyridine-1(2H)-carboxamide (106 mg, 0.232 mmol) in tetrahydrofuran (4 mL) was added hydrochloric acid (3M, 4 mL) at room temperature, and continued to stir the reaction solution for 2 hours.

Saturated sodium bicarbonate solution (50 mL) was added to the reaction mixture to quench the reaction, extracted with ethyl acetate (50 mL), and the organic phase was obtained by separation. The organic phase was washed with saturated brine (50 mL), dried over anhydrous sodium sulfate, filtered with suction, and evaporated to dryness. The residue was purified by column chromatography, eluting with petroleum ether/ethyl acetate=1:1, and the fractions containing the product were concentrated to give Compound 1. The relevant test data are as follows:

$^1$H NMR (DMSO-d$_6$, 400 MHz), δ 12.91 (s, 1H), 9.95 (s, 1H), 8.30 (s, 1H), 8.02 (d, J=7.6 Hz, 1H), 7.78 (d, J=7.6 Hz, 1H), 7.52 (s, 1H), 7.03 (t, J=5.6 Hz, 1H), 5.60 (dt, J=20.4 Hz, J=6.8 Hz, 1H), 3.53 (t, J=5.8 Hz, 2H), 3.39 (dd, J=11.4 Hz, 5.8 Hz, 2H), 3.29 (s, 3H), 2.81-2.86 (m, 2H), 2.00-2.02 (m, 2H).

ESI-MS: 411.2 [M+H]$^+$.

Example 2

Compound 2: Preparation of N-(5-cyano-44(2-methoxyethyl)amino)pyridin-2-yl)-7-formyl-4-hydroxy-3,4-dihydro-2,4-methylene-1,8-naphthyridine-1(2H)-carboxamide

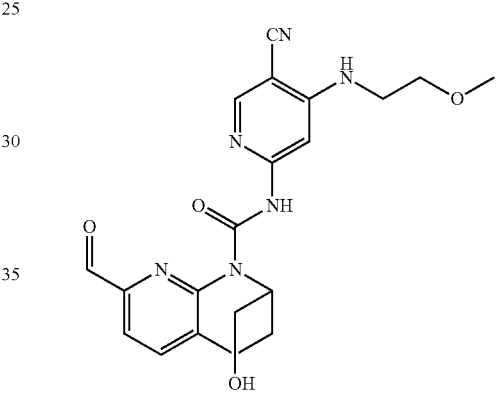

The First Step: Preparation of N-(5-cyano-4-((2-methoxyethyl)amino)pyridin-2-yl)-7-(dimethoxymethyl)-4-(((tert-butyldiphenyl)silyl)oxy)-3,4-dihydro-2,4-methylene-1,8-naphthyridine-1(2H)-carboxamide

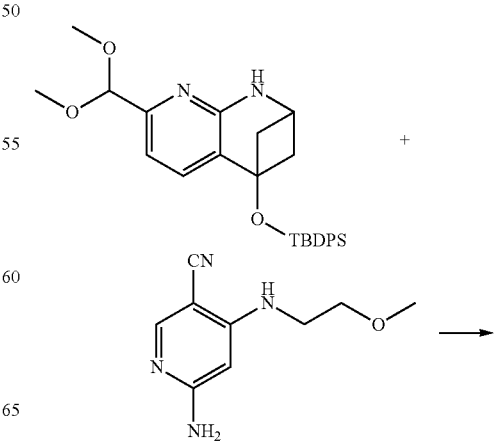

-continued

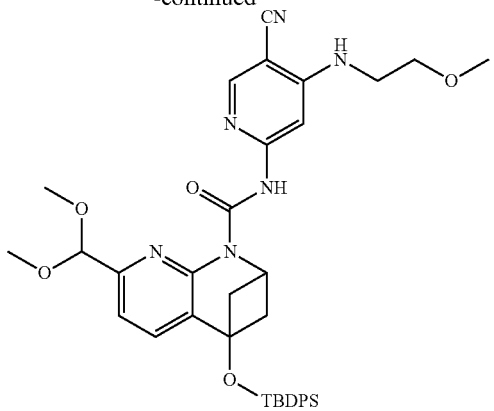

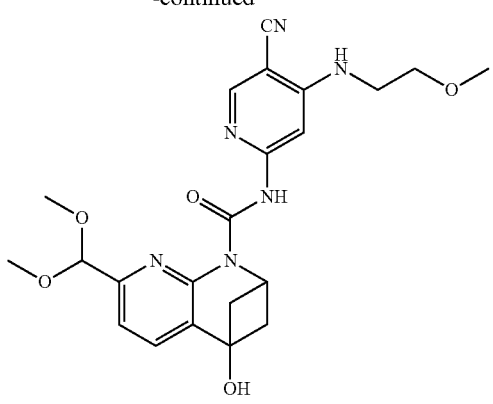

To a solution of bis(1H-1,2,4-triazol-1-yl)methanone (170 mg, 1.04 mmol) in N,N-dimethylformamide (3 mL) was added 6-amino-4-((2-methoxyethyl)amino)nicotinonitrile (Intermediate 2, 200 mg, 1.04 mmol) at 0° C. and stirred at room temperature for 2 hours. To this solution were then added 7-(dimethoxymethyl))-4-((tert-butyldiphenylsilyl) oxy)-1,2,3,4-tetrahydro-2,4-methylene-1,8-naphthyridine (Intermediate 17, 200 mg, 0.42 mmol) in N,N-dimethylformamide (2 mL) and triethylamine (0.5 mL, 3.61 mmol), and the reaction solution was continued to stir for 16 hours.

Water (50 mL) was added to the reaction mixture to quench the reaction, extracted with dichloromethane (50 mL), and the organic phase was obtained by separation. The organic phase was washed with saturated brine (50 mL), dried over anhydrous sodium sulfate, and filtered with suction, and evaporated to dryness. The residue was purified by column chromatography, eluting with petroleum ether/ ethyl acetate=2:1, and the fractions containing the product were concentrated to give N-(5-cyano-4-(2-methoxyethyl) amino)pyridin-2-yl)-7-(dimethoxymethyl)-4-((tert-butyldiphenylsilyl)oxy)-3,4-dihydro-2,4-methylene-1,8-naphthyridine-1(2H)-carboxamide. The relevant test data are as follows:

ESI-MS: 693.3 [M+H]+.

The Second Step: Preparation of N-(5-cyano-4-((2-methoxyethyl)amino)pyridin-2-yl)-7-(dimethoxymethyl)-4-hydroxy-3,4-dihydro-2,4-methylene-1,8-naphthyridine-1(2H)-carboxamide At 0° C., to a solution of N-(5-cyano-4-((2-methoxyethyl) amino)pyridin-2-yl)-7-(dimethoxymethyl)-4-((tert-butyldiphenyl silyl)oxy)-3,4-dihydro-2,4-methylene-1,8-naphthyridine-1(2H)-carboxamide (60 mg, 0.09 mmol) in tetrahydrofuran (4 mL) was added dropwise tetrabutylammonium fluoride in tetrahydrofuran (1 M, 0.18 mL, 0.18 mmol), and the reaction solution was continued to stir at room temperature for 1 hour.

Water (50 mL) was added to the reaction mixture to quench the reaction, extracted with ethyl acetate (50 mL), and the organic phase was obtained by separation. The organic phase was washed with saturated brine (50 mL), dried over anhydrous sodium sulfate, filtered with suction, and evaporated to dryness. The residue was purified by column chromatography, eluting with dichloromethane/ methanol=10:1, and the fractions containing the product were concentrated to give N-(5-cyano-((2-methoxyethyl) amino)pyridin-2-yl)-7-(dimethoxymethyl)-4-hydroxy-3,4-dihydro-2,4-methylene-1,8-naphthyridine-1(2H)-carboxamide. The relevant test data are as follows:

ESI-MS: 455.2 [M+H]+.

The Third Step: Preparation of N-(5-cyano-4-((2-methoxyethyl)amino)pyridin-2-yl)-7-formyl-4-hydroxy-3,4-dihydro-2,4-methylene-1,8-naphthyridine-1(2H)-carboxamide

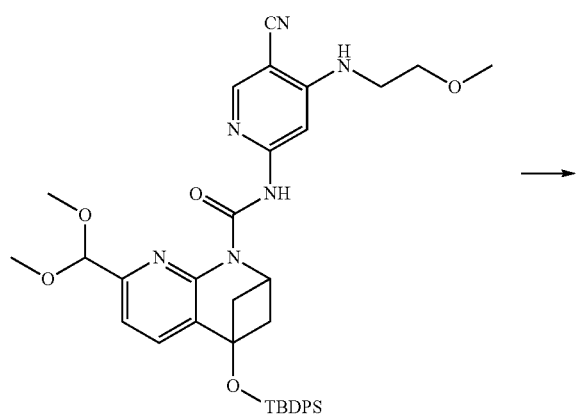

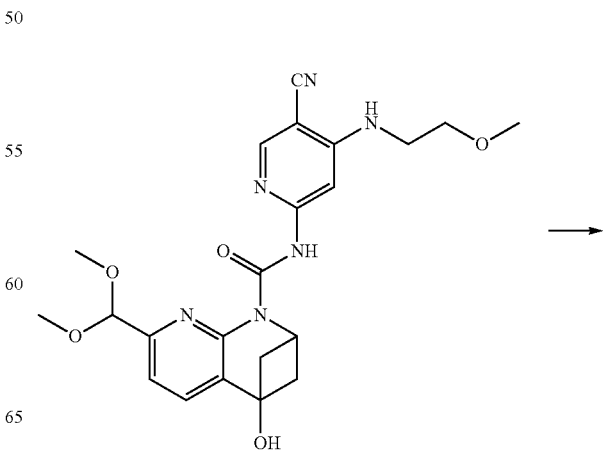

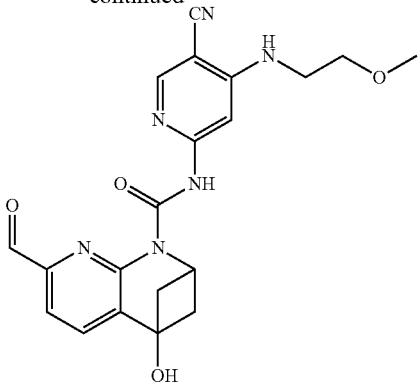

At room temperature, to N-(5-cyano-4-((2-methoxyethyl)amino)pyridin-2-yl)-7-(dimethoxymethyl)-4-hydroxy-3,4-dihydro-2,4-methylene-1,8-naphthyridine-1(2H)-carboxamide (32 mg, 0.07 mmol) in tetrahydrofuran (2 mL) was added hydrochloric acid (3 M, 2 mL), and the reaction solution was continued to stir for 2 hours.

Saturated sodium bicarbonate solution (50 mL) was added to the reaction mixture to quench the reaction, extracted with ethyl acetate (50 mL), and the organic phase was obtained by separation. The organic phase was washed with saturated brine (50 mL), dried over anhydrous sodium sulfate, filtered with suction, and evaporated to dryness. The residue was purified by column chromatography, eluting with dichloromethane/methanol=10:1, and the fraction containing the product was concentrated to obtain Compound 2. The relevant test data of the product are as follows:

$^1$H NMR (DMSO-d$_6$, 400 MHz), δ 13.12 (s, 1H), 9.94 (s, 1H), 8.29 (s, 1H), 8.01 (d, J=7.2 Hz, 1H), 7.75 (d, J=7.6 Hz, 1H), 7.54 (s, 1H), 7.00 (t, J=5.6 Hz, 1H), 6.88 (s, 1H), 5.49 (t, J=6.0 Hz, 1H), 3.53 (t, J=5.8 Hz, 2H), 3.39 (dd, J=11.4 Hz, 5.8 Hz, 2H), 3.29 (s, 3H), 2.45-2.47 (m, 2H), 1.72-1.74 (m, 2H).

ESI-MS: 409.2 [M+H]$^+$.

Example 3

Compound 3: Preparation of N-(5-cyano-44(2-methoxyethyl)amino)pyridin-2-yl)-7-formyl-4-methoxy-3,4-dihydro-2,4-methylene-1,8-naphthyridine-1(2H)-carboxamide

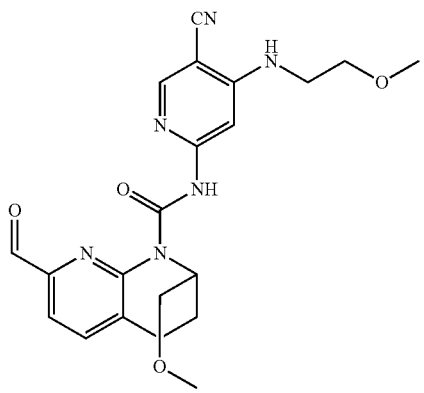 [SMILES: COCCNc1cc(NC(=O)N2c3nc(C=O)ccc3CCC2COC)ncc1C#N]

Taking Intermediate 21 and Intermediate 2 as starting materials, Compound 3 was obtained by reacting in a manner similar to the preparation of Compound 1 of example 1. The relevant test data are as follows:

$^1$H NMR (DMSO-d$_6$, 400 MHz), δ 13.06 (s, 1H), 9.95 (s, 1H), 8.29 (s, 1H), 7.98 (d, J=7.2 Hz, 1H), 7.75 (d, J=7.6 Hz, 1H), 7.54 (s, 1H), 7.00 (t, J=5.8 Hz, 1H), 5.50 (t, J=6.4 Hz, 1H), 3.53 (t, J=5.8 Hz, 2H), 3.47 (s, 3H), 3.40 (dd, J=11.6 Hz, 5.6 Hz, 2H), 3.29 (s, 3H), 2.79-2.83 (m, 2H), 1.60-1.63 (m, 2H).

ESI-MS: 423.2 [M+H]$^+$.

Example 4

Compound 4: Preparation of N-(5-cyano-44(2-methoxyethyl)amino)pyridin-2-yl)-4-fluoro-7-formyl-64(4-methyl-2-oxo piperazin-1-yl)methyl)-3,4-dihydro-2,4-methylene-1,8-naphthyridine-1(2H)-carboxamide

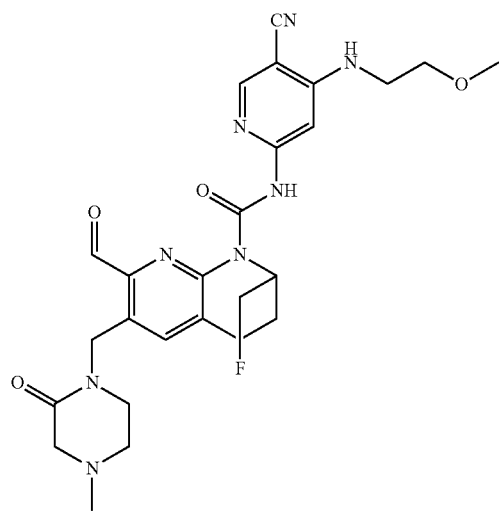 [SMILES: COCCNc1cc(NC(=O)N2c3nc(C=O)c(CN4CCN(C)CC4=O)cc3CCC2CF)ncc1C#N]

The First Step: Preparation of N-(5-cyano-44(2-methoxyethyl)amino)pyridin-2-yl)-7-(dimethoxymethyl)-4-fluoro-6-((4-methyl-2-oxopiperazin-1-yl)methyl)-3,4-dihydro-2,4-methylene-1,8-naphthyridine-1(2H)-carboxamide

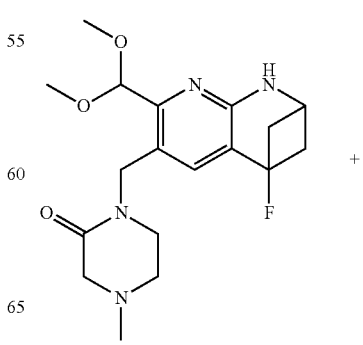

-continued

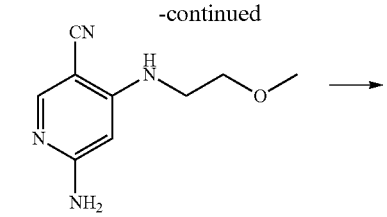

The Second Step: Preparation of N-(5-cyano-4-((2-methoxyethyl)amino)pyridin-2-yl)-4-fluoro-7-formyl-6-((4-methyl-2-oxo piperazin-1-yl)methyl)-3,4-dihydro-2,4-methylene-1,8-naphthyridine-1(2H)-carboxamide

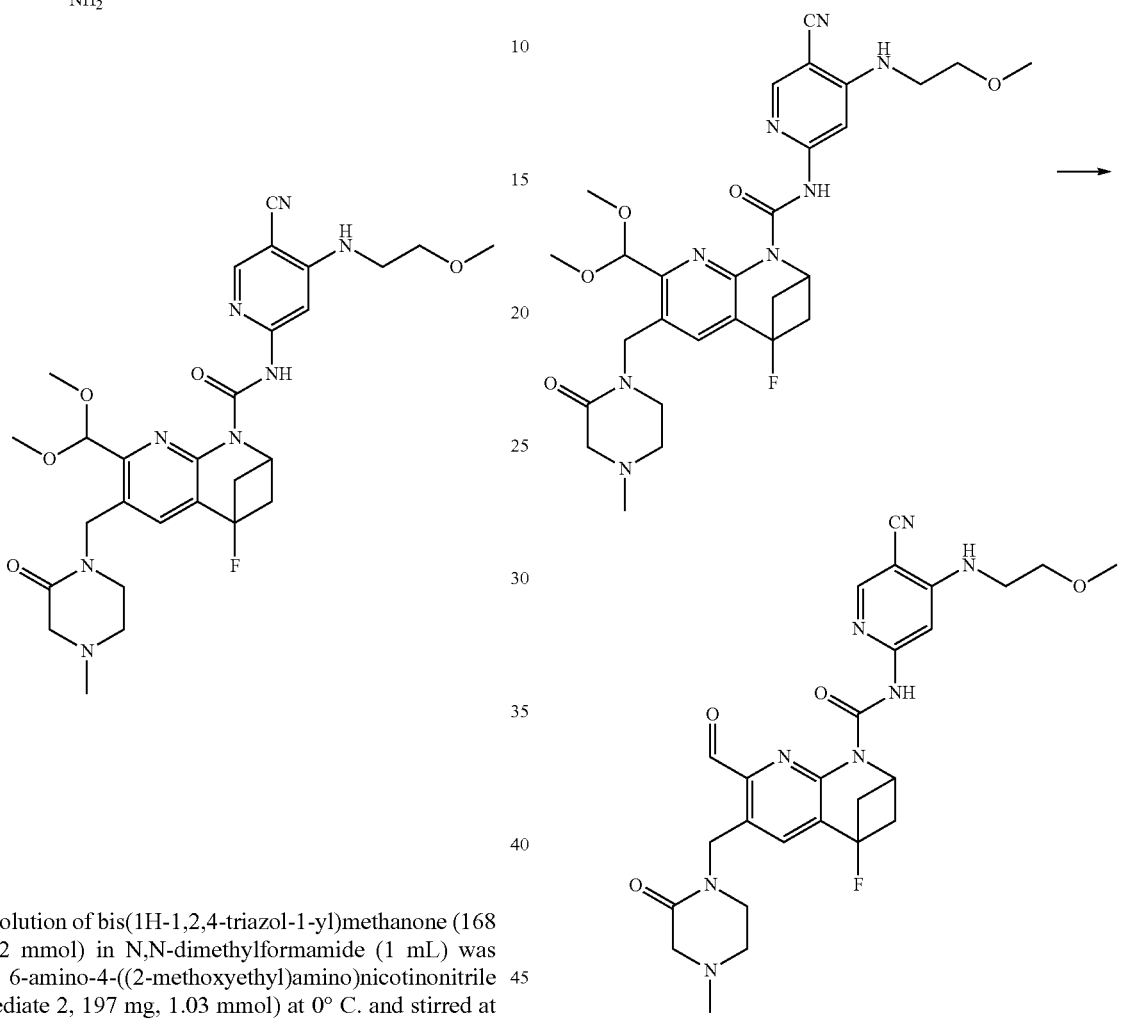

To a solution of bis(1H-1,2,4-triazol-1-yl)methanone (168 mg, 1.02 mmol) in N,N-dimethylformamide (1 mL) was added 6-amino-4-((2-methoxyethyl)amino)nicotinonitrile (Intermediate 2, 197 mg, 1.03 mmol) at 0° C. and stirred at room temperature for 1 hour. To this solution was then added 1-((7-(dimethoxymethyl)-4-fluoro-1,2,3,4-tetrahydro-2,4-methylene-1,8-naphthyridin-6-yl)methyl)-4-methylpiperazin-2-one (Intermediate 49, 149 mg, 0.41 mmol) in N,N-dimethylformamide (1 mL), and the reaction solution was continued to stir for 16 hours.

Water (50 mL) was added to the reaction mixture to quench the reaction, extracted with dichloromethane (50 mL), and the organic phase was obtained by separation. The organic phase was washed with saturated brine (50 mL), dried over anhydrous sodium sulfate, filtered with suction, and evaporated to dryness. The residue was purified by column chromatography, eluting with a gradient of ethyl acetate and dichloromethane/methanol=10:1, and the fractions containing the product were concentrated to give N-(5-cyano-4-(2-methoxyethyl)amino)pyridin-2-yl)-7-(dimethoxymethyl)-4-fluoro-6-(4-methyl-2-oxopiperazin-1-yl)methyl)-3,4-dihydro-2,4-methylene-1,8-naphthyridine-1 (2H)-carboxamide. The relevant test data are as follows:

ESI-MS: 583.3 [M+H]$^+$.

At room temperature, to a solution of N-(5-cyano-4-((2-methoxyethyl)amino)pyridin-2-yl)-7-(dimethoxymethyl)-4-fluoro-6-((4-methyl-2-oxopiperazin-1-yl)methyl)-3,4-dihydro-2,4-methylene-1,8-naphthyridine-1(2H)-carboxamide (107 mg, 0.18 mmol) in tetrahydrofuran (4 mL) was added hydrochloric acid (3 M, 4 mL), and the reaction solution was continued to stir for 30 min.

Saturated sodium bicarbonate solution (50 mL) was added to the reaction mixture to quench the reaction, extracted with ethyl acetate (50 mL), and the organic phase was obtained by separation. The organic phase was washed with saturated brine (50 mL), dried over anhydrous sodium sulfate, filtered with suction, and evaporated to dryness. The residue was purified by column chromatography, eluted with dichloromethane/methanol=10:1, and the fractions containing the product were concentrated to obtain Compound 4. The relevant test data are as follows:

$^1$H NMR (DMSO-$d_6$, 400 MHz), δ 12.90 (s, 1H), 10.13 (s, 1H), 8.31 (s, 1H), 7.64 (s, 1H), 7.53 (s, 1H), 7.03 (t, J=5.2

Hz, 1H), 5.55-5.65 (m, 1H), 4.98 (s, 2H), 3.54 (t, J=5.8 Hz, 2H), 3.41 (m, 2H), 3.30 (s, 3H), 3.29 (m, 2H), 3.07 (s, 2H), 2.86 (qd, J=6.8 Hz, 2.0 Hz, 2H), 2.62 (t, J=5.4 Hz, 2H), 2.25 (s, 3H), 2.45 (qd, J=6.8 Hz, 2.0 Hz, 2H).

ESI-MS: 537.3 [M+H]⁺.

Example 5

Compound 5: Preparation of N-(5-cyano-4-((2-methoxyethyl)amino)pyridin-2-yl)-7-formyl-4-hydroxy-6-((4-methyl-2-oxopiperazin-1-yl)methyl)-3,4-dihydro-2,4-methylene-1,8-naphthyridine-1(2H)-carboxamide

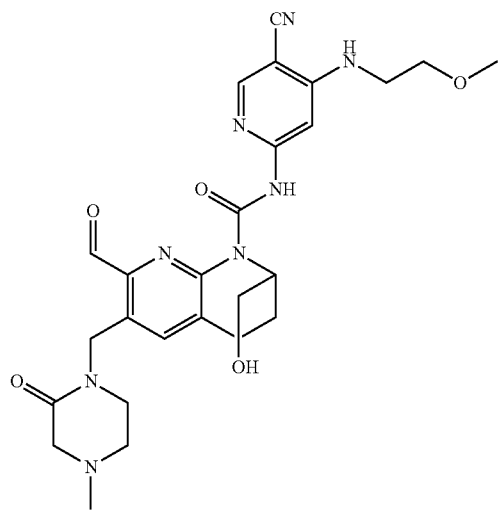 [SMILES: COCCNc1cc(NC(=O)N2c3nc(C=O)c(CN4CCN(C)CC4=O)cc3CCC2CO)ncc1C#N]

The First Step: Preparation of N-(5-cyano-44(2-methoxyethyl)amino)pyridin-2-yl)-7-(dimethoxymethyl)-4-((tert-butyldiphenylsilyl)oxy)-6-((4-methyl-2-oxopiperazin-1-yl)methyl)-3,4-dihydro-2,4-methylene-1,8-naphthyridine-1(2H)-carboxamide

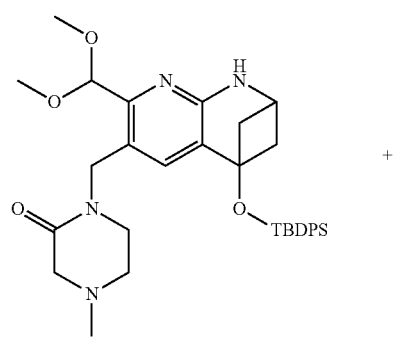

+

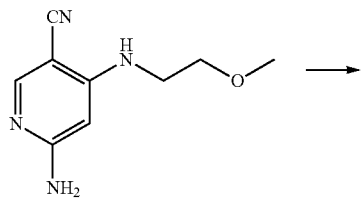

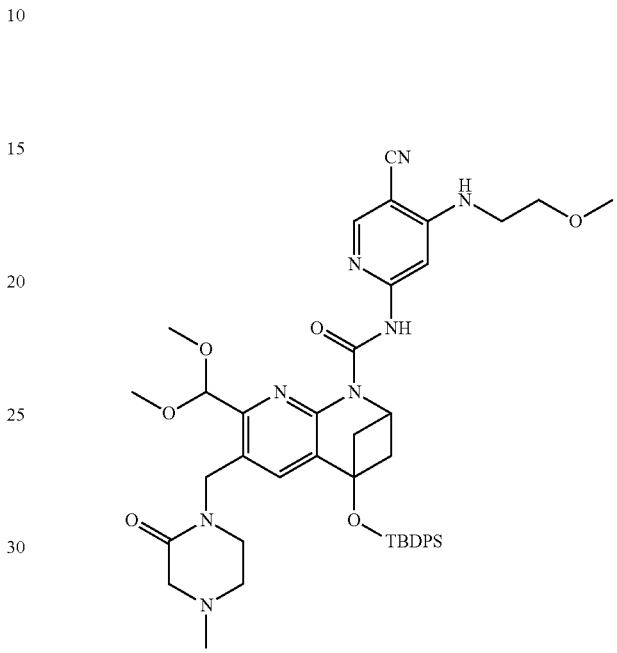

To a solution of bis(1H-1,2,4-triazol-1-yl)methanone (317 mg, 1.94 mmol) in N,N-dimethylformamide (1 mL) was added 6-amino-4-((2-methoxyethyl)amino)nicotinonitrile (Intermediate 2, 372 mg, 1.94 mmol) at 0° C. and stirred at room temperature for 1 hour. To this solution was then added 1-((7-(dimethoxymethyl)-4-((tert-butyldiphenylsilyl)oxy)-1,2,3,4-tetrahydro-2,4-methylene-1,8-naphthyridin-6-yl)methyl)-4-methylpiperazin-2-one (Intermediate 50, 465 mg, 0.77 mmol) in N,N-dimethylformamide (1 mL) and the reaction solution was continued to stir for 16 hours.

Water (50 mL) was added to the reaction mixture to quench the reaction, extracted with dichloromethane (50 mL), and the organic phase was obtained by separation. The organic phase was washed with saturated brine (50 mL), dried over anhydrous sodium sulfate, and filtered with suction, and evaporated to dryness. The residue was purified by column chromatography, eluting with a gradient of ethyl acetate and dichloromethane/methanol=10:1, and the fractions containing the product were concentrated to give N-(5-cyano-4-((2-methoxyethyl)amino)pyridin-2-yl)-7-(dimethoxymethyl)-4-((tert-butyldiphenylsilyl)oxy)-6-((4-methyl-2-oxopiperazin-1-yl)methyl)-3,4-dihydro-2,4-methylene-1,8-naphthyridine-1(2H)-carboxamide. The relevant test data of the product are as follows:

ESI-MS: 820.2 [M+H]⁺.

The Second Step: Preparation of N-(5-cyano-44(2-methoxyethyl)amino)pyridin-2-yl)-7-(dimethoxymethyl)-4-hydroxy-6-((4-methyl-2-oxopiperazin-1-yl)methyl)-3,4-dihydro-2,4-methylene-1,8-naphthyridine-1(2H)-carboxamide

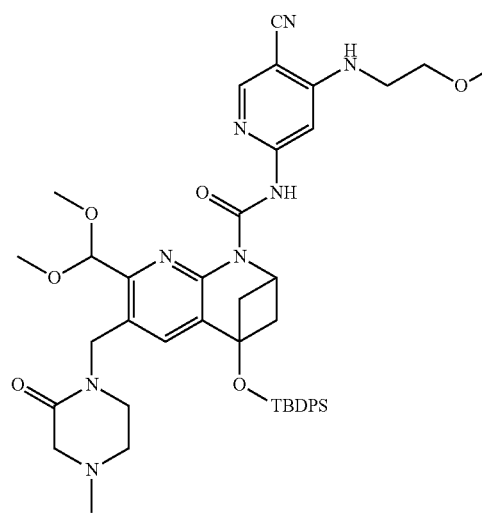

At 0° C., to a solution of N-(5-cyano-4-((2-methoxyethyl)amino)pyridin-2-yl)-7-(dimethoxymethyl)-4-((tert-butyldiphenyl silyl)oxy)-64(4-methyl-2-oxopiperazin-1-yl)methyl)-3,4-dihydro-2,4-methylene-,8-naphthyridine-1(2H)-carboxamide (250 mg, 0.31 mmol) in tetrahydrofuran (5 mL) was added dropwise a solution of tetrabutylammonium fluoride in tetrahydrofuran (1 M, 0.6 mL, 0.60 mmol), and then continued to stir the reaction solution at room temperature for 1 hour.

Water (50 mL) was added to the reaction mixture to quench the reaction, extracted with ethyl acetate (50 mL), and the organic phase was obtained by separation. The organic phase was washed with saturated brine (50 mL), dried over anhydrous sodium sulfate, filtered with suction, and evaporated to dryness. The residue was purified by column chromatography, eluting with dichloromethane/methanol=10:1, and the fractions containing the product were concentrated to give N-(5-cyano-4-((2-methoxyethyl)amino)pyridin-2-yl)-7-(dimethoxymethyl)-4-hydroxy-6-((4-methyl-2-oxopiperazin-1-yl)methyl)-3,4-dihydro-2,4-methylene-1,8-naphthyridine-1(2H)-carboxamide. The relevant test data are as follows:
ESI-MS: 581.2 [M+H]$^+$.

The Third Step: Preparation of N-(5-cyano-44(2-methoxyethyl)amino)pyridin-2-yl)-7-formyl-4-hydroxy-6-((4-methyl-2-oxopiperazin-1-yl)methyl)-3,4-dihydro-2,4-methylene-1,8-naphthyridine-1(2H)-carboxamide

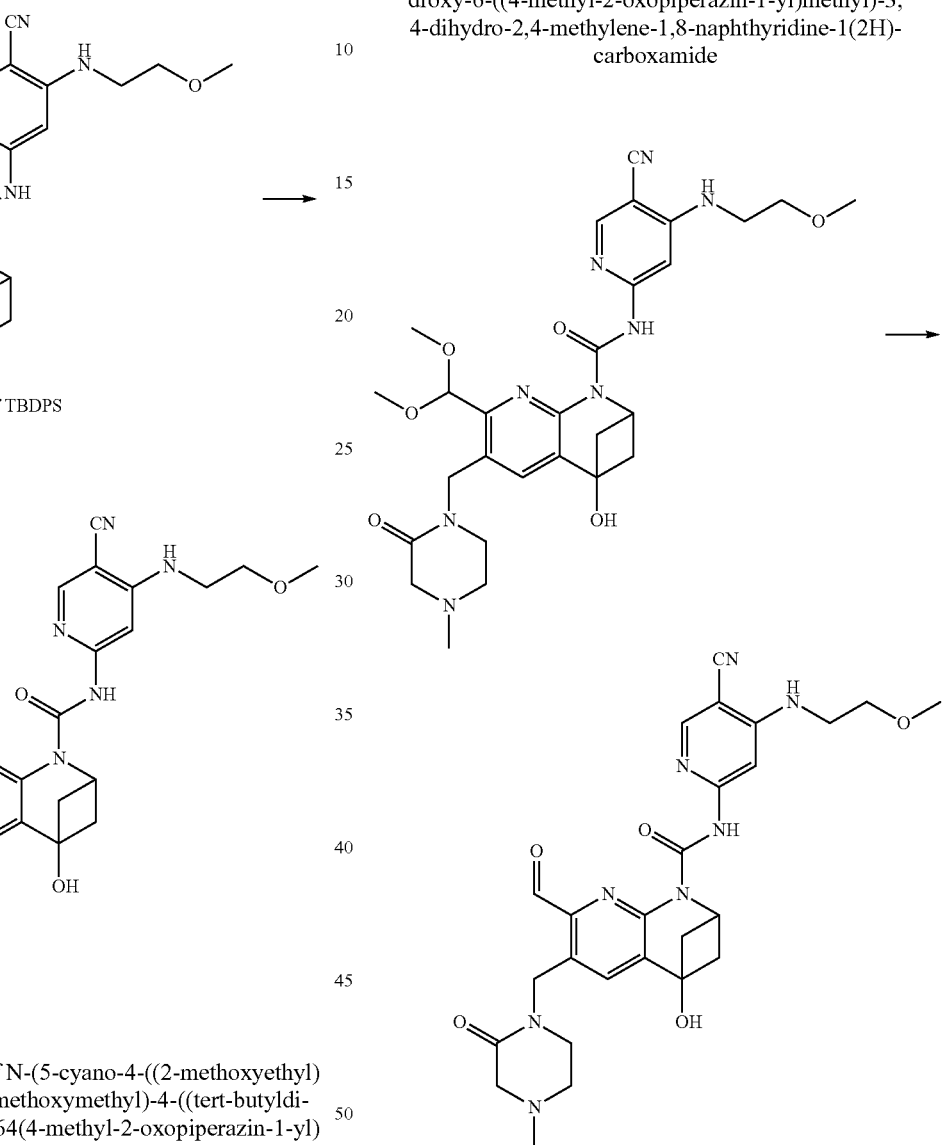

At room temperature, to a solution of N-(5-cyano-4-((2-methoxyethyl)amino)pyridin-2-yl)-7-(dimethoxymethyl)-4-hydroxy-6-((4-methyl-2-oxopiperazin-1-yl)methyl)-3,4-dihydro-2,4-methylene-1,8-naphthyridine-1(2H)-carboxamide (55 mg, 0.095 mmol) in tetrahydrofuran (4 mL) was added hydrochloric acid (3 M, 4 mL), and the reaction solution was continued to stir for 30 min.

Saturated sodium bicarbonate solution (50 mL) was added to the reaction mixture to quench the reaction, extracted with ethyl acetate (50 mL), and the organic phase was obtained by separation. The organic phase was washed with saturated brine (50 mL), and dried over anhydrous sodium sulfate, filtered with suction, and evaporated to dryness. The residue was purified by column chromatography, eluted with dichloromethane/methanol=10:1, and the fractions containing the product was concentrated to obtain Compound 5. The relevant test data of the product are as follows:

$^1$H NMR (DMSO-d$_6$, 400 MHz), δ 13.10 (s, 1H), 10.11 (s, 1H), 8.29 (s, 1H), 7.72 (s, 1H), 7.53 (s, 1H), 6.99 (t, J=5.4 Hz, 1H), 6.89 (s, 1H), 5.46 (t, J=6.2 Hz, 1H), 4.96 (s, 2H), 3.53 (t, J=5.8 Hz, 2H), 3.39 (dd, J=11.0 Hz, 5.8 Hz, 2H), 3.29 (s, 3H), 3.27 (m, 2H), 3.05 (s, 2H), 2.61 (t, J=5.2 Hz, 2H), 2.48 (m, 2H), 2.24 (s, 3H), 1.72-1.74 (m, 2H).

ESI-MS: 535.3 [M+H]$^+$.

Example 6

Compound 6: Preparation of (R)—N-(5-cyano-4-((1-methoxyprop-2-yl)amino)pyridin-2-yl)-4-fluoro-7-formyl-6-((4-methyl-2-oxopiperazin-1-yl)methyl)-3,4-dihydro-2,4-methylene-1,8-naphthyridine-1(2H)-carboxamide

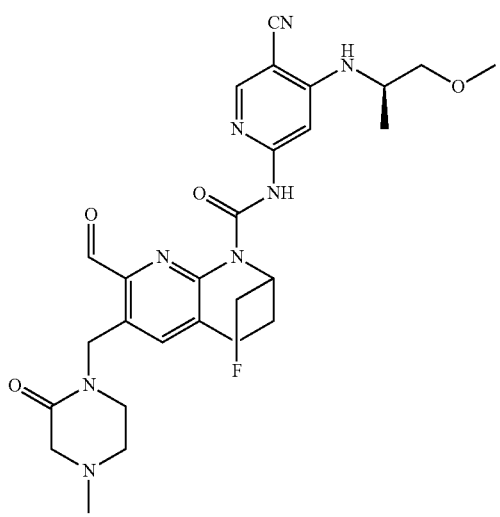 [SMILES: COC[C@@H](C)Nc1cc(NC(=O)N2c3nc(C=O)c(CN4CCN(C)CC4=O)cc3CCC2CF)ncc1C#N]

According to the method similar to preparing Compound 4 in Example 4, Compound 6 was prepared by reacting Intermediate 49 and Intermediate 3 as starting materials. The relevant test data of the product are as follows:

$^1$H NMR (DMSO-d$_6$, 400 MHz), δ 12.90 (s, 1H), 10.13 (s, 1H), 8.31 (s, 1H), 7.64 (s, 1H), 7.56 (s, 1H), 6.69 (d, J=7.6 Hz, 1H), 5.59 (dt, J=20.4 Hz, 6.4 Hz, 1H), 4.98 (s, 2H), 3.95-4.02 (m, 1H), 3.83-4.90 (m, 1H), 3.50 (dd, J=9.6 Hz, 6.4 Hz, 1H), 3.39 (dd, J=9.6 Hz, 5.6 Hz, 1H), 3.31 (s, 2H), 3.30 (s, 3H), 3.06 (s, 2H), 2.85 (m, 2H), 2.62 (t, J=5.6 Hz, 2H), 2.25 (s, 3H), 2.01-2-03 (m, 2H), 1.20 (d, J=7.6 Hz, 3H).
ESI-MS: 551.2 [M+H]$^+$.

Example 7

Compound 7: Preparation of N-(5-cyano-44(2-methoxyethyl)amino)pyridin-2-yl)-4-fluoro-7-formyl-64(4-methylpiperazin-1-yl)methyl)-3,4-dihydro-2,4-methylene-1,8-naphthyridine-1(2H)-carboxamide

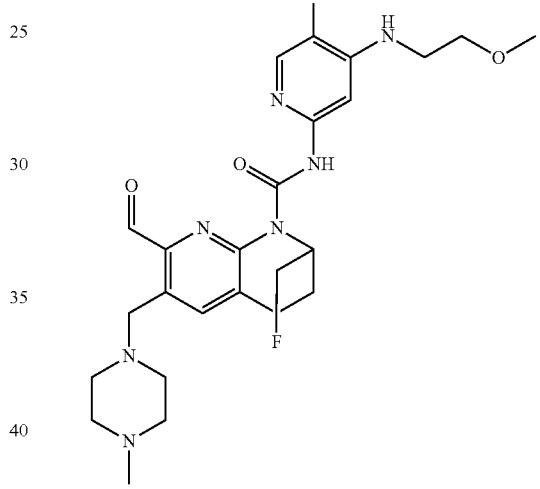

According to the method similar to preparing Compound 4 in Example 4, Compound 7 was prepared by reacting Intermediate 54 and Intermediate 2 as starting materials. The relevant test data of the product are as follows:

$^1$H NMR (DMSO-d$_6$, 400 MHz), δ 12.90 (s, 1H), 10.20 (s, 1H), 8.30 (s, 1H), 7.96 (s, 1H), 7.53 (s, 1H), 7.02 (t, J=5.8 Hz, 1H), 5.59 (dt, J=20.4 Hz, 6.6 Hz, 1H), 3.90 (s, 2H), 3.54 (t, J=5.8 Hz, 2H), 3.40 (dd, J=11.0 Hz, 5.4 Hz, 2H), 3.30 (s, 3H), 2.81-2.87 (m, 2H), 2.47-2.48 (m, 4H), 2.33-2.34 (m, 4H), 2.18 (s, 3H), 2.02-2.04 (m, 2H).

ESI-MS: 523.3 [M+H]$^+$.

207
Example 8

Compound 8: Preparation of N-(5-cyano-4-((2-methoxyethyl)amino)pyridin-2-yl)-4-fluoro-7-formyl-64(2-(dimethylamino)-N-methylacetamido)methyl)-3,4-dihydro-2,4-methylene-1,8-naphthyridine-1(2H)-carboxamide

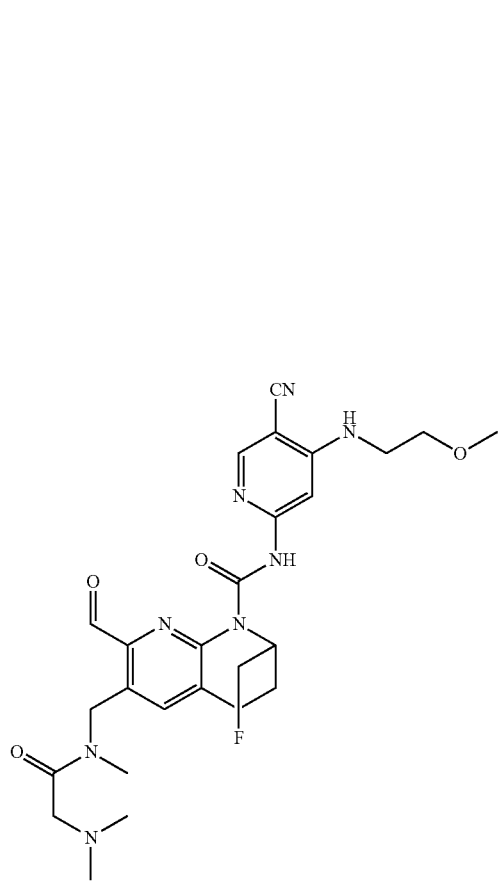 [SMILES: COCCNc1cc(NC(=O)N2c3nc(C=O)c(CN(C)C(=O)CN(C)C)cc3CCC2CF)ncc1C#N]

According to the method similar to preparing Compound 4 in Example 4, Compound 8 was prepared by reacting Intermediate 57 and Intermediate 2 as starting materials. The relevant test data of the product are as follows:

$^1$H NMR (DMSO-d$_6$, 400 MHz), 12.91 (s, 1H), 10.11 (s, 1H), 8.30 (s, 1H), 7.61 (s, 1H), 7.52 (s, 1H), 7.05 (t, J=5.4 Hz, 1H), 5.54-5.63 (m, 1H), 4.94 (s, 2H), 3.53 (t, J=5.8 Hz, 2H), 3.40 (dd, J=11.2 Hz, J=5.6 Hz, 2H), 3.29 (s, 3H), 3.06 (s, 2H), 2.85-2.87 (m, 2H), 2.31 (s, 6H), 2.00-2.02 (m, 2H).

ESI-MS: 539.3 [M+H]$^+$.

208
Example 9

Compound 9: Preparation of N-(5-cyano-4-(2-methoxyethoxy)pyridin-2-yl)-4-fluoro-7-formyl-64(4-methyl-2-oxopiperazin-1-yl)methyl)-3,4-dihydro-2,4-methylene-1,8-naphthyridine-1(2H)-carboxamide

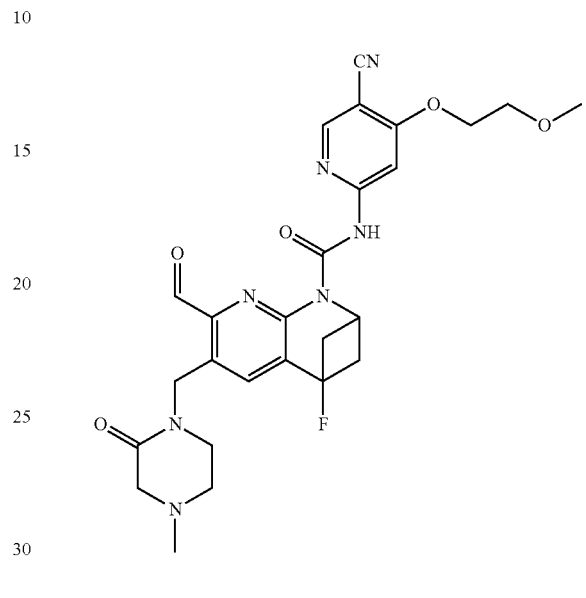

The First Step: Preparation of N-(5-cyano-4-(2-methoxyethoxy)pyridin-2-yl)-7-(dimethoxymethyl)-4-fluoro-6-((4-methyl)-2-oxopiperazin-1-yl)methyl)-3,4-dihydro-2,4-methylene-1,8-naphthyridine-1(2H)-carboxamide

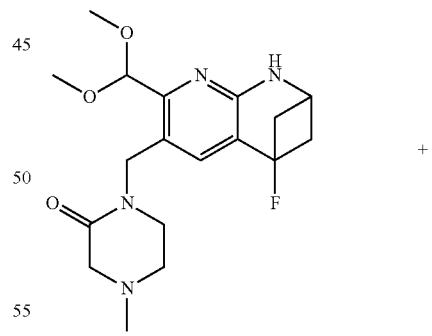

+

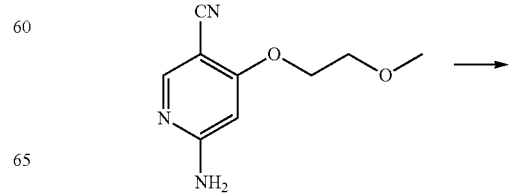

210

The Second Step: Preparation of N-(5-cyano-4-(2-methoxyethoxy)pyridin-2-yl)-4-fluoro-7-formyl-64(4-methyl-2-oxopiperazin-1-yl)methyl)-3,4-dihydro-2,4-methylene-1,8-naphthyridine-1(2H)-carboxamide

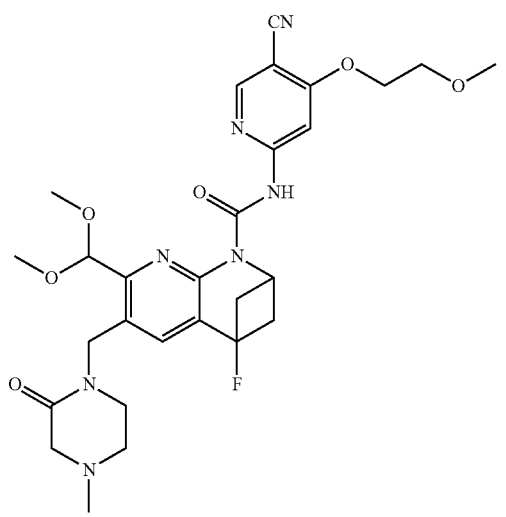

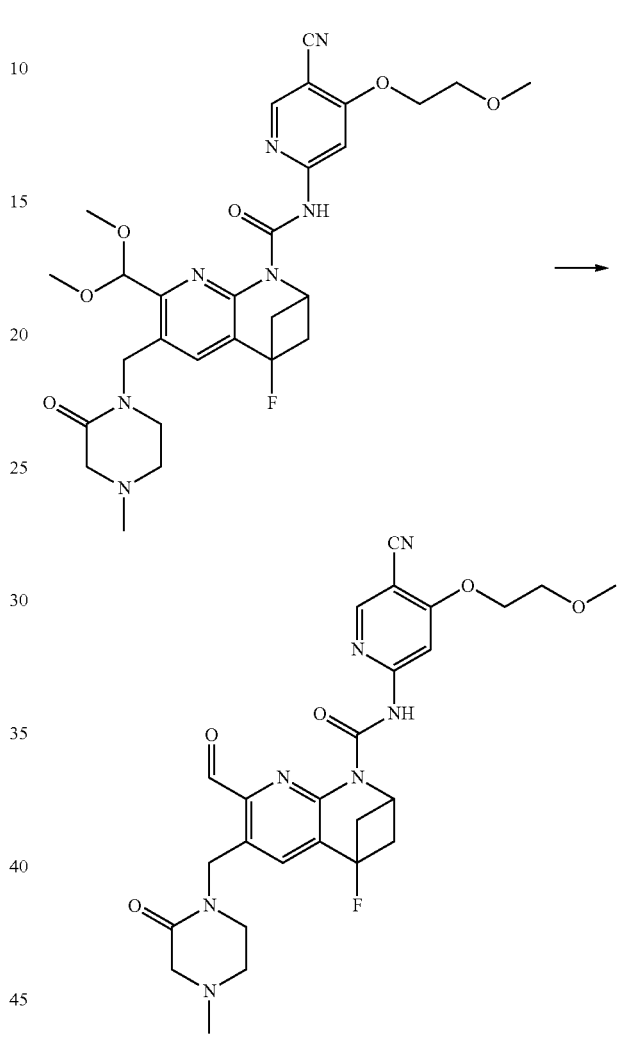

At room temperature, to a solution of bis(trichloromethyl) carbonate (33 mg, 0.110 mmol) in tetrahydrofuran (2.5 mL) was added triethylamine (89 mg, 0.879 mmol) and 14(7-(dimethoxymethyl)-4-fluoro-1,2,3,4-tetrahydro-2,4-methylene-1,8-naphthyridin-6-yl)methyl)-4-methylpiperazin-2-one (Intermediate 49, 100 mg, 0.275 mmol), and then stirred for 1 hour under nitrogen protection to obtain Intermediate 4. After that, 6-amino-4-(2-methoxyethoxy) nicotinonitrile (Intermediate 6, 64 mg, 0.330 mmol) was added to the reaction system and continued to stir for 2 hours.

Saturated aqueous sodium bicarbonate solution (50 mL) was added to the reaction mixture to quench the reaction, extracted with ethyl acetate (50 mL), and the organic phase was obtained by separation. The organic phase was washed with saturated brine (50 mL), dried over anhydrous sodium sulfate, filtered with suction, and evaporated to dryness. The residue was purified by column chromatography, eluting with a gradient of petroleum ether/ethyl acetate=1:1 and ethyl acetate/methanol=10:1, and the fractions were concentrated to give N-(5-cyano-4-(2-methoxyethoxy)pyridin-2-yl)-7-(dimethoxymethyl)-4-fluoro-6-((4-methyl-2-oxopiperazin-1-yl)methyl)-3,4-dihydro-2,4-methylene-1,8-naphthyridine-1(2H)-carboxamide, The relevant test data are as follows:

ESI-MS: 584.3 [M+H]$^+$.

At room temperature, to N-(5-cyano-4-(2-methoxyethoxy)pyridin-2-yl)-7-(dimethoxymethyl)-4-fluoro-64(4-methyl-2-oxopiperazin-1-yl)methyl)-3,4-dihydro-2,4-methylene-1,8-naphthyridine-1(2H)-carboxamide (20 mg, 0.034 mmol) in tetrahydrofuran (3 mL) was added hydrochloric acid (3 M, 3 mL) and the reaction was continued to stir for 30 min.

Saturated sodium bicarbonate solution (50 mL) was added to the reaction mixture to quench the reaction, extracted with ethyl acetate (50 mL), and the organic phase was obtained by separation. The organic phase was washed with saturated brine (50 mL), dried over anhydrous sodium sulfate, filtered with suction, and evaporated to dryness. The residue was purified by column chromatography, eluted with dichloromethane/methanol=10:1, and the fractions containing the product was concentrated to obtain Compound 9. The relevant test data of the product are as follows:

$^1$H NMR (DMSO-d$_6$, 400 MHz), δ 13.25 (s, 1H), 10.16 (s, 1H), 8.64 (s, 1H), 7.94 (s, 1H), 7.66 (s, 1H), 5.58 (dt, J=20.4

Hz, 6 Hz, 1H), 4.98 (s, 2H), 4.36 (t, J=4 Hz, 2H), 3.75 (t, J=4 Hz, 2H), 3.35 (s, 3H), 3.29-3.31 (m, 2H), 3.05 (s, 2H), 2.84-2.89 (m, 2H), 2.61 (t, J=5.2 Hz, 2.0 Hz, 2H), 2.24 (s, 3H), 2.01-2.06 (m, 2H).

ESI-MS: 538.2 [M+H]⁺.

Example 10

Compound 10: Preparation of N-(5-cyano-4-((tetra-hydrofuran-3-yl)amino)pyridin-2-yl)-4-fluoro-7-formyl-6-((4-methyl-2-oxopiperazin-1-yl)methyl)-3,4-dihydro-2,4-methylene-1,8-naphthyridine-1(2H)-carboxamide

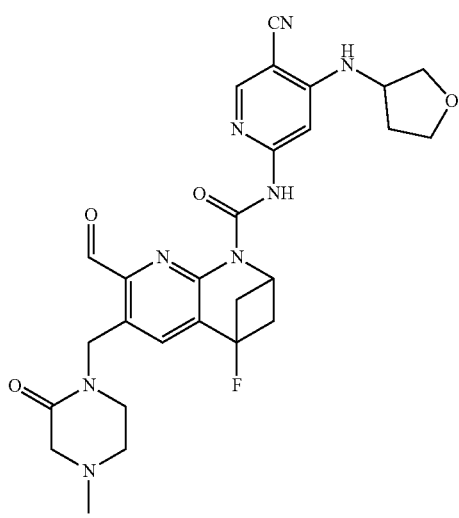 [SMILES: CN1CCN(Cc2cc3c(nc2C=O)N(C(=O)Nc2cc(NC4CCOC4)c(C#N)cn2)C2CC3(F)C2)C(=O)C1]

According to the method similar to preparing Compound 9 in Example 9, Compound 10 was prepared by reacting Intermediate 49 and Intermediate 4 as starting materials. The relevant test data of the product are as follows:

¹H NMR (DMSO-d₆, 400 MHz), δ 12.93 (s, 1H), 10.13 (s, 1H), 8.34 (s, 1H), 7.64 (s, 1H), 7.53 (s, 1H), 7.18 (d, J=5.2 Hz, 1H), 5.59 (dt, J=20 Hz, 6.8 Hz, 1H), 4.98 (s, 2H), 3.85-3.93 (m, 2H), 3.71-3.79 (m, 2H), 3.31 (s, 3H), 3.06 (s, 2H), 2.83-2.88 (m, 2H), 2.62 (t, J=5.6 Hz, 2H), 2.25 (s, 3H), 2.02 (m, 2H).

ESI-MS: 549.2 [M+H]⁺.

Example 11

Compound 11: Preparation of N-(5-cyano-4-(((trans)-2-methoxycyclopentyl)amino)pyridin-2-yl)-4-fluoro-7-formyl-64(4-methyl-2-oxopiperazin-1-yl)methyl)-3,4-dihydro-2,4-methylene-1,8-naphthyridine-1(2H)-carboxamide

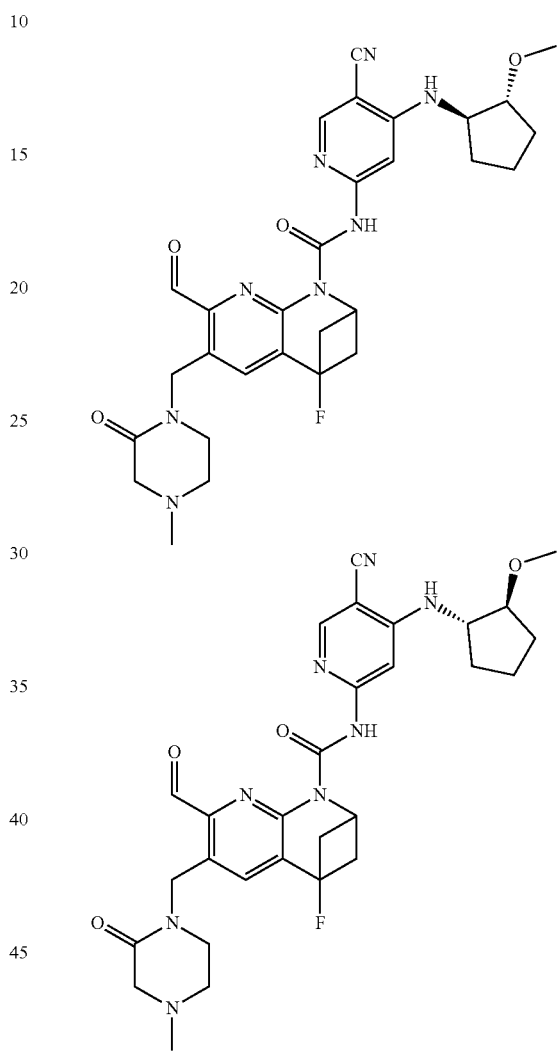

According to the method similar to preparing Compound 9 in Example 9, Compound 11 was prepared by reacting Intermediate 49 and Intermediate 5 as starting materials. The relevant test data of the product are as follows:

¹H NMR (DMSO-d₆, 400 MHz), δ 12.89 (s, 1H), 10.12 (s, 1H), 8.30 (s, 1H), 7.63 (s, 1H), 7.60 (s, 1H), 6.96 (d, J=7.2 Hz, 1H), 5.58 (dt, J=20.4 Hz, 6.6 Hz, 1H), 4.97 (s, 2H), 3.75-3.82 (m, 2H), 3.30 (m, 2H), 3.27 (s, 3H), 3.05 (s, 2H), 2.82-2.87 (m, 2H), 2.61 (t, J=5.4 Hz, 2H), 2.24 (s, 3H), 2.00-2.02 (m, 2H), 1.86-1.95 (m, 2H), 1.58-1.73 (m, 4H).

ESI-MS: 577.2 [M+H]⁺.

Chiral resolution conditions: equipment: SFC, chromatographic column: chiralpak-AS, mobile phase: CO₂-EtOH. The compound with shorter retention time on the SFC machine is named P1, and the longer retention time is named P2. One of P1 and P2 is Compound 11A, and the other is Compound 11B.

Example 12

Preparation of N-(5-cyano-4-(((cis)-2-methoxycyclopentyl)amino)pyridin-2-yl)-4-fluoro-7-formyl-64(4-methyl-2-oxopiperazin-1-yl)methyl)-3,4-dihydro-2,4-methylene-1,8-naphthyridine-1(2H)-carboxamide

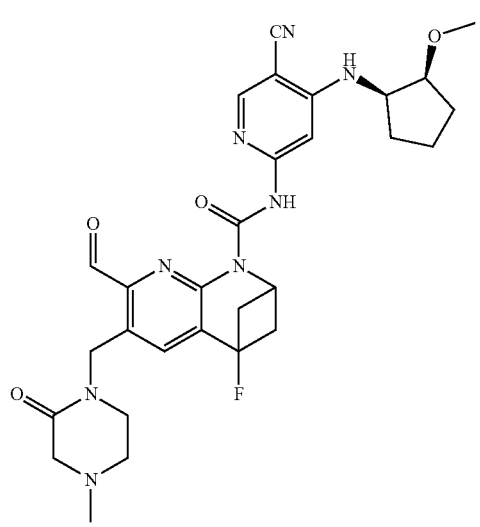

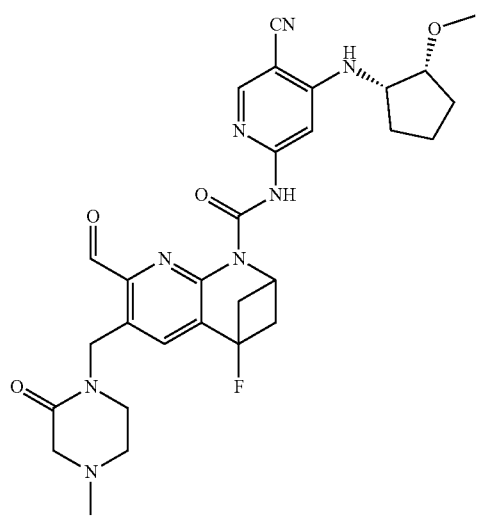

According to the method similar to preparing Compound 9 in Example 9, Compound 12 was prepared by reacting Intermediate 49 and Intermediate 59 as starting materials. The relevant test data of the product are as follows:

ESI-MS: 577.2 [M+H]$^+$.

Chiral resolution conditions: equipment: SFC, chromatographic column: chiralpak-AS, mobile phase: $CO_2$-EtOH. The compound with shorter retention time on the SFC machine is named P1, and the longer retention time is named P2. One of P1 and P2 is Compound 12A, and the other is Compound 12B.

Example 13

Compound 13: Preparation of N-(5-cyano-4-((2-methoxyethyl)amino)pyridin-2-yl)-4-fluoro-7-formyl-64(3-oxomorpholinyl) methyl)-3,4-dihydro-2,4-methylene-1,8-naphthyridine-1(2H)-carboxamide

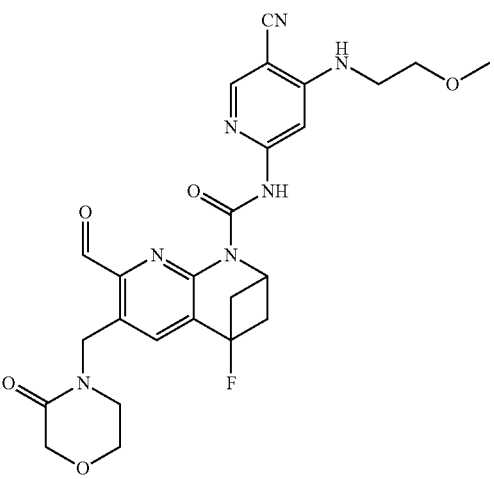 [SMILES: COCCNc1cc(NC(=O)N2c3nc(C=O)c(CN4CCOCC4=O)cc3C3(F)CC2C3)ncc1C#N]

According to the method similar to preparing Compound 9 in Example 9, Compound 13 was prepared by reacting Intermediate 52 and Intermediate 2 as starting materials. The relevant test data of the product are as follows:

ESI-MS: 524.5 [M+H]$^+$.

Example 14

Compound 14: Preparation of N-(5-cyano-4-((2-methoxyethyl)amino)pyridin-2-yl)-4-fluoro-7-formyl-64(2-oxo-1,3-oxazepan-3-yl)methyl)-3,4-dihydro-2,4-methylene-1,8-naphthyridine-1(2H)-carboxamide

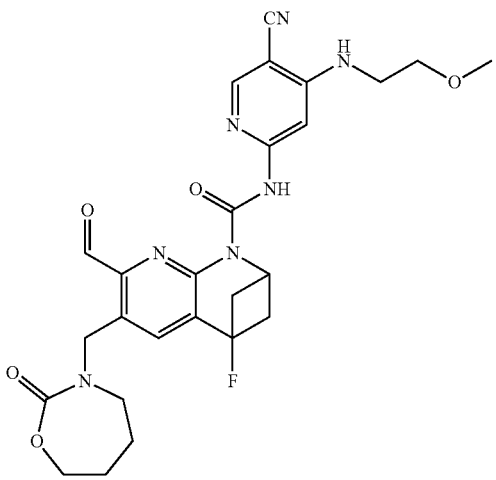 [SMILES: COCCNc1cc(NC(=O)N2c3nc(C=O)c(CN4CCCCOC4=O)cc3C3(F)CC2C3)ncc1C#N]

According to the method similar to preparing Compound 9 in Example 9, Compound 14 was prepared by reacting Intermediate 55 and Intermediate 2 as starting materials. The relevant test data of the product are as follows:

$^1$H NMR (DMSO-d$_6$, 400 MHz), δ 12.91 (s, 1H), 10.10 (s, 1H), 8.30 (s, 1H), 7.75 (s, 1H), 7.52 (s, 1H), 7.05 (t, J=5.8 Hz, 1H), 5.60 (m, 1H), 4.85 (s, 2H), 4.07 (s, 2H), 3.53 (t, J=5.8 Hz, 2H), 3.39 (m, 4H), 3.29 (s, 3H), 2.86 (m, 2H), 2.02-2.03 (m, 2H), 1.78-1.79 (m, 2H), 1.62 (m, 2H).

ESI-MS: 538.3 [M+H]$^+$.

Example 15

Compound 15: Preparation of N-(5-cyano-4-((2-methoxyethyl)amino)pyridin-2-yl)-4-fluoro-7-formyl-6-((N-methylacetamido) methyl)-3,4-dihydro-2,4-methylene-1,8-naphthyridine-1(2H)-carboxamide

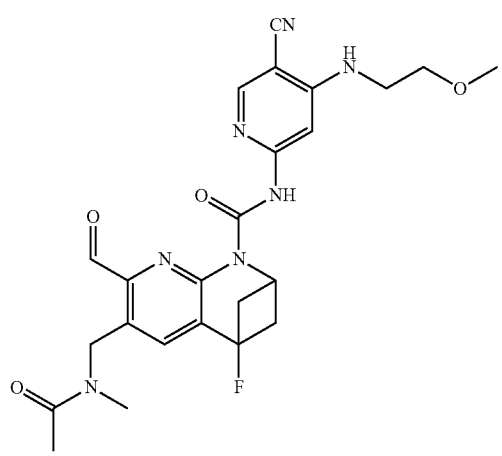 [SMILES: COCCNc1cc(NC(=O)N2c3nc(C=O)c(CN(C)C(C)=O)cc3C3(F)CC2C3)ncc1C#N]

According to the method similar to preparing Compound 9 in Example 9, Compound 15 was prepared by reacting Intermediate 58 and Intermediate 2 as starting materials. The relevant test data of the product are as follows:

ESI-MS: 495.2 [M+H]$^+$.

Example 16

Compound 16: Preparation of N-(5-(trifluoromethyl)pyridin-2-yl)-4-fluoro-7-formyl-6-((4-methyl-2-oxopiperazin-1-yl)methyl)-3,4-dihydro-2,4-methylene-1,8-naphthyridine-1(2H)-carboxamide

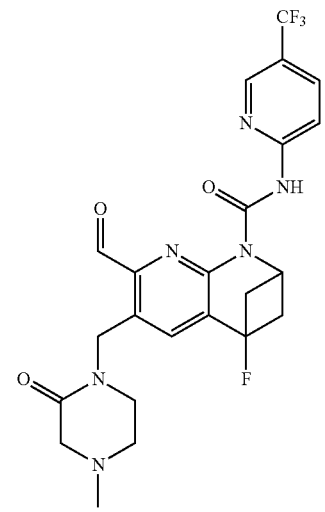 [SMILES: CN1CCN(Cc2cc3c(nc2C=O)N(C(=O)Nc2ccc(C(F)(F)F)cn2)C2CC3(F)C2)C(=O)C1]

According to the method similar to preparing Compound 9 in Example 9, Compound 16 was prepared by reacting Intermediate 49 and 2-amino-5-(trifluoromethyl)pyridine as starting materials. The relevant test data of the product are as follows:

$^1$H NMR (DMSO-d$_6$, 400 MHz), δ 13.25 (s, 1H), 10.19 (s, 1H), 8.79 (s, 1H), 8.29 (d, J=8.8 Hz, 1H), 8.24 (dd, J=8.8 Hz, 2.0 Hz, 1H), 7.67 (s, 1H), 5.51 (dt, J=20.4 Hz, 6.4 Hz, 1H), 4.99 (s, 2H), 3.31 (s, 2H), 3.07 (s, 2H), 2.85-2.90 (m, 2H), 2.62 (t, J=5.6 Hz, 2H), 2.25 (s, 3H), 2.02-2.08 (m, 2H).

ESI-MS: 507.2 [M+H]$^+$.

Example 17

Compound 17: Preparation of N-(5-cyano-4-(((trans)-2-hydroxycyclopentyl)amino)pyridin-2-yl)-4-fluoro-7-formyl-6-((4-methyl-2-oxopiperazin-1-yl)methyl)-3,4-dihydro-2,4-methylene-1,8-naphthyridine-1(21-1)-carboxamide

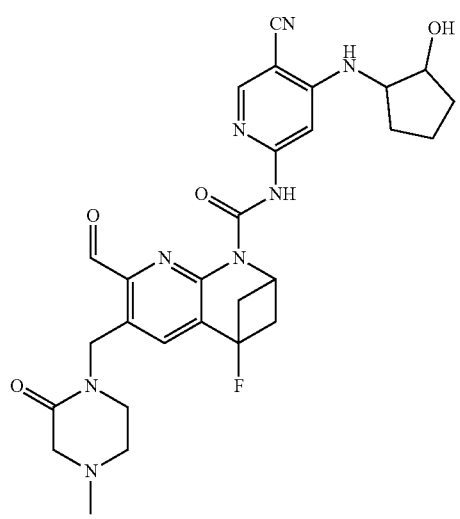 [SMILES: CN1CCN(Cc2cc3c(nc2C=O)N(C(=O)Nc2cc(NC4CCCC4O)c(C#N)cn2)C2CC3(F)C2)C(=O)C1]

According to the method similar to preparing Compound 5 in Example 5, Compound 17 was prepared by reacting Intermediate 49 and Intermediate 9 as starting materials. The relevant test data of the product are as follows:

¹H NMR (DMSO-d₆, 400 MHz), δ 12.87 (s, 1H), 10.12 (s, 1H), 8.29 (s, 1H), 7.63 (s, 1H), 7.57 (s, 1H), 6.84 (d, J=6.8 Hz, 1H), 5.83-5.54 (m, 1H), 4.97 (s, 2H), 4.93 (d, J=4.8 Hz, 1H), 4.11-4.04 (m, 1H), 3.64-3.55 Cm, 1H), 3.30 (t, J=4.0 Hz, 2H), 3.05 (s, 2H), 2.87-2.82 (dd, J=13.8 Hz, 7.0 Hz, 2H), 2.6 (t, J=5.2 Hz, 2H), 3.17 (s, 3H), 2.15-2.06 (m, 1H), 2.04-1.99 (dd, J=14.8 Hz, 7.2 Hz, 2H), 1.92-1.84 (m, 1H), 1.75-1.60 (m, 2H), 1.55-1.45 (m, 2H).

ESI-MS: 563.3 [M+H]⁺.

Example 18

Compound 18: Preparation of N-(5-cyano-4-((2-methoxyethyl)amino)pyridin-2-yl)-7-formyl-6-((4-methyl-2-oxopiperazin-1-yl)methyl)-3,4-dihydro-2,4-methylene-1,8-naphthyridine-1(2H)-carboxamide

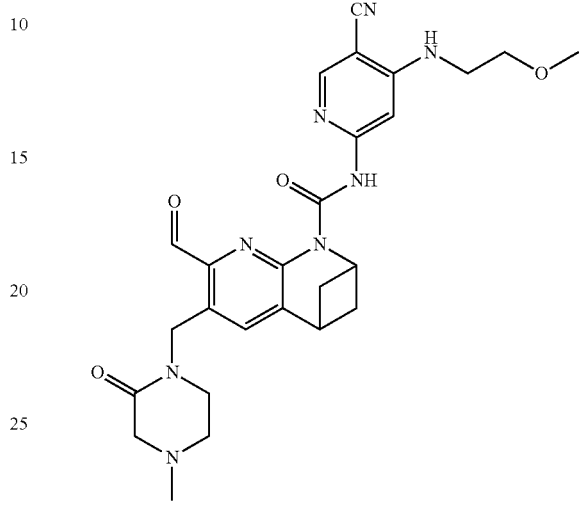

According to the method similar to preparing Compound 4 in Example 4, Compound 18 was prepared by reacting Intermediate 51 and Intermediate 2 as starting materials. The relevant test data of the product are as follows:

¹H NMR (DMSO-d₆, 400 MHz), δ 13.23 (s, 1H), 10.09 (s, 1H), 8.29 (s, 1H), 7.55 (s, 1H), 7.53 (s, 1H), 7.00 (t, J=5.4 Hz, 1H), 5.51-5.55 (dd, J=11.2 Hz, 5.2 Hz, 1H), 4.91 (s, 2H), 3.63 (dd, J=11.2 Hz, 5.2 Hz, 1H), 3.53 (t, J=5.6 Hz, 2H), 3.39 (dt, J=5.6 Hz, 5.6 Hz, 2H), 3.29 (s, 3H), 3.27-3.30 (m, 2H), 3.06 (s, 2H), 2.61-2.65 (m, 4H), 2.24 (s, 3H), 1.45 (dd, J=7.0 Hz, 2.6 Hz, 2H).

ESI-MS: 519.1 [M+H]⁺.

Example 19

Compound 19: Preparation of N-(5-cyano-4-(((trans)-2-methoxycyclopentyl)amino)pyridin-2-yl)-4-fluoro-7-formyl-3,4-dihydro-2,4-methylene-1,8-naphthyridine-1(2H)-carboxamide

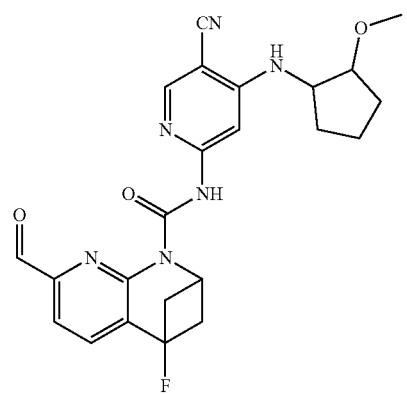 [SMILES: COC1CCCC1Nc1cc(NC(=O)N2c3nc(C=O)ccc3C3(F)CC2C3)ncc1C#N]

The First Step: Preparation of phenyl 7-(dimethoxymethyl)-4-fluoro-3,4-dihydro-2,4-methylene-1,8-naphthyridine-1(2H)-carboxylate

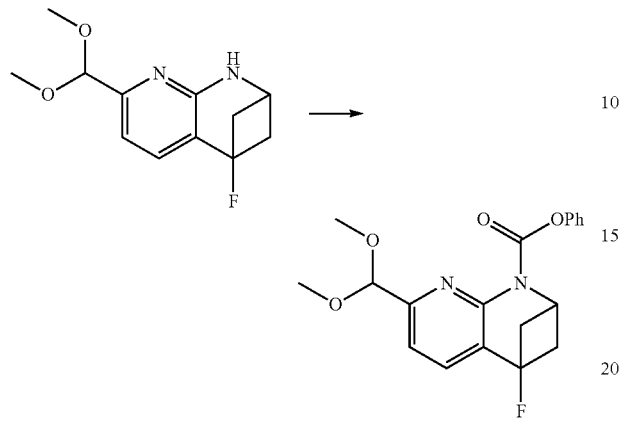

To 7-(dimethoxymethyl)-4-fluoro-1,2,3,4-tetrahydro-2,4-methylene-1,8-naphthyridine (Intermediate 16, 100 mg, 0.42 mmol) in tetrahydrofuran (5 mL) was added LiHMDS (1 M, 0.6 mL, 0.60 mmol) at −15° C. and stirred at 0° C. for 1 h.

After the reaction was completed, saturated ammonium chloride solution (50 mL) was added to the reaction solution to quench the reaction, extracted with ethyl acetate (50 mL), and the organic phase was obtained by separation. The organic phase was washed with saturated brine (50 mL), dried over anhydrous sodium sulfate, filtered with suction, and evaporated to dryness. The residue was purified by column chromatography, eluting with petroleum ether/ethyl acetate=5:1, and the fractions containing the product were concentrated to give phenyl 7-(dimethoxymethyl)-4-fluoro-3,4-dihydro-2,4-methylene-1,8-naphthyridine-1(2H)-carboxylate. The relevant test data are as follows:

ESI-MS: 359.3 [M+H]$^+$.

The Second Step: Preparation of N-(5-cyano-4-(((trans)-2-methoxycyclopentyl)amino)pyridin-2-yl)-4-fluoro-7-(dimethoxymethyl)-3,4-dihydro-2,4-methylene-1,8-naphthyridine-1(2H)-carboxamide

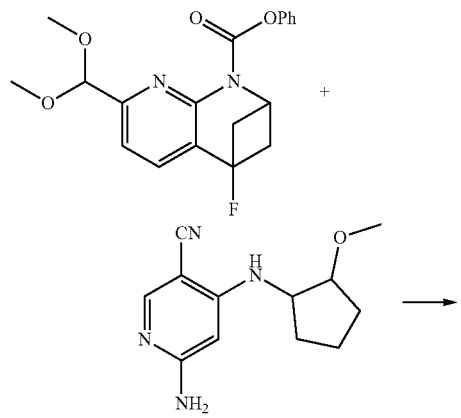

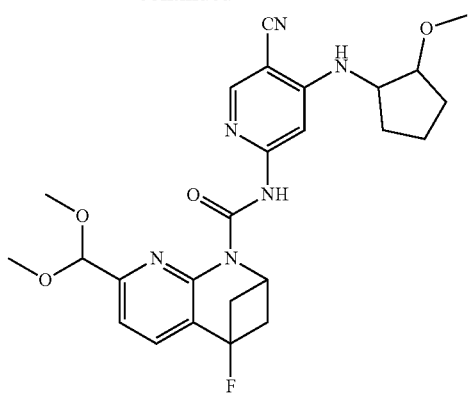

To a solution of phenyl 7-(dimethoxymethyl)-4-fluoro-3,4-dihydro-2,4-methylene-1,8-naphthyridine-1(2H)-carboxylate (45 mg, 0.13 mmol) and 6-amino-4-(trans-(2-methoxycyclopentyl)amino)nicotinonitrile (Intermediate 5, 44 mg, 0.19 mmol) in tetrahydrofuran (1 mL) was added LiHMDS (1 M, 0.6 mL, 0.60 mmol) at −15° C. and stirred at room temperature for 1 hour.

After the reaction was completed, saturated ammonium chloride solution (50 mL) was added to the reaction solution to quench the reaction, extracted with ethyl acetate (50 mL), and the organic phase was obtained by separation. The organic phase was washed with saturated brine (50 mL), dried over anhydrous sodium sulfate, filtered with suction, and evaporated to dryness. The residue was purified by column chromatography, eluting with petroleum ether/ethyl acetate=4:1, and the fractions containing the product were concentrated to give N-(5-cyano-4-(((trans)-2-methoxycyclopentyl)amino)pyridin-2-yl)-4-fluoro-7-(dimethoxymethyl)-3,4-dihydro-2,4-methylene-1,8-naphthyridine-1(2H)-carboxamide. The relevant test data are as follows:

ESI-MS: 497.5 [M+H]$^+$.

The Third Step: Preparation of N-(5-cyano-4-(((trans)-2-methoxycyclopentyl)amino)pyridin-2-yl)-4-fluoro-7-formyl-3,4-dihydro-2,4-methylene-1,8-naphthyridine-1(2H)-carboxamide

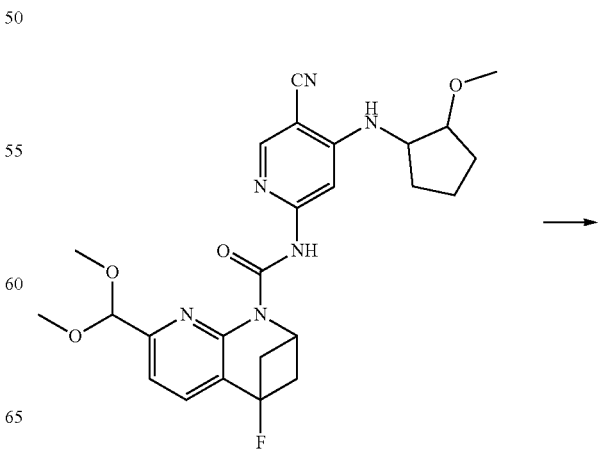

-continued

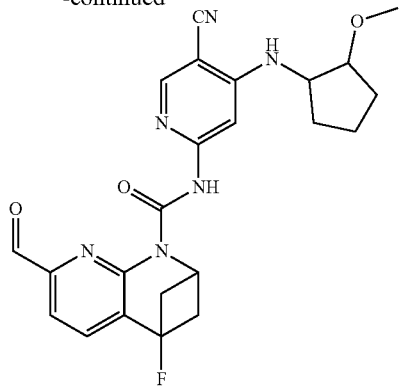

At room temperature, to a solution of N-(5-cyano-4-(((trans)-2-methoxycyclopentyl)amino)pyridin-2-yl)-4-fluoro-7-(dimethoxymethyl)-3,4-dihydro-2,4-methylene-1,8-naphthyridine-1(2H)-carboxamide (79 mg, 0.16 mmol) in tetrahydrofuran (2 mL) was added hydrochloric acid (3M, 2 mL) and continued to stir the reaction solution for 1 hour.

Saturated sodium bicarbonate solution (50 mL) was added to the reaction mixture to quench the reaction, extracted with ethyl acetate (50 mL), and the organic phase was obtained by separation. The organic phase was washed with saturated brine (50 mL), dried over anhydrous sodium sulfate, filtered with suction, and evaporated to dryness. The residue was purified by column chromatography, eluted with petroleum ether/ethyl acetate=3:1, and the fractions containing the product was concentrated to obtain Compound 19. The relevant test data of the product are as follows:

$^1$H NMR (DMSO-d$_6$, 400 MHz), δ 12.91 (s, 1H), 9.96 (s, 1H), 8.30 (s, 1H), 8.02 (d, J=7.6 Hz, 1H), 7.78 (d, J=7.6 Hz, 1H), 7.61 (s, 1H), 6.97 (d, J=6.8 Hz, 1H), 5.60 (dt, J=20.4 Hz, 1H), 3.82-3.79 (m, 1H), 3.78-3.73 (m, 1H), 3.27 (s, 3H), 2.86-2.81 (m, 2H), 2.10-2.05 (m, 1H), 2.03-1.98 (m, 2H), 1.93-1.86 (m, 1H), 1.73-1.56 (m, 4H).

ESI-MS: 451.4 [M+H]$^+$.

Example 20

Compound 20: Preparation of N-(5-cyano-4-(((trans)-2-hydroxycyclopentyl)amino)pyridin-2-yl)-4-fluoro-7-formyl-3,4-dihydro-2,4-methylene-1,8-naphthyridine-1(2H)-carboxamide

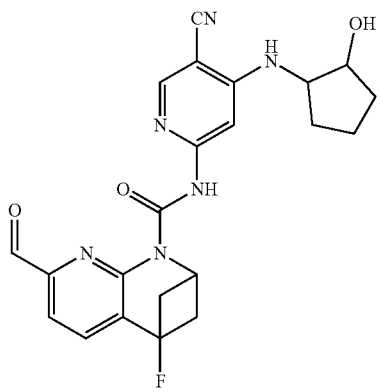 [SMILES: N#Cc1cnc(NC(=O)N2c3nc(C=O)ccc3C3(F)CC2C3)cc1NC1CCCC1O]

According to the method similar to preparing Compound 9 in Example 9, Compound 20 was prepared by reacting Intermediate 16 and Intermediate 9 as starting materials. The relevant test data of the product are as follows:

$^1$H NMR (DMSO-d$_6$, 400 MHz), δ 12.88 (s, 1H), 9.96 (s, 1H), 8.29 (s, 1H), 8.02 (d, J=7.6 Hz, 1H), 7.78 (d, J=7.6 Hz, 1H), 7.58 (s, 1H), 6.83 (d, J=6.8 Hz, 1H), 5.65-5.57 (m, 1H), 4.93 (d, J=4.8 Hz, 1H), 4.11-4.05 (m, 1H), 3.64-3.58 (m, 1H), 2.86-2.80 (m, 2H), 2.15-2.07 (m, 1H), 2.04-1.98 (m, 2H), 1.92-1.84 (m, 1H), 1.72-1.63 (m, 2H), 1.55-1.46 (m, 2H).

ESI-MS: 437.2 [M+H]$^+$.

Example 21

Compound 21: Preparation of N-(5-cyano-44(2-methoxyethyl)amino)pyridin-2-yl)-4-fluoro-7-formyl-6-ethyl-3,4-dihydro-2,4-methylene-1,8-naphthyridine-1(2H)-carboxamide

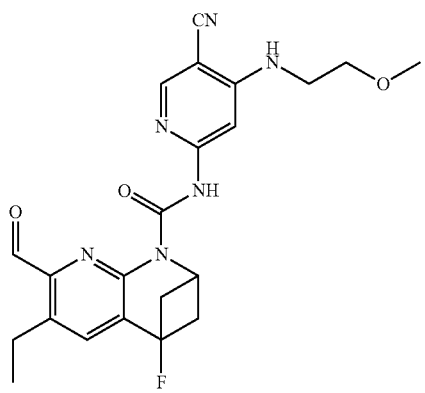 [SMILES: CCc1cc2c(nc1C=O)N(C(=O)Nc1cc(NCCOC)c(C#N)cn1)C1CC2(F)C1]

According to the method similar to preparing Compound 1 in Example 1, Compound 21 was prepared by reacting Intermediate 48 and Intermediate 2 as starting materials. The relevant test data of the product are as follows:

$^1$H NMR (DMSO-d$_6$, 400 MHz), δ 12.97 (s, 1H), 10.09 (s, 1H), 8.28 (s, 1H), 7.85 (s, 1H), 7.51 (s, 1H), 7.01 (t, J=5.6 Hz, 1H), 5.57 (dt, J=20.4 Hz, 6.4 Hz, 1H), 3.53 (t, J=6 Hz, 2H), 3.39 (dt, J=5.6 Hz, 5.6 Hz, 2H), 3.29 (s, 3H), 3.06 (q, J=7.6 Hz, 2H), 2.84 (dd, J=6.8 Hz, 2.0 Hz, 2H), 2.01 (dd, J=6.8 Hz, 2.0 Hz, 2H), 1.2 (t, J=7.6 Hz, 3H).

ESI-MS: 439.2 [M+H]$^+$.

Example 22

Compound 22 Preparation of N-(5-cyano-4-((2-(2-methoxyethoxy)ethyl)amino)pyridin-2-yl)-7-formyl-4-methoxy-3,4-dihydro-2,4-methylene-1,8-naphthyridine-1(2H)-carboxamide

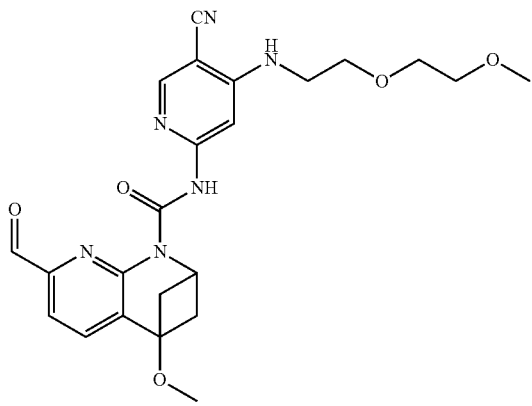 [SMILES: COCCOCCNc1cc(NC(=O)N2c3nc(C=O)ccc3C3(OC)CC2C3)ncc1C#N]

According to the method similar to preparing Compound 1 in Example 1, Compound 22 was prepared by reacting Intermediate 21 and Intermediate 7 as starting materials. The relevant test data of the product are as follows:

$^1$H NMR (DMSO-d$_6$, 400 MHz), δ 13.06 (s, 1H), 9.95 (s, 1H), 8.30 (s, 1H), 7.98 (d, J=7.6 Hz, 1H), 7.74 (s, J=7.6 Hz, 1H), 7.54 (s, J, 1H), 6.98 (t, J=5.6 Hz, 1H), 5.50 (t, J=6.4 Hz, 1H), 3.61 (t, J=5.6 Hz, 2H), 3.55-3.58 (m, 2H), 3.47 (s, 3H), 3.44-3.46 (m, 2H), 3.39 (q, J=5.6 Hz, 2H), 3.24 (s, 3H), 2.82 (m, 2H), 1.61 (dd, J=6.8 Hz, 2.4 Hz, 2H).

ESI-MS: 467.0 [M+H]$^+$.

Example 23

Compound 23: Preparation of N-(5-cyano-4-(azetidin-3-ylamino)pyridin-2-yl)-7-formyl-4-fluoro-3,4-dihydro-2,4-methylene-1,8-naphthyridine-1(2H)-carboxamide

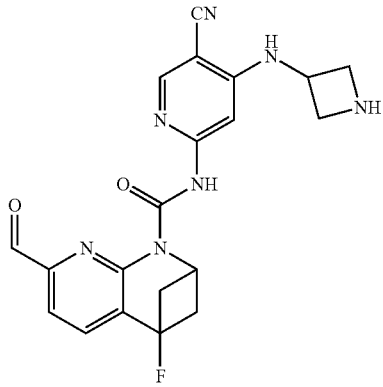 [SMILES: N#Cc1cnc(NC(=O)N2c3nc(C=O)ccc3C3(F)CC2C3)cc1NC1CNC1]

According to the method similar to preparing Compound 1 in Example 1, Compound 23 was prepared by reacting Intermediate 16 and Intermediate 8 as starting materials. The relevant test data of the product are as follows:

ESI-MS: 408.0 [M+H]$^+$.

Example 24

Compound 24: Preparation of (R)—N-(5-cyano-44(1-methoxyprop-2-yl)amino)pyridin-2-yl)-7-formyl-6-((4-methyl-2-oxopiperazin-1-yl)methyl)-3,4-dihydro-2,4-methylene-1,8-naphthyridine-1(2H)-carboxamide

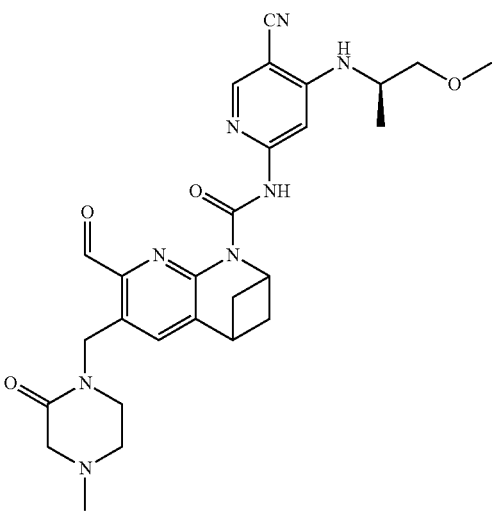 [SMILES: COC[C@@H](C)Nc1cc(NC(=O)N2c3nc(C=O)c(CN4CCN(C)CC4=O)cc3C3CC2C3)ncc1C#N]

According to the method similar to preparing Compound 4 in Example 4, Compound 24 was prepared by reacting Intermediate 51 and Intermediate 3 as starting materials. The relevant test data of the product are as follows:

$^1$H NMR (DMSO-d$_6$, 400 MHz), δ 13.22 (s, 1H), 10.09 (s, 1H), 8.29 (s, 1H), 7.57 (s, 1H), 7.56 (s, 1H), 6.61 (d, J=8.4 Hz, 1H), 5.53 (dd, J=11.2 Hz, 5.2 Hz, 1H), 4.91 (s, 2H), 3.85 (dt, J=13.6 Hz, 6.4 Hz, 1H), 3.62 (dt, J=6.0 Hz, 5.2 Hz, 1H), 3.49 (dd, J=9.6 Hz, 6.4 Hz, 1H), 3.39 (dd, J=9.8 Hz, 5.8 Hz, 1H), 3.29 (s, 3H), 3.29-3.28 (m, 2H), 3.08 (s, 2H), 2.66-2.59 (m, 4H), 2.25 (s, 3H), 1.46 (dd, J=7.2 Hz, 2.4 Hz, 2H), 1.19 (d, J=6.8 Hz, 3H).

ESI-MS: 533.2 [M+H]$^+$.

Example 25

Compound 25: Preparation of N-(5-cyano-4-(methoxyethoxy)pyridin-2-yl)-7-formyl-6-((4-methyl-2-oxopiperazin-1-yl) methyl)-3,4-dihydro-2,4-methylene-1,8-naphthyridine-1(2H)-carboxamide

Example 26

Compound 26: Preparation of N-(5-cyano-4-(((trans)-2-methoxycyclopentyl)amino)pyridin-2-yl)-7-formyl-6-((4-methyl-2-oxopiperazin-1-yl)methyl)-3,4-dihydro-2,4-methylene-1,8-naphthyridine-1(2H)-carboxamide

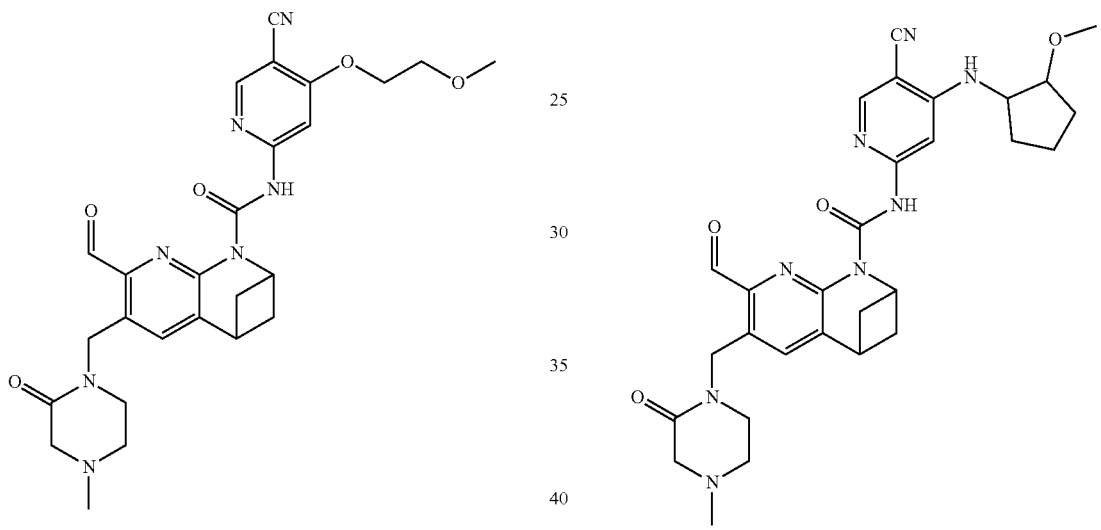

According to the method similar to preparing Compound 4 in Example 4, Compound 25 was prepared by reacting Intermediate 51 and Intermediate 6 as starting materials. The relevant test data of the product are as follows:

$^1$H NMR (DMSO-$d_6$, 400 MHz), δ 13.58 (s, 1H), 10.13 (s, 1H), 8.62 (s, 1H), 7.95 (s, 1H), 7.58 (s, 1H), 5.54 (dd, J=11.2 Hz, 5.2 Hz, 1H), 4.92 (s, 2H), 4.35 (t, J=4.4 Hz, 2H), 3.75 (t, J=4.4 Hz, 2H), 3.64 (dt, J=6.0 Hz, 5.2 Hz, 1H), 3.35 (s, 3H), 3.31-3.29 (m, 2H), 3.08 (s, 2H), 2.65-2.61 (m, 4H), 2.25 (s, 3H), 1.48 (dd, J=7.2 Hz, 2.4 Hz, 2H).

ESI-MS: 520.2 [M+H]$^+$.

According to the method similar to preparing Compound 4 in Example 4, Compound 26 was prepared by reacting Intermediate 51 and Intermediate 5 as starting materials. The relevant test data of the product are as follows:

$^1$H NMR (DMSO-$d_6$, 400 MHz), δ 13.22 (s, 1H), 10.09 (s, 1H), 8.29 (s, 1H), 7.61 (s, 1H), 7.55 (s, 1H), 6.92 (d, J=7.2 Hz, 1H), 5.53 (dd, J=11.2 Hz, 5.2 Hz, 1H), 4.91 (s, 2H), 3.83-3.80 (m, 1H), 3.78-3.73 (m, 1H), 3.63 (dt, J=6.4 Hz, 5.2 Hz, 1H), 3.30-3.28 (m, 2H), 3.27 (s, 3H), 3.07 (s, 2H), 2.66-2.59 (m, 4H), 2.25 (s, 3H), 2.09-2.03 (m, 1H), 1.93-1.86 (m, 1H), 1.74-1.55 (m, 4H), 1.45 (dd, J=7.0 Hz, 2.6 Hz, 2H).

ESI-MS: 559.2 [M+H]$^+$.

Example 27

Compound 27: Preparation of N-(5-cyano-4-((2-methoxyethyl)amino)pyridin-2-yl)-7-formyl-6-((3-oxomorpholinyl)methyl)-3,4-dihydro-2,4-methylene-1,8-naphthyridine-1(2H)-carboxamide

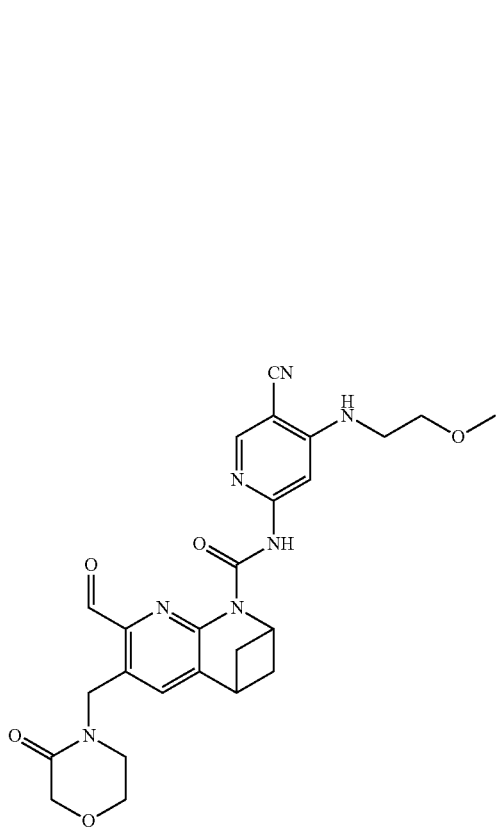 [SMILES: COCCNc1cc(NC(=O)N2c3nc(C=O)c(CN4CCOCC4=O)cc3C3CC2C3)ncc1C#N]

According to the method similar to preparing Compound 1 in Example 1, Compound 27 was prepared by reacting Intermediate 53 and Intermediate 2 as starting materials. The relevant test data of the product are as follows:

$^1$H NMR (DMSO-d$_6$, 400 MHz), δ 13.22 (s, 1H), 10.09 (s, 1H), 8.29 (s, 1H), 7.65 (s, 1H), 7.54 (s, 1H), 6.98 (t, J=5.8 Hz, 1H), 5.54 (dd, J=11.2 Hz, 5.2 Hz, 1H), 4.95 (s, 2H), 4.16 (s, 2H), 3.89 (t, J=5.0 Hz, 2H), 3.65 (dt, J=6.0 Hz, 5.2 Hz, 1H), 3.53 (t, J=5.8 Hz, 2H), 3.40-3.39 (m, 2H), 3.36 (t, J=5.0 Hz, 2H), 3.29 (s, 3H), 3.29-3.28 (m, 2H), 2.65-2.60 (m, 2H), 1.46 (dd, J=7.0 Hz, 2.6 Hz, 2H).

ESI-MS: 506.2 [M+H]$^+$.

Example 28

Compound 28: Preparation of N-(5-cyano-44(2-methoxyethyl)amino)pyridin-2-yl)-7-formyl-6-((2-oxo-1,3-oxazepan-3-yl)methyl)-3,4-dihydro-2,4-methylene-1,8-naphthyridine-1(2H)-carboxamide

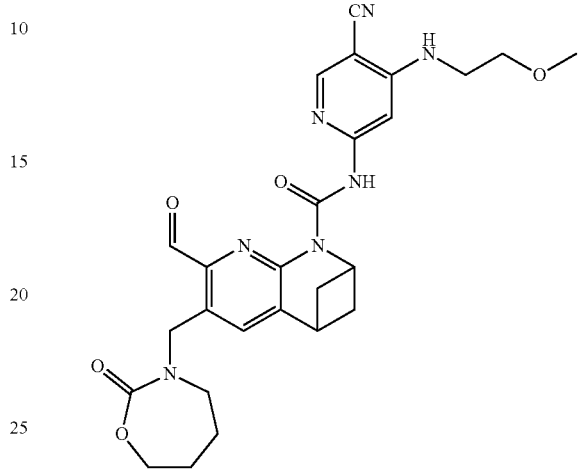

According to the method similar to preparing Compound 1 in Example 1, Compound 28 was prepared by reacting Intermediate 56 and Intermediate 2 as starting materials. The relevant test data of the product are as follows:

$^1$H NMR (DMSO-d$_6$, 400 MHz), δ 13.23 (s, 1H), 10.07 (s, 1H), 8.29 (s, 1H), 7.73 (s, 1H), 7.53 (s, 1H), 6.98 (t, J=5.6 Hz, 1H), 5.54 (dd, J=11.6 Hz, 5.2 Hz, 1H), 4.81 (s, 2H), 4.09 (t, J=5.2 Hz, 2H), 3.68 (dt, J=6.0 Hz, 5.2 Hz, 1H), 3.53 (t, J=5.8 Hz, 2H), 3.42-3.37 (m, 2H), 3.29 (s, 3H), 3.29-3.28 (m, 2H), 2.65-2.60 (m, 2H), 1.79-1.75 (m, 2H), 1.64-1.60 (m, 2H), 1.46 (dd, J=7.0 Hz, 2.6 Hz, 2H).

ESI-MS: 520.3 [M+H]$^+$.

Example 29

Compound 29: Preparation of N-(5-cyano-4-((2-methoxyethyl)amino)pyridin-2-yl)-4-(2-(dimethylamino)ethoxy)-7-formyl-3,4-dihydro-2,4-methylene-1,8-naphthyridine-1(2H)-carboxamide

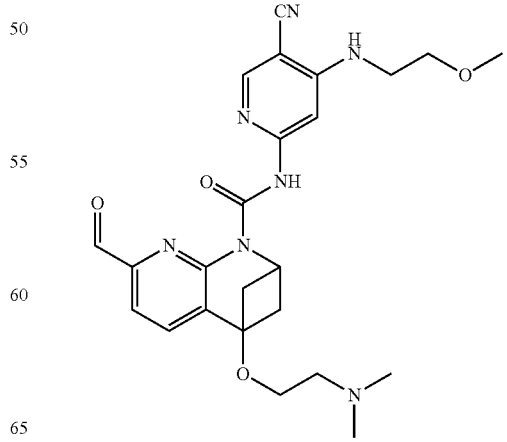

According to the method similar to preparing Compound 4 in Example 4, Compound 29 was prepared by reacting Intermediate 23 and Intermediate 2 as starting materials. The relevant test data of the product are as follows:

¹H NMR (DMSO-d₆, 400 MHz), δ 13.07 (s, 1H), 9.95 (s, 1H), 8.30 (s, 1H), 8.05 (d, J=7.6 Hz, 1H), 7.77 (d, J=7.6 Hz, 1H), 7.54 (s, 1H), 7.02 (t, J=4.8 Hz, 1H), 5.50 (t, J=6.2 Hz, 1H), 3.75 (t, J=5.4 Hz, 2H), 3.53 (t, J=5.8 Hz, 2H), 3.40 (dt, J=5.6 Hz, 5.8 Hz, 2H), 3.29 (s, 3H), 2.84-2.80 (m, 2H), 2.72-2.65 (m, 2H), 2.32 (s, 6H), 1.66 (dd, J=6.8 Hz, 2.0 Hz, 2H).

ESI-MS: 408.1 [M+H]⁺.

Example 30

Compound 30: Preparation of N-(5-cyano-4-((2-methoxyethyl)amino)pyridin-2-yl)-4-(2-(dimethylamino)acetamido)-7-formyl-3,4-dihydro-2,4-methylene-1,8-naphthyridine-1(2H)-carboxamide

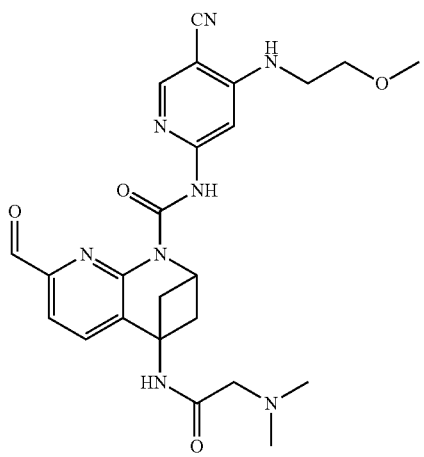 [SMILES: COCCNc1cc(NC(=O)N2c3nc(C=O)ccc3C3(NC(=O)CN(C)C)CC2C3)ncc1C#N]

According to the method similar to preparing Compound 4 in Example 4, Compound 30 was prepared by reacting Intermediate 31 and Intermediate 2 as starting materials. The relevant test data of the product are as follows:

¹H NMR (DMSO-d₆, 400 MHz), δ 13.16 (s, 1H), 9.94 (s, 1H), 8.76 (s, 1H), 8.29 (s, 1H), 7.70 (d, J=7.6 Hz, 1H), 7.64 (d, J=7.6 Hz, 1H), 7.54 (s, 1H), 7.00 (t, J=5.6 Hz, 1H), 5.61 (t, J=5.6 Hz, 1H), 3.52 (t, J=5.6 Hz, 2H), 3.40 (dt, J=5.6 Hz, 5.6 Hz, 2H), 3.29 (s, 3H), 3.03 (s, 2H), 2.52 (m, 2H), 2.30 (s, 6H), 1.92 (dd, J=7.2 Hz, 2.4 Hz, 2H).

ESI-MS: 493.1 [M+H]⁺.

Example 31

Compound 31: Preparation of N-(5-cyano-44(2-methoxyethyl)amino)pyridin-2-yl)-4-(1-methylpiperidine-4-carboxamido)-7-formyl-3,4-dihydro-2,4-methylene-1,8-naphthyridine-1(2H)-carboxamide

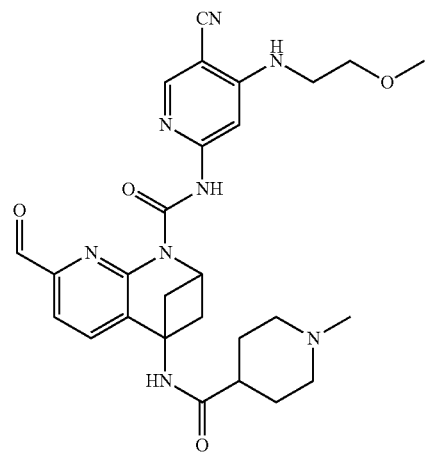 [SMILES: COCCNc1cc(NC(=O)N2c3nc(C=O)ccc3C3(NC(=O)C4CCN(C)CC4)CC2C3)ncc1C#N]

According to the method similar to preparing Compound 4 in Example 4, Compound 31 was prepared by reacting Intermediate 32 and Intermediate 2 as starting materials. The relevant test data of the product are as follows:

ESI-MS: 533.2 [M+H]⁺.

Example 32

Compound 32: Preparation of N-(5-cyano-4-((2-methoxyethyl)amino)pyridin-2-yl)-4-(1-methyl-1H-pyrazole-4-carboxamido)-7-formyl-3,4-dihydro-2,4-methylene-1,8-naphthyridine-1(2H)-carboxamide

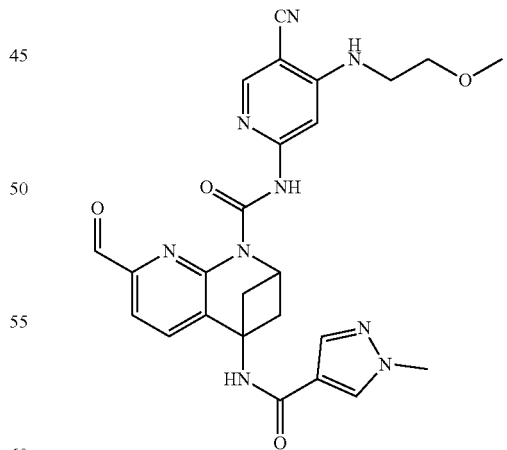

According to the method similar to preparing Compound 1 in Example 1, Compound 32 was prepared by reacting Intermediate 33 and Intermediate 2 as starting materials. The relevant test data of the product are as follows:

¹H NMR (DMSO-d₆, 400 MHz), δ 13.18 (s, 1H), 9.95 (s, 1H), 8.98 (s, 1H), 8.30 (s, 1H), 8.21 (s, 1H), 7.94 (s, 1H), 7.70 (d, J=7.6 Hz, 1H), 7.61 (d, J=7.6 Hz, 1H), 7.56 (s, 1H), 7.02 (t, J=5.6 Hz, 1H), 5.65 (t, J=5.6 Hz, 1H), 3.89 (s, 3H), 3.54 (t, J=5.6 Hz, 2H), 3.40 (dt, J=5.6 Hz, 5.6 Hz, 2H), 3.30 (s, 3H), 2.60 (m, 2H), 1.99 (dd, J=7.2 Hz, 2.4 Hz, 2H).
ESI-MS: 516.1 [M+H]⁺.

Example 33

Compound 33: Preparation of N-(5-cyano-4-(((trans)-2-methoxycyclopentyl)amino)pyridin-2-yl)-4-(2-(dimethylamino)acetamido)-7-formyl-3,4-dihydro-2,4-methylene-1,8-naphthyridine-1(2H)-carboxamide

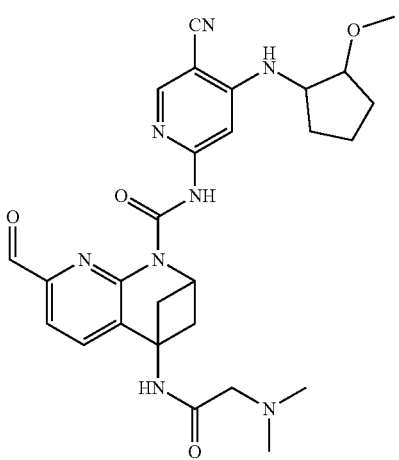 [SMILES: COC1CCCC1Nc1cc(NC(=O)N2c3nc(C=O)ccc3C3(NC(=O)CN(C)C)CC2C3)ncc1C#N]

According to the method similar to preparing Compound 4 in Example 4, Compound 33 was prepared by reacting Intermediate 31 and Intermediate 5 as starting materials. The relevant test data of the product are as follows:
ESI-MS: 533.1 [M+H]⁺.

Example 34

Compound 34: Preparation of N-(5-cyano-4-((2-methoxyethyl)amino)pyridin-2-yl)-4-(methyl(tetrahydrofuran-3-yl)amino)-7-formyl-3,4-dihydro-2,4-methylene-1,8-naphthyridine-1(2H)-carboxamide

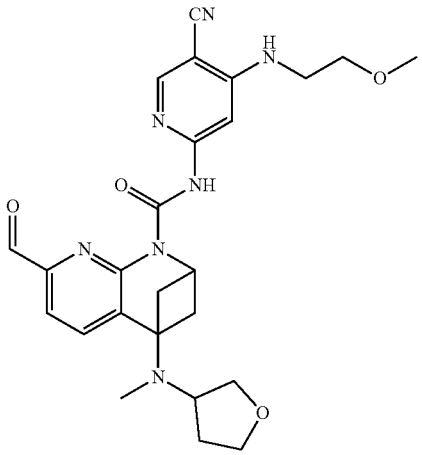 [SMILES: COCCNc1cc(NC(=O)N2c3nc(C=O)ccc3C3(N(C)C4CCOC4)CC2C3)ncc1C#N]

According to the method similar to preparing Compound 4 in Example 4, Compound 34 was prepared by reacting Intermediate 41 and Intermediate 2 as starting materials. The relevant test data of the product are as follows:
¹H NMR (DMSO-d₆, 400 MHz), δ 13.17 (s, 1H), 9.95 (s, 1H), 8.29 (s, 1H), 7.97 (d, J=7.2 Hz, 1H), 7.75 (d, J=7.6 Hz, 1H), 7.54 (s, 1H), 6.99 (t, J=5.4 Hz, 1H), 5.49 (t, J=6.0 Hz, 1H), 3.83-3.77 (m, 2H), 3.62-3.50 (m, 4H), 3.42-3.37 (m, 2H), 3.29 (s, 3H), 2.63 (dd, J=9.0 Hz, 5.8 Hz, 2H), 2.27 (s, 3H), 2.26 (m, 1H), 1.56-1.54 (m, 2H), 1.27-1.25 (m, 2H).
ESI-MS: 492.2 [M+H]⁺.

Example 35

Compound 35: Preparation of N-(5-cyano-4-((2-methoxyethyl)amino)pyridin-2-yl)-4-(2-(pyrrolidin-1-yl)ethoxy)-7-formyl-3,4-dihydro-2,4-methylene-1,8-naphthyridine-1(2H)-carboxamide

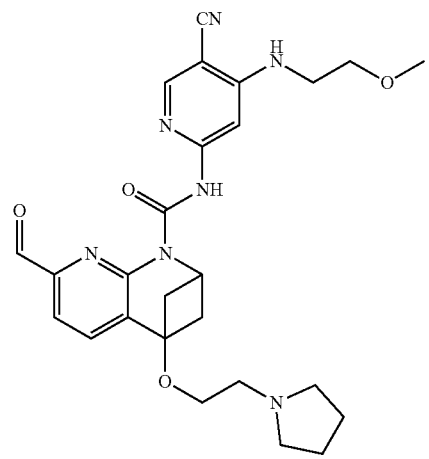 [SMILES: COCCNc1cc(NC(=O)N2c3nc(C=O)ccc3C3(OCCN4CCCC4)CC2C3)ncc1C#N]

According to the method similar to preparing Compound 4 in Example 4, Compound 35 was prepared by reacting Intermediate 26 and Intermediate 2 as starting materials. The relevant test data of the product are as follows:
¹H NMR (DMSO-d₆, 400 MHz), δ 13.06 (s, 1H), 9.96 (s, 1H), 8.30 (s, 1H), 8.16 (d, J=7.6 Hz, 1H), 7.76 (d, J=7.6 Hz, 1H), 7.54 (s, 1H), 7.02 (t, J=5.4 Hz, 1H), 5.52 (t, J=6.2 Hz, 1H), 3.94 (m, 2H), 3.53 (t, J=5.8 Hz, 2H), 3.40 (dt, J=5.6 Hz, 5.4 Hz, 2H), 3.29 (s, 3H), 3.29-3.28 (m, 2H), 2.89-2.85 (m, 2H), 2.51-2.50 (m, 4H), 1.92-1.91 (m, 4H), 1.68 (dd, J=6.8 Hz, 2.0 Hz, 2H).
ESI-MS: 505.8 [M+H]⁺.

Example 36

Compound 36: Preparation of N-(5-cyano-4-((2-methoxyethyl)amino)pyridin-2-yl)-4-(2-methoxy-ethoxy)-7-formyl-3,4-dihydro-2,4-methylene-1,8-naphthyridine-1(2H)-carboxamide

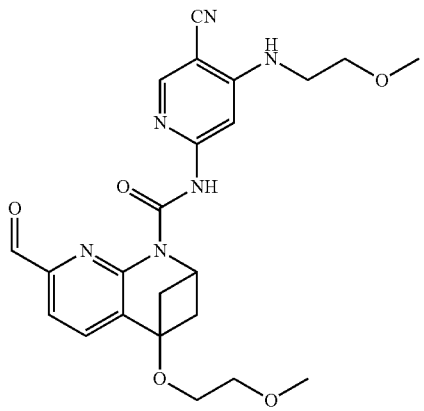 [SMILES: COCCNc1cc(NC(=O)N2c3nc(C=O)ccc3C3(OCCOC)CC2C3)ncc1C#N]

According to the method similar to preparing Compound 1 in Example 1, Compound 36 was prepared by reacting Intermediate 22 and Intermediate 2 as starting materials. The relevant test data of the product are as follows:

$^1$H NMR (DMSO-d$_6$, 400 MHz), δ 13.06 (s, 1H), 9.95 (s, 1H), 8.29 (s, 1H), 8.02 (d, J=7.6 Hz, 1H), 7.76 (d, J=7.6 Hz, 1H), 7.53 (s, 1H), 7.00 (t, J=5.6 Hz, 1H), 5.50 (t, J=6.4 Hz, 1H), 3.78-3.75 (m, 2H), 3.61-3.59 (m, 2H), 3.53 (t, J=5.8 Hz, 2H), 3.40 (dt, J=5.6 Hz, 5.6 Hz, 2H), 3.33 (s, 3H), 3.29 (s, 3H), 2.77 (dt, J=6.8 Hz, 2.0 Hz, 2H), 1.67 (dd, J=6.8 Hz, 2.0 Hz, 2H).

ESI-MS: 467.2 [M+H]$^+$.

Example 37

Compound 37: Preparation of N-(5-cyano-4-((2-methoxyethyl)amino)pyridin-2-yl)-4-propionamido-7-formyl-3,4-dihydro-2,4-methylene-1,8-naphthyridine-1(2H)-carboxamide

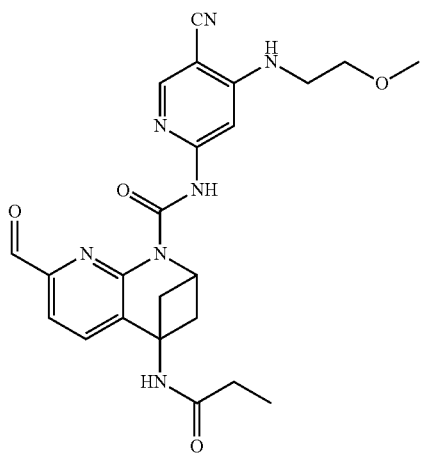 [SMILES: CCC(=O)NC12CC(C1)N(C(=O)Nc1cc(NCCOC)c(C#N)cn1)c1nc(C=O)ccc12]

According to the method similar to preparing Compound 1 in Example 1, Compound 37 was prepared by reacting Intermediate 34 and Intermediate 2 as starting materials. The relevant test data of the product are as follows:

$^1$H NMR (DMSO-d$_6$, 400 MHz), δ 13.16 (s, 1H), 9.94 (s, 1H), 8.75 (s, 1H), 8.30 (s, 1H), 7.70 (d, J=7.6 Hz, 1H), 7.62 (d, J=7.6 Hz, 1H), 7.54 (s, 1H), 7.00 (t, J=5.6 Hz, 1H), 5.61 (t, J=5.8 Hz, 1H), 3.53 (t, J=5.8 Hz, 2H), 3.40 (dt, J=6.0 Hz, 5.2 Hz, 2H), 3.29 (s, 3H), 2.48-2.46 (m, 2H), 2.27 (q, J=7.6 Hz, 2H), 1.90 (dd, J=7.2 Hz, 2.4 Hz, 2H), 1.08 (t, J=7.6 Hz, 3H).

ESI-MS: 464.2 [M+H]$^+$.

Example 38

Compound 38: Preparation of N-(5-cyano-4-((2-methoxyethyl)amino)pyridin-2-yl)-4-ethanesulfonamido-7-formyl-3,4-dihydro-2, 4-methylene-1,8-naphthyridine-1(2H)-carboxamide

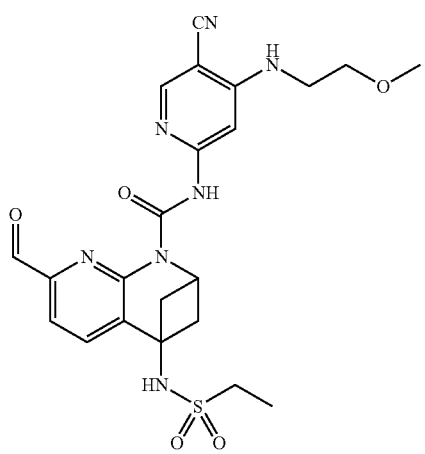 [SMILES: CCS(=O)(=O)NC12CC(C1)N(C(=O)Nc1cc(NCCOC)c(C#N)cn1)c1nc(C=O)ccc12]

According to the method similar to preparing Compound 1 in Example 1, Compound 38 was prepared by reacting Intermediate 40 and Intermediate 2 as starting materials. The relevant test data of the product are as follows:

$^1$H NMR (DMSO-d$_6$, 400 MHz), δ 13.14 (s, 1H), 9.95 (s, 1H), 8.34 (s, 1H), 8.30 (s, 1H), 8.09 (d, J=7.6 Hz, 1H), 7.81 (d, J=7.6 Hz, 1H), 7.53 (s, 1H), 7.02 (t, J=5.6 Hz, 1H), 5.60 (t, J=6.0 Hz, 1H), 3.53 (t, J=6.0 Hz, 2H), 3.40 (dt, J=5.6 Hz, 5.6 Hz, 2H), 3.29 (s, 3H), 3.18 (q, J=7.2 Hz, 2H), 2.74 (dt, J=6.8 Hz, 2.4 Hz, 2H), 1.80 (dt, J=6.8 Hz, 2.4 Hz, 2H), 1.31 (t, J=7.2 Hz, 3H).

ESI-MS: 500.1 [M+H]$^+$.

Example 39

Compound 39: Preparation of N-(5-cyano-44(2-methoxyethyl)amino)pyridin-2-yl)-4-(2-(morpholin-4-yl)ethoxy)-7-formyl-3,4-dihydro-2,4-methylene-1,8-naphthyridine-1(2H)-carboxamide

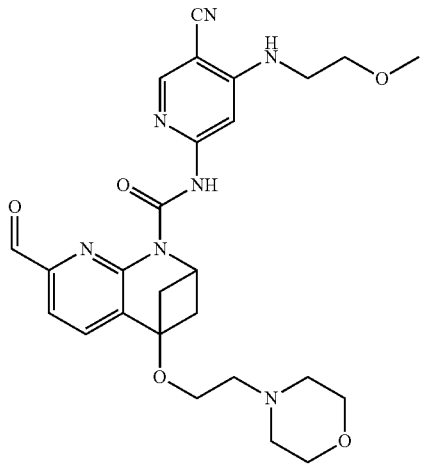 [SMILES: COCCNc1cc(NC(=O)N2c3nc(C=O)ccc3C3(OCCN4CCOCC4)CC2C3)ncc1C#N]

According to the method similar to preparing Compound 4 in Example 4, Compound 39 was prepared by reacting Intermediate 27 and Intermediate 2 as starting materials. The relevant test data of the product are as follows:

$^1$H NMR (DMSO-$d_6$, 400 MHz), δ 13.06 (s, 1H), 9.95 (s, 1H), 8.29 (s, 1H), 8.08 (d, J=7.2 Hz, 1H), 7.76 (d, J=7.6 Hz, 1H), 7.53 (s, 1H), 7.01 (t, J=5.6 Hz, 1H), 5.50 (t, J=6.2 Hz, 1H), 3.74 (t, J=5.6 Hz, 2H), 3.60 (t, J=4.6 Hz, 4H), 3.53 (t, J=5.6 Hz, 2H), 3.39 (dt, J=5.6 Hz, 5.6 Hz, 2H), 3.29 (s, 3H), 2.78 (dt, J=6.6 Hz, 2.0 Hz, 2H), 2.62 (t, J=5.8 Hz, 2H), 2.50-2.46 (m, 4H), 1.67 (dd, J=6.8 Hz, 2.0 Hz, 2H).

ESI-MS: 522.3 [M+H]$^+$.

Example 40

Compound 40: Preparation of N-(5-cyano-44(2-methoxyethyl)amino)pyridin-2-yl)-4-(1-methylpyrrolidine-3-carboxamido)-7-formyl-3,4-dihydro-2,4-methylene-1,8-naphthyridine-1(2H)-carboxamide

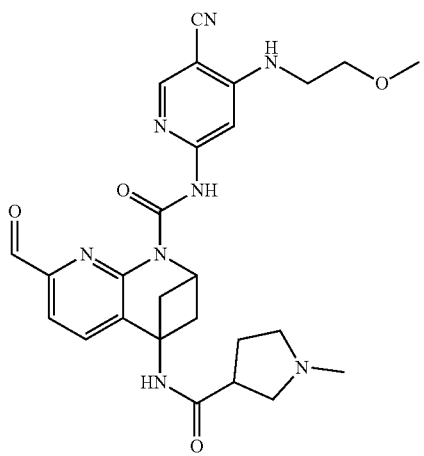 [SMILES: COCCNc1cc(NC(=O)N2c3nc(C=O)ccc3C3(NC(=O)C4CCN(C)C4)CC2C3)ncc1C#N]

According to the method similar to preparing Compound 4 in Example 4, Compound 40 was prepared by reacting Intermediate 35 and Intermediate 2 as starting materials. The relevant test data of the product are as follows:

$^1$H NMR (DMSO-$d_6$, 400 MHz), δ 13.15 (s, 1H), 9.95 (s, 1H), 9.04 (s, 1H), 8.30 (s, 1H), 7.70 (d, J=7.6 Hz, 1H), 7.64 (d, J=7.6 Hz, 1H), 7.54 (s, 1H), 7.02 (t, J=5.6 Hz, 1H), 5.62 (t, J=5.8 Hz, 1H), 3.53 (t, J=5.8 Hz, 2H), 3.42-3.39 (m, 3H), 3.29 (s, 3H), 2.63 (s, 3H), 2.52 (m, 4H), 2.22-2.12 (m, 4H), 1.93-1.91 (m, 2H), 1.23 (t, J=7.2 Hz, 2H).

ESI-MS: 519.2 [M+H]$^+$.

Example 41

Compound 41: Preparation of N-(5-cyano-44(2-methoxyethyl)amino)pyridin-2-yl)-4-(2(pyrrolidin-1-yl)acetamido)-7-formyl-3,4-dihydro-2,4-methylene-1,8-naphthyridine-1(2H)-carboxamide

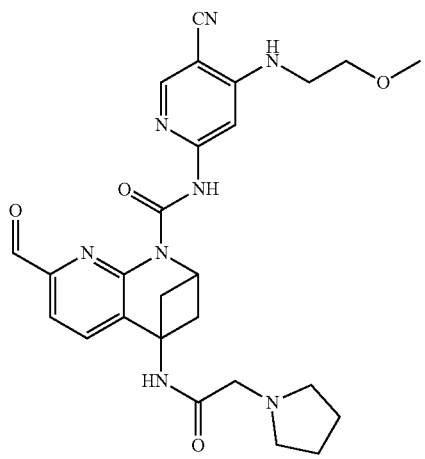 [SMILES: COCCNc1cc(NC(=O)N2c3nc(C=O)ccc3C3(NC(=O)CN4CCCC4)CC2C3)ncc1C#N]

According to the method similar to preparing Compound 4 in Example 4, Compound 41 was prepared by reacting Intermediate 36 and Intermediate 2 as starting materials. The relevant test data of the product are as follows:

$^1$H NMR (DMSO-$d_6$, 400 MHz), δ 13.16 (s, 1H), 9.95 (s, 1H), 8.80 (s, 1H), 8.30 (s, 1H), 7.71 (d, J=7.6 Hz, 1H), 7.65 (d, J=7.6 Hz, 1H), 7.55 (s, 1H), 7.01 (t, J=5.4 Hz, 1H), 5.61 (t, J=5.8 Hz, 1H), 3.53 (t, J=5.8 Hz, 2H), 3.40 (dt, J=5.6 Hz, 5.6 Hz, 2H), 3.29 (s, 3H), 3.29 (s, 2H), 2.72 (m, 2H), 2.55 (m, 4H), 1.92 (dd, J=7.4 Hz, 2.2 Hz, 2H), 1.79 (m, 4H).

ESI-MS: 519.2 [M+H]$^+$.

Example 42

Compound 42: Preparation of N-(5-cyano-44(2-methoxyethyl)amino)pyridin-2-yl)-4-(N,1-dimethyl-1H-pyrazole-4-carboxamido)-7-formyl-3,4-dihydro-2,4-methylene-1,8-naphthyridine-1(2H)-carboxamide

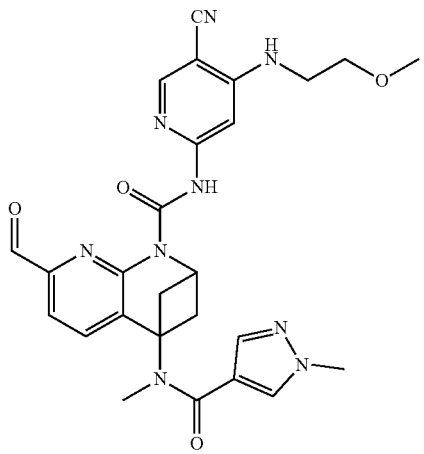 [SMILES: COCCNc1cc(NC(=O)N2c3nc(C=O)ccc3C3(N(C)C(=O)c4cnn(C)c4)CC2C3)ncc1C#N]

According to the method similar to preparing Compound 1 in Example 1, Compound 42 was prepared by reacting Intermediate 42 and Intermediate 2 as starting materials. The relevant test data of the product are as follows:
ESI-MS: 530.1 [M+H]+.

Example 43

Compound 43: Preparation of N-(5-cyano-4-((2-methoxyethyl)amino)pyridin-2-yl)-7-formyl-4-(4-methyl-2-oxopiperazin-1-yl)-3,4-dihydro-2,4-methylene-1,8-naphthyridine-1(2H)-carboxamide

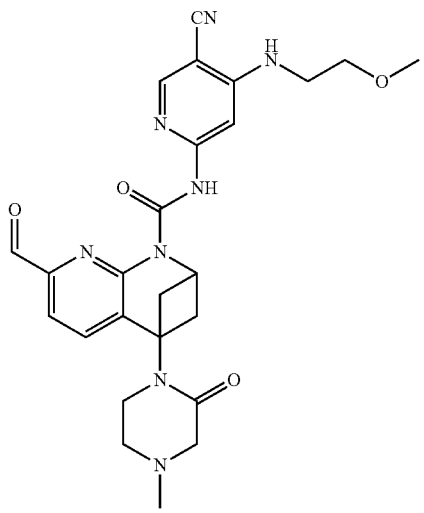 [SMILES: COCCNc1cc(NC(=O)N2c3nc(C=O)ccc3C3(N4CCN(C)CC4=O)CC2C3)ncc1C#N]

According to the method similar to preparing Compound 4 in Example 4, Compound 43 was prepared by reacting Intermediate 44 and Intermediate 2 as starting materials. The relevant test data of the product are as follows:

$^1$H NMR (DMSO-d$_6$, 400 MHz), δ 13.12 (s, 1H), 9.95 (s, 1H), 8.34 (s, 1H), 8.30 (s, 1H), 7.71 (d, J=7.6 Hz, 1H), 7.56-7.55 (m, 2H), 7.01 (t, J=5.6 Hz, 1H), 5.58 (t, J=5.8 Hz, 1H), 3.53 (t, J=5.8 Hz, 2H), 3.40 (dt, J=5.6 Hz, 5.6 Hz, 2H), 3.29 (s, 3H), 3.20-3.00 (m, 4H), 2.83-2.71 (m, 3H), 2.73 (dd, J=10.4 Hz, 6.0 Hz, 1H), 2.31 (s, 3H), 2.14 (t, J=5.2 Hz, 1H), 1.81 (t, J=5.2 Hz, 1H).
ESI-MS: 505.2 [M+H]+.

Example 44

Compound 44: Preparation of N-(5-cyano-4-((2-methoxyethyl)amino)pyridin-2-yl)-7-formyl-4-(morpholine-4-carboxamido)-3,4-dihydro-2,4-methylene-1,8-naphthyridine-1(2H)-carboxamide

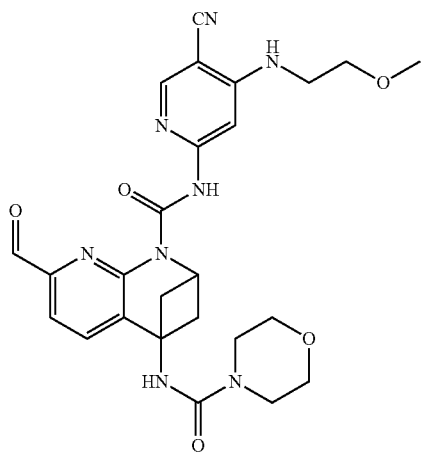 [SMILES: COCCNc1cc(NC(=O)N2c3nc(C=O)ccc3C3(NC(=O)N4CCOCC4)CC2C3)ncc1C#N]

According to the method similar to preparing Compound 1 in Example 1, Compound 44 was prepared by reacting Intermediate 43 and Intermediate 2 as starting materials. The relevant test data of the product are as follows:

$^1$H NMR (DMSO-d$_6$, 400 MHz), δ 13.18 (s, 1H), 9.95 (s, 1H), 8.30 (s, 1H), 7.72 (d, J=7.6 Hz, 1H), 7.64 (d, J=7.6 Hz, 1H), 7.55 (s, 1H), 7.48 (s, 1H), 7.00 (t, J=5.6 Hz, 1H), 5.60 (t, J=5.6 Hz, 1H), 3.61 (t, J=3.6 Hz, 4H), 3.53 (t, J=6.0 Hz, 2H), 3.40 (dt, J=5.6 Hz, 5.6 Hz, 2H), 3.36 (t, J=4.8 Hz, 4H), 3.29 (s, 3H), 2.50 (m, 2H), 1.88 (dd, J=7.2 Hz, 2.4 Hz, 2H).
ESI-MS: 521.2 [M+H]+.

Example 45

Compound 45: Preparation of N-(5-cyano-4-((2-methoxyethyl)amino)pyridin-2-yl)-4-(2-(morpholin-4-yl)-2-oxoethoxy)-7-formyl-3,4-dihydro-2,4-methylene-1,8-naphthyridine-1(2H)-carboxamide

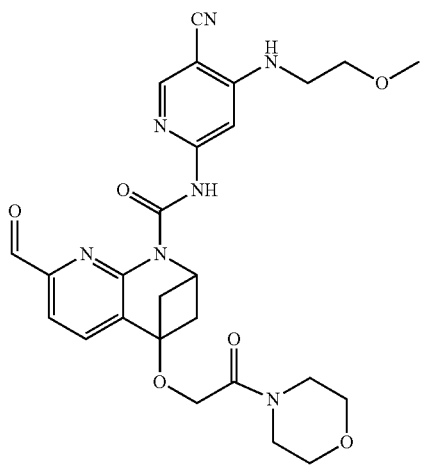 [SMILES: COCCNc1cc(NC(=O)N2c3nc(C=O)ccc3C3(OCC(=O)N4CCOCC4)CC2C3)ncc1C#N]

According to the method similar to preparing Compound 4 in Example 4, Compound 45 was prepared by reacting Intermediate 29 and Intermediate 2 as starting materials. The relevant test data of the product are as follows:

$^1$H NMR (DMSO-d$_6$, 400 MHz), δ 13.07 (s, 1H), 9.96 (s, 1H), 8.30 (s, 1H), 8.07 (d, J=7.2 Hz, 1H), 7.78 (d, J=7.6 Hz, 1H), 7.54 (s, 1H), 7.01 (t, J=5.6 Hz, 1H), 5.49 (t, J=6.4 Hz, 1H), 4.49 (s, 2H), 3.58 (m, 4H), 3.53 (t, J=5.6 Hz, 2H), 3.46 (t, J=4.8 Hz, 4H), 3.40 (dt, J=5.6 Hz, 5.2 Hz, 2H), 3.29 (s, 3H), 2.83 (dt, J=6.8 Hz, 2.4 Hz, 2H), 1.64 (dd, J=7.2 Hz, 2.4 Hz, 2H).

ESI-MS: 536.3 [M+H]$^+$.

Example 46

Compound 46: Preparation of N-(5-cyano-4-((2-methoxyethyl)amino)pyridin-2-yl)-4-(2-(4-methylpiperazin-1-yl)-2-oxoethoxy)-7-formyl-3,4-dihydro-2,4-methylene-1,8-naphthyridine-1(2H)-carboxamide

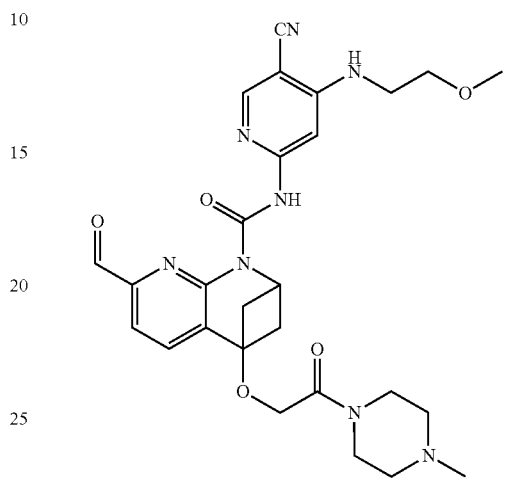

According to the method similar to preparing Compound 4 in Example 4, Compound 46 was prepared by reacting Intermediate 30 and Intermediate 2 as starting materials. The relevant test data of the product are as follows:

ESI-MS: 549.3 [M+H]$^+$.

Example 47

Compound 47: Preparation of N-(5-cyano-4-((2-methoxyethyl)amino)pyridin-2-yl)-4-(2-hydroxyacetamido)-7-formyl-3,4-dihydro-2,4-methylene-1,8-naphthyridine-1(2H)-carboxamide

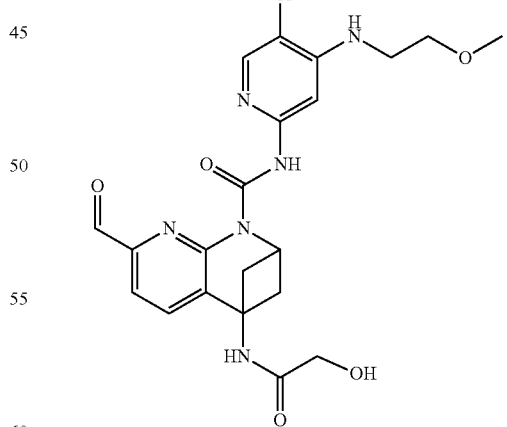

According to the method similar to preparing Compound 2 in Example 2, Compound 47 was prepared by reacting Intermediate 37 and Intermediate 2 as starting materials. The relevant test data of the product are as follows:

$^1$H NMR (DMSO-d$_6$, 400 MHz), δ 13.17 (s, 1H), 9.95 (s, 1H), 8.78 (s, 1H), 8.30 (s, 1H), 7.71 (d, J=7.6 Hz, 1H), 7.66

(d, J=7.6 Hz, 1H), 7.54 (s, 1H), 7.02 (t, J=5.2 Hz, 1H), 5.61 (t, J=6 Hz, 1H), 3.96 (s, 2H), 3.53 (t, J=6.0 Hz, 2H), 3.40 (dt, J=5.2 Hz, 5.2 Hz, 2H), 3.29 (s, 3H), 2.56 (m, 2H), 1.92 (m, 2H).

ESI-MS: 466.1 [M+H]⁺.

Example 48

Compound 48: Preparation of N-(5-cyano-4-((2-methoxyethyl)amino)pyridin-2-yl)-4-(pyridine-2-carboxamido)-7-formyl-3,4-dihydro-2,4-methylene-1,8-naphthyridine-1(2H)-carboxamide

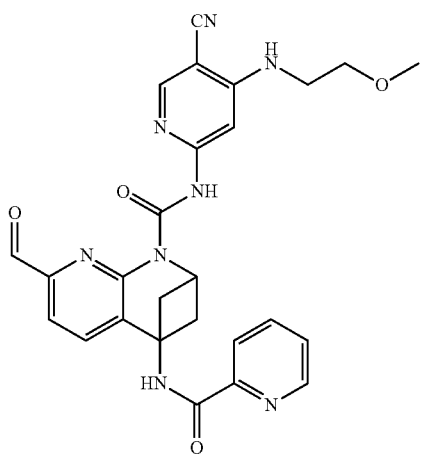 [SMILES: COCCNc1cc(NC(=O)N2c3nc(C=O)ccc3C3(NC(=O)c4ccccn4)CC2C3)ncc1C#N]

According to the method similar to preparing Compound 1 in Example 1, Compound 48 was prepared by reacting Intermediate 38 and Intermediate 2 as starting materials. The relevant test data of the product are as follows:

¹H NMR (DMSO-d₆, 400 MHz), δ 13.18 (s, 1H), 9.95 (s, 1H), 9.79 (s, 1H), 8.73 (dt, J=4.8 Hz, 1.2 Hz, 1H), 8.31 (s, 1H), 8.04-8.07 (m, 2H), 7.69 (d, J=7.6 Hz, 1H), 7.67 (dd, J=8.8 Hz, 2.4 Hz, 1H), 7.64 (d, J=7.6 Hz, 1H), 7.56 (s, 1H), 7.01 (t, J=5.6 Hz, 1H), 5.65 (t, J=5.6 Hz, 1H), 3.54 (t, J=6.0 Hz, 2H), 3.41 (dt, J=5.6 Hz, 5.6 Hz, 2H), 3.30 (s, 3H), 2.66-2.70 (m, 2H), 2.03 (dd, J=7.6 Hz, 2.4 Hz, 2H).

ESI-MS: 513.2 [M+H]⁺.

Example 49

Compound 49: Preparation of N-(5-cyano-44(2-methoxyethyl)amino)pyridin-2-yl)-4-(1H-pyrazole-2-carboxamido)-7-formyl-3,4-dihydro-2,4-methylene-1,8-naphthyridine-1(2H)-carboxamide

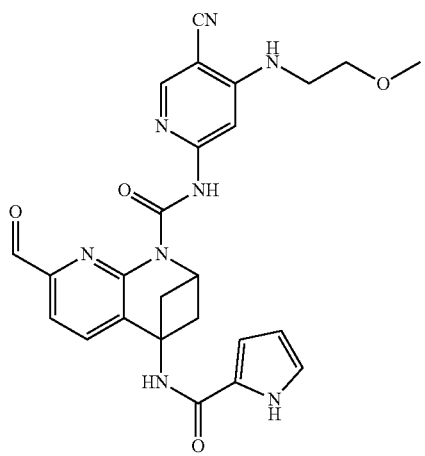 [SMILES: COCCNc1cc(NC(=O)N2c3nc(C=O)ccc3C3(NC(=O)c4ccc[nH]4)CC2C3)ncc1C#N]

According to the method similar to preparing Compound 1 in Example 1, Compound 49 was prepared by reacting Intermediate 39 and Intermediate 2 as starting materials. The relevant test data of the product are as follows:

¹H NMR (DMSO-d₆, 400 MHz), δ 13.18 (s, 1H), 11.51 (s, 1H), 9.95 (s, 1H), 8.91 (s, 1H), 8.31 (s, 1H), 7.71 (d, J=7.6 Hz, 1H), 7.65 (d, J=7.6 Hz, 1H), 7.56 (s, 1H), 7.01 (t, J=5.6 Hz, 1H), 6.95 (s, 1H), 6.93 (s, 1H), 6.15 (s, 1H), 5.66 (t, J=5.6 Hz, 1H), 3.54 (t, J=6.0 Hz, 2H), 3.41 (dt, J=5.6 Hz, 5.6 Hz, 2H), 3.30 (s, 3H), 2.63-2.60 (m, 2H), 2.00 (dd, J=7.6 Hz, 2.4 Hz, 2H).

ESI-MS: 501.2 [M+H]⁺.

Comparative Example

Positive Control Compound: N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide

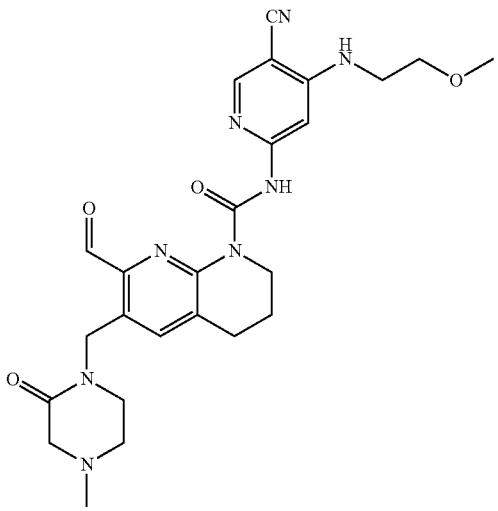 [SMILES: COCCNc1cc(NC(=O)N2CCCc3cc(CN4CCN(C)CC4=O)c(C=O)nc32)ncc1C#N]

According to the method described in WO2016151500A1, the positive control compound was prepared. The relevant test data of the product are as follows:

$^1$H NMR (DMSO-$d_6$, 400 MHz), δ 13.46 (s, 1H), 10.07 (s, 1H), 8.26 (s, 1H), 7.52 (s, 1H), 7.51 (s, 1H), 6.95 (t, J=5.6 Hz, 1H), 4.89 (s, 2H), 3.96 (t, J=5.8 Hz, 2H), 3.53 (t, J=5.8 Hz, 2H), 3.39 (dt, J=5.8 Hz, 5.6 Hz, 2H), 3.29 (s, 3H), 3.27 (t, J=6.0 Hz, 2H), 3.05 (s, 2H), 2.93 (t, J=6.0 Hz, 2H), 2.62 (t, J=5.6 Hz, 2H), 2.24 (s, 3H), 1.96-1.90 (m, 2H).

ESI-MS: 507.3 [M+H]$^+$.

Biological Test Evaluation

In Vitro Biochemical Kinase Analysis of FGFR4

FGFR4 protein kinase detection kit was purchased from Cisbio (HTRF KinEASE-TK kit). Prepare 1× kinase reaction buffer. Transfer 10 nL of a diluted compound to each well of a reaction plate (784075, Greiner) with an Echo 550, and seal the plate with sealing film. The reaction plate was centrifuged at 1000 g for 1 minute. Prepare 2×FGFR4 using 1× kinase reaction buffer, add 5 μL of kinase to each well of the reaction plate, seal the plate, centrifuge at 1000 g for 30 seconds, and incubate it at room temperature for 10 minutes. Prepare a mixture of 2×TK-substrate-biotin and ATP using 1× kinase reaction buffer, add 5 μL of TK-substrate-biotin/ATP mixture to the reaction plate, seal the plate with sealing film, centrifuge at 1000 g for 30 seconds, and react at room temperature for 40 minutes. Prepare 2×Sa-XL 665 and TK-antibody-Cryptate mixture using HTRF detection buffer, add 10 μL Sa-XL 665 and TK-antibody-Cryptate mixture to each well, centrifuge at 1000 g for 30 seconds, and react at room temperature for 1 hour. Envision 2104 read fluorescence signals at 615 nm (Cryptate) and at 665 nm (XL665). IC$_{50}$ of the compound was calculated using the GraphPad nonlinear fitting formula.

In Vitro Cell Proliferation Assay of FGFR4 (CellTiter-Glo Luminescent Cell Viability Assay, CTG Assay)

Hep 3B hepatoma cells were purchased from Cell Resource Center of Peking Union College, and HuH-7 hepatoma cells were purchased from Shanghai Biological Technology Co., Ltd. enzyme research. The cells were prepared at a concentration of 3×10$^4$/mL, which was then added with 100 μL to each well of a 96-well transparent flat-bottom black-walled plate to make 3000 cells per well. Incubate overnight at 37° C. in 5% CO$_2$ incubator. Dilute a compound and add it to the wells having the cells, then add cell culture medium to 200 μL per well. Put in CO$_2$ incubator for incubation. After 96 hours, 100 μL of culture medium was removed from each well, 100 μL of CTG was added, and the 96-well plate was placed on a shaker for 10 minutes, and placed in the shade at room temperature for 45 minutes. Data was read out by SoftMax Pro i3X Microplate Reader of MD, analyzed by the software GraphPad Prism 5.0, and S-shaped dose-response curve was drawn, then the EC$_{50}$ values were calculated.

Compounds 1 to 49 prepared in Example 1 to 49 were tested according to the above method, and the relevant results are shown in Table 1.

TABLE 1

| Compound | FGFR4 IC$_{50}$(nM) | Hep 3B EC$_{50}$(nM) | HuH-7 EC$_{50}$(nM) |
|---|---|---|---|
| 1 | 0.4 | 15.1 | 62.0 |
| 2 | 2.2 | 8.1 | 52.0 |
| 3 | 1.6 | 13.4 | 42.0 |
| 4 | 0.7 | 6.4 | 12.0 |
| 5 | 1.8 | 27.0 | 49.0 |
| 6 | 2.1 | 3.3 | 5.9 |
| 7 | 5.1 | 669.3 | >1000 |
| 8 | 2.6 | 11.8 | 28.0 |
| 9 | 4.9 | 58.0 | 71.0 |
| 10 | 3.8 | 10.0 | 20.0 |
| 11-P1 | 1.3 | 5.6 | 0.2 |
| 11-P2 | 9.8 | 32.1 | 73.1 |
| 12-P1 | 2.1 | 8.6 | 0.9 |
| 12-P2 | 10.9 | 39.0 | 95.2 |
| 13 | 6.9 | 12.6 | 74.0 |
| 14 | 3.3 | 7.8 | 28.0 |
| 16 | 23.2 | 637.8 | >1000 |
| 17 | 0.7 | n.d. | 0.6 |
| 18 | 2.5 | 5.6 | 15.1 |
| 19 | 0.8 | 6.0 | 31.6 |
| 20 | 0.6 | 1.2 | 24.0 |
| 21 | 2.1 | 15.8 | 28.4 |
| 22 | 4.7 | 125 | 125 |
| 23 | n.d. | 101.9 | n.d. |
| 24 | 0.6 | 1.4 | 1.7 |
| 25 | 2.5 | 19.3 | 25.4 |
| 26 | 0.3 | 1.3 | 1.0 |
| 27 | 1.4 | 6.7 | 9.7 |
| 28 | 1.1 | 7.2 | 6.9 |
| 29 | 1.1 | 1.2 | 0.2 |
| 30 | 1.4 | n.d. | 0.8 |
| 31 | 1.1 | 5.5 | 4.5 |
| 32 | 0.5 | 1.7 | 0.7 |
| 33 | 0.3 | 0.3 | 0.08 |
| 34 | 1.2 | 10.7 | n.d. |
| 35 | 1.1 | 2.2 | n.d. |
| 36 | 2.5 | 8.5 | 11.8 |
| 37 | 2.5 | 6.4 | n.d. |
| 38 | 2.3 | 9.5 | 19.2 |
| 39 | 1.6 | 7.8 | 10.0 |
| 40 | 3.4 | 24.9 | 39.6 |
| 41 | 3.4 | 11.9 | 13.3 |
| 42 | 3.2 | 7.2 | n.d. |
| 43 | 3.1 | 6.5 | n.d. |
| 44 | 2.5 | 12.3 | n.d. |
| 45 | 1.8 | 11.4 | n.d. |
| 47 | 2.8 | 17.8 | n.d. |
| 48 | 1.6 | n.d. | n.d. |

TABLE 1-continued

| Compound | FGFR4 IC$_{50}$(nM) | Hep 3B EC$_{50}$(nM) | HuH-7 EC$_{50}$(nM) |
|---|---|---|---|
| 49 | 1.6 | n.d. | n.d. |
| Positive Control Compound | 2.1 | 15.0 | 52.0 |

From the data shown in Table 1, the compounds of the present disclosure have strong inhibitory effects on the activity of FGFR4 kinase and proliferations of Hep 3B cells and HuH-7 cells with high FGFR4 expression.

In Vivo Efficacy Test

Reagents and Materials

Human hepatoma Hep3B cells and cell culture medium (EMEM) were purchased from ATCC. Antibiotics (penicillin, streptomycin) and Tryspin-EDTA were purchased from Gibco. Phosphate buffered saline (PBS) and fetal bovine serum (FBS) were purchased from Hyclone. Matrigel was purchased from Corning. Nu/Nu nude mice 6-8 weeks, female, purchased from Vitalriver.

Experiments

Human hepatoma Hep3B cells were cultured in monolayer in vitro, and cultured in EMEM with 10% fetal bovine serum, 100 U/mL penicillin and 100 µg/mL streptomycin, 37° C., 5% CO$_2$. Trypsin-EDTA was used twice a week for routine digestion and passage. When cell saturation reached 80%-90%, cells were harvested, counted, and seeded. 0.2 mL of 10×10$^6$ Hep3B cells were subcutaneously seeded on the right back of each nude mouse (PBS:Matrigel=1:1). Administration was started when the average tumor volume reached 128 mm$^3$.

The mice were administered by gavage, twice a day. Control group was given pure water. Three treatment groups were administered Compound 4, at the doses of 10 mg/kg, 30 mg/kg, and 60 mg/kg, respectively. Tumors were measured and weighed twice a week. By day 16, the average tumor volume in the control group had reached the humanitarian endpoint (2000 mm$^3$), and the experiment was terminated.

Figure 2:
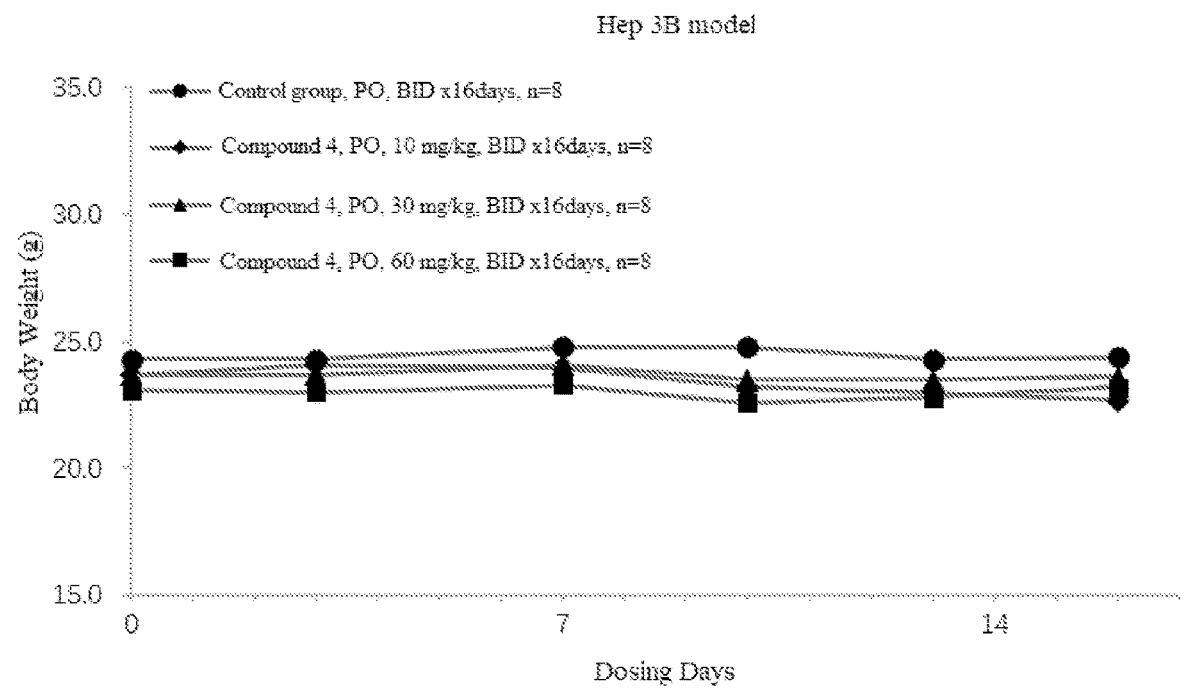

The data was processed by software such as Excel. The experimental results are shown in FIG. 1 and FIG. 2. When compound 4 was administered at a dose of 30 mg/kg and 60 mg/kg, the tumor inhibition rates were 78% and 97%, respectively. The tumor inhibition effect was obvious in Hep 3B tumor models.

In addition, FGFR4 is highly expressed in the liver and is involved in the regulation of fat storage, energy expenditure and body weight, and in particular has been shown to play an important role in lipid metabolism (Huang, X. et al., Diabetes, 2007, 56: 2501-2510). Experiments have shown that after inhibiting the expression of FGFR4 in the liver of obese mice, there are significant weight loss, as well as improvements in glucose metabolism and lipid levels (WO2009046141). It is reasonable to speculate that inhibiting the physiological activity of FGFR4 should also promote lipid metabolism, thus becoming a potential therapeutic drug for obesity.

Unless otherwise defined, the terms used in the present disclosure are the meanings commonly understood by those skilled in the art.

The embodiments described in the present disclosure are only for exemplary purposes and are not intended to limit the protection scope of the present disclosure. Those skilled in the art can make various other substitutions, changes and improvements within the scope of the present disclosure.

Therefore, the present disclosure are not limited to the above-described embodiments, but only by the claims.

The invention claimed is:

1. A compound of formula (I) or a pharmaceutically acceptable salt, solvate, active metabolite, polymorph, isotopic label, isomer or prodrug thereof,

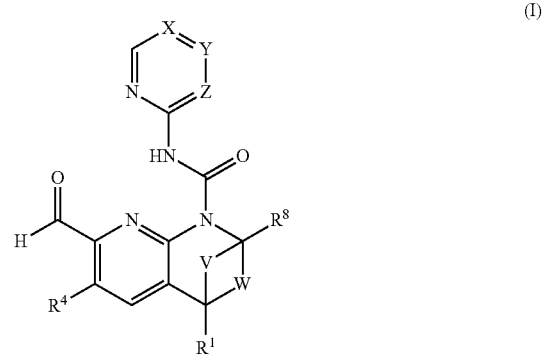

(I)

wherein, V and W are independently selected from C$_1$~C$_4$ alkylene or cyclopropylene, and V, W and the carbon atom connecting R$^8$ and the carbon atom connecting R$^1$ together form a 4-6 membered carbocyclic group;

X is selected from C(R$^X$) or N; Y is selected from C(R$^Y$) or N; Z is selected from CH or N; and at most one of X, Y, and Z is N;

R$^X$ is selected from:
1) hydrogen, halogen, cyano, C$_3$~C$_6$ cycloalkyl, ethynyl; or
2) C$_1$~C$_6$ alkyl, which is unsubstituted or substituted by one or more groups selected from halogen and hydroxyl;

R$^Y$ is selected from:
1) hydrogen, halogen, cyano, C$_1$~C$_3$ alkylthio group;
2) C$_1$~C$_6$ alkyl, which is unsubstituted or substituted by one or more hydroxyl;
3) C$_3$~C$_6$ cycloalkyl, which is unsubstituted or substituted by one or more hydroxyl;
4) C$_3$~C$_6$ cycloalkoxy, which is unsubstituted or substituted by one or more groups selected from the group consisting of hydroxyl, C$_1$~C$_3$ alkoxy and CH$_3$OCH$_2$—;
5) C$_1$~C$_6$ alkoxy, which is unsubstituted or substituted by one or more groups selected from the group consisting of hydroxyl, halogen, C$_1$~C$_3$ alkoxy, C$_1$~C$_3$ alkoxy optionally substituted by one or more C$_1$~C$_3$ alkoxy, C$_3$~C$_6$ cycloalkoxy, —NR$^{Y1}$R$^{Y2}$; or
6) —NR$^{Y1}$R$^{Y3}$, —O—(CH$_2$)$_{0-1}$—R$^{Y7}$ or —CHR$^{Y8}$R$^{Y9}$;

R$^{Y1}$ is selected from hydrogen or C$_1$~C$_6$ alkyl;

R$^{Y2}$ is selected from hydrogen, unsubstituted or hydroxy-substituted C$_1$~C$_3$ alkyl;

R$^{Y3}$ is selected from:
1) C$_1$~C$_6$ alkyl, which is unsubstituted or substituted by one or more selected from the group consisting of hydroxyl, halogen, C$_1$~C$_3$ alkoxy, C$_1$~C$_3$ alkoxy optionally substituted by one or more C$_1$~C$_3$ alkoxy, C$_1$~C$_3$ haloalkoxy, —S(=O)$_2$R$^{Y5}$, cyclopropyl optionally substituted by one or more C$_1$~C$_3$ alkoxy, and —NR$^{Y1}$R$^{Y2}$;
2) C$_3$~C$_6$ cycloalkyl, which is unsubstituted or substituted by one or more selected from the group consisting of hydroxyl, halogen, C$_1$~C$_3$ alkoxy, C$_1$~C$_3$ haloalkoxy, —NHS(=O)$_2$CH$_3$, and —NR$^{Y1}$R$^{Y2}$;

3) $C_5\sim C_8$ bicycloalkyl, which is unsubstituted or substituted with one or more groups selected from the group consisting of hydroxy, hydroxymethyl, and $C_1\sim C_3$ alkyl; or
4) —$(CH_2)_{0-1}$—$R^{Y4}$, —C(=O) $R^{Y5}$, —S(=O)$_2R^{Y5}$; or
$R^{Y1}$, $R^{Y3}$ and the N atom to which they are attached together form a 4-6 membered aliphatic heterocyclyl that is unsubstituted or optionally substituted by one or more $R^{Y6}$;
$R^{Y4}$ is selected from:
1) 4-6 membered saturated heterocyclyl which is unsubstituted or substituted by one or more groups selected from the group consisting of $C_1\sim C_3$ alkyl, —S(=O)$_2R^{Y5}$ and oxo;
2) phenyl, which is unsubstituted or substituted by one or more —S(=O)$_2R^{Y5}$;
$R^{Y5}$ is selected from $C_1\sim C_3$ alkyl;
$R^{Y6}$ is selected from:
1) hydroxyl, $C_1\sim C_3$ alkoxy;
2) $C_1\sim C_3$ alkyl which is unsubstituted or substituted by one or more —$NR^{Y1}R^{Y2}$, or
3) Two $R^{Y6}$ connected to the same carbon atom together with the carbon atom to which they are connected form an 5-membered saturated heterocyclyl which is unsubstituted or substituted with one or more $C_1\sim C_3$ alkyl;
$R^{Y7}$ is selected from:
1) quinuclidinyl; or
2) 4-6 membered saturated heterocyclyl, which is unsubstituted or optionally substituted by one or more groups selected from the group consisting of $C_1\sim C_3$ alkyl and oxo;
$R^{Y8}$, $R^{Y9}$ and the carbon atoms to which they are attached together form a 6-membered saturated aliphatic heterocyclyl;
or
$R^X$, $R^Y$ and the carbon atoms to which they are attached together form a fused heterocyclyl that is unsubstituted or optionally substituted by one or more $C_1\sim C_3$ alkyl, and the fused heterocyclyl includes two fused cyclic groups, and the number of ring atoms of the fused heterocyclyl is 9-10;
$R^1$ is selected from:
1) hydrogen, halogen, cyano, —$N_3$, carboxyl, ethynyl; or
2) $C_1\sim C_3$ alkyl, which is unsubstituted or substituted by one or more groups selected from the group consisting of hydroxyl and halogen;
3) —$OR^2$, —$(CH_2)_{0-1}NR^2R^3$ or —C(=O)—$NR^2R^3$;
$R^2$ is selected from:
1) hydrogen; or
2) $C_3\sim C_6$ cycloalkyl, which is unsubstituted or substituted by one or more groups selected from the group consisting of hydroxyl, halogen, $C_1\sim C_3$ alkoxy, and —$NR^{Y1}R^{Y2}$;
3) $C_1\sim C_3$ alkyl, which is unsubstituted or substituted by one or more groups selected from the group consisting of hydroxyl, halogen, $C_1\sim C_3$ alkoxy, $C_1\sim C_3$ alkoxy optionally substituted by one or more $C_1\sim C_3$ alkoxy, $C_1\sim C_3$ haloalkoxy, —$NR^{Y1}R^{Y3}$ and —C(=O)—$NR^{Y1}R^{Y3}$; or
4) —$(CH_2)_{0-1}$—$R^{Y4}$;
$R^3$ is selected from:
1) hydrogen, $C_1\sim C_3$ alkyl; or
2) $C_1\sim C_4$ acyl, which is unsubstituted or substituted by one or more groups selected from the group consisting of hydroxyl, $C_3\sim C_6$ cycloalkyl, $C_1\sim C_3$ alkoxy, —$NR^{Y1}R^{Y3}$, and $R^{Y4}$;
3) —C(=O)—$R^9$, —S(=O)$_2R^{Y5}$;

or
$R^2$, $R^3$ and the N atom to which they are attached together form a 4-6 membered saturated heterocyclyl which is unsubstituted or substituted with one or more $R^7$;
$R^4$ is selected from:
1) hydrogen, halogen, —$CH_2CO_2H$, —C(=O) H;
2) $C_1\sim C_3$ alkyl, which is unsubstituted or substituted by one or more groups selected from the group consisting of hydroxyl, halogen, $C_1\sim C_3$ alkoxy, $C_1\sim C_3$ haloalkoxy;
3) $C_3\sim C_6$ cycloalkyl, which is unsubstituted or substituted by one or more groups selected from the group consisting of hydroxyl, halogen, $C_1\sim C_3$ alkoxy, $C_1\sim C_3$ haloalkoxy;
4) 5- or 6-membered heterocyclyl, which is unsubstituted or substituted by one or more groups selected from the group consisting of $C_1\sim C_3$ alkyl, $C_1\sim C_3$ haloalkyl, oxetanyl and oxo; or
5) —$CH_2NR^5R^6$, —$CH(CH_3)NR^5R^6$, —$C(CH_3)_2NR^5R^6$;
$R^5$ is selected from $C_3\sim C_6$ cycloalkyl, $C_1\sim C_3$ alkyl which is unsubstituted or substituted by one or more —$NR^{Y1}R^{Y2}$;
$R^6$ is selected from:
1) $C_1\sim C_3$ alkyl, $C_4\sim C_7$ cycloalkylformyl, —S(=O)$_2R^{Y5}$; or
2) $C_1\sim C_4$ acyl, which is unsubstituted or substituted by one or more groups selected from the group consisting of hydroxyl, $C_1\sim C_3$ alkoxy, —$NR^{Y1}R^{Y2}$;
or
$R^5$, $R^6$ and the N atom to which they are attached together form a 4-7 membered saturated heterocyclyl which is unsubstituted or substituted with one or more $R^7$;
$R^7$ is selected from:
1) $C_1\sim C_4$ acyl, hydroxyl, oxo, —$NR^{Y1}R^{Y2}$; or
2) $C_1\sim C_3$ alkyl, which is unsubstituted or substituted by one or more hydroxyl groups;
or
Two $R^7$ connected to the same carbon atom and the carbon atom connected to them together form a 4-6 membered saturated heterocyclyl;
$R^8$ is selected from hydrogen or $C_1\sim C_3$ alkyl;
$R^9$ is 4-6 membered saturated heterocyclic or aromatic heterocyclyl, which is unsubstituted or substituted by one or more groups selected from the group consisting of $C_1\sim C_3$ alkyl and oxo.
2. The compound of formula (I) according to claim 1, or a pharmaceutically acceptable salt, solvate, active metabolite, polymorph, isotopic label, isomer or prodrug thereof, wherein the compound is represented by formula (Ia):

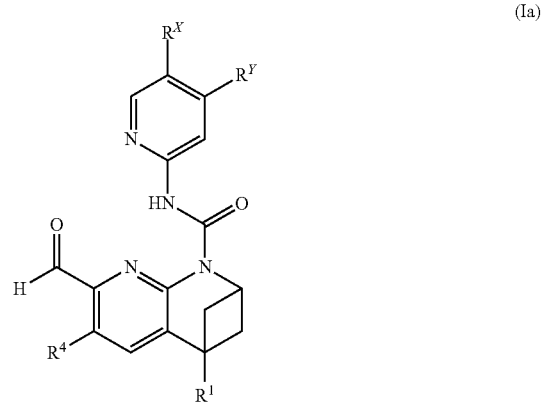

(Ia)

wherein, $R^X$ is selected from halogen, cyano, $C_1$~$C_3$ haloalkyl;
$R^Y$ is selected from:
1) hydrogen, halogen, $C_1$~$C_3$ alkyl, $C_3$~$C_6$ cycloalkyl;
2) $C_3$~$C_6$ cycloalkoxy, which is unsubstituted or substituted by one or more groups selected from the group consisting of hydroxyl and $C_1$~$C_3$ alkoxy;
3) $C_1$~$C_6$ alkoxy, which is unsubstituted or substituted by one or more groups selected from the group consisting of hydroxyl, halogen, $C_1$~$C_3$ alkyl, $C_1$~$C_3$ alkoxy optionally substituted by one or more $C_1$~$C_3$ alkoxy, $C_3$~$C_6$ cycloalkoxy, —$NR^{Y1}R^{Y2}$, or
4) —$NR^{Y1}R^{Y3}$ or —O—$(CH_2)_{0-1}$—$R^{Y7}$;

$R^{Y2}$ is selected from $C_1$~$C_3$ alkyl;
$R^{Y3}$ is selected from:
1) $C_1$~$C_3$ alkyl, which is unsubstituted or substituted by one or more selected from the group consisting of hydroxyl, halogen, $C_1$~$C_3$ alkoxy, $C_1$~$C_3$ alkoxy optionally substituted by one or more $C_1$~$C_3$ alkoxy, $C_1$~$C_3$ haloalkoxy, and —$NR^{Y1}R^{Y2}$;
2) $C_3$~$C_6$ cycloalkyl, which is unsubstituted or substituted by one or more selected from the group consisting of hydroxyl, $C_1$~$C_3$ alkoxy, and $C_1$~$C_3$ haloalkoxy;
3) —$(CH_2)_{0-1}$—$R^{Y4}$, —C(=O) $R^{Y5}$, —S(=O)$_2$$R^{Y5}$; or
$R^{Y1}$, $R^{Y3}$ and the N atom to which they are attached together form a 4-6 membered aliphatic heterocyclyl that is unsubstituted or optionally substituted by one or more $R^{Y6}$;

$R^{Y6}$ is selected from:
1) hydroxyl, $C_1$~$C_3$ alkyl; or
2) two $R^{Y6}$ connected to the same carbon atom together with the carbon atom to which they are connected form an 5-membered saturated heterocyclyl which is unsubstituted or substituted with one or more $C_1$~$C_3$ alkyl;

$R^1$ is selected from:
1) hydrogen, halogen, cyano; or
2) —$OR_2$, —$(CH_2)_{0-1}NR^2R^3$ or —C(=O)—$NR^2R^3$;

$R^2$ is selected from:
1) hydrogen; or
2) $C_3$~$C_6$ cycloalkyl, which is unsubstituted or substituted by one or more groups selected from the group consisting of hydroxyl, halogen, $C_1$~$C_3$ alkoxy, and —$NR^{Y1}R^{Y2}$,
3) $C_1$~$C_3$ alkyl, which is unsubstituted or substituted by one or more groups selected from the group consisting of hydroxyl, halogen, $C_1$~$C_3$ alkoxy, $C_1$~$C_3$ alkoxy optionally substituted by one or more $C_1$~$C_3$ alkoxy, $C_1$~$C_3$ haloalkoxy, —$NR^{Y1}R^{Y3}$ and —C(=O)—$NR^{Y1}R^{Y3}$; or
4) —$(CH_2)_{0-1}$—$R^{Y4}$;

$R^3$ is selected from:
1) hydrogen, $C_1$~$C_3$ alkyl; or
2) $C_1$~$C_4$ acyl, which is unsubstituted or substituted by one or more groups selected from the group consisting of hydroxyl, $C_3$~$C_6$ cycloalkyl, $C_1$~$C_3$ alkoxy, —$NR^{Y1}R^{Y3}$, and $R^{Y4}$;
3) —C(=O)—$R^9$, —S(=O)$_2$$R^{Y5}$;
or
$R^2$, $R^3$ and the N atom to which they are attached together form a 4-6 membered saturated heterocyclyl which is unsubstituted or substituted with one or more $R^7$;

$R^4$ is selected from:
1) hydrogen, halogen, $C_3$~$C_6$ cycloalkyl;
2) $C_1$~$C_3$ alkyl, which is unsubstituted or substituted by one or more groups selected from the group consisting of hydroxyl, halogen, and $C_1$~$C_3$ alkoxy; or 3) —$CH_2NR^5R^6$;
$R^6$ is selected from:
1) $C_1$~$C_3$ alkyl;
2) $C_1$~$C_4$ acyl, which is unsubstituted or substituted by one or more groups selected from the group consisting of hydroxyl, $C_1$~$C_3$ alkoxy, —$NR^{Y1}R^{Y2}$;
or
$R^5$, $R^6$ and the N atom to which they are attached together form a 5-7 membered saturated heterocyclyl which is unsubstituted or substituted with one or more $R^7$.

3. The compound of formula (I) according to claim 1, or a pharmaceutically acceptable salt, solvate, active metabolite, polymorph, isotopic label, isomer or prodrug thereof, wherein Y is C($R^Y$), $R^Y$ is selected from the group consisting of —$NHCH_2CH_2OCH_3$, —$NHCH(CH_3)CH_2OCH_3$, —$OCH_2CH_2OCH_3$, —$OCH_3$, —$OCH_2CH_3$, —OCH($CH_3$)$CH_3$, —$NHCH_2CH_2F$, —$NHCH(CH_3)CH_3$, —$NHCH_2CH_2OCF_3$, —OCH($CH_3$)$CH_2OCH_3$, —SCH($CH_3$)$CH_3$, —$NHCH_2CH_2S(=O)_2CH_3$, —$NHCH_2CH_2N(CH_3)_2$, —$NHCH_2CH_2NHCH_3$, —$NHCH_2CH_2OCH_2CH_2OCH_3$, and one of the following structures:

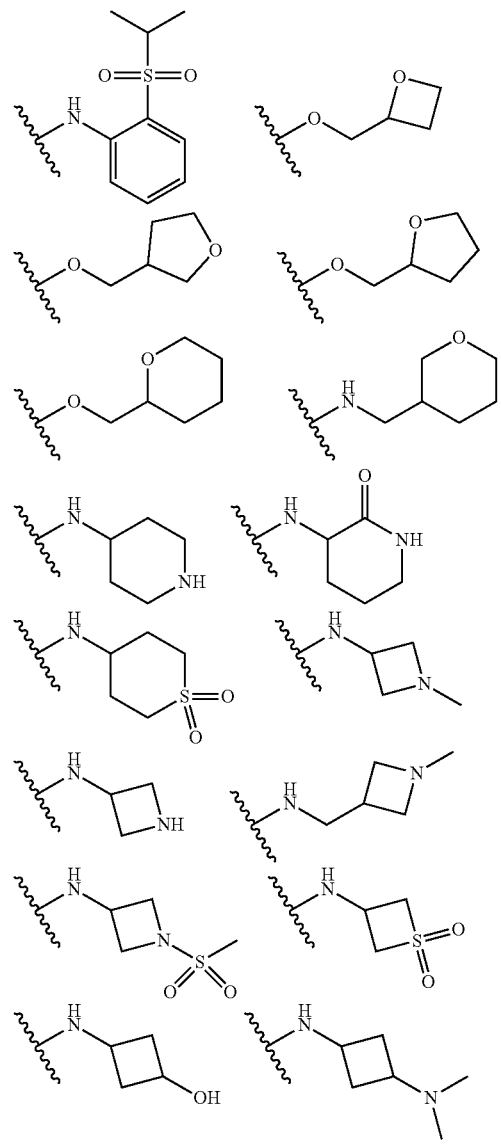

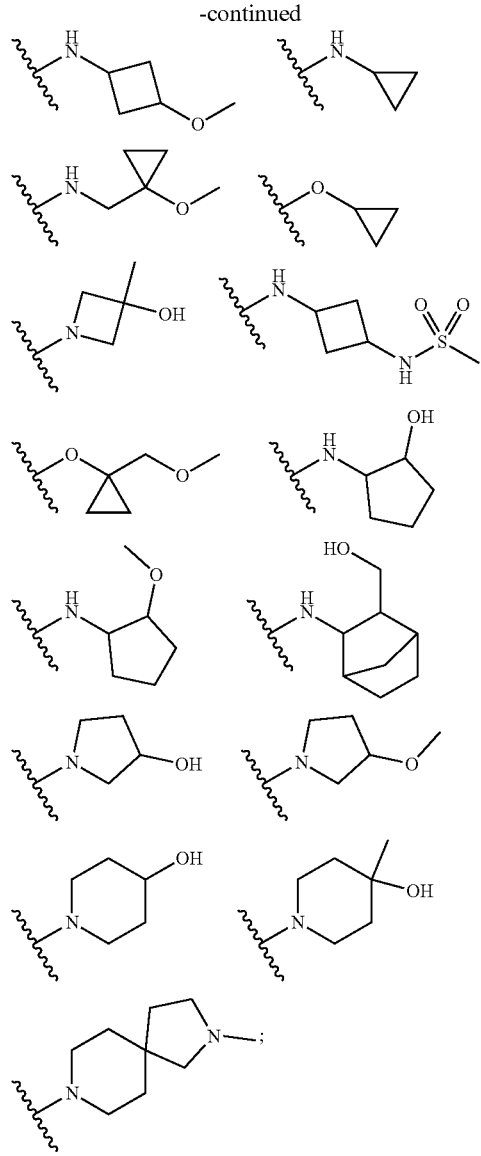

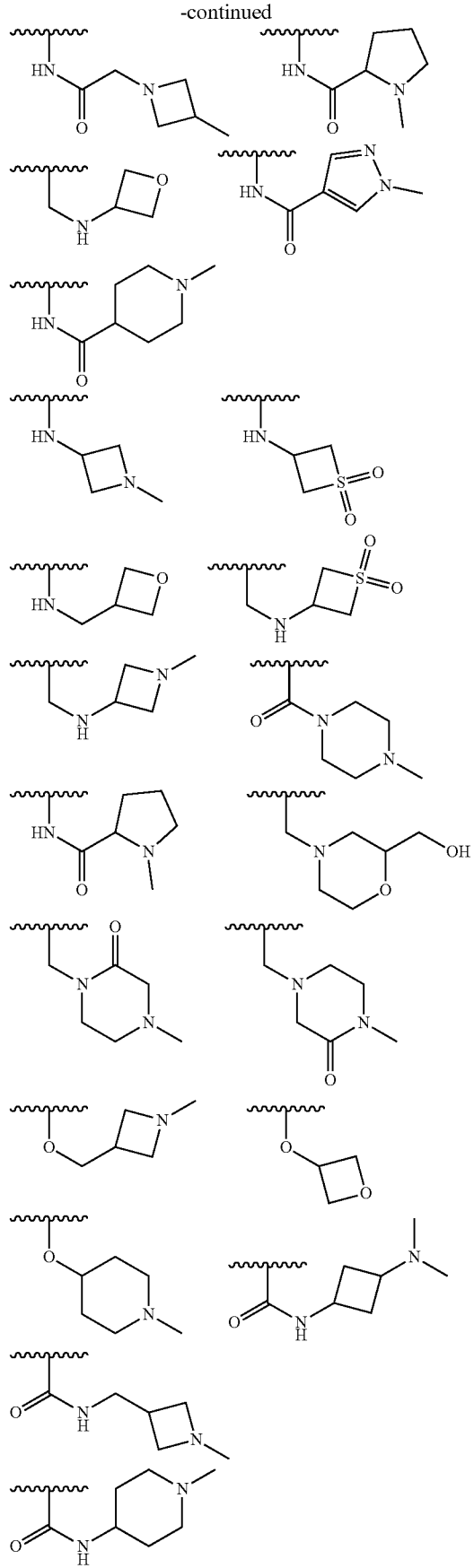

R[1] is selected from the group consisting of —F, —OH, —OCH$_3$, —CH$_2$OH, —N$_3$, —NH$_2$, —CN, —H, —N(CH$_3$) C(=O) CH$_2$N(CH$_3$)$_2$, —NHC(=O) CH$_2$N (CH$_3$)$_2$, —NHCH$_2$CH$_2$N(CH$_3$)$_2$, —C≡CH, —CH$_3$, —COOH, —NHCH$_2$CH$_2$OCH$_3$, —C(=O)N(CH$_3$) CH$_2$CH$_2$N(CH$_3$)$_2$, —C(=O) NHCH$_2$C(=O)N(CH$_3$)$_2$, —C(=O) NHCH$_2$CH$_2$N(CH$_3$)$_2$, —CH$_2$NHCH$_2$CH$_2$N (CH$_3$)$_2$, —CH$_2$NHC(=O) CH$_2$N(CH$_3$)$_2$, —N(CH$_3$) CH$_2$C(=O)N(CH$_3$)$_2$, —OCH$_2$CH$_2$N(CH$_3$)$_2$, —OCH$_2$CH$_2$OCH$_3$, —NHCH$_2$C(=O)N(CH$_3$)$_2$, and one of the following structures:

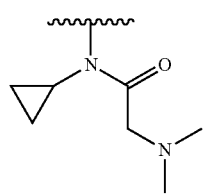

-continued

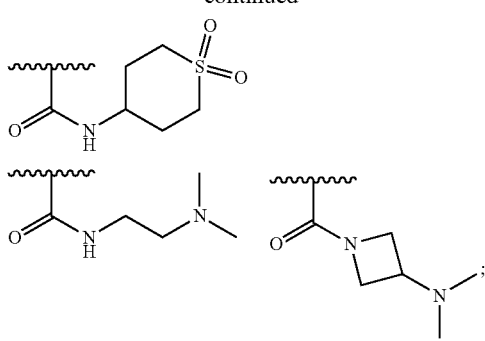

R⁴ is selected from the group consisting of —H, —N(CH₃) C(=O) CH₂N(CH₃)₂, —CH₂N(CH₃) C(=O) CH₃, —CH₂N(CH₃) C(=O) CH₂OH, —CH₂N(CH₃) C(=O) CH₂OCH₃, and one of the following structures:

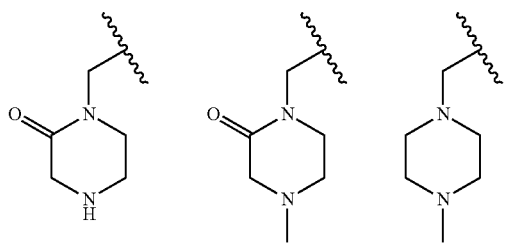

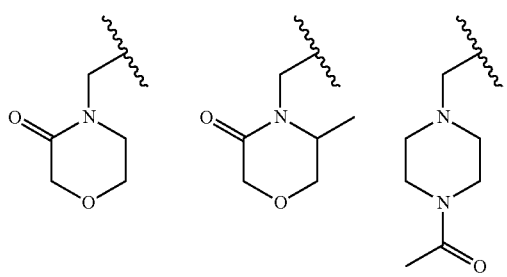

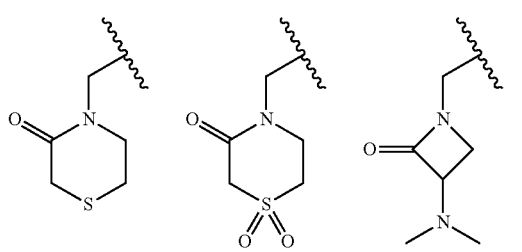

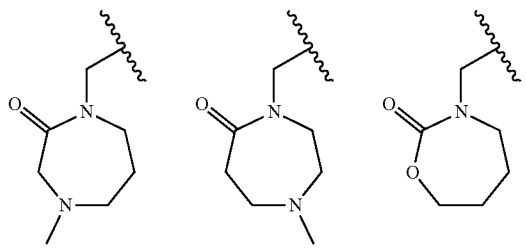

-continued

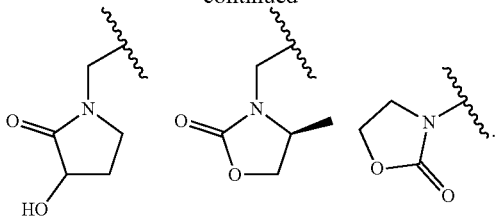

4. The compound of formula (I) according to claim 1, or a pharmaceutically acceptable salt, solvate, active metabolite, polymorph, isotopic label, isomer or prodrug thereof, wherein the compound is represented by the following structure:

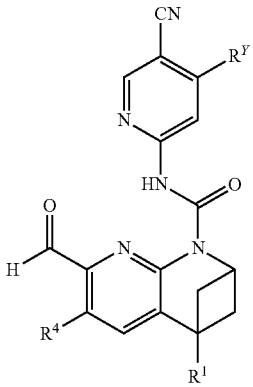

(Ia-1)

$R^Y$ is selected from:
1) hydrogen, $C_1$~$C_3$ alkylthio;
2) $C_1$~$C_3$ alkoxy, which is unsubstituted or substituted by one or more $C_1$~$C_3$ alkoxy;
3) —$NR^{Y1}R^{Y3}$; or
4) $C_3$~$C_6$ cycloalkoxy, which is unsubstituted or substituted by one or more groups selected from the group consisting of hydroxyl and $C_1$~$C_3$ alkoxy;

$R^{Y1}$ is hydrogen;
$R^{Y3}$ is selected from:
1) $C_1$~$C_3$ alkyl, which is unsubstituted or substituted by one or more selected from the group consisting of halogen, $C_1$~$C_3$ alkoxy, $C_1$~$C_3$ alkoxy optionally substituted by one or more $C_1$~$C_3$ alkoxy, $C_1$~$C_3$ haloalkoxy, and —N($R^{Y2}$)₂;
2) —(CH₂)₀₋₁—$R^{Y4}$, —S(=O)₂$R^{Y5}$;
3) $C_3$~$C_6$ cycloalkyl, which is unsubstituted or substituted by one or more selected from the group consisting of hydroxyl, and $C_1$~$C_3$ alkoxy;
or
$R^{Y1}$, $R^{Y3}$ and the N atom to which they are attached together form a 4-6 membered aliphatic heterocyclyl that is unsubstituted or optionally substituted by one or more $R^{Y6}$;
$R^{Y2}$ is selected from $C_1$~$C_3$ alkyl;
$R^{Y4}$ is selected from 4-6 membered saturated heterocyclyl which is unsubstituted or substituted by one or more groups selected from the group consisting of $C_1$~$C_3$ alkyl and oxo;
$R^{Y5}$ is selected from $C_1$~$C_3$ alkyl;
$R^{Y6}$ is selected from hydroxyl or $C_1$~$C_3$ alkyl;

$R^1$ is selected from:
1) hydrogen, halogen, cyano; or
2) —$OR^2$, $NR^2R^3$;

$R^4$ is selected from hydrogen, halogen, $C_1$~$C_3$ alkyl, —$CH_2NR^5R^6$;

$R^5$ is selected from $C_1$~$C_3$ alkyl;

$R^6$ is selected from $C_1$~$C_4$ acyl, which is unsubstituted or substituted by one or more groups selected from the group consisting of hydroxyl, $C_1$~$C_3$ alkoxy, —$N(R^{y2})_2$;

or $R^5$, $R^6$ and the N atom to which they are attached together form a 6-7 membered saturated heterocyclyl which is unsubstituted or substituted with one or more $R^7$;

$R^7$ is selected from oxo, $C_1$~$C_3$ alkyl.

5. The compound of formula (I) according to claim 1, or a pharmaceutically acceptable salt, solvate, active metabolite, polymorph, isotopic label, isomer or prodrug thereof, wherein the compound is selected from:

1

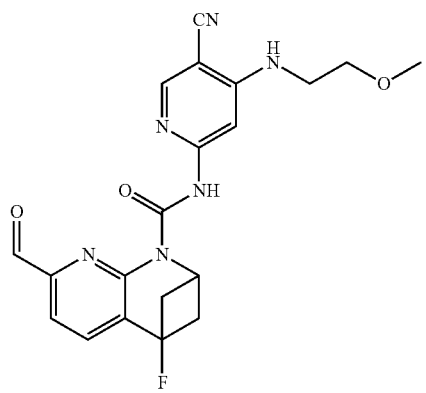

2

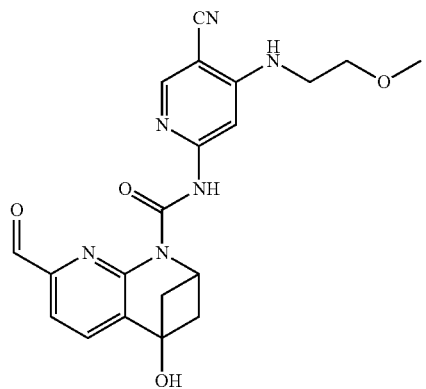

3

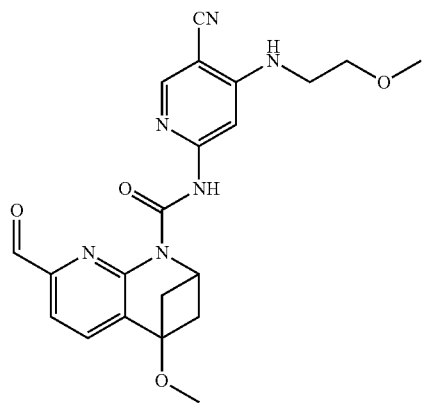

4

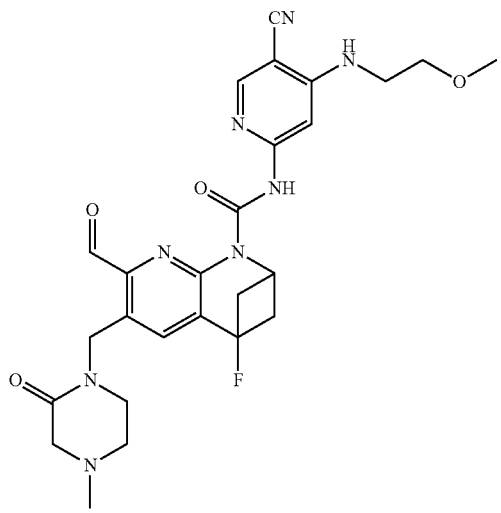

5

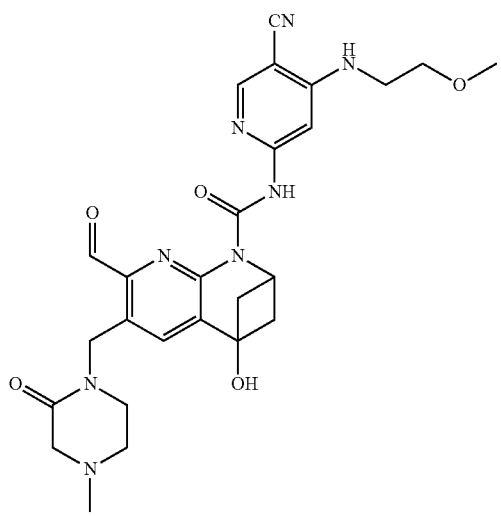

6

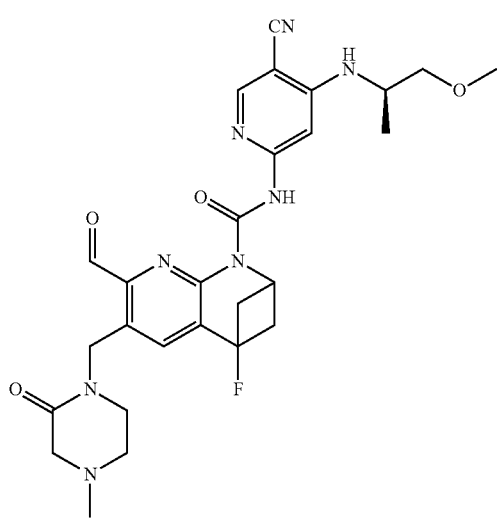

7
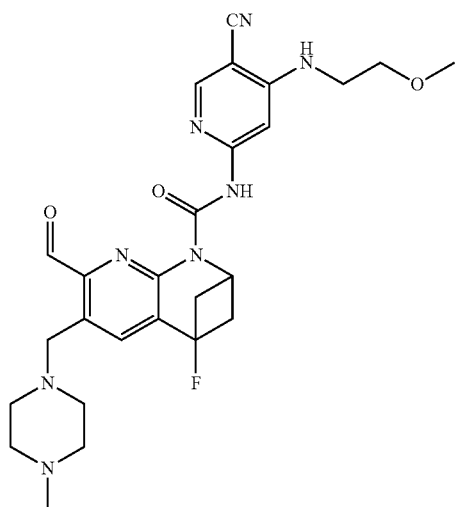
8
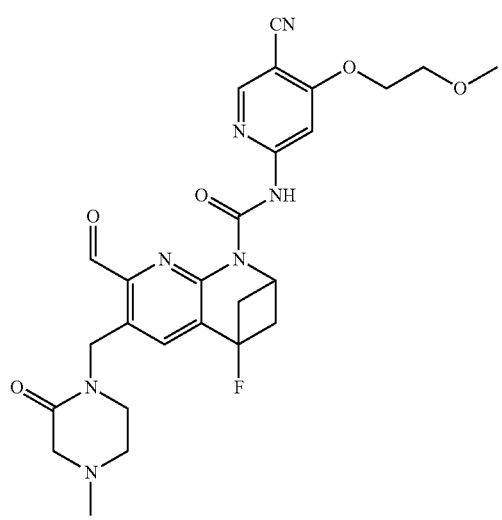
9
10
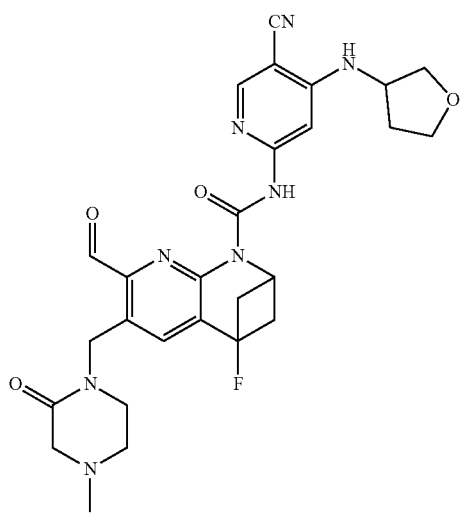
11A
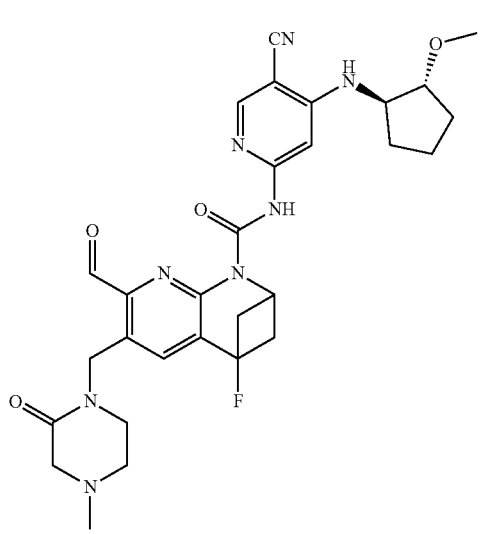
11B
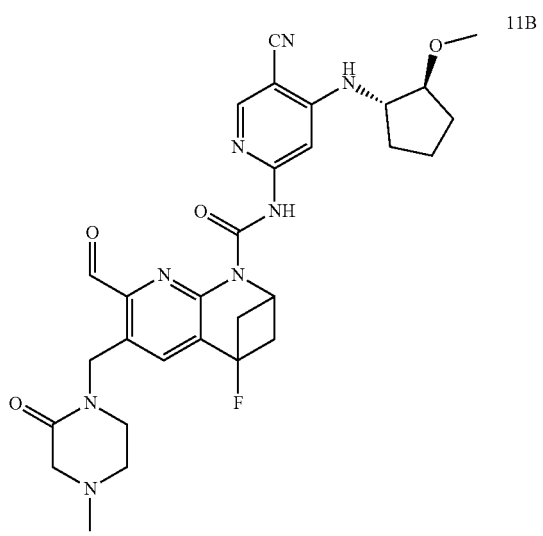

259
-continued
260
-continued
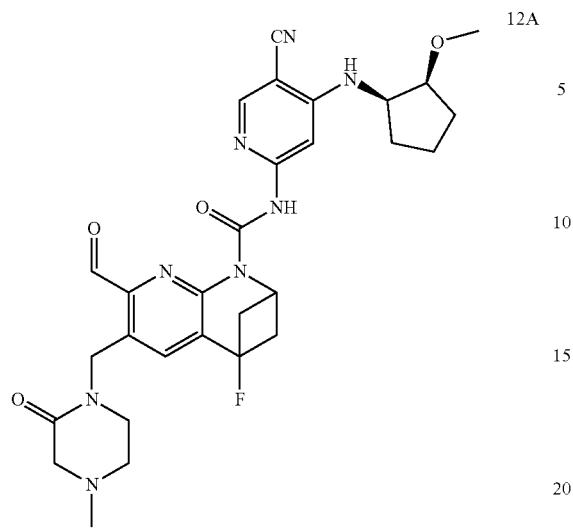
12A
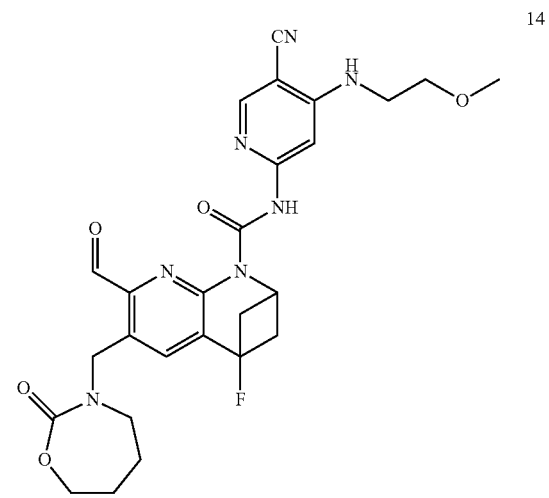
14
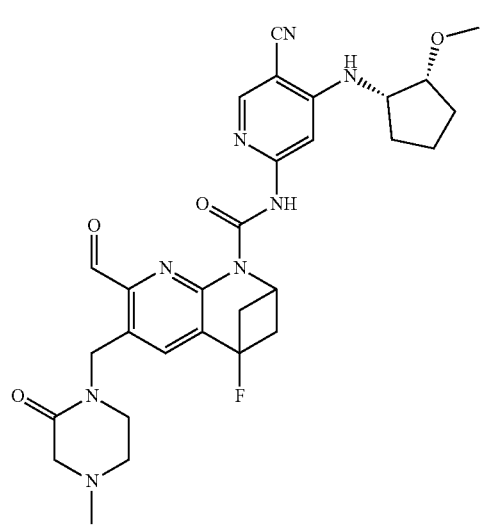
12B
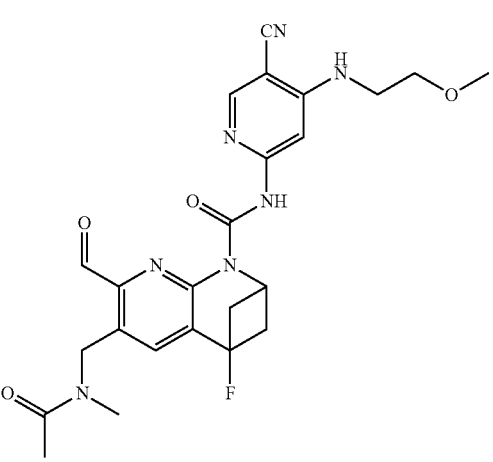
15
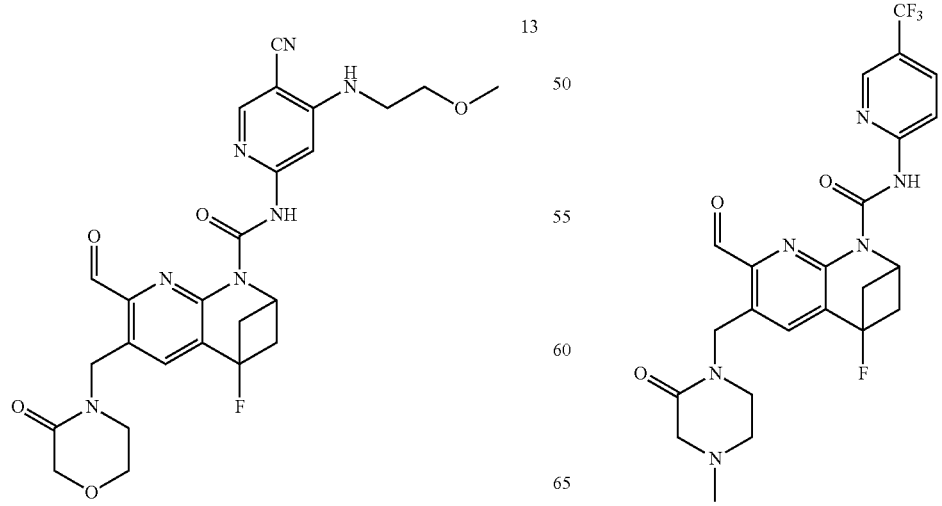
13
16

17
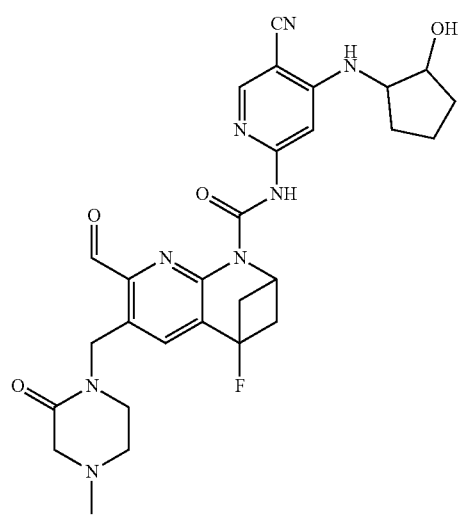
18
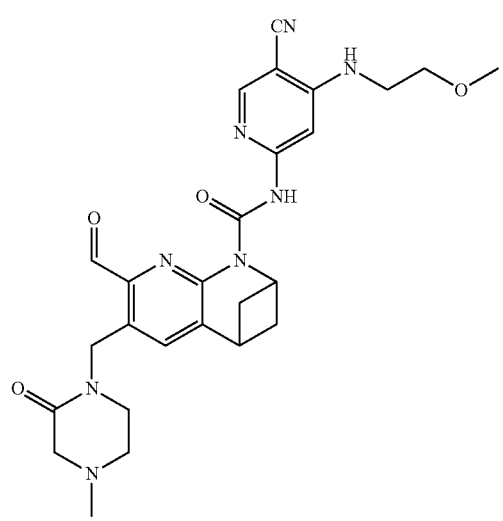
19
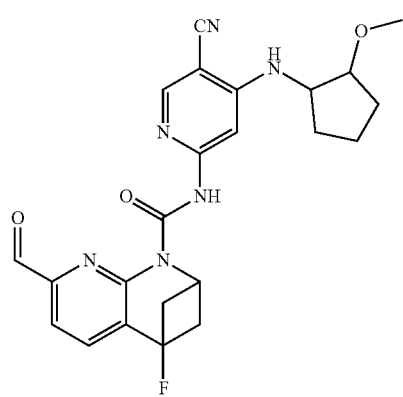
20
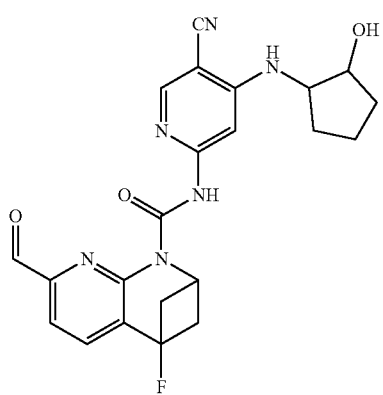
21
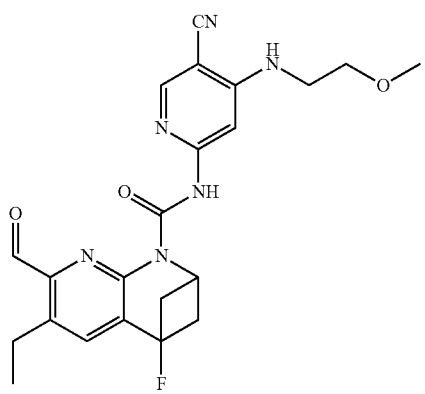
22
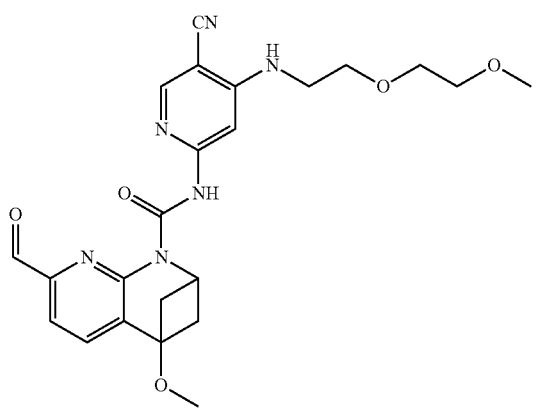
23
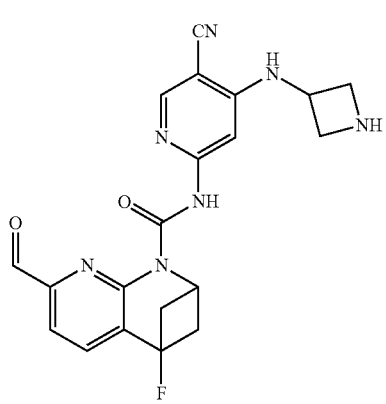

263
24
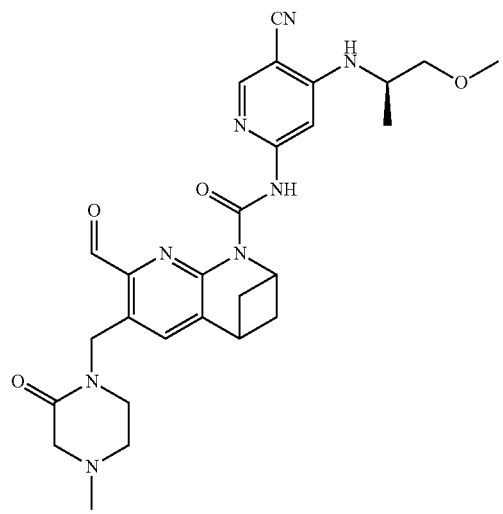
25
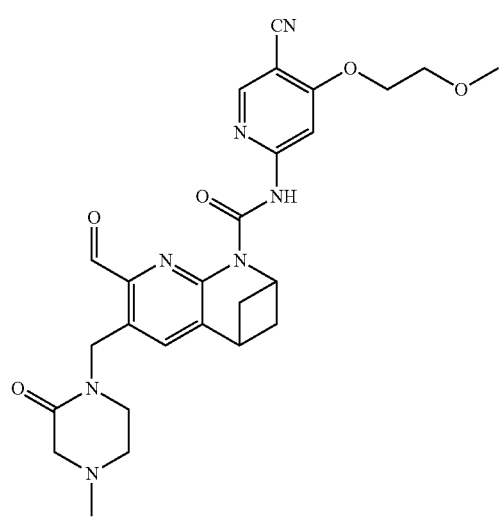
26
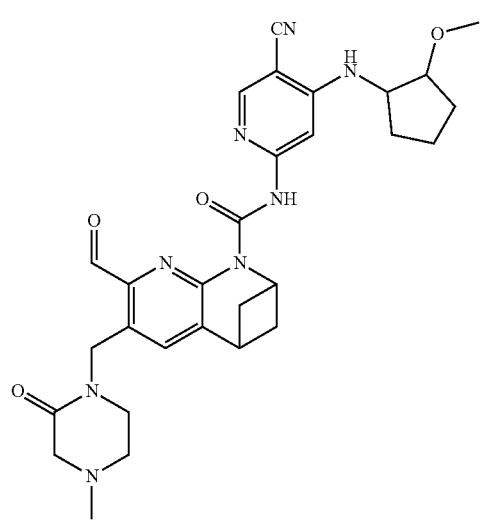
264
27
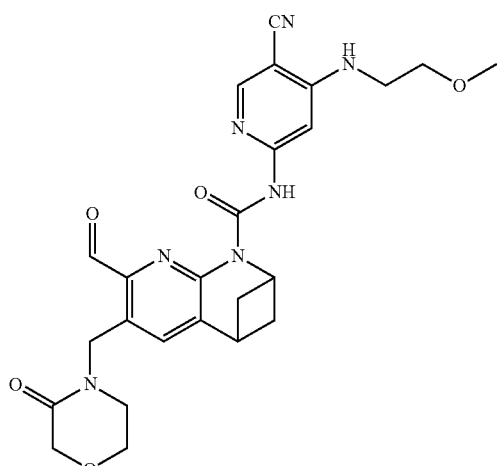
28
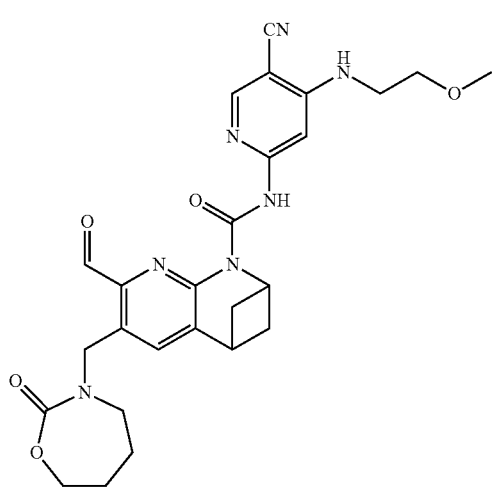
29
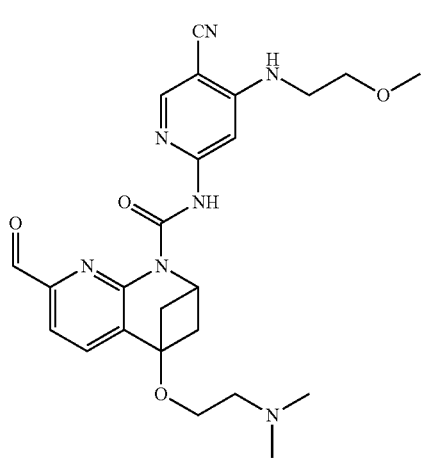

30
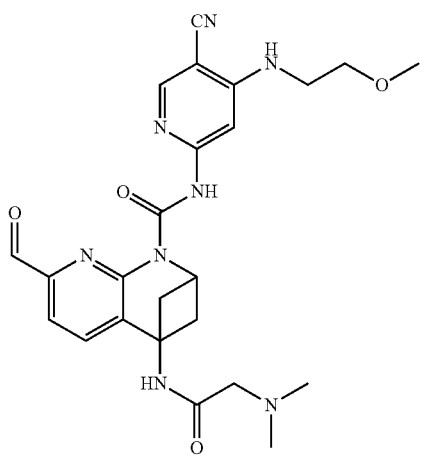
31
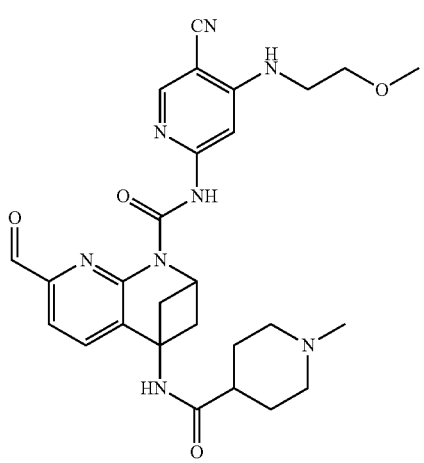
32
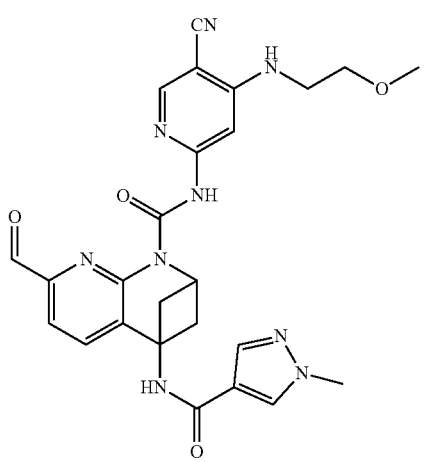
33
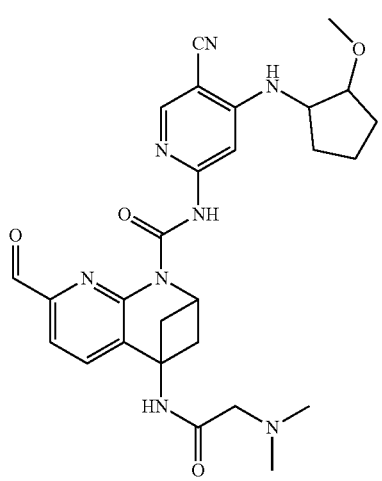
34
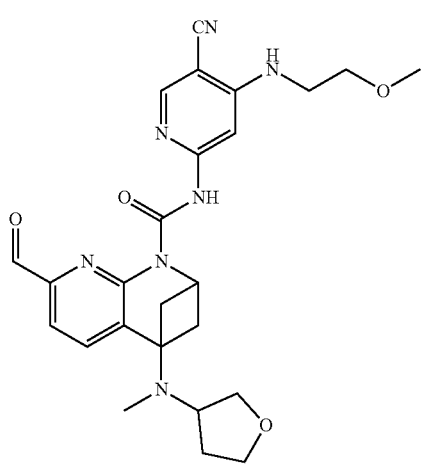
35
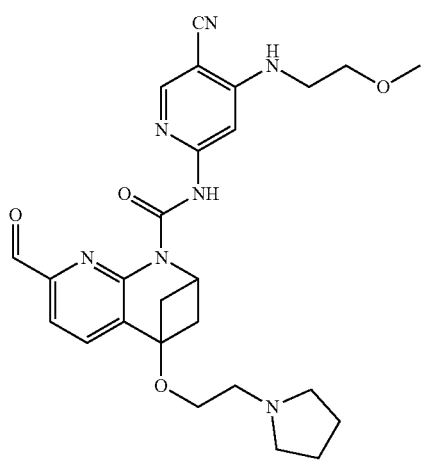

36
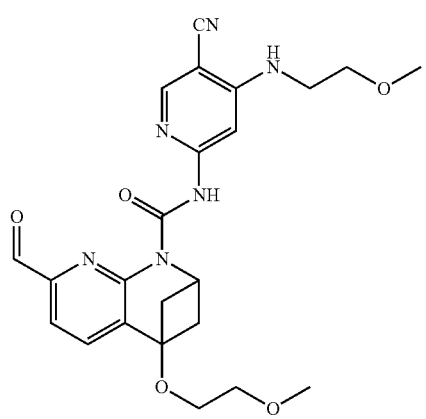
37
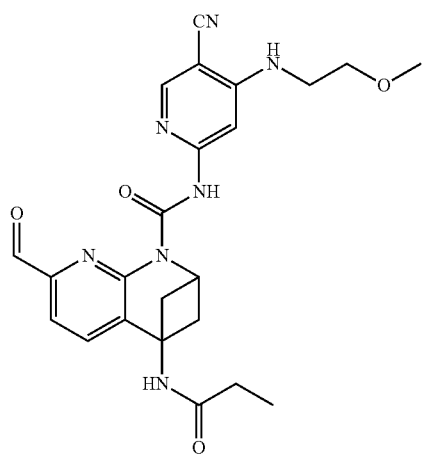
38
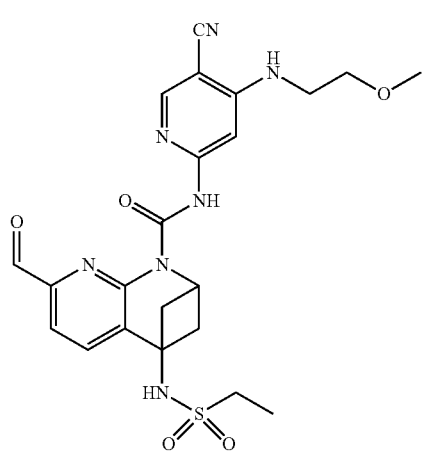
39
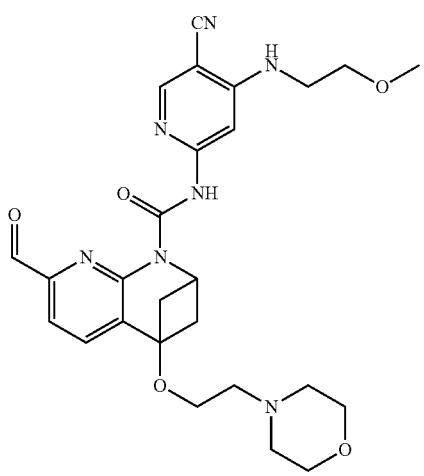
40
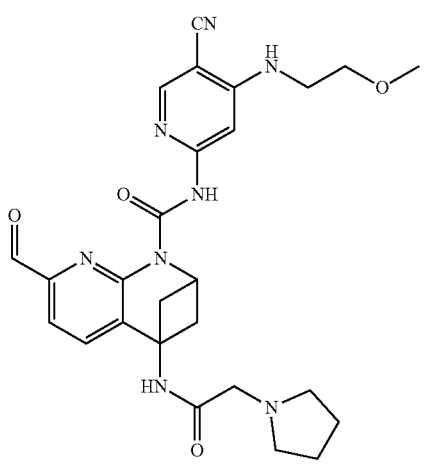
41

269
-continued
42
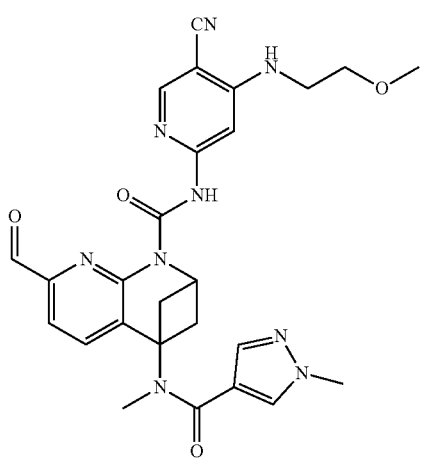
43
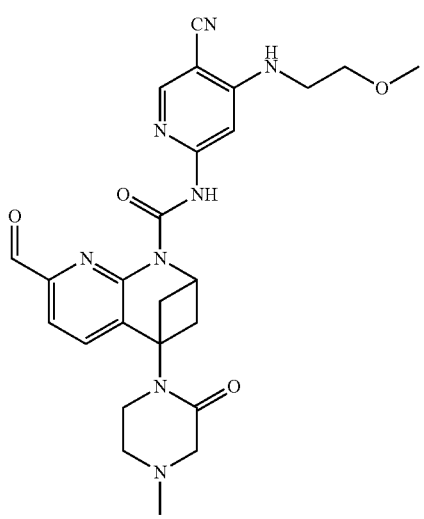
44
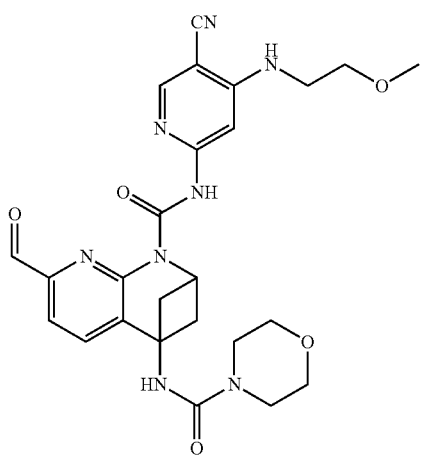
270
-continued
45
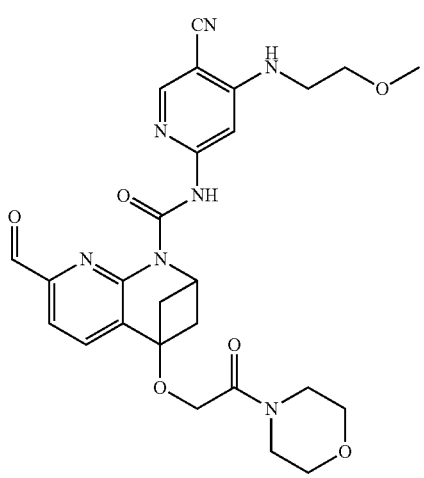
46
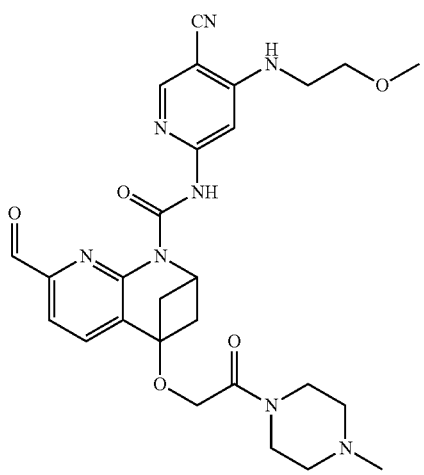
47
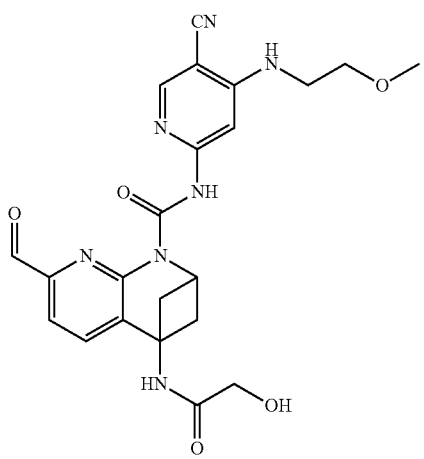

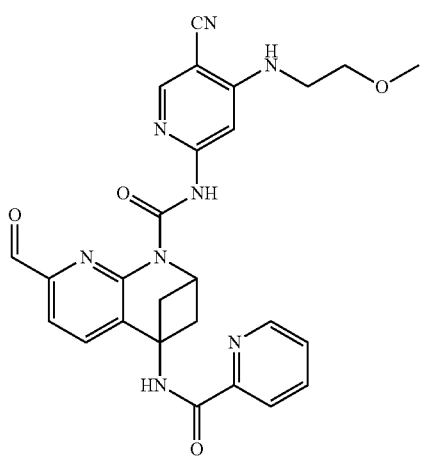
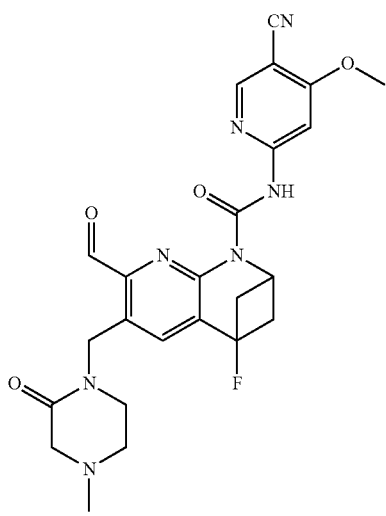
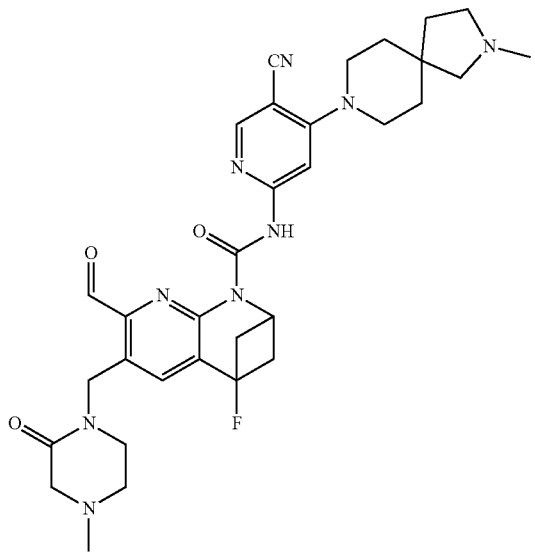
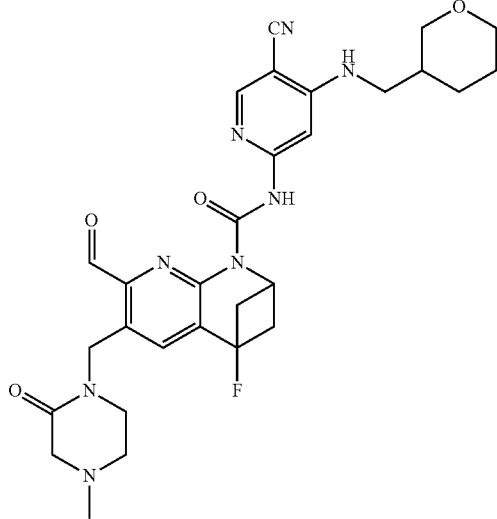

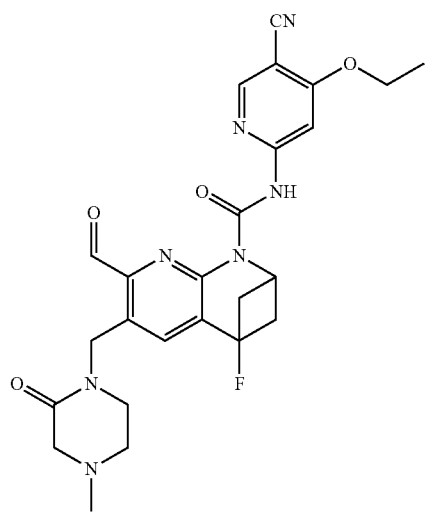
54
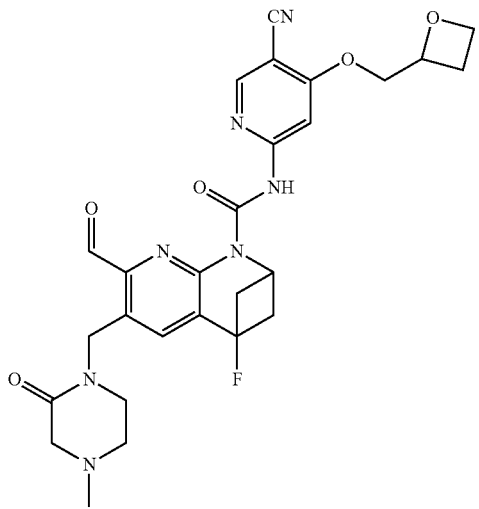
57
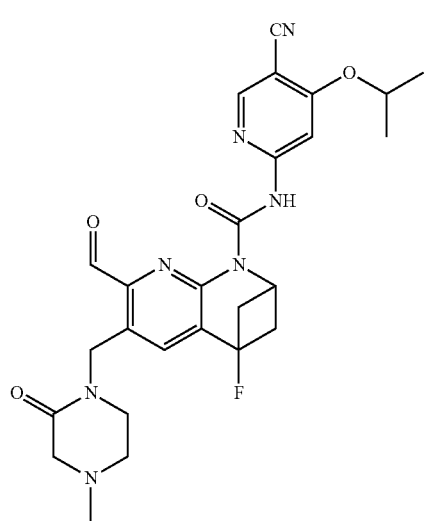
55
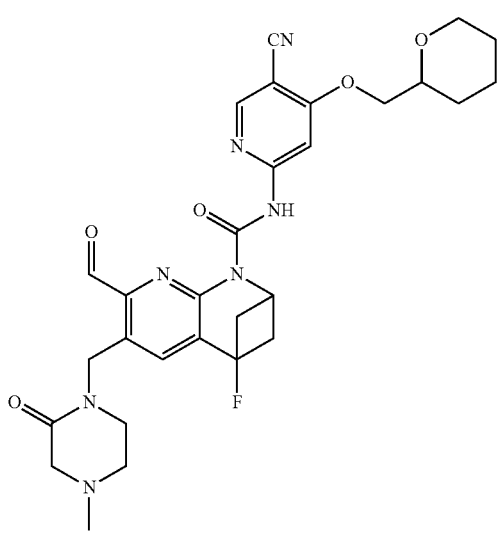
58
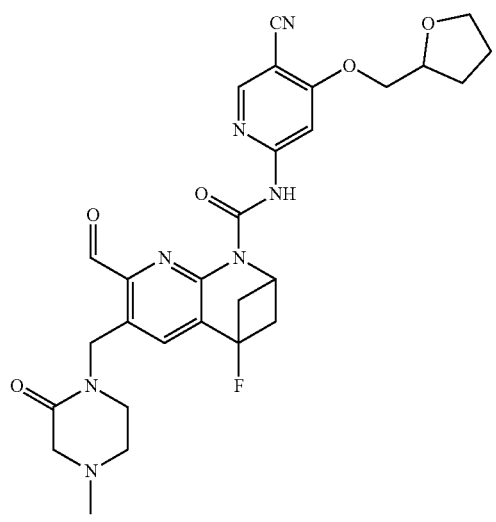
56
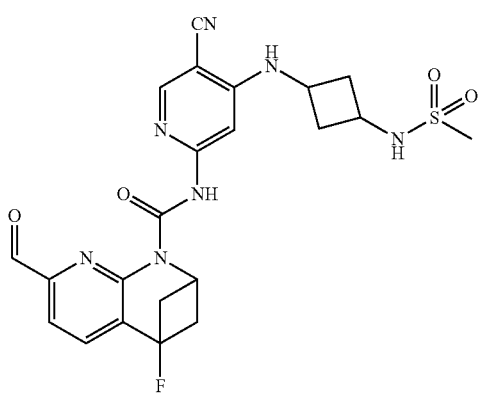
59

60 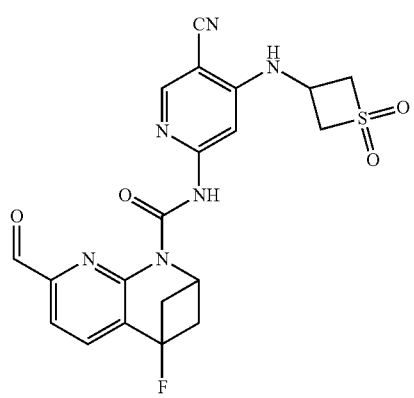
61 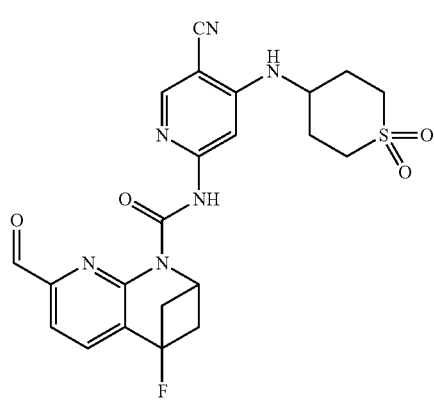
62 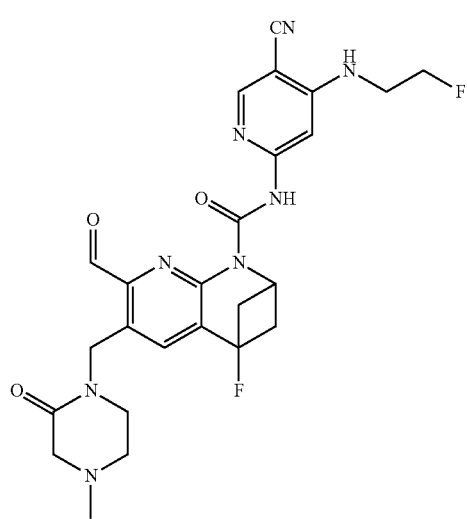
63 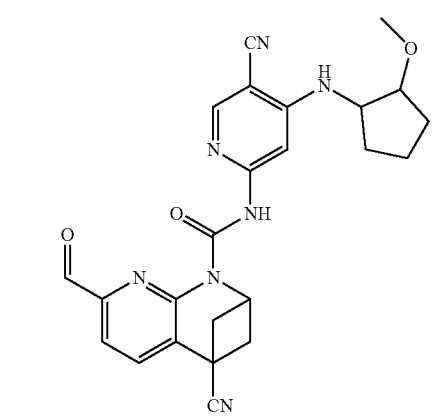
64 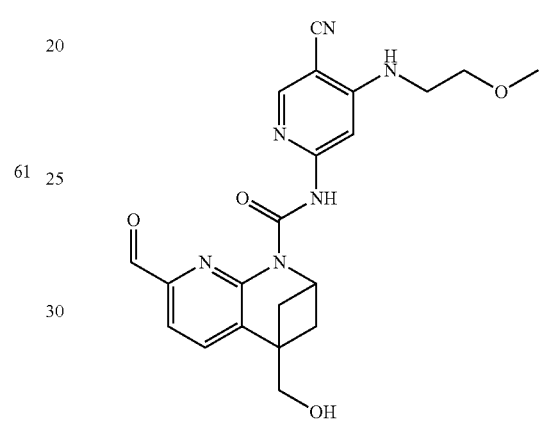
65 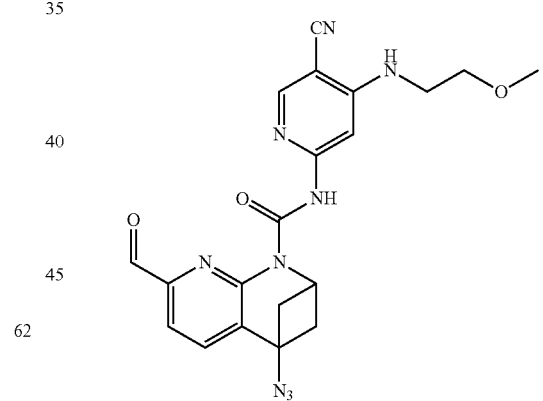
66 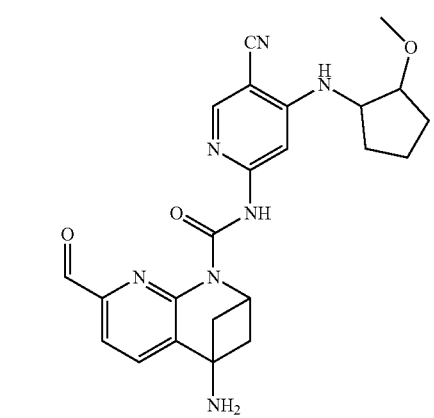

67
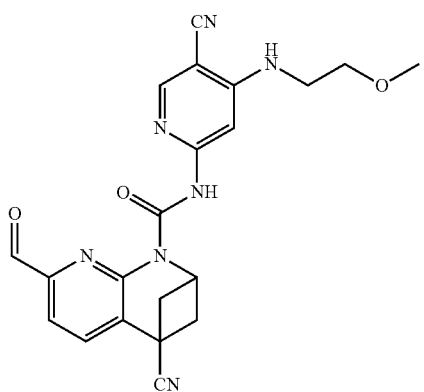
68
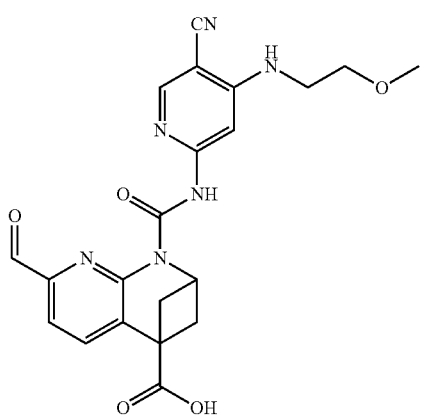
69
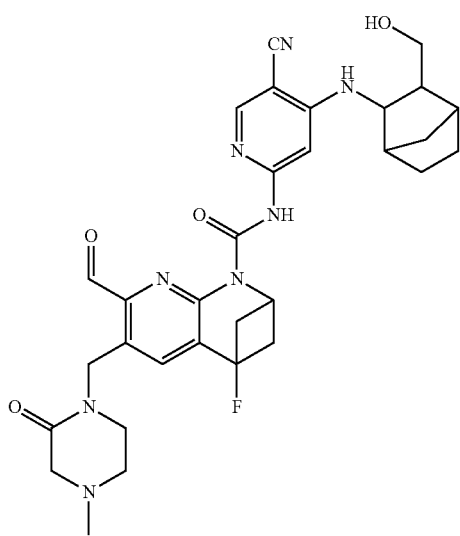
70
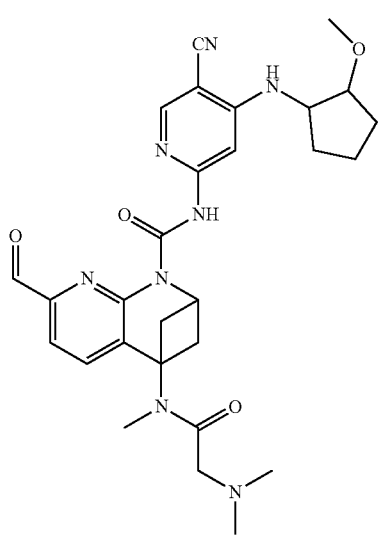
71
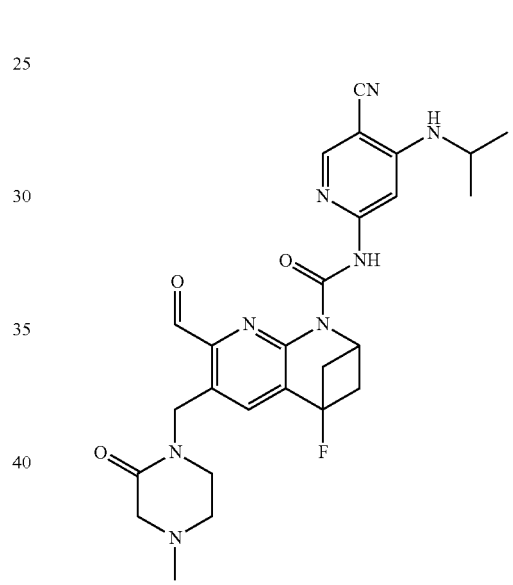
72
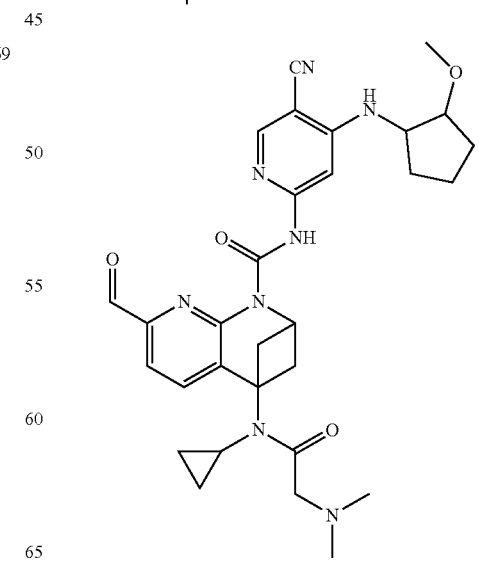

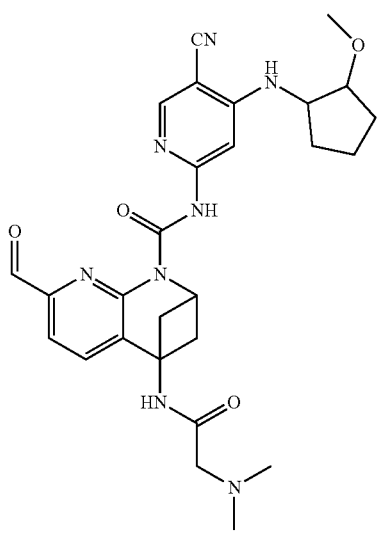
73
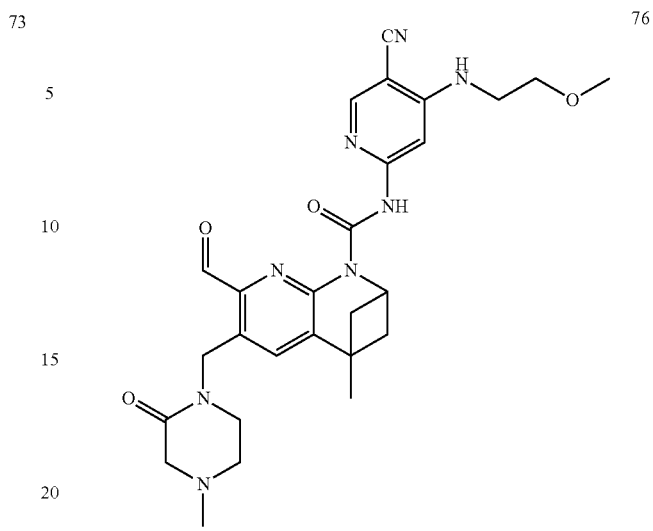
76
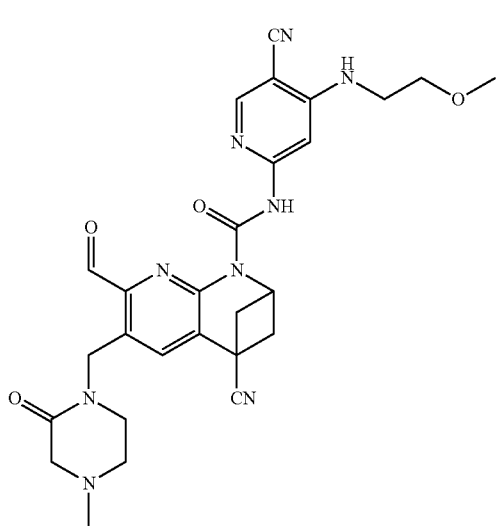
74
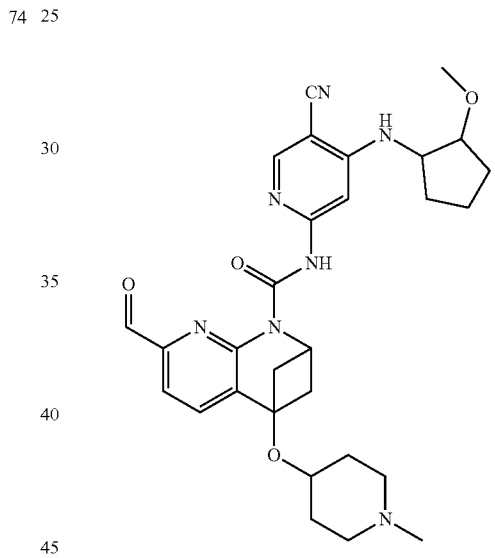
77
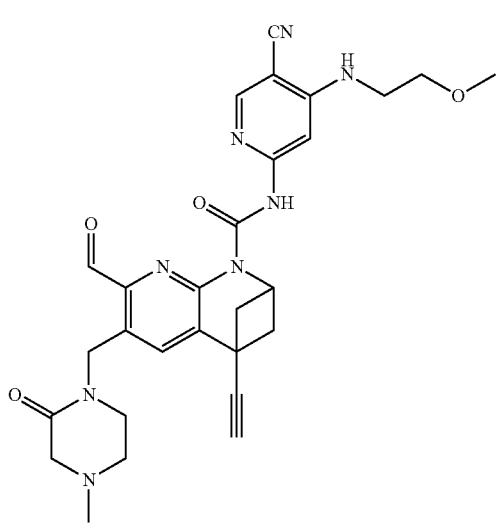
75
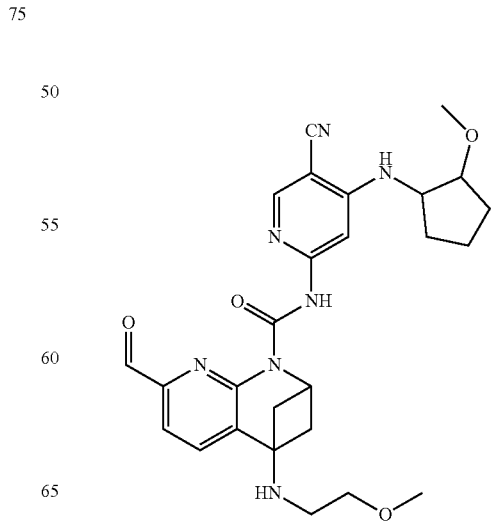
78

79
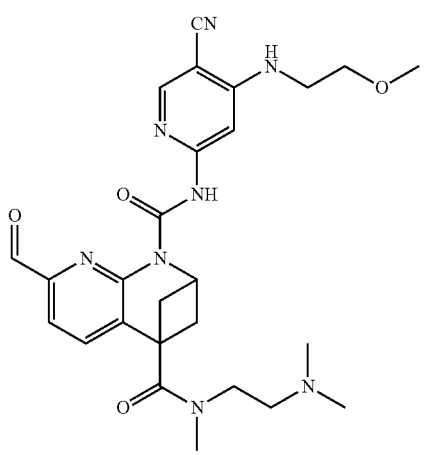
80
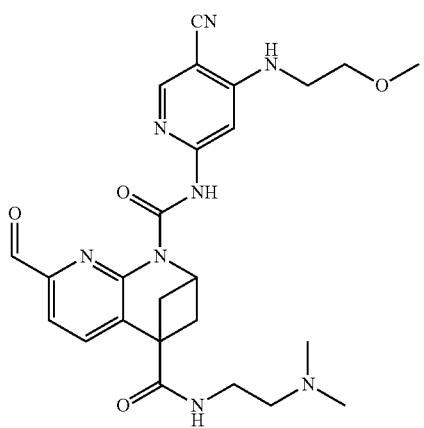
81
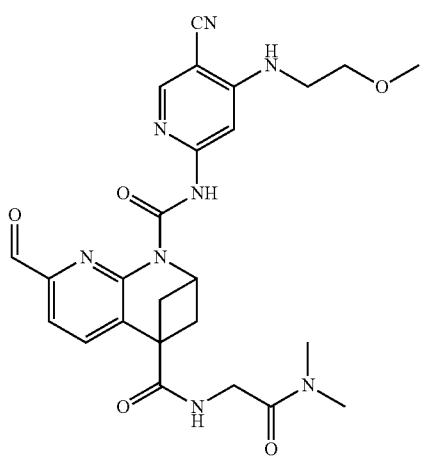
82
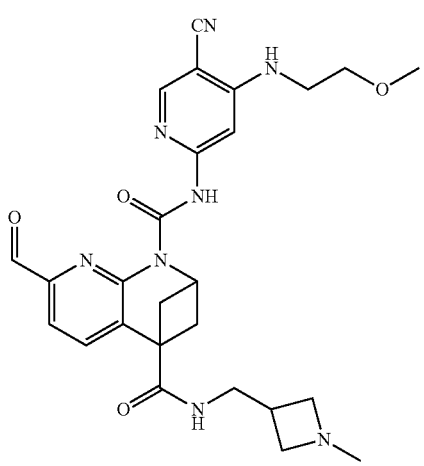
83
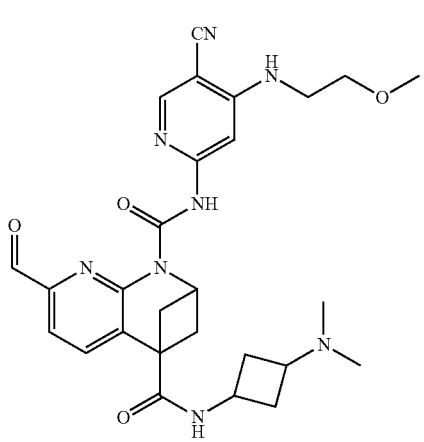
84
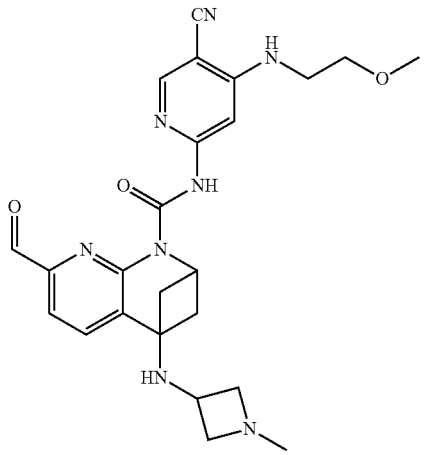

85
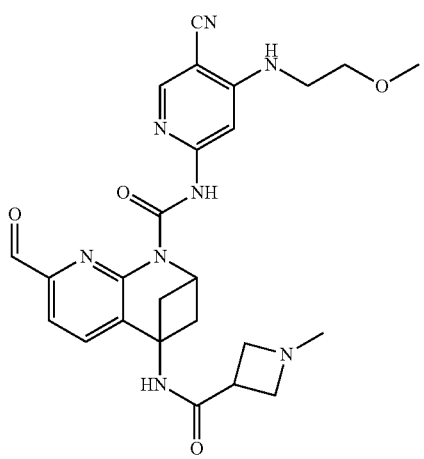
86
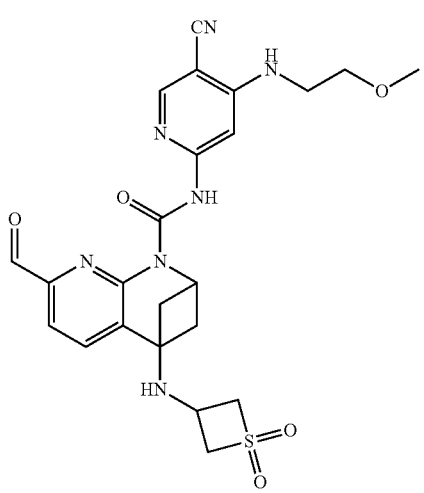
87
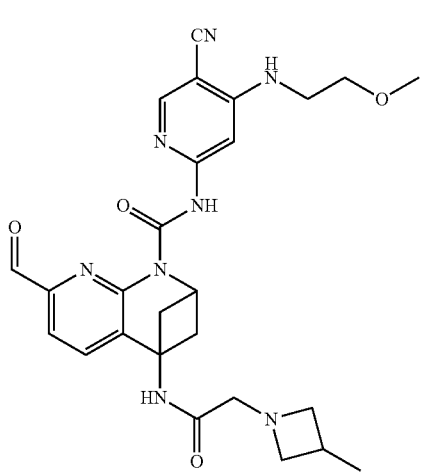
88
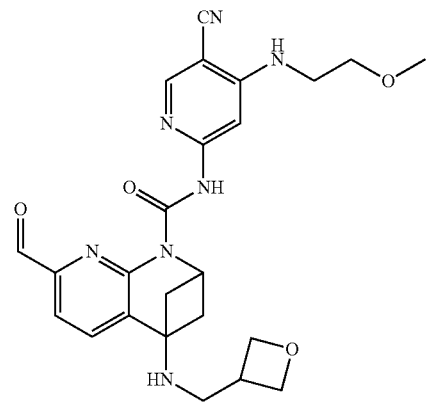
89
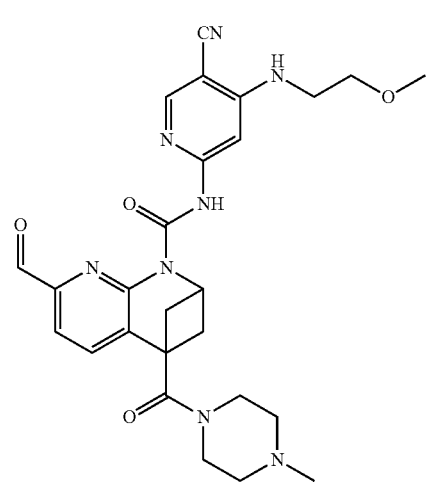
90
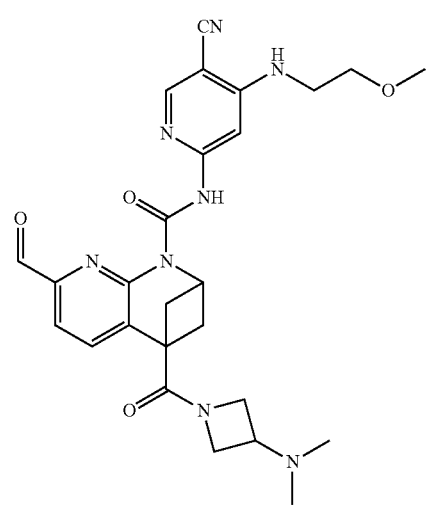

91
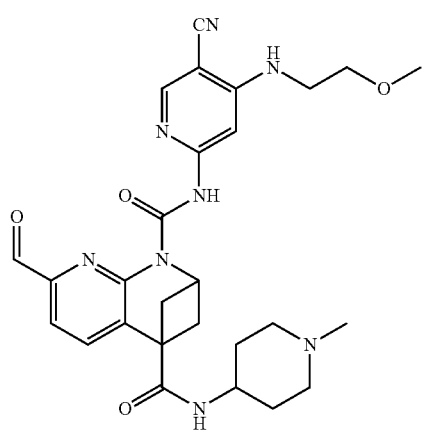
92
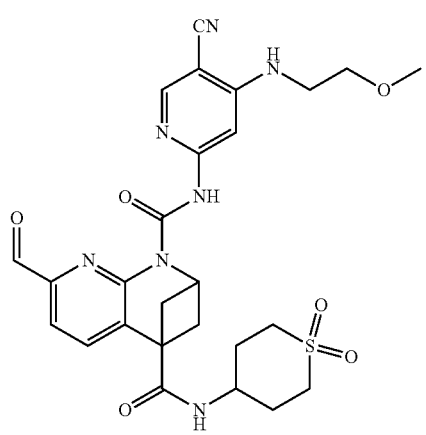
93
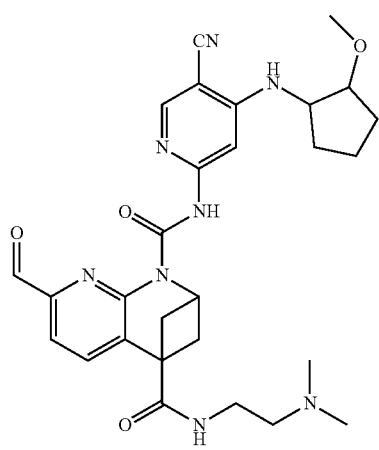
94
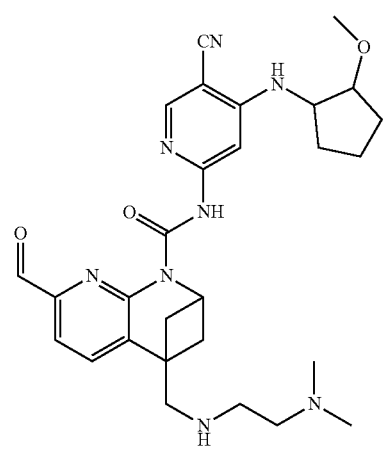
95
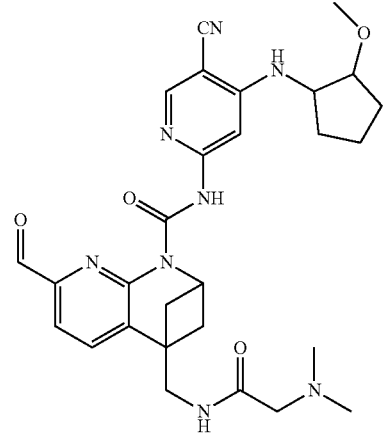
96
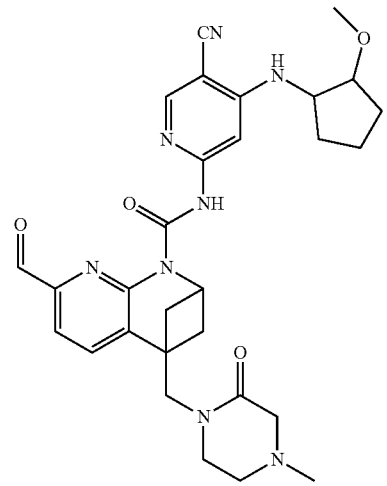

97
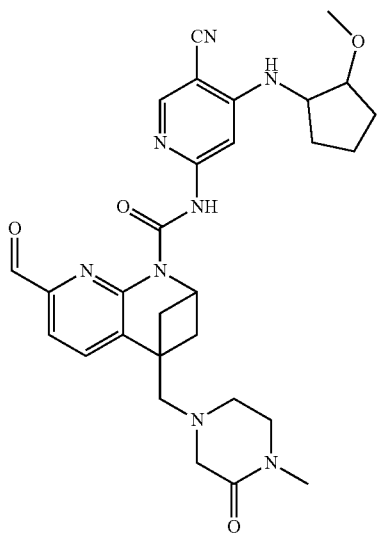
98
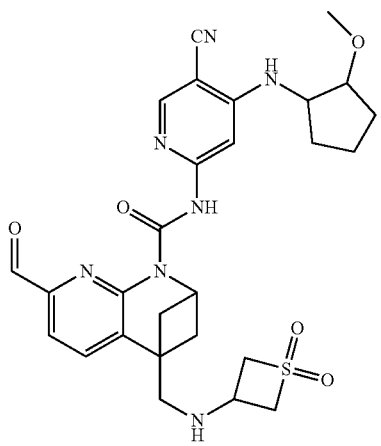
99
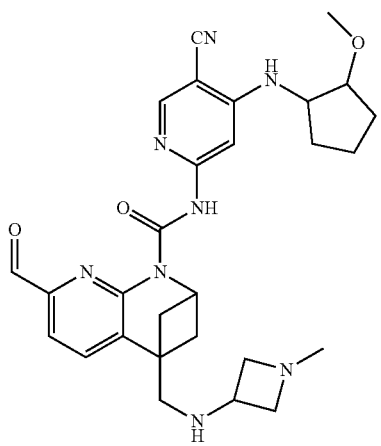
100
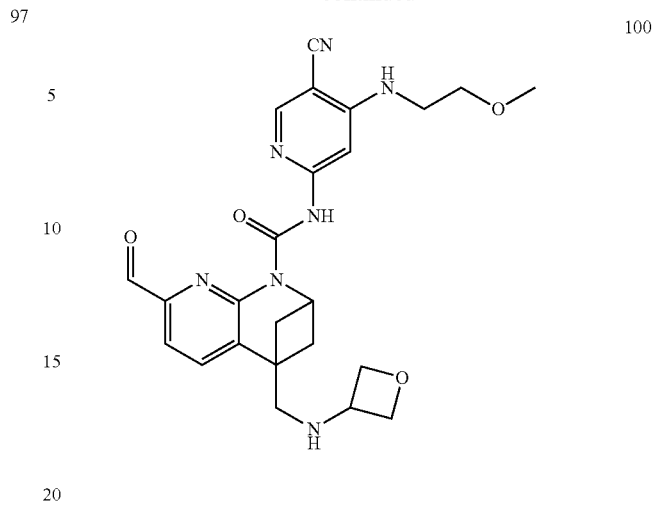
101
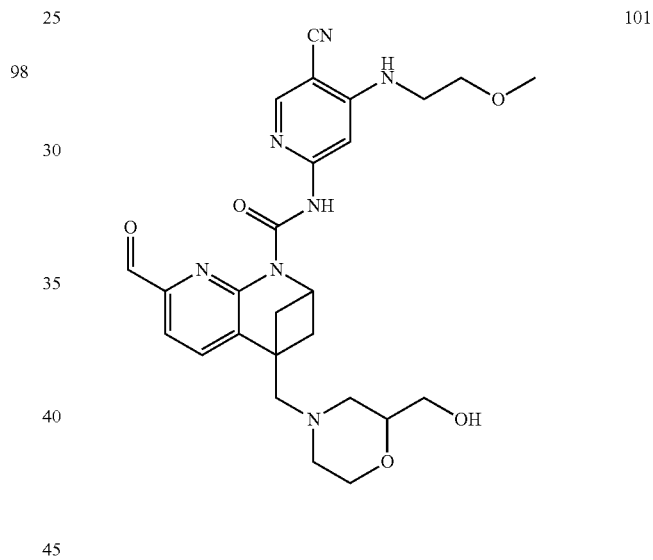
102
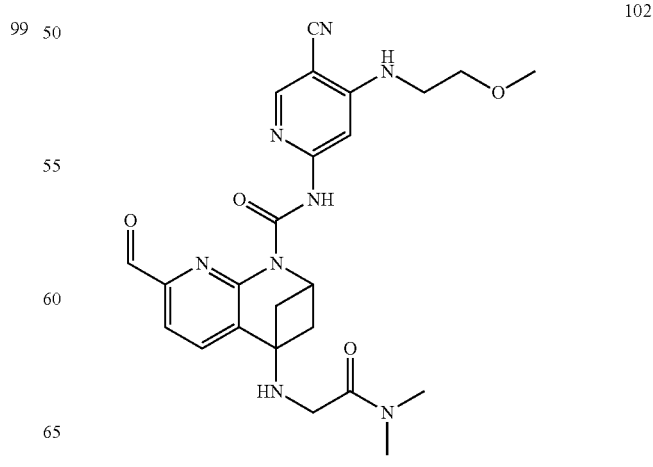

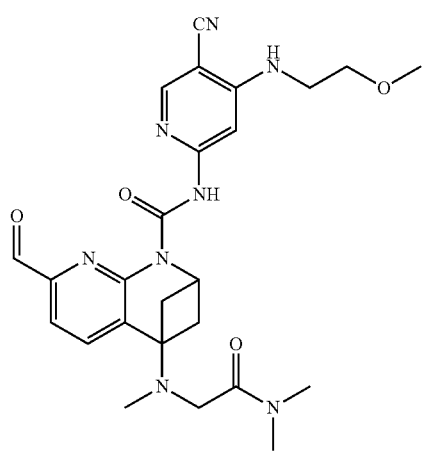
103
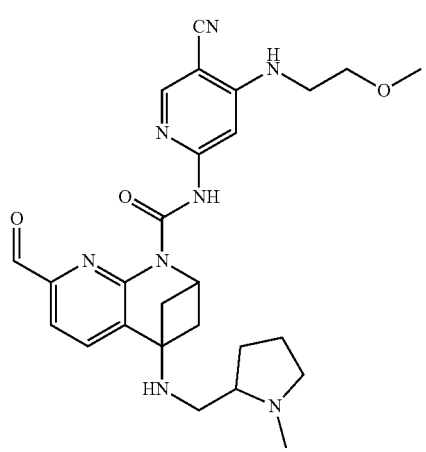
104
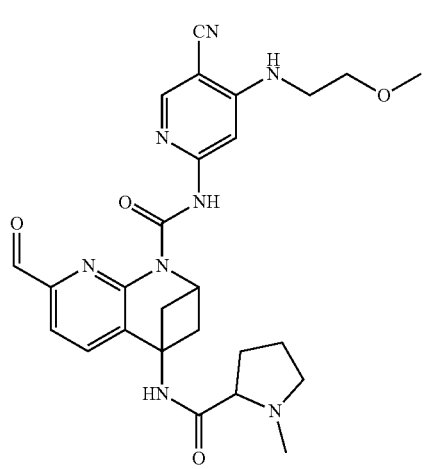
105
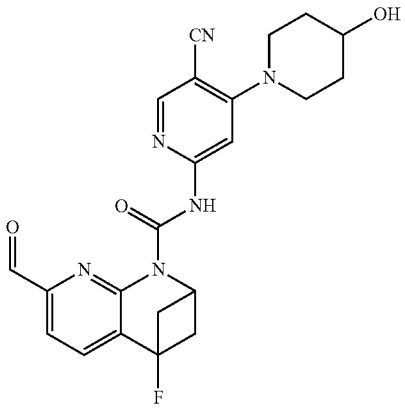
106
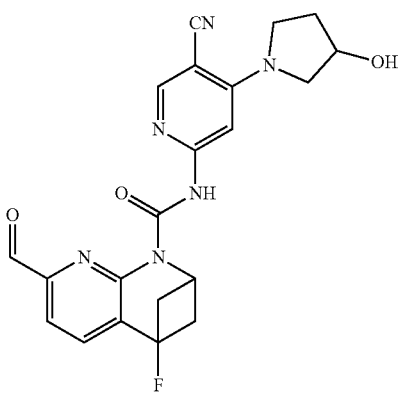
107
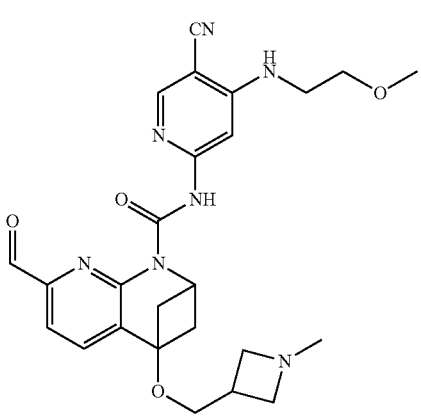
108

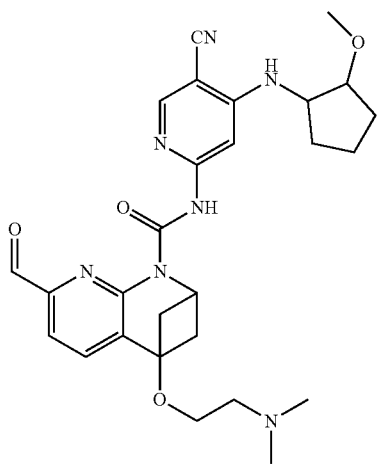
109
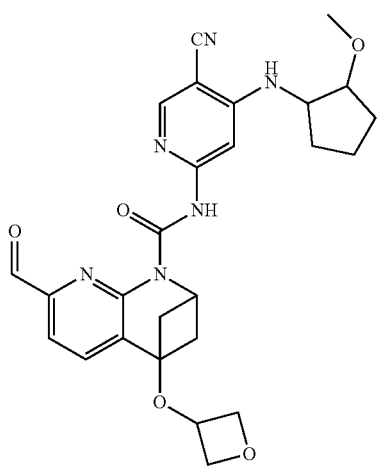
110
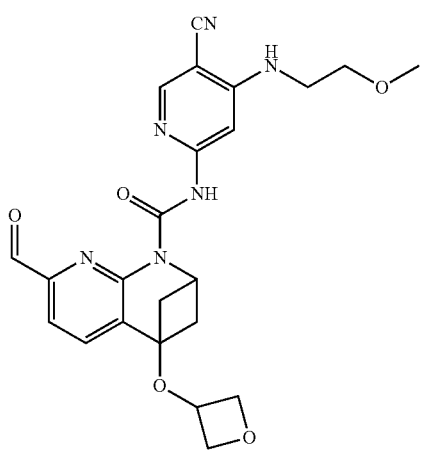
111
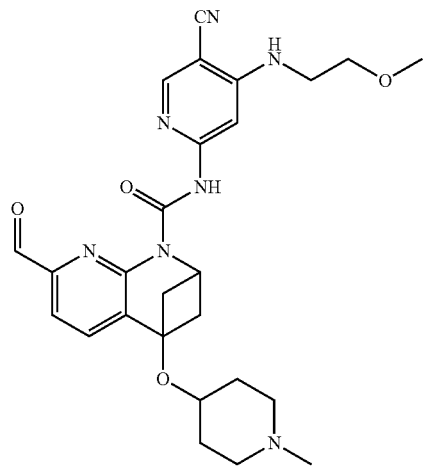
112
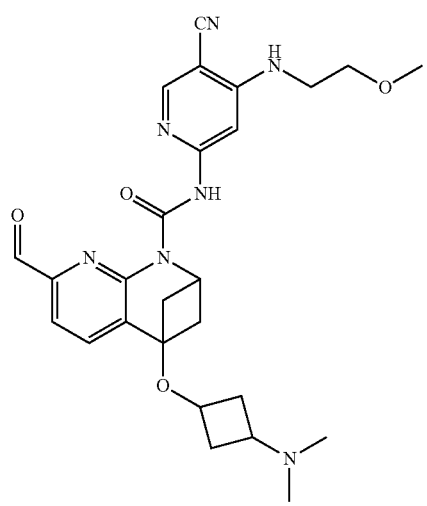
113
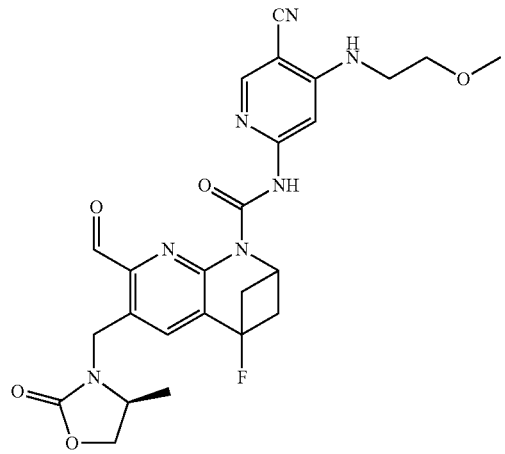
114

115
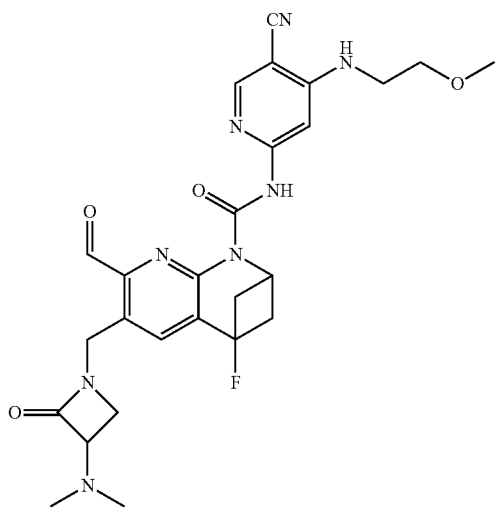
116
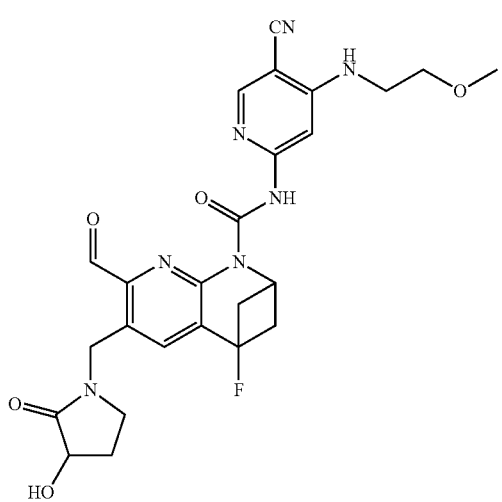
117
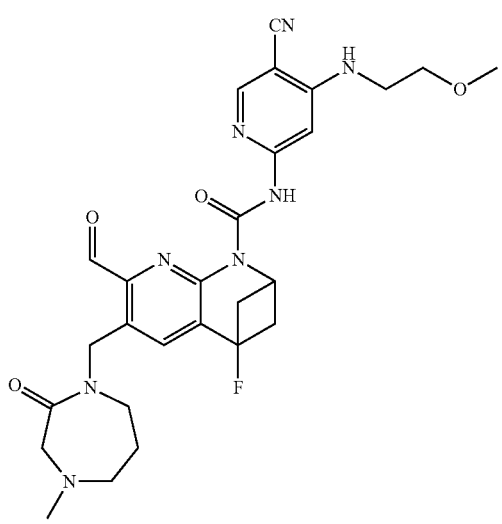
118
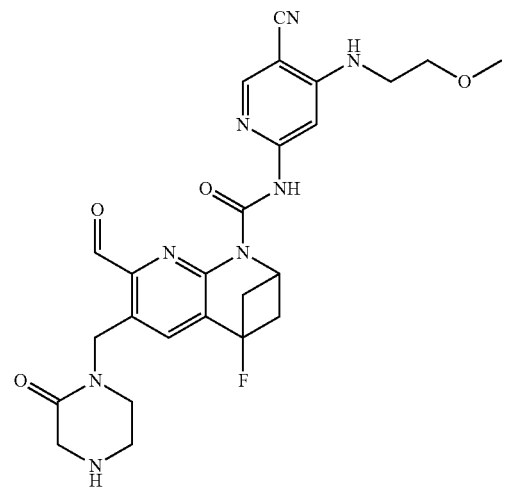
119
119
120
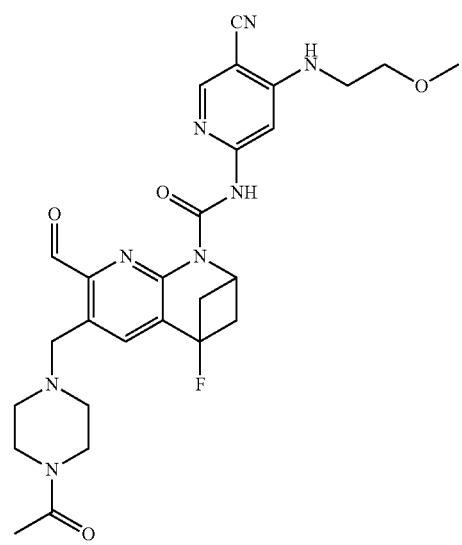

121
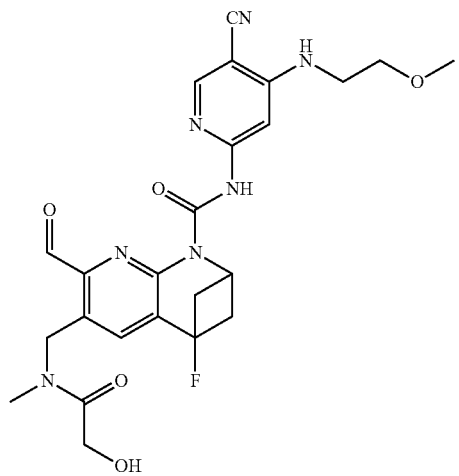
122
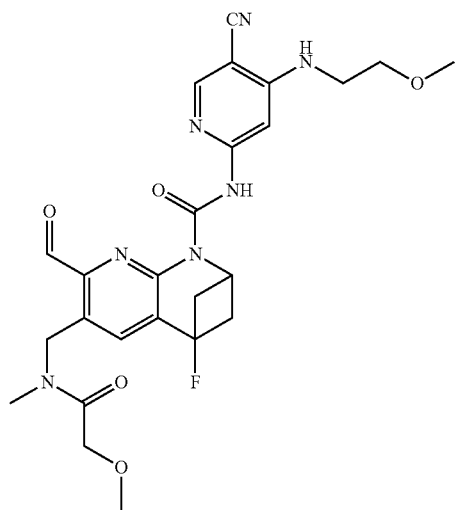
123
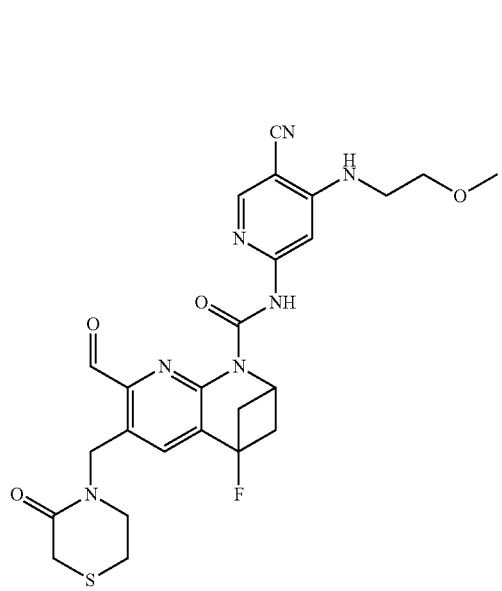
124
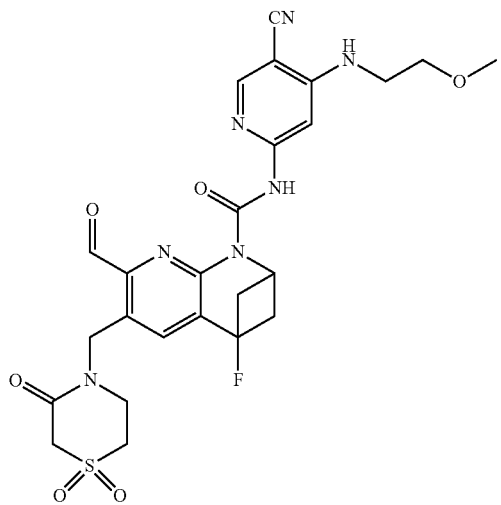
125
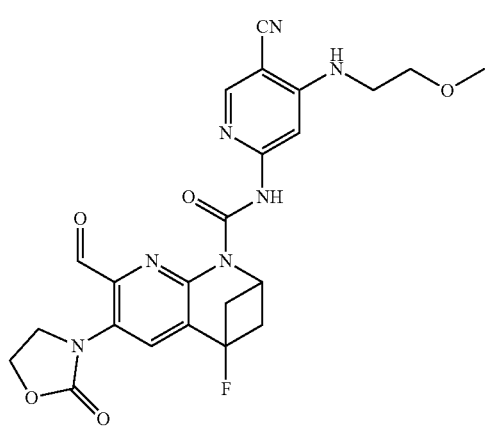
126
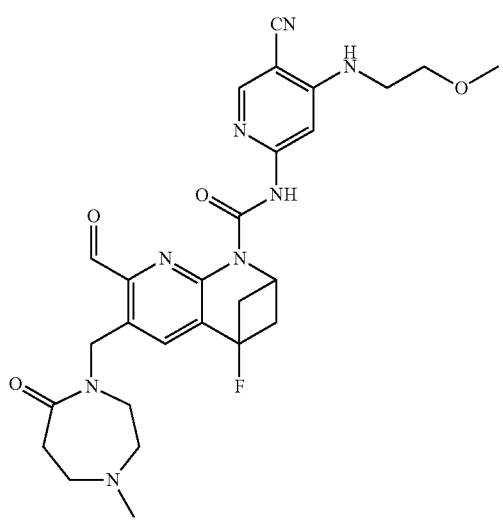

297
-continued
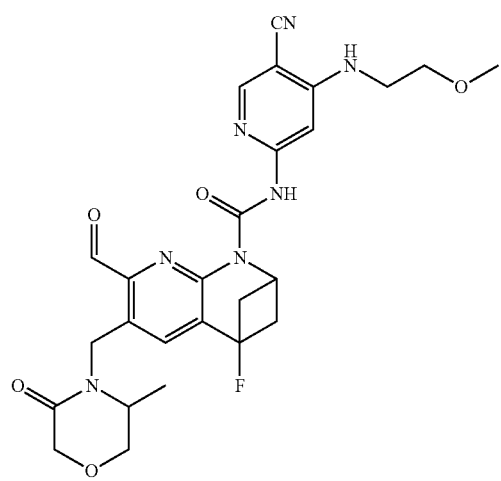
127
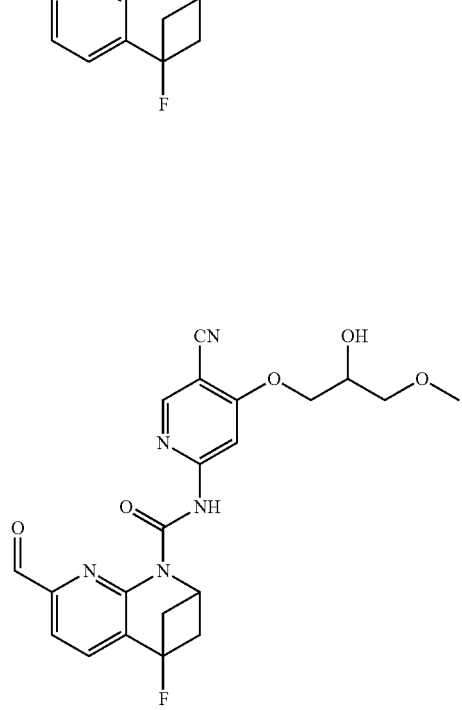
128
129
298
-continued
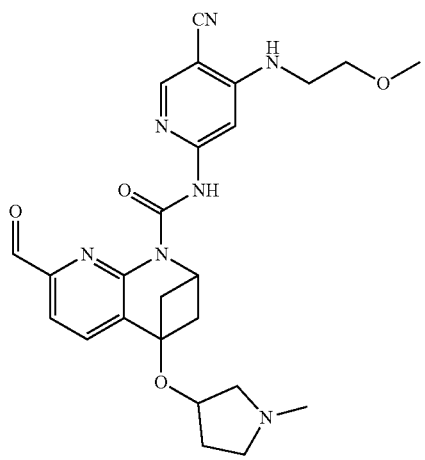
130
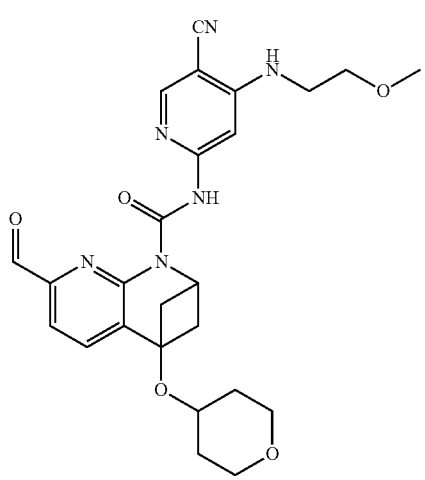
131
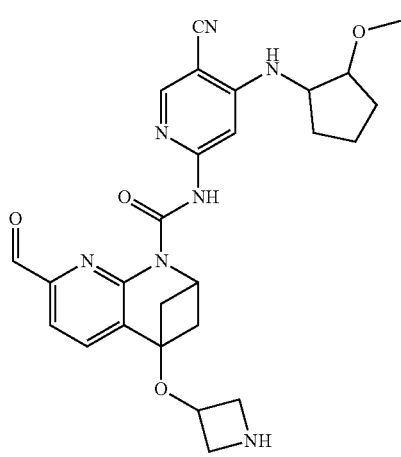
132

| 133 | 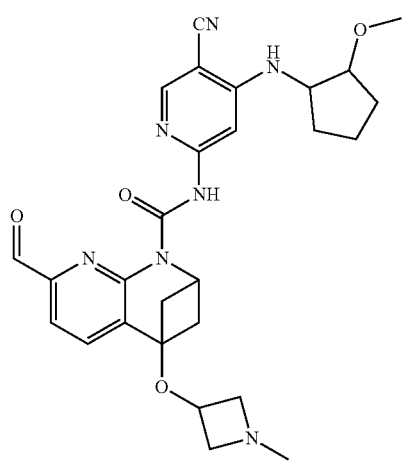 | 136 | 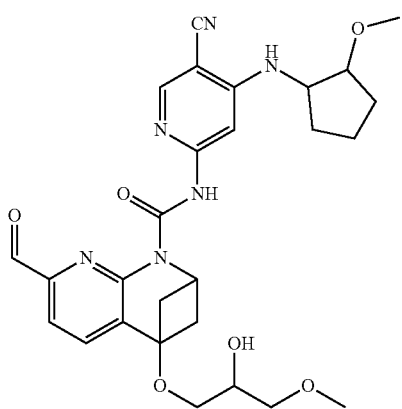 |
| --- | --- | --- | --- |
| 134 | 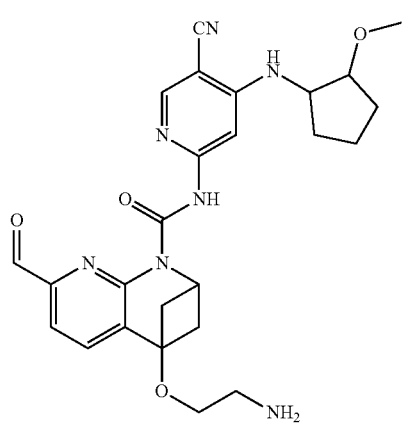 | 137 | 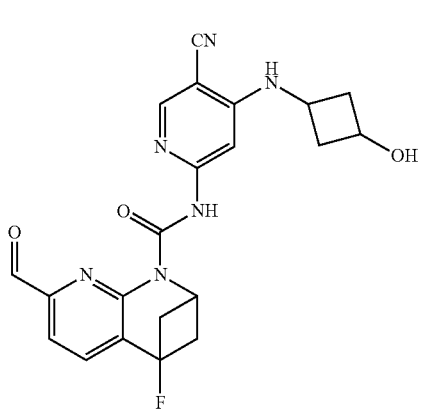 |
| 135 | 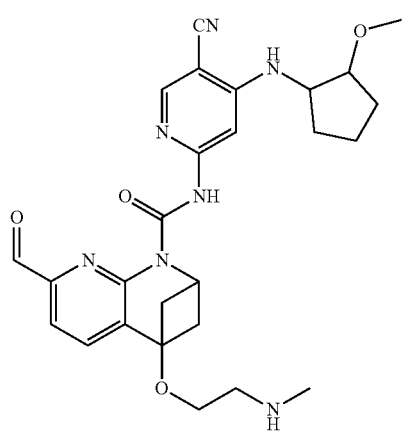 | 138 | 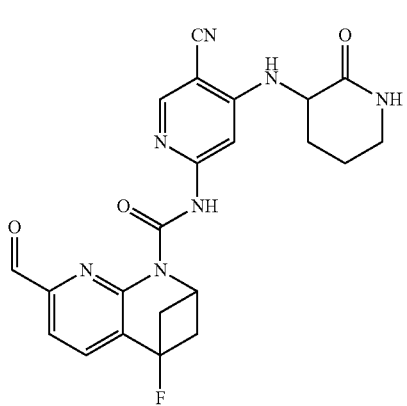 |

-continued
139
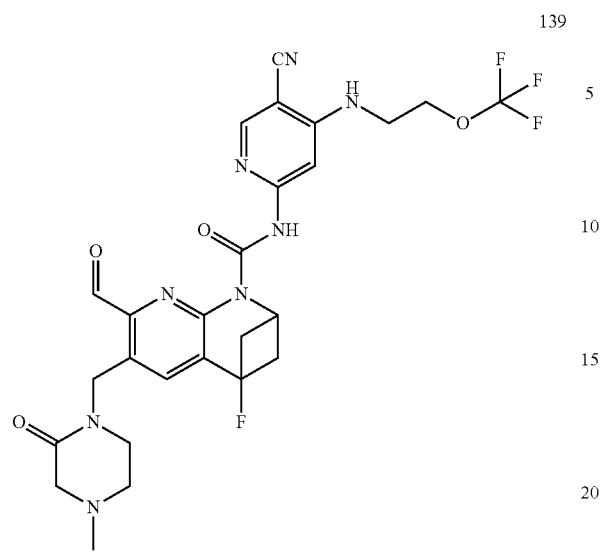
140
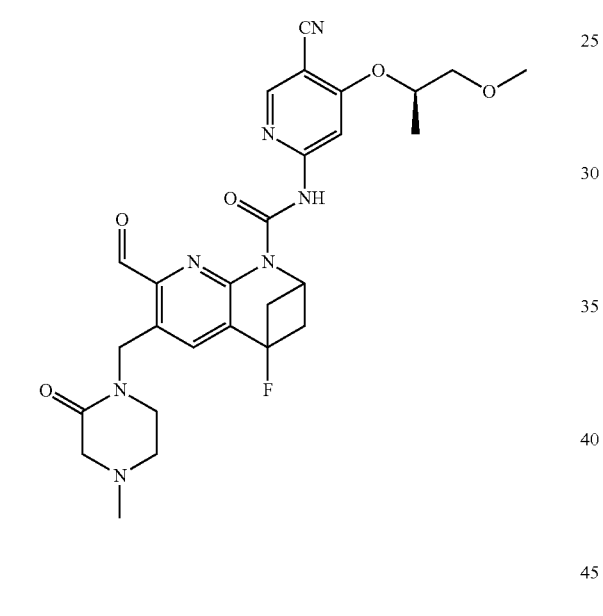
141
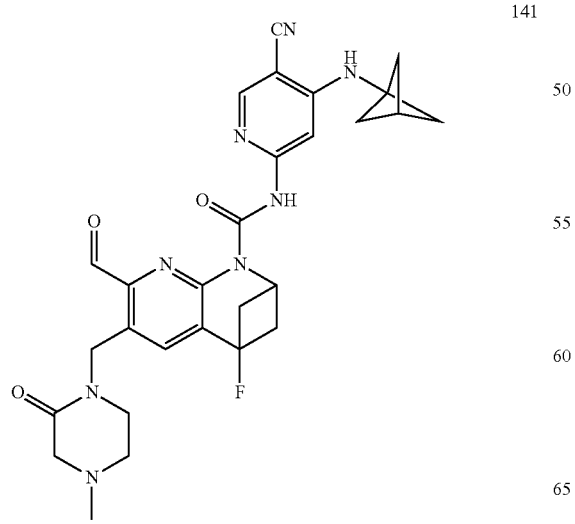
142
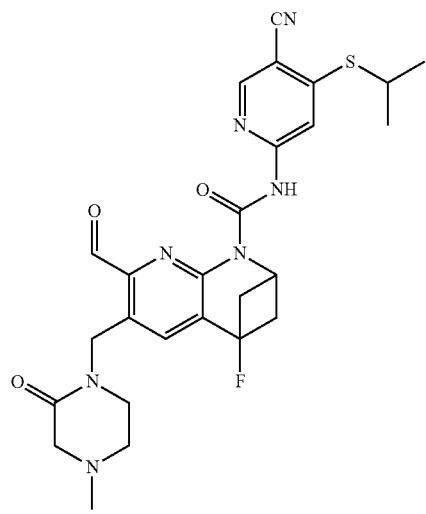
143
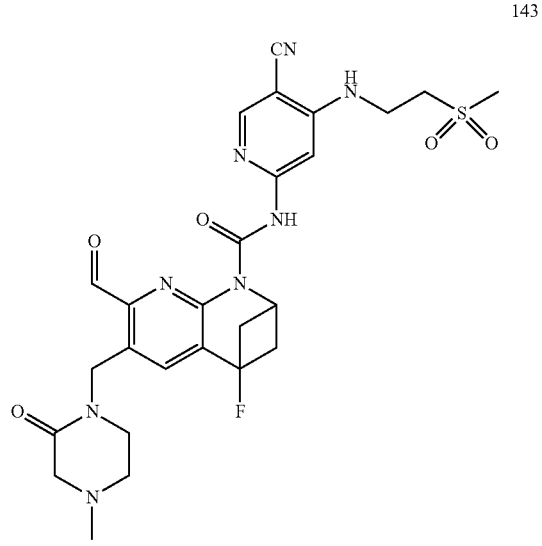
144
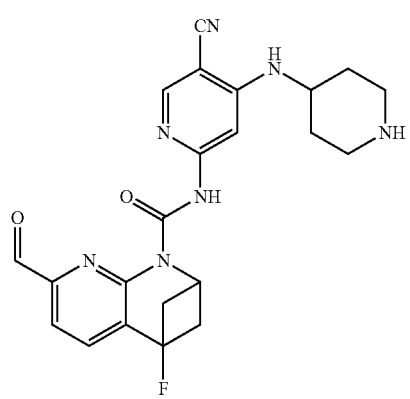

303
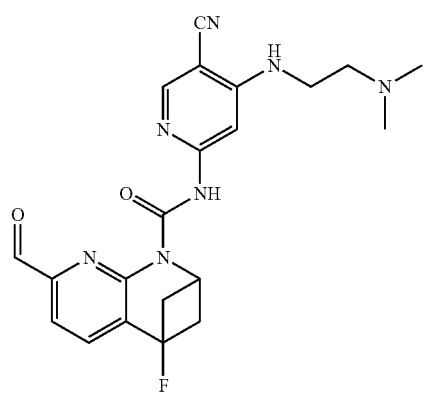
145
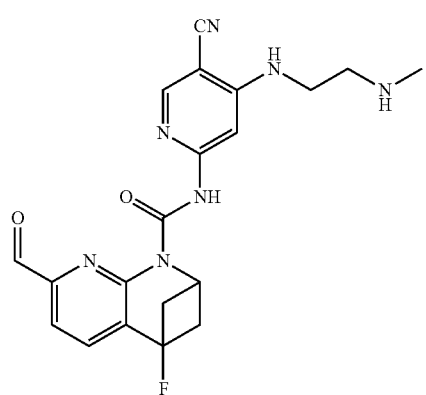
146
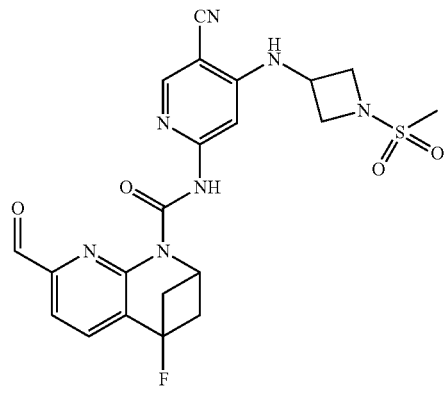
147
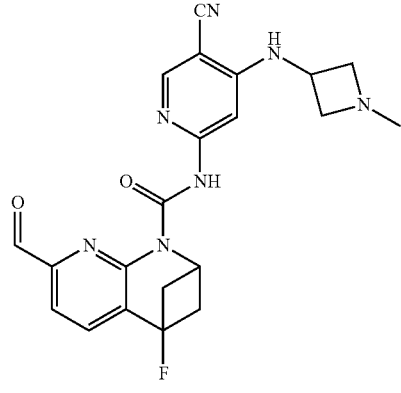
148
304
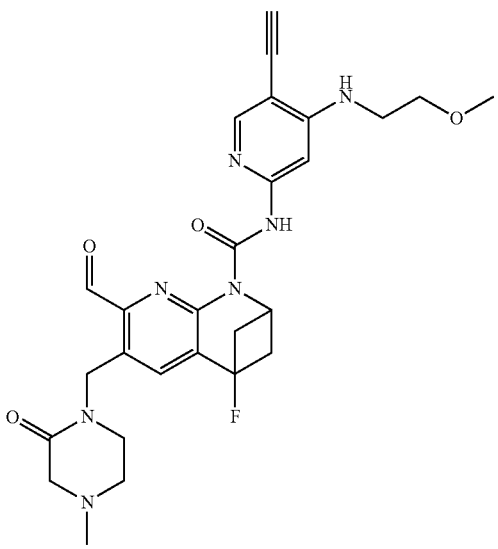
149
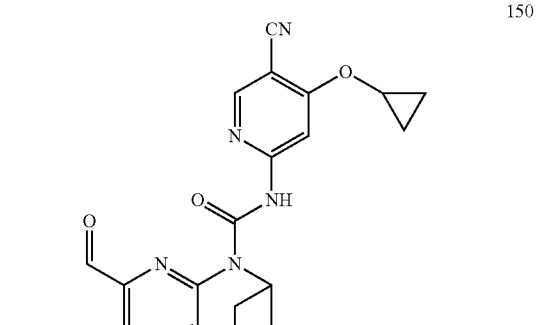
150
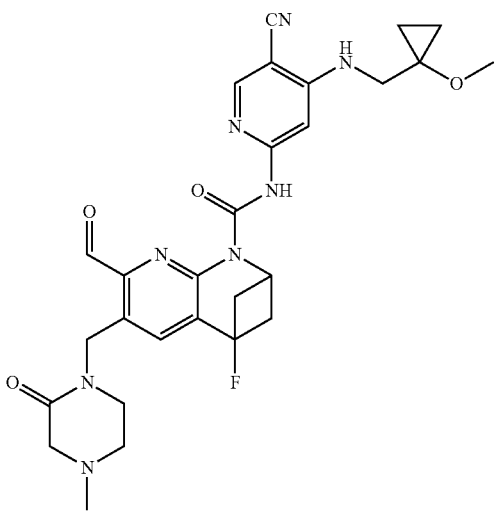
151

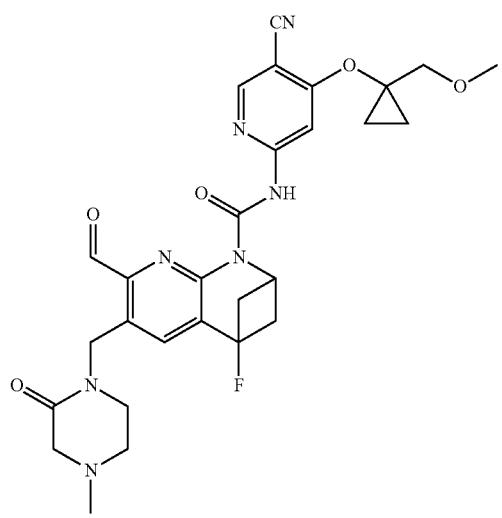
152
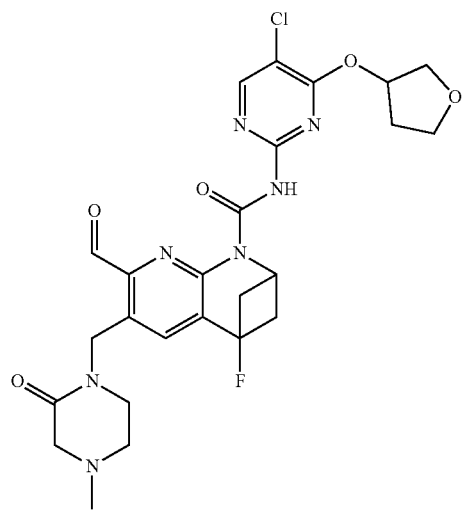
155
153
156
154
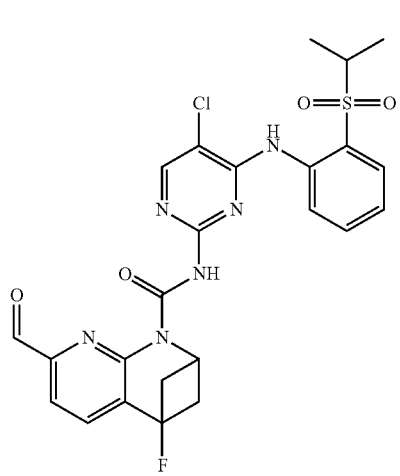
157

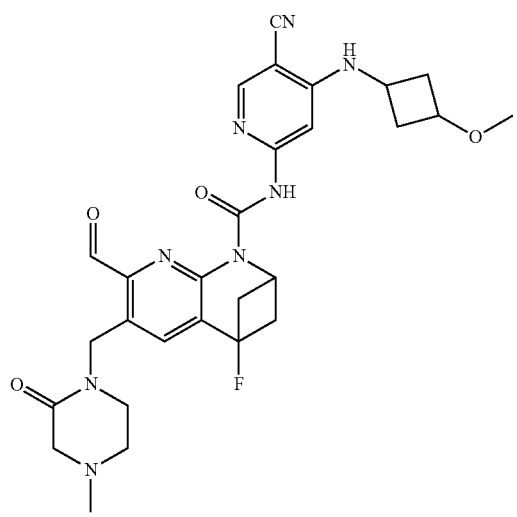
158
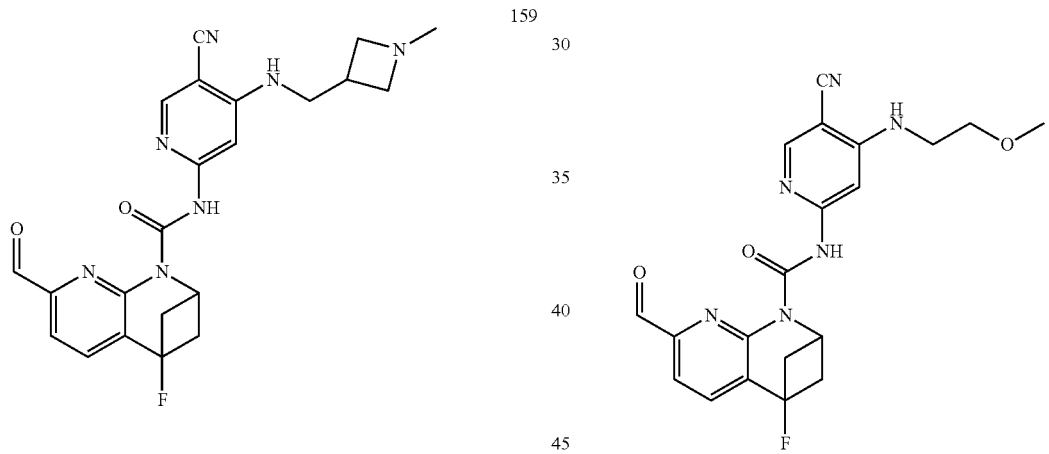
159
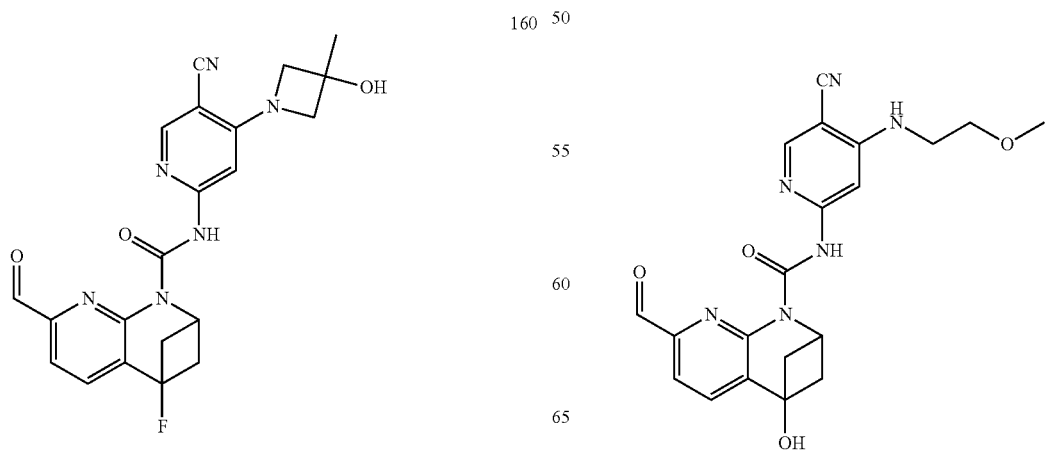
160
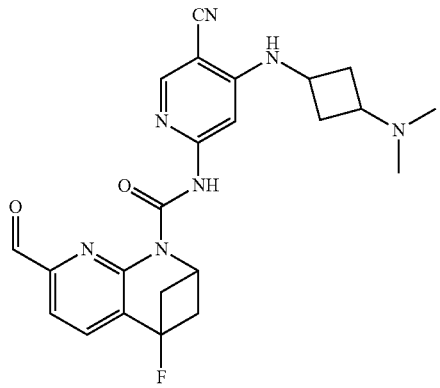
161
6. The compound of formula (I) according to claim 1, or a pharmaceutically acceptable salt, solvate, active metabolite, polymorph, isotopic label, isomer or prodrug thereof, wherein the compound is selected from:

| | |
|---|---|
| 3 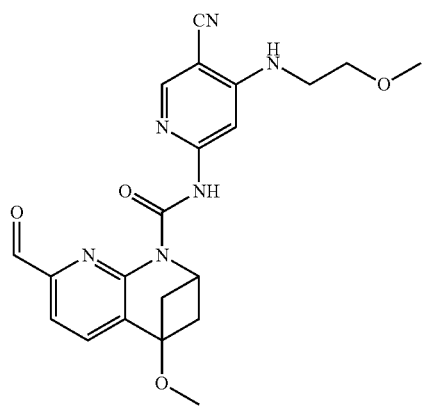 | 6 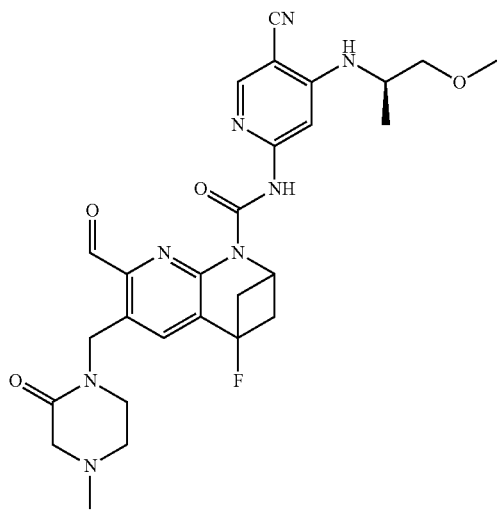 |
| 4 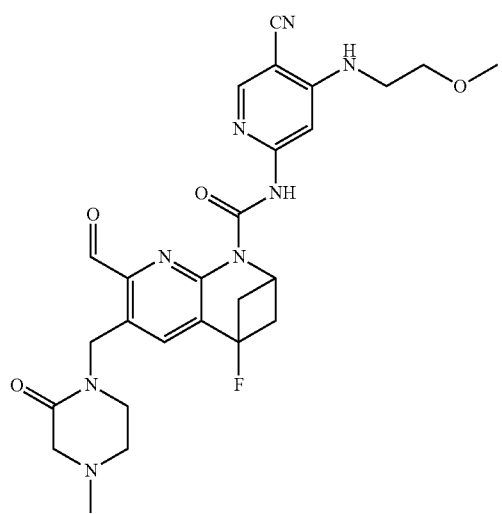 | 7 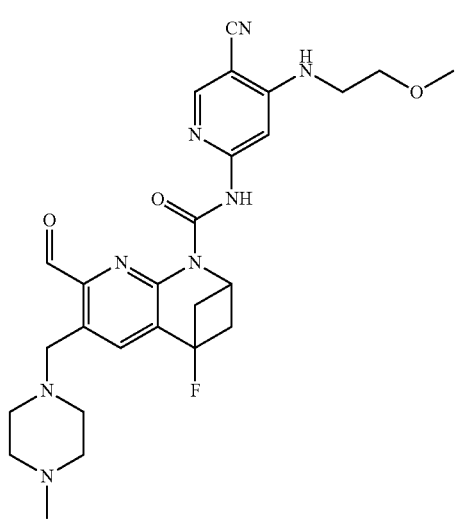 |
| 5 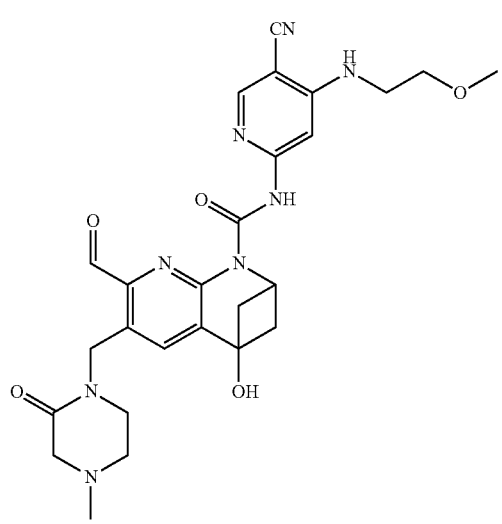 | 8 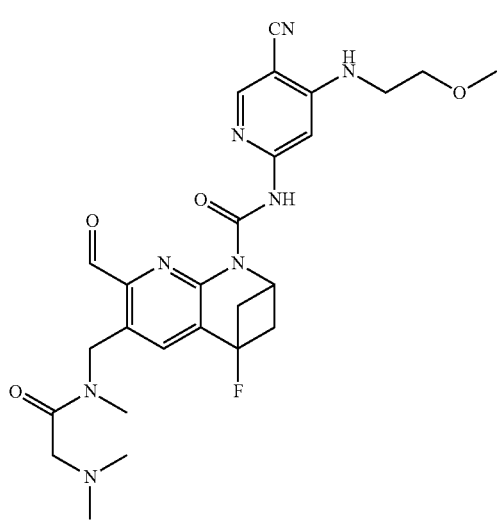 |

311
-continued
9
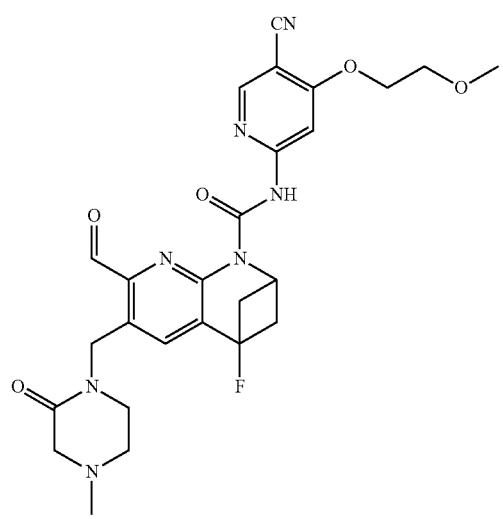
10
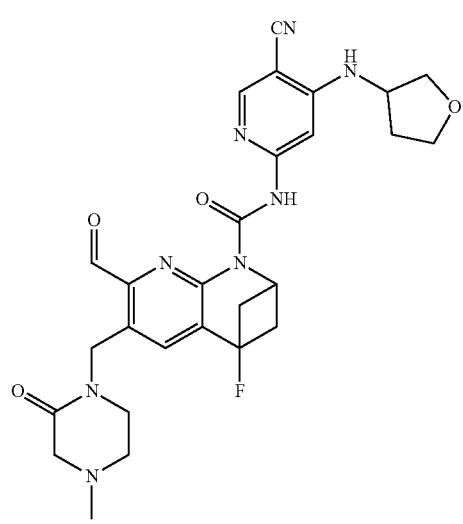
11A
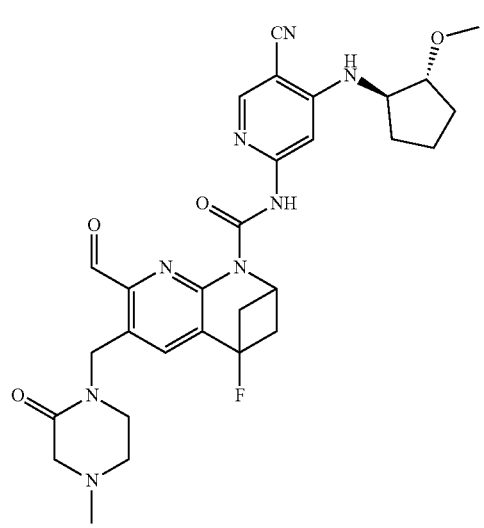
312
-continued
11B
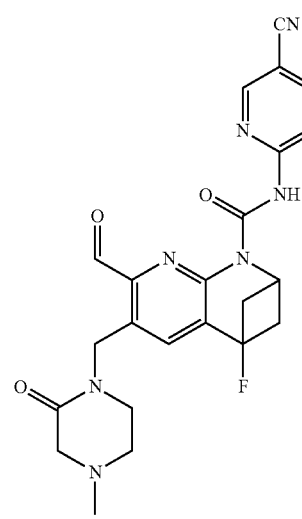
12A
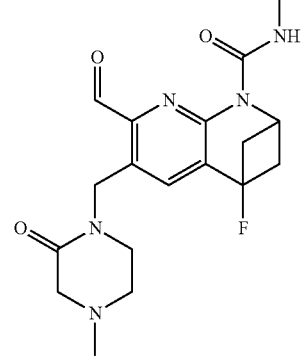
12B
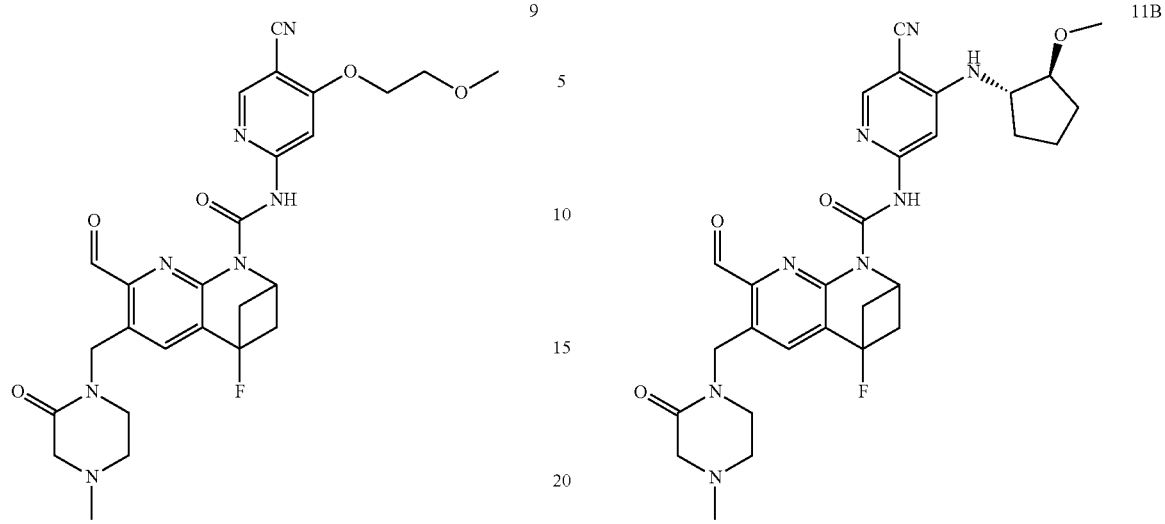

13
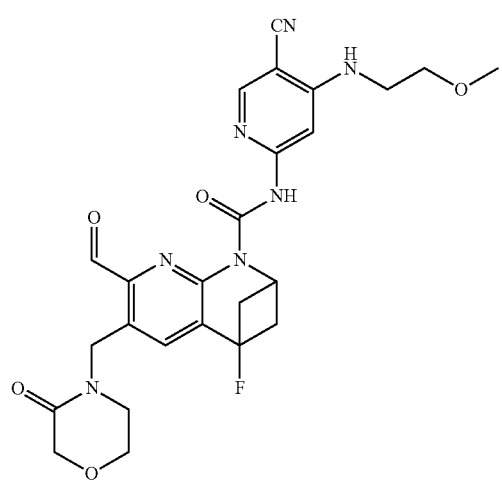
14
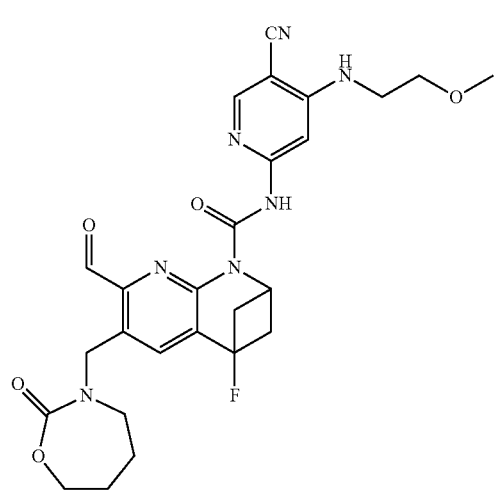
15
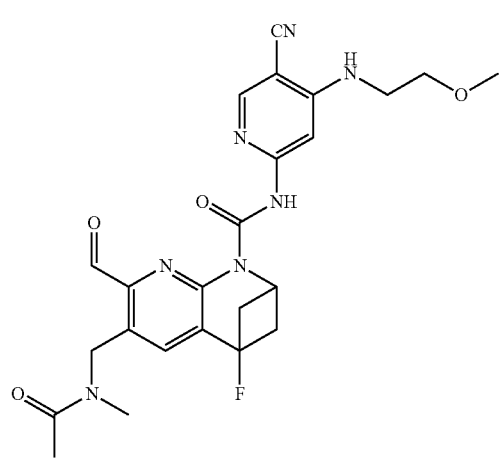
16
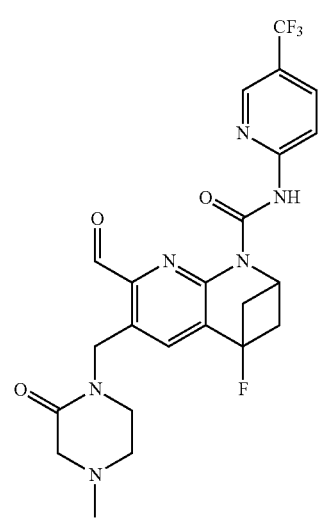
17
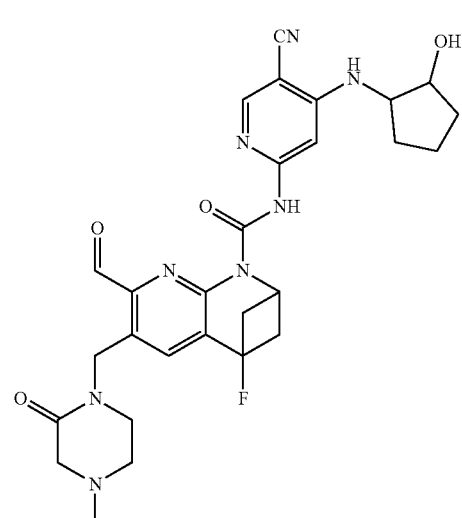
18
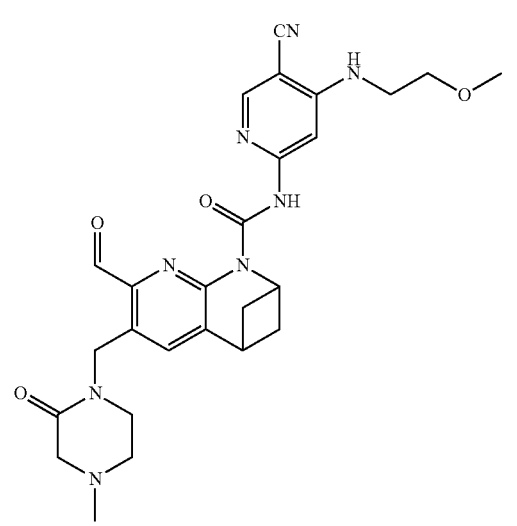

19
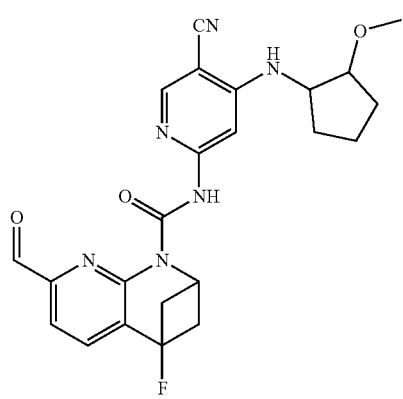
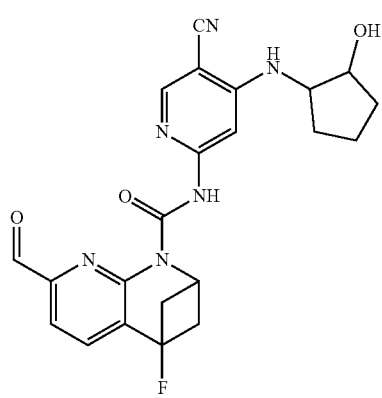
21
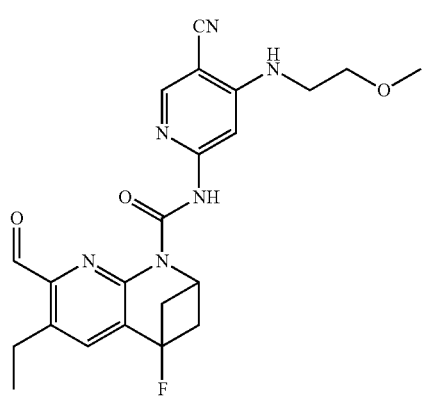
22
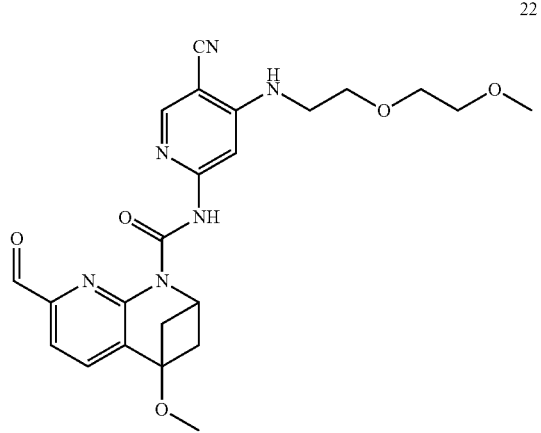
23
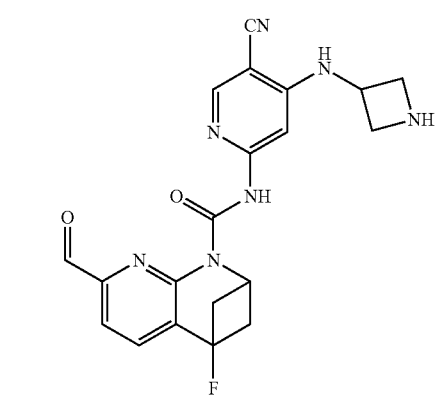
24
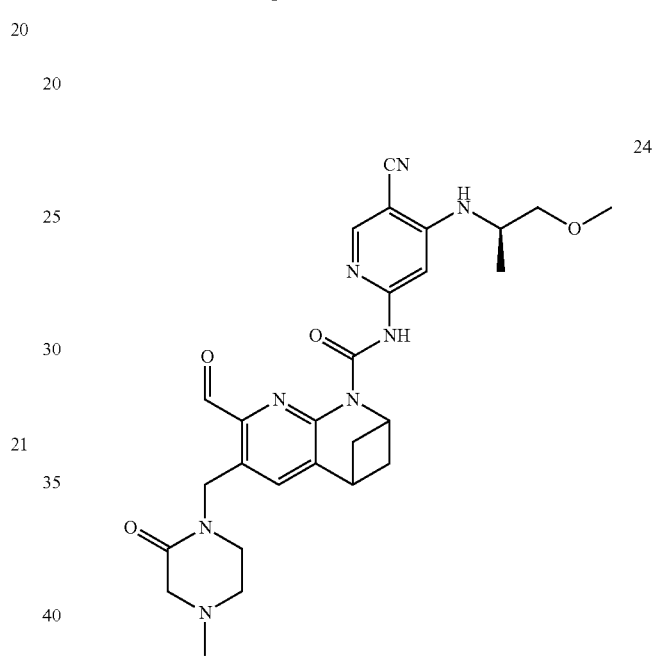
25
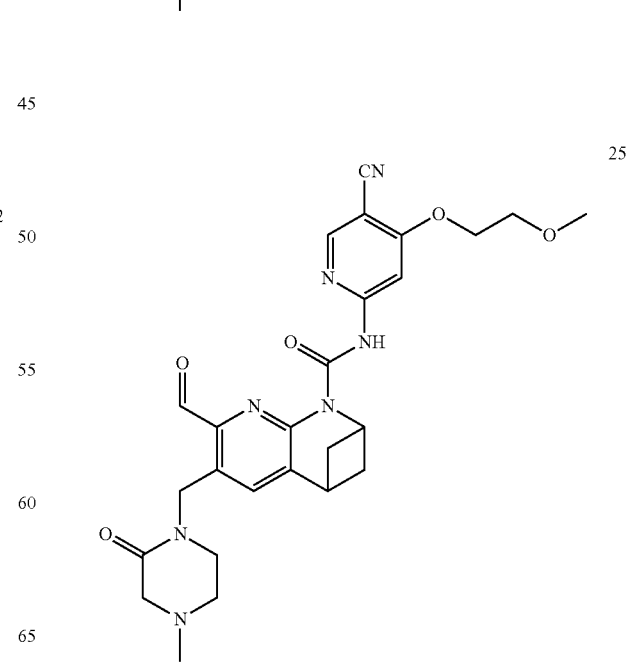

26
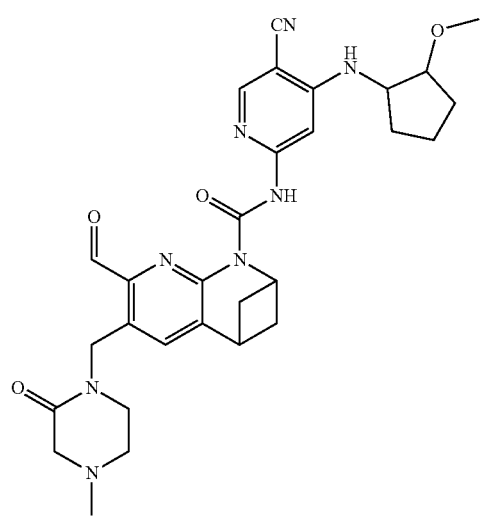
27
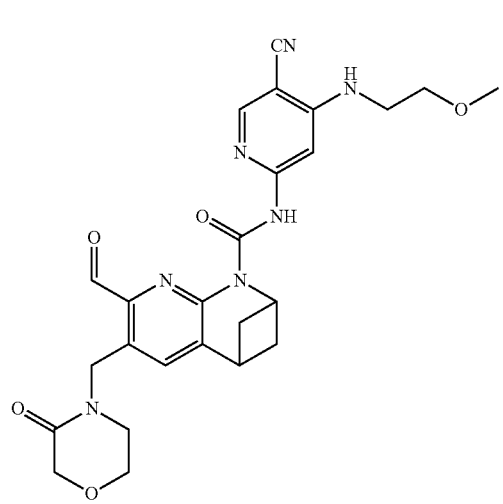
28
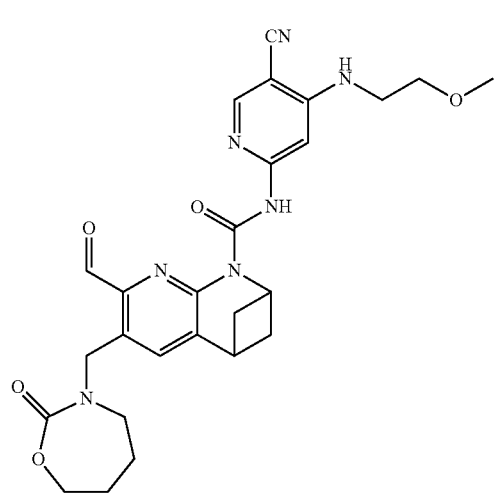
29
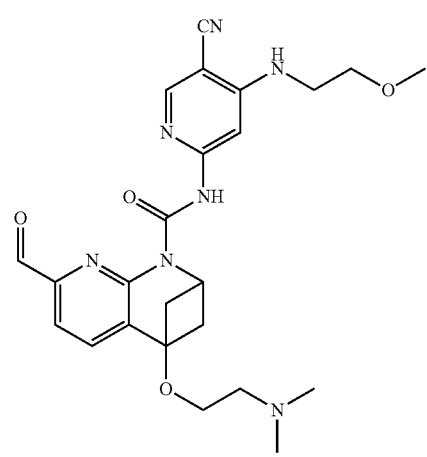
30
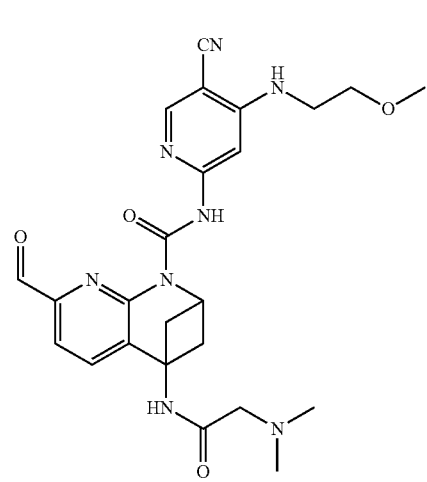
31
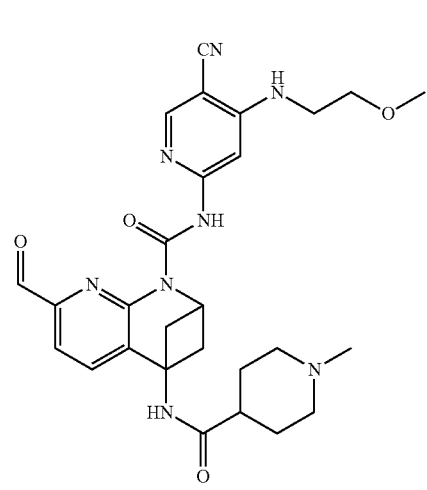

| 32 | 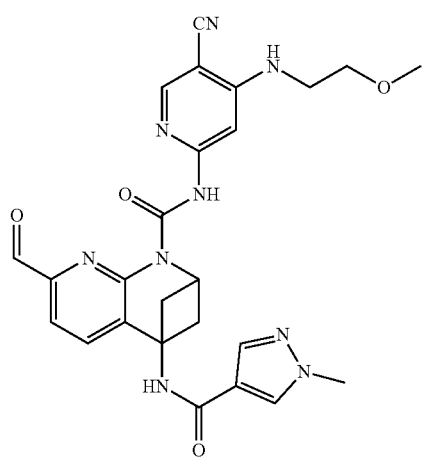 |
| --- | --- |
| 33 | 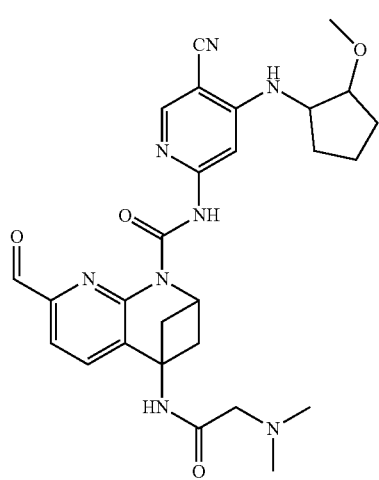 |
| 34 | 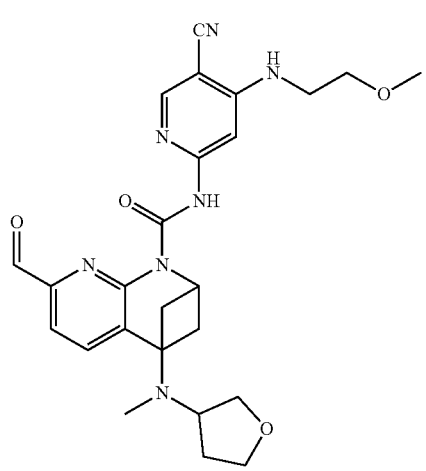 |
| 35 | 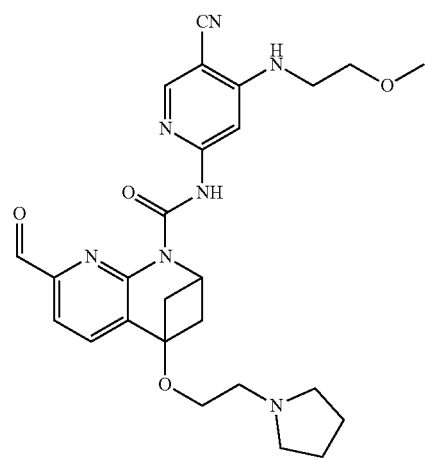 |
| --- | --- |
| 36 | 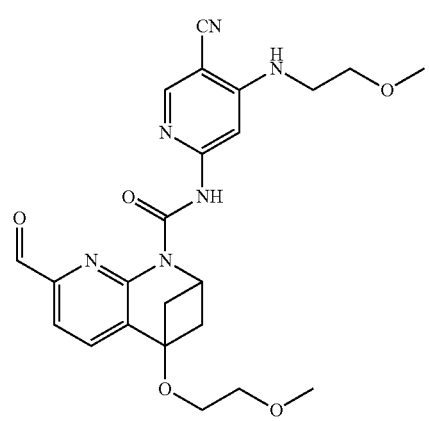 |
| 37 | 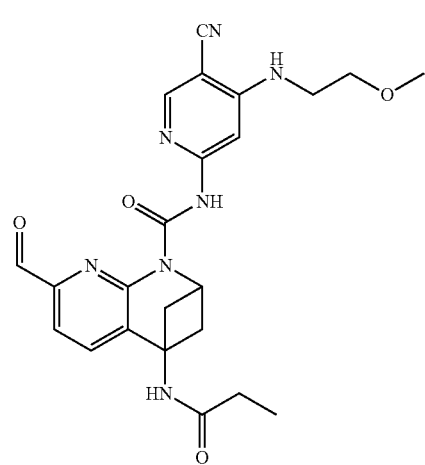 |

38
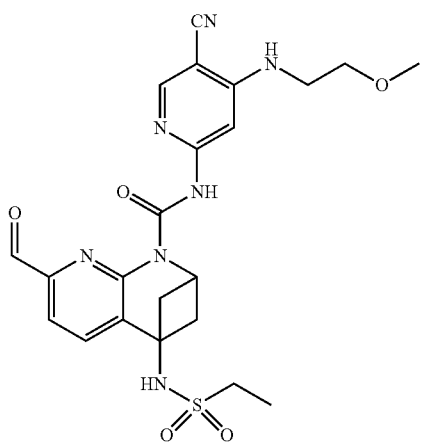
39
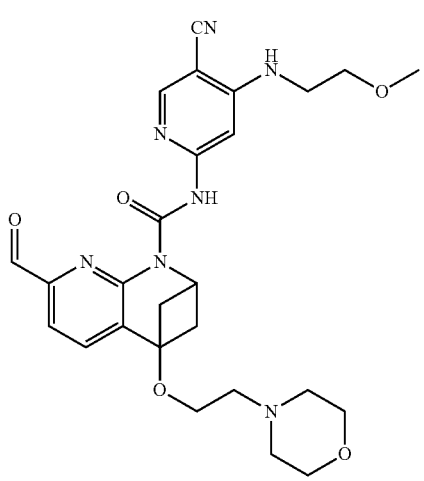
40
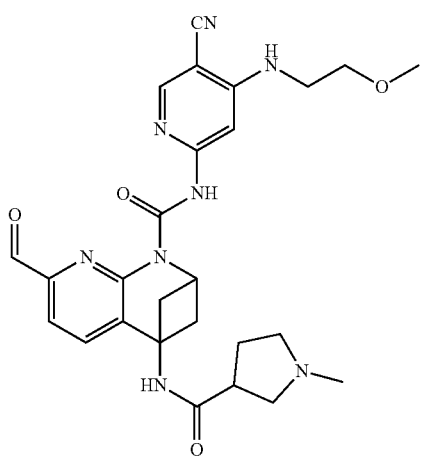
41
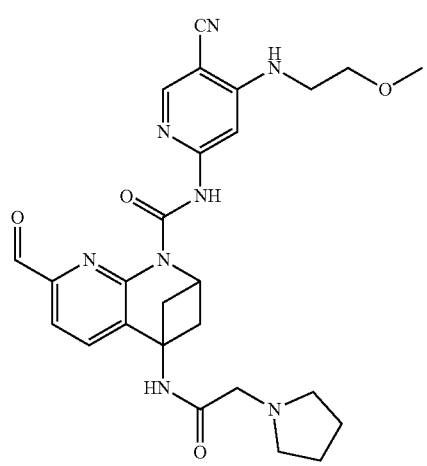
42
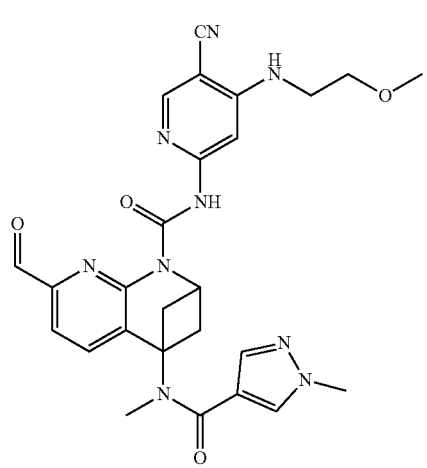
43
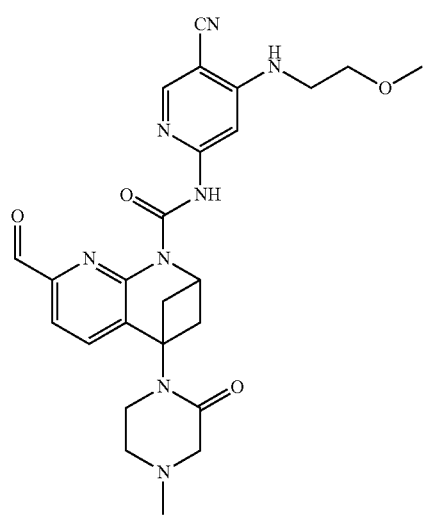

44

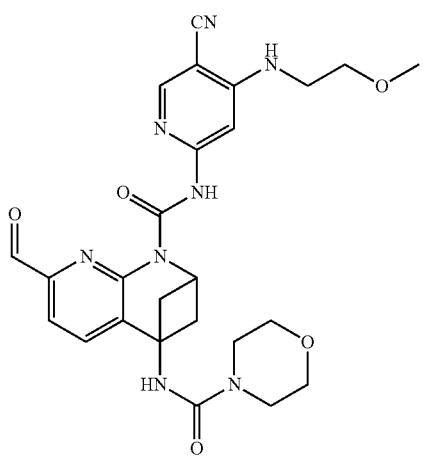

45

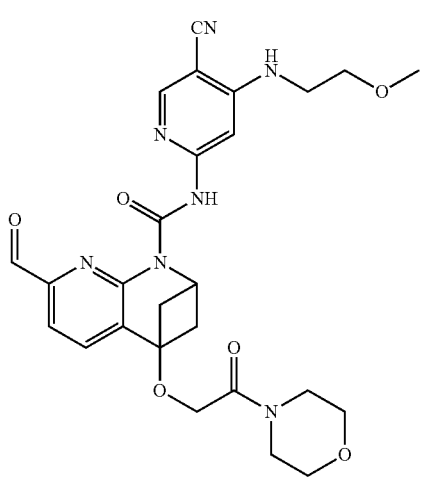

46

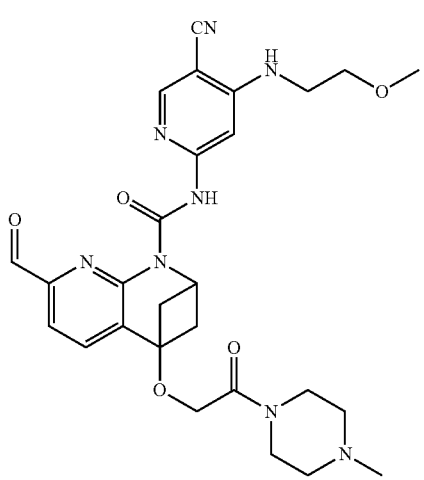

47

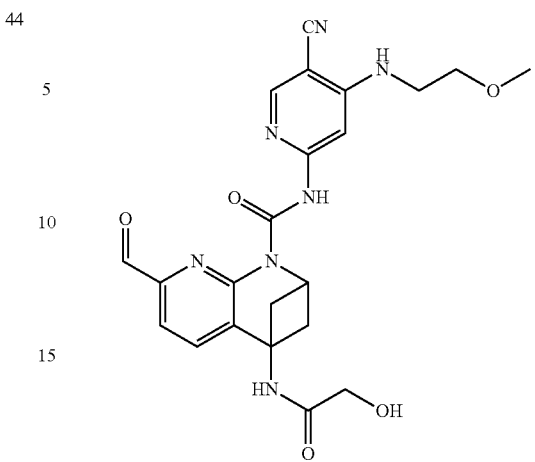

48

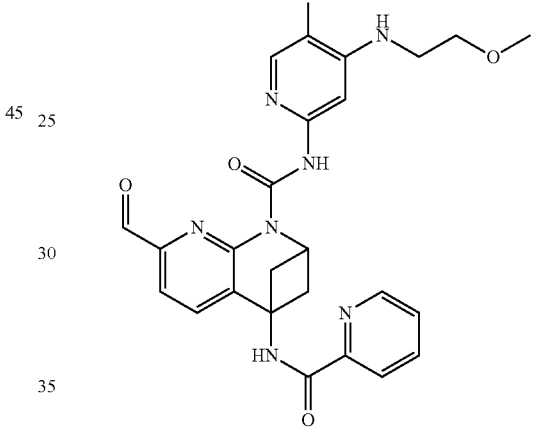

49

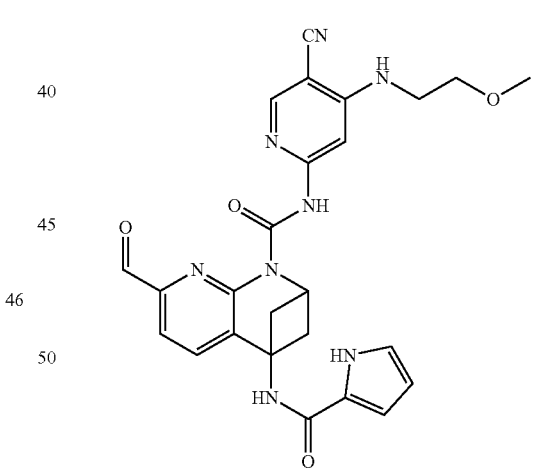

7. A pharmaceutical composition comprising the compound of formula (I) or a pharmaceutically acceptable salt, solvate, active metabolite, polymorph, isotopic label, isomer or pro-drug thereof according to claim 1, and a pharmaceutically acceptable carrier.

8. A method of preventing or treating a disease mediated by FGFR4, FGF19, or KLB, comprising administering to a patient in need thereof a therapeutically effective amount of the compound of formula (I) or a pharmaceutically acceptable salt, solvate, active metabolite, polymorph, isotopic label, isomer or pro-drug thereof according to claim 1.

9. A method of treating benign or malignant tumors or obesity, comprising administering to a patient in need thereof a therapeutically effective amount of the compound of formula (I) or a pharmaceutically acceptable salt, solvate, active metabolite, polymorph, isotopic label, isomer or pro-drug thereof according to claim 1.

10. The method according to claim 9, wherein the malignant tumor is selected from the group consisting of hepatocellular carcinoma, cholangiocarcinoma, breast cancer, nasopharyngeal cancer, oral cancer, glioblastoma, prostate cancer, rhabdomyosarcoma, esophageal squamous cell carcinoma, malignant peripheral nerve sheath tumor, gastric cancer, ovary cancer, lung cancer, colorectal cancer, and skin cancer.

11. A method preventing or treating a disease mediated by FGFR4, FGF19, or KLB, comprising administering to a patient in need thereof a therapeutically effective amount of the compound of formula (I) or a pharmaceutically acceptable salt, solvate, active metabolite, polymorph, isotopic label, isomer or pro-drug thereof according to claim 6.

12. A method of treating benign or malignant tumors or obesity, comprising administering to a patient in need thereof a therapeutically effective amount of the compound of formula (I) or a pharmaceutically acceptable salt, solvate, active metabolite, polymorph, isotopic label, isomer or pro-drug thereof according to claim 6.

13. The method according to claim 12, wherein the malignant tumor is selected from the group consisting of hepatocellular carcinoma, cholangiocarcinoma, breast cancer, nasopharyngeal cancer, oral cancer, glioblastoma, prostate cancer, rhabdomyosarcoma, esophageal squamous cell carcinoma, malignant peripheral nerve sheath tumor, gastric cancer, ovary cancer, lung cancer, colorectal cancer, and skin cancer.

* * * * *